United States Patent
Jeong

(10) Patent No.: US 7,986,412 B2
(45) Date of Patent: *Jul. 26, 2011

(54) INTERFEROMETRIC DEFECT DETECTION AND CLASSIFICATION

(75) Inventor: Hwan J. Jeong, Los Altos, CA (US)

(73) Assignee: JZW LLC, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/959,194

(22) Filed: Dec. 2, 2010

(65) Prior Publication Data

US 2011/0075151 A1 Mar. 31, 2011

(51) Int. Cl.
*G01B 9/02* (2006.01)
(52) U.S. Cl. ........................................ 356/450
(58) Field of Classification Search ................... 356/496, 356/450, 237.1, 239.1
See application file for complete search history.

(56) References Cited

U.S. PATENT DOCUMENTS

| | | |
|---|---|---|
| 6,259,055 B1 | 7/2001 | Sokol et al. |
| 6,501,551 B1 | 12/2002 | Tearney et al. |
| 6,934,035 B2 | 8/2005 | Yang et al. |
| 7,061,625 B1 | 6/2006 | Hwang et al. |
| 7,095,507 B1 | 8/2006 | Hwang et al. |
| 7,138,629 B2 | 11/2006 | Noji et al. |
| 7,209,239 B2 | 4/2007 | Hwang et al. |
| 7,259,869 B2 | 8/2007 | Hwang et al. |
| 7,351,969 B2 | 4/2008 | Watanabe et al. |
| 7,357,513 B2 | 4/2008 | Watson et al. |
| 7,365,858 B2 | 4/2008 | Fang-Yen et al. |
| 7,428,057 B2 | 9/2008 | De Lega et al. |
| 7,446,882 B2 | 11/2008 | De Lega et al. |
| 7,616,323 B2 | 11/2009 | De Lega et al. |
| 7,864,334 B2* | 1/2011 | Jeong ............................ 356/496 |
| 2002/0066318 A1 | 6/2002 | Dubois et al. |
| 2004/0160604 A1* | 8/2004 | Meeks et al. .................. 356/364 |
| 2005/0105097 A1 | 5/2005 | Fang-Yen et al. |
| 2006/0132804 A1 | 6/2006 | Dubois et al. |
| 2006/0158657 A1 | 7/2006 | De Lega et al. |

(Continued)

OTHER PUBLICATIONS

Aug. 5, 2009 International Search Report in connection with counterpart International Application No. PCT/US2009/045999.

(Continued)

*Primary Examiner* — Tarifur R Chowdhury
*Assistant Examiner* — Jonathan M Hansen
(74) *Attorney, Agent, or Firm* — Cooper & Dunham, LLP

(57) ABSTRACT

Systems and methods for using common-path interferometric imaging for defect detection and classification are described. An illumination source generates and directs coherent light toward the sample. An optical imaging system collects light reflected or transmitted from the sample including a scattered component and a specular component that is predominantly undiffracted by the sample. A variable phase controlling system is used to adjust the relative phase of the scattered component and the specular component so as to change the way they interfere at the image plane. The resultant signal is compared to a reference signal for the same location on the sample and a difference above threshold is considered to be a defect. The process is repeated multiple times each with a different relative phase shift and each defect location and the difference signals are stored in memory. This data is then used to calculate an amplitude and phase for each defect, which can be used for defect detection and classification. This method is expected to detect much smaller defects than current inspection systems and to find defects that are transparent to these systems.

22 Claims, 60 Drawing Sheets

U.S. PATENT DOCUMENTS

| | | |
|---|---|---|
| 2006/0158658 A1 | 7/2006 | Colonna De Lega et al. |
| 2006/0158659 A1 | 7/2006 | Colonna De Lega et al. |
| 2006/0215174 A1 | 9/2006 | Dubois et al. |
| 2008/0007726 A1 | 1/2008 | Fairley et al. |
| 2008/0024766 A1 | 1/2008 | Mieher et al. |
| 2008/0088849 A1 | 4/2008 | De Lega et al. |
| 2008/0221814 A1 | 9/2008 | Trainer |
| 2008/0266547 A1 | 10/2008 | Clark et al. |
| 2008/0291465 A1 | 11/2008 | Lorraine et al. |
| 2009/0296096 A1 | 12/2009 | Jeong |
| 2010/0134786 A1 | 6/2010 | De Lega et al. |

OTHER PUBLICATIONS

Aug. 5, 2009 Notification of Transmittal of the International Search Report and the Written Opinion of the International Searching Authority, or the Declaration in connection with counterpart International Application No. PCT/US2009/045999.

Aug. 5, 2009 Written Opinion of the International Searching Authority in connection with counterpart International Application No. PCT/US2009/045999.

* cited by examiner

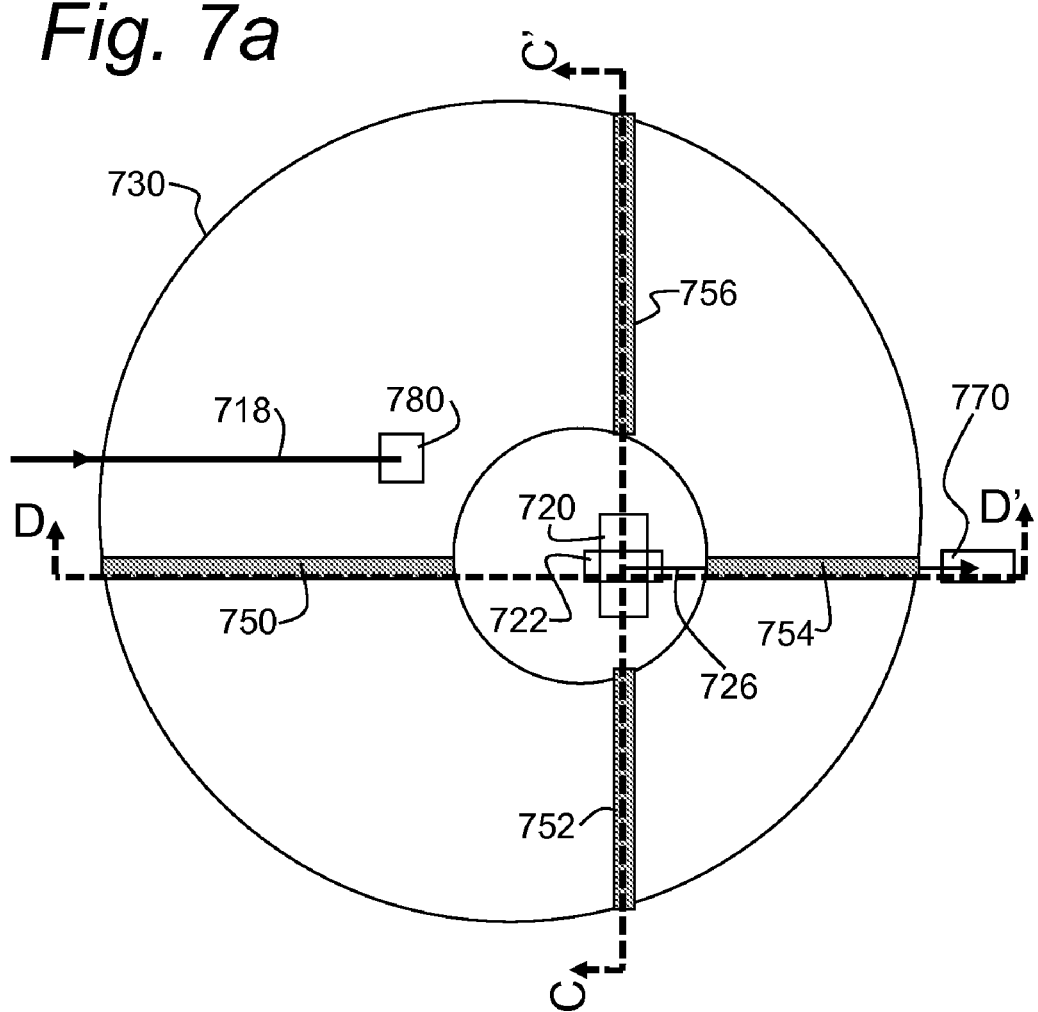
Fig. 7a
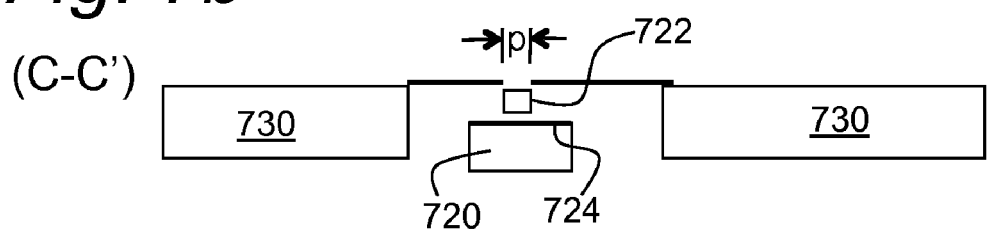
Fig. 7b (C-C')
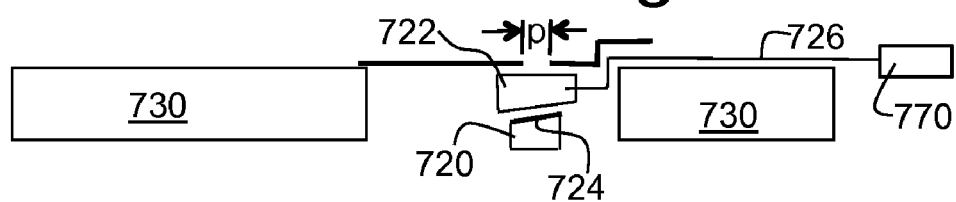
Fig. 7c (D-D')

(E-E')

(F-F')

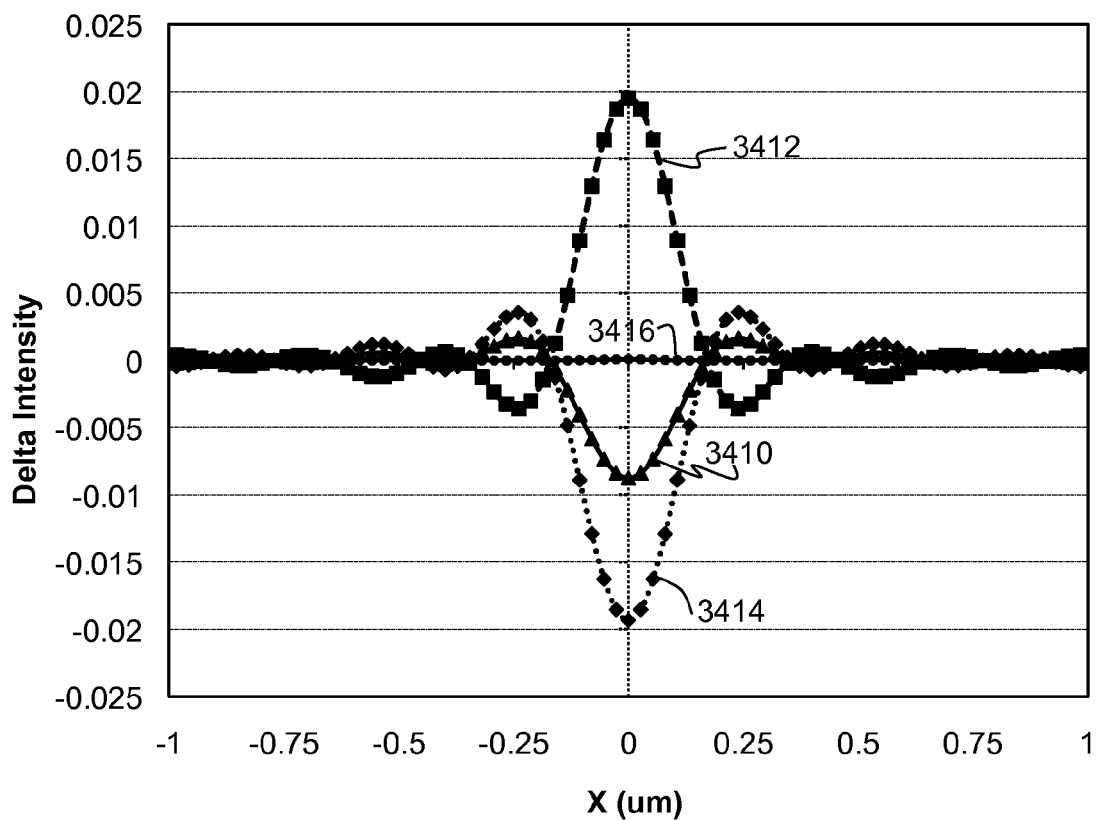
Fig. 34
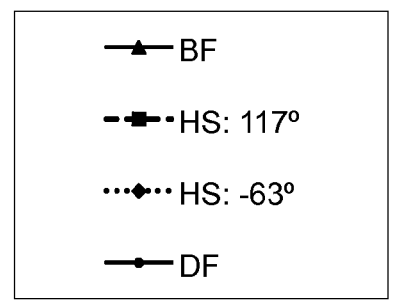

INTERFEROMETRIC DEFECT DETECTION AND CLASSIFICATION

CROSS-REFERENCE TO RELATED APPLICATIONS

This patent application claims the benefit of U.S. patent application Ser. No. 12/190,144 filed Aug. 12, 2008, of U.S. Provisional Ser. No. 61/130,729 filed Jun. 3, 2008, of U.S. Provisional Ser. No. 61/135,616 filed Jul. 22, 2008, of U.S. Provisional Ser. No. 61/189,508 filed Aug. 20, 2008, of U.S. Provisional Ser. No. 61/189,509 filed Aug. 20, 2008, of U.S. Provisional Ser. No. 61/189,510 filed Aug. 20, 2008 and of U.S. Provisional Ser. No. 61/210,513 filed Mar. 19, 2009, each of which is incorporated by reference herein.

FIELD

This patent specification relates to common-path interferometry. More particularly, the patent specification relates to high resolution common-path interferometric imaging for use in detecting and classifying defects in microlithographic devices such as semiconductor devices and integrated circuits and defects in photolithographic reticles.

BACKGROUND

Optical defect detection technology has been one of the key technologies limiting our ability to make ever smaller transistors. It has, up till now, provided both high performance and high throughput, which other technologies like electron beam microscopy could not offer. However, as the geometries employed in IC chips have continued to decrease, it has become harder to detect defects reliably. Design rules of future generations of IC chips are so small that there is a real possibility that none of the current optical defect detection technologies will work. Therefore, in order to extend the life of optical inspection technology into future equipment generations, a major overhaul of optical defect detection technology is needed.

Optical defect detection systems in use today include both bright field systems and dark field systems. Unlike bright field systems, dark field systems attempt to exclude the unscattered illumination beam from the image. However, limitations of the current dark field and bright field defect detection systems exist which cause difficulty in reliably detecting defects, especially as the design rules progressively decrease. Separate path interferometric techniques have been proposed according to which two beams, probe and reference beams, are generated using a beam splitter and brought to an image sensor through different paths or subsystems. For example, separate path systems designed for defect detection are discussed in U.S. Pat. Nos. 7,061,625, 7,095,507, 7,209,239 and 7,259,869. These and the other patents identified in this patent specification, as well as all non-patent references identified in this patent specification, are hereby incorporated by reference. Another separate path system which is designed for high resolution surface profiling is the Linnik interferometer (see, M. Francon, "Optical Interferometry," Academic Press, New York and London, 1966, p 289.) These separate path interferometric systems are, in principle, capable of amplifying the defect signal or measuring both the amplitude and phase of the defect signal. However, these systems are not only complex and expensive but also have serious drawbacks; photon noise and sample pattern noise can be excessive and also they are unstable due to the two different paths the probe and reference beams take. Small environmental perturbations like floor vibrations, acoustic disturbances, temperature gradients, etc., can easily destabilize the system. Consequently, it is difficult to use this kind of separate path interferometric system in industrial environments.

Conventional phase-contrast microscopes are designed to provide a fixed amount of phase control to specular component, usually $\pi/2$ or $-\pi/2$. These systems commonly use extended light sources such as an arc or halogen lamp. Although they are generally suitable for observing biological samples, conventional phase-contrast microscopes are not generally well suited for detecting the wide variety of defects that exist in semiconductor wafers and/or reticles.

U.S. Pat. No. 7,295,303 discusses approaches similar to phase-contrast microscopy that are not well suited for detecting a wide variety of defects that exist in semiconductor wafers and/or reticles.

U.S. Pat. No. 7,365,858 and U.S. Application Publication No. 2005/0105097 A1 discuss a system for imaging biological samples. Two modes of operation are discussed, a "phase mode" and an "amplitude mode." The goal in the discussed amplitude mode is to obtain high contrast raw images. In phase mode, the discussed techniques attempt to extract phase information only. The discussions mention liquid crystal spatial light modulation which is performed in a pupil conjugate through the use of beam splitters and additional lens groups, which are prone to illumination power losses.

U.S. Pat. No. 6,674,522 and U.S. Application Publication No. 2008/0226157 A1 discuss defect detection systems and methods for lithographic masks. They utilize a defocus or Zernike point spread function to detect defects. Their methods are not only complex and require a large amount of computing resources but also not suitable for the detection of small defects.

SUMMARY

A common-path interferometric imaging system and method are provided. According to some embodiments, a common-path interferometric imaging system for the detection and classification of defects in a sample is provided. The system includes an illumination source for generating light, which includes wavelengths as short as EUV (13.5 nm) and wavelengths as long as 10 microns in the far infrared, directed toward the sample; an optical imaging system for collecting a portion of the light from the sample including a scattered component of the light that is predominantly scattered by the sample, and a specular component of the light that is predominantly undiffracted, or specularly reflected or transmitted, by the sample; a variable phase controlling system for adjusting the relative phase of the scattered component and the specular component and a sensing system for measuring the intensity of the combined scattered and specular components, and a processing system to determine from outputs of the sensing system if points on the sample are likely to include defects.

An accurate positioning system allows the intensity signal from each point on the sample to be accurately referenced to and compared with a reference signal for that point by a computer. If the difference exceeds predetermined positive and negative thresholds, then this location on the sample is recorded and displayed as a possible defect location along with the level of the sample and reference signals corresponding to that location.

Under some conditions it is possible that a defect could be missed with a given phase shift setting so this process can be repeated with a different phase shift setting. A second scan with a different phase shift is very likely to detect any defects missed during the first scan but two scans don't provide the additional information needed to accurately characterize the defect. However a third scan with a third phase shift does provide sufficient data to characterize both the phase and amplitude of the defect and this data, together with their location with respect to the circuit elements, is useful in grouping together like defects and in determining their likely effect on product yield if left uncorrected.

The reference signal with which the signal from the sample is compared may be generated by a computer from the pattern image that is expected to be on the sample, assuming the defect is not present. If multiple copies of the pattern are available and some are known to be defect free, or the defects are known to be randomly distributed, then the reference signal can be generated by a similar common-path interferometric imaging system using the same phase shift and wavelength to scan the corresponding position on one or more neighboring die on the same wafer, or the corresponding position on one or more die on a similar wafer.

BRIEF DESCRIPTION OF THE DRAWINGS

The inventive body of work will be readily understood by referring to the following detailed description in conjunction with the accompanying drawings, in which:

FIGS. 7a-7c show an example of a compensation plate with Fourier filter strips for use with an interferometric defect detection system, according to some embodiments;

FIGS. 33 through 35b are graphs showing results of numerical simulations;

DETAILED DESCRIPTION

Figure 1:
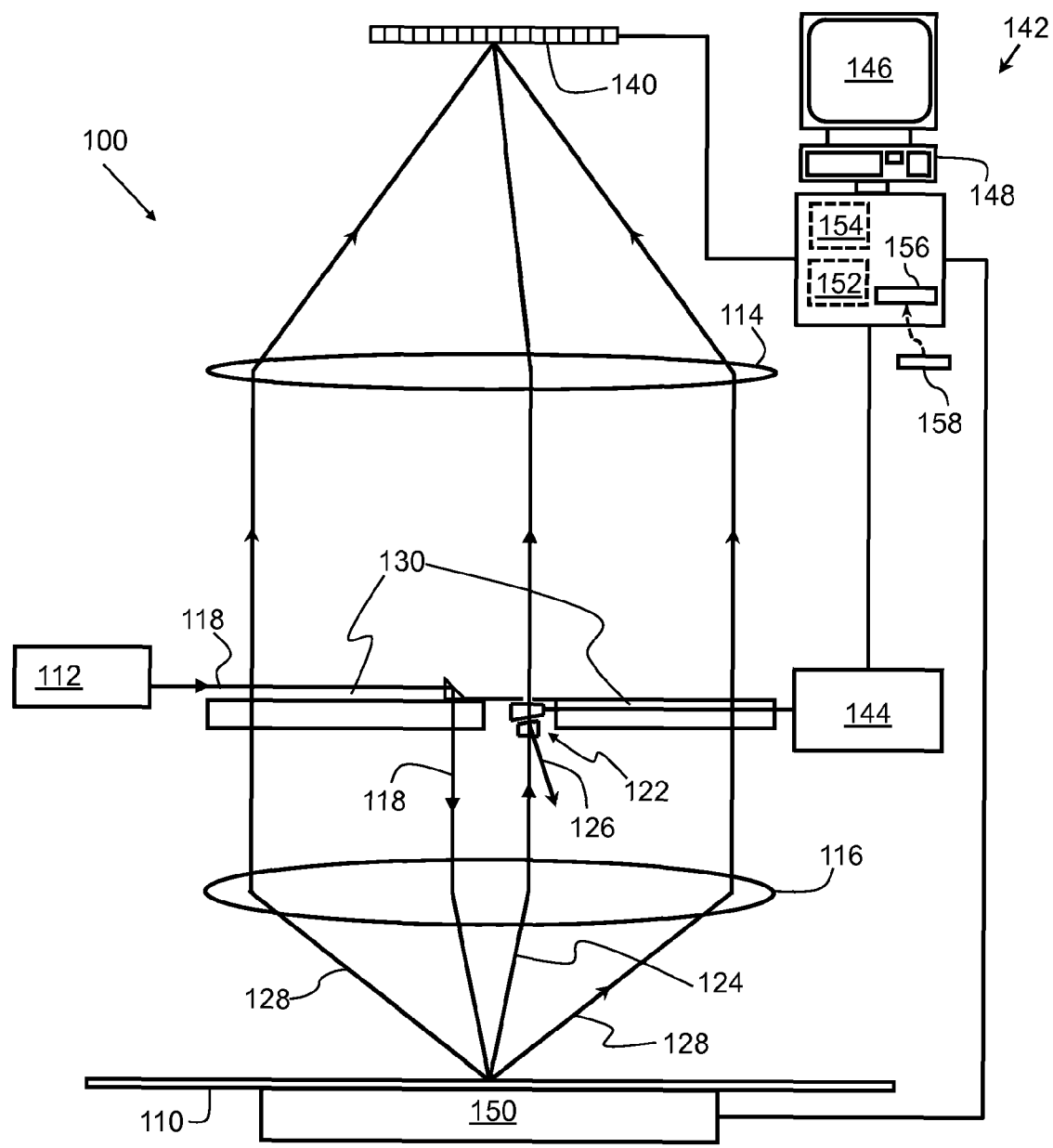
FIG. 1 shows an example of an interferometric defect detection system, according to some embodiments.

A detailed description of the inventive body of work is provided below. While several embodiments are described, it should be understood that the inventive body of work is not limited to any one embodiment, but instead encompasses numerous alternatives, modifications, and equivalents, as well as combinations of features from the different embodiments. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work. The words "reticle" and "mask" are used herein interchangeably and refer to a patterned object that is used as a master to create other patterned objects.

The optical field can be described with complex amplitudes. Complex amplitudes can be conveniently represented in a Cartesian or in a polar coordinate system. It is represented by real and imaginary parts in a Cartesian coordinate system and amplitude and phase in a polar coordinate system. Therefore, the three phrases: "complex amplitude", "real and imaginary parts," and "amplitude and phase" are equivalent to each other as used herein, and the three terms are treated equivalently and can be exchanged with one another.

Also, the word "light" is used as shorthand for electromagnetic radiation having a relatively wide range of possible wavelengths, as discussed below. In addition, the specular component of reflection in practice is "substantially specular," meaning that it includes not only specularly reflected light but can also include a relatively small amount of scattered light.

I. Defect Signal Equation

Starting from the first principle, when a ray of light with a narrow temporal frequency bandwidth hits a sample such as a wafer, most of the light is absorbed or specularly reflected (or undiffracted) and a small part of the light is scattered (or diffracted) by both circuit patterns and defects in the wafer. The light ray can be decomposed into several electrical field components. Each field component of the ray is defined as follows.

$b \equiv |b|\exp(i\phi_b)$; Complex amplitude of the specular component, where $\phi_b$ is the phase of specular component which can be set to zero without losing the generality of the signal equation, $a \equiv |a|\exp(i(\phi_a+\phi_b)) \equiv (a_x+ia_y)\exp(i\phi_b)$; Complex amplitude of the portion of the light ray scattered by circuit patterns whose polarization is the same as that of b, and where $\phi_a$ is the phase of a relative to the phase of b, and $a_x$ and $a_y$ are the real and imaginary components of a respectively when the real axis is oriented to the direction of b, $s \equiv |s|\exp(i(\phi_s+\phi_b)) \equiv (s_x+is_y)\exp(i\phi_b)$; Complex amplitude of the portion of the light ray scattered by defects whose polarization is the same as that of b, also called signal, and where $\phi_s$ is the phase of s relative to that of b and $s_x$ and $s_y$ are the real and imaginary components of s respectively when the real axis is oriented to the direction of b, $$a + s = |a|\exp(i(\varphi_a + \varphi_b)) + |s|\exp(i(\varphi_s + \varphi_b))$$
$$= ((a_x + s_x) + i(a_y + s_y))\exp(i\varphi_b)$$

$q_a \equiv |q_a|\exp(i(\phi_{qa}+\phi_b))$; Complex amplitude of the portion of the light ray scattered by circuit patterns whose polarization is orthogonal to that of b, $q_s \equiv |q_s|\exp(i(\phi_{qs}+\phi_b))$; Complex amplitude of the portion of the light ray scattered by defects whose polarization is orthogonal to that of b, and $g \equiv |g|\exp(i(\phi_g+\phi_b))$; Complex amplitude of any stray light present. Stray light is undesirable non-image-forming light which is generated by unwanted reflections from lens surfaces and mechanical components.

The light intensity that an image sensor detects can be expressed as follows. Note that, in imaging, light of narrow temporal frequency bandwidth can be treated like the light of a single temporal frequency with the same intensity. This is not only intuitively correct but can also be easily proved mathematically.

The light intensity, I, detected by a detector element at the image plane is the sum of the squares of the electric field amplitudes for the specular, scattered and stray light components and is given by:

$$I \equiv |b + a + s|^2 + |q_a + q_s|^2 + |g|^2 \qquad (1)$$
$$= |b|^2 + |a + s|^2 + |q_a + q_s|^2 + |g|^2 + (ba^* + b^*a) + (bs^* + b^*s) \qquad (1a)$$
$$= |b|^2 + |a + s|^2 + |q_a + q_s|^2 + |g|^2 + 2|b||a|\cos(\varphi_a) + 2|b||s|\cos(\varphi_s) \qquad (1b)$$
$$= |b|^2 + |a + s|^2 + |q_a + q_s|^2 + |g|^2 + 2|b|(a_x + s_x) \qquad (1c)$$

where b*, a* and s* are the complex conjugates of b, a and s respectively.

The specular component, b, is separated out in equation (1a) because it can be physically separated from other image intensity components at the pupil plane. Note that all complex amplitudes are functions of position on the sample. Additionally, only relative phases between different components matter. Therefore, the absolute phase of specular component, $\phi_b$, does not play any role and can be set to zero without losing generality. Also notice that if $\phi_b$ is set to zero, the complex amplitude of the specular component defines the direction of the real axis of the complex plane coordinate system used herein.

The optical path length difference of the stray light with respect to the specular component is assumed to be larger than the coherence length of the illumination light. Therefore, stray light is added incoherently, without considering its relative phase, in the equation (1).

Equation (1c) shows that the image comprises not only a defect signal, s, but also many other unwanted components. In order to find a defect, components other than the defect signal need to be removed to the extent possible. This is commonly done by die-to-die subtraction of the image of, e.g., neighboring die from the image of the current die. Note that in general at least two die-to-die subtractions, for example, [(current die image)−(left die image)] and [(current die image)−(right die image)], are required in order to correctly identify defect signals. Defects that show up in both subtracted images belong to a current die. Defects that show up in only one of the two subtracted images belong to neighboring dies. Therefore, by comparing two subtracted images, we can tell which defects belong to which die unambiguously. For memory area inspection, cell-to-cell image subtractions rather than die-to-die image subtractions are performed in order to minimize noise from wafer patterns. This method works effectively because the chance of having defects at the same locations in two different dies is negligibly small. The image intensity difference after die-to-die subtraction can be expressed as follows.

$$\Delta I \equiv I - I(s = q_s = 0) \tag{2}$$

$$= |a+s|^2 - |a|^2 + |q_a + q_s|^2 - |q_a|^2 + bs^* + b^*s \tag{2a}$$

$$= |a+s|^2 - |a|^2 + |q_a + q_s|^2 - |q_a|^2 + 2|b|s_x \tag{2b}$$

$$= |a+s|^2 - |a|^2 + |q_a + q_s|^2 - |q_a|^2 + 2|b||s|\cos(\varphi_s) \tag{2c}$$

Equation (2c) is a general defect signal equation. Note that the definition of defect herein includes not only the defects of interest but also the defects of little or no interest. A good example of the defects of little interest is sample pattern noise. The sample pattern noise is actually not a noise but a defect as this term is used herein. That is, s, the defect signal includes the sample pattern noise as well as the defect signal of interest. Detailed discussions on sample pattern noise will be presented in later sections. Equation (2c) shows that the comparison of the two signals with and without a defect present is a mixed bag of different signal components. The first four terms constitute the dark field signal because they exist even if the specular component is filtered out (herein they will sometimes be called the "dark field term"). Dark field systems detect this part of the signal. Note that the raw dark field signal, the first four terms in equation (1b), is always positive. But, this is not the part that is of interest. Rather, it is the difference signal, equation (2c), that is used to find defects. The dark field part of the defect signal, i.e. the first four terms in equation (2c), is a combination of both positive and negative terms whose magnitudes depend not only on the defect pattern but also on circuit patterns around the defect. Therefore, the dark field part of a defect signal can either be positive, negative, or zero depending on the circuit pattern around the defect. This means that dark field systems cannot detect defects in a consistent manner.

Furthermore, as the defect size gets much smaller than the wavelength, the magnitude of the dark field signal becomes so small that it can be easily swamped by noise. The last term in the signal equation is the interference term (herein it will be sometimes called the "interference part"). That is, the last term originates from interference between the defect signal amplitude and the specular component. The sign and magnitude of the interference term depends not only on the strength of the specular component but also on the relative phase between the defect signal amplitude and the specular component. If the phase difference between the defect signal and the specular component is ±90° then the defect signal may not be detected.

Current bright field systems detect both dark field and interference terms simultaneously without controlling the relative phase between the defect signal amplitude and the specular component. In this case, not only can the defect signal be low but also the dark field terms and the interference terms can either bolster or cancel each other depending on the nature of the defect itself and the surrounding circuit patterns. This means that the current bright field systems cannot offer consistent defect detection performance either.

Therefore, both current dark field and bright field systems are severely handicapped. More signal analysis shows that the bright field system can be fatally blind to some types of defects. This will be shown in a later section describing the High Sensitivity Mode.

The solutions described herein can be described at least theoretically in connection with signal equation (2c), but it should be understood that theoretical explanations can pertain to idealized circumstances that should not limit the practical aspects of the operation of embodiments disclosed in this patent specification. The signal equation shows the importance of controlling the relative phase between the defect signal amplitude and the specular component for consistent performance. By controlling the relative phase, both the sign and the magnitude of the interference term can be controlled. For example, if we set the relative phase to zero, the magnitude of the interference term attains a positive maximum. If we set the relative phase to 180°, the magnitude of the interference term attains a minimum (or a negative maximum). Thus, controlling the relative phase between the specular and scattered components can be used to maximize the magnitude of interference term, and can also be used to change its sign. It should be understood that references to maximizing in this patent specification refer to at increasing a parameter preferably but not necessarily to a practical maximum thereof, and references to minimizing refer to reducing a parameter preferably but not necessarily to a practical minimum thereof.

Owing to this capability of changing the sign by altering the relative phase shift, it is always possible to match the signs of the interference term and the dark field term. When the signs of the interference and dark field terms are the same, they bolster each other. Maximizing the defect signal through the control of relative phase between the defect signal amplitude and the specular component results in consistent system performance. Another important feature that equation (2c) reveals is the possibility of determining both the amplitude and phase of the interference term by scanning the sample multiple times with a different relative phase value for each sample scan.

The determination of both the amplitude and phase of the interference term facilitates not only high defect detection sensitivity but also a much more accurate defect classification. For example, the defect size can be estimated from the amplitude information and the defect type can be determined from the phase information. Note that the optical signal amplitude of the defect does not directly provide the physical size of the defect. Rather, it provides only an 'optical size' of the defect. The relationship between the physical size and the optical size can be complicated making it difficult to estimate the physical size of the defect accurately from the optical signal amplitude alone. However, we can establish a general correlation between the physical size and the optical sizes through experiments or simulations. Then, the physical size of defects can be approximately estimated from the correlation. If other data such as likely defect composition data, reticle pattern data, etc, are additionally used, a more accurate characterization of defects will be possible.

A more accurate characterization of defects allows a more accurate decision as whether or not they likely require repair. This possibility will be explored in a later section of Catch-all Mode. Accurate defect classification is usually as important as reliable defect detection because it can save time in the defect review process which is one of the more expensive processes in semiconductor manufacturing.

The relative phase can be controlled by controlling either the phase of the specular component or the phase of the scattered component. However, it is usually easier to control the phase of the specular component because the etendue of the specular component is much smaller than that of the scattered component. The control of the relative phase between scattered and specular components is one of the key features of the interferometric defect detection and classification technology disclosed herein. Its importance will be demonstrated with examples in later sections.

The signal equation reveals another important fact: the interference term, $2|b||s|\cos(\phi_s)$, is actually the defect signal amplified by the specular component, b. That is, even if the original defect signal is small, it can be amplified by the specular component by a large amount because the specular component is usually very intense. Furthermore, this amplification process turns out to be a noiseless. See, e.g., Philip C. D. Hobbs. "Building Electro-Optical Systems; Making it all work," John Wiley & Sons, Inc., 2000, pp 30-32 and p 123, which is incorporated by reference herein. This signal amplification process is so ideal that it does not degrade but rather maintains the signal-to-noise ratio. This kind of amplification is called "noiseless parametric amplification" where $|b|$ is the amplification parameter. A basic theoretical explanation for the noiseless amplification is as follows. Both the magnitude of the interference term and the photon noise are proportional to $|b|$. Therefore, the signal-to-noise ratio, the ratio between the two quantities, is independent of $|b|$. The factor '2' in the interference term comes from the fact that there are actually two signal amplifiers that coherently work with each other. One amplifier is represented by $bs^*$ and the other amplifier is represented by $b^*s$. They are mutually coherent but can either be mutually constructive or destructive depending on the relative phase between the defect signal and the specular component.

In order to maximize the amplification of the defect signal, the two amplifiers need to be configured to work in a mutually constructive way by controlling the relative phase between the defect signal and the specular component. The mutual construction becomes a maximum when the relative phase is set to either 0° or 180°. A complete mutual destruction happens when the relative phase is ±90°. In the case of noise, the story is different. We can see from equation (1b) that there is only one noise amplifier which is represented by $|b|^2$ in the equation and is the main source of photon noise. This means that the specular component can amplify the signal two times more than the signal-noise.

Consequently, the specular component can increase the signal-to-noise ratio of the signal up to two times the intrinsic signal-to-noise ratio inherent in the signal itself if the dynamic range of the image sensor is sufficiently large. The price paid for the factor '2' is that the relative phase between the scattered and the specular components must be controlled in order to maximize the amplification. Therefore, increasing the signal-to-noise ratio requires phase control. Phase control requires knowledge about the relative phase in order to add more information to the signal. Thus, the increase in the signal-to-noise ratio does not violate the law of information conservation.

The intrinsic signal-to-noise ratio is the ratio between the signal and the signal-noise, the noise contained in the signal itself. Signal-noise is also called intrinsic noise. The dynamic range of a detector is the ratio between the maximum signal range of the detector and the minimum detectable signal, which is usually assumed to be the noise level of the detector. Dynamic range is usually defined as the total number of gray levels the detector can provide, i.e. the maximum signal range divided by the noise level.

No electronic amplifiers, including even the cleanest electronic amplifiers, such as the dynodes inside a photo-multiplier tube, can increase the signal-to-noise ratio. They can only reduce the signal-to-noise ratio. The noiseless amplification by the specular component is special in the sense that it can actually increase the signal-to-noise ratio. It is the best amplifier known so far. It is the most suitable amplifier for weak signals such as the signals from tiny defects and it beats all electronic amplifiers in performance.

The systems and methods disclosed herein fully utilize the power of the noiseless amplification by the specular component in order to reliably detect tiny defects. The interferometric detection herein is a version of homodyne detection in which the two interfering beams have the same temporal frequency.

It is noted that the specular component is a double-edged sword. If it is utilized as an amplifier by controlling its phase properly, its benefit can be huge. However, if it is not utilized, it does not stay neutral but becomes harmful in that it can be a major source of photon noise. This additional noise indicates that bright field inspection systems can perform even worse than dark field inspection systems in certain instances. This is one of the reasons why the existing bright field systems do not perform consistently. One of main ideas described herein is utilizing the specular component in the most beneficial way.

The examples shown in the following tables demonstrate the power of noiseless amplification. Examples are selected to represent the real world of high-end defect detection in the future. In the examples, the relative phase between the specular and scattered components is set to 0° or 180° in order to maximize the noiseless amplification. The defect signal level in a single pixel of a typical high-end image sensor such as scientific grade CCD, TDI CCD (Time Delay and Integration CCD), etc. is considered. Detector noise is assumed to be additive and independent of the signal level. Light intensities are expressed in the unit of light-generated electrons in the detector rather than photons in the light beam because what we eventually care about is the number of electrons generated in the detector.

In the example shown in the first table, the defect signal is very weak compared with the detector noise but still quite strong compared with its intrinsic noise. The first table below shows how an undetectably weak defect signal for conventional defect detection system can become an easily detectable signal through a large, noiseless amplification provided by a strong specular component and a large image sensor dynamic range. In this example the signal-to-noise ratio was increased from 0.25 to 12.0 by the noiseless amplification process.

|  | Without Noiseless Amplification | With Noiseless Amplification |
| --- | --- | --- |
| Signal: $|s|^2$ | 50 electrons | 50 electrons |
| Intrinsic Noise | $\sqrt{50}$ = 7.07 electrons | $\sqrt{50}$ = 7.07 electrons |
| Intrinsic SNR | 7.07 | 7.07 |
| Detector Full Well Capacity | 200,000 electrons | 200,000 electrons |
| Detector Noise | 200 electrons | 200 electrons |
| Min Detectable Signal | 200 electrons | 200 electrons |
| Dynamic Range | $\frac{200,000}{200} = 1,000$ | $\frac{200,000}{200} = 1,000$ |

-continued

|  | Without Noiseless Amplification | With Noiseless Amplification |
|---|---|---|
| Specular Component: $\|b\|^2$ | 0 | 100,000 electrons |
| Gain: | 1× | $\dfrac{2 \times \sqrt{100,000} \times \sqrt{50}}{50} = 89.4\times$ |
| Amplified Signal | 50 electrons | $50 \times 89.4 = 4{,}472$ electrons |
| Raw Image Contrast | $\dfrac{50 - 0}{50 + 0} = 100\%$ | $\dfrac{104{,}472 - 100{,}000}{104{,}472 + 100{,}000} = 2.2\%$ |
| # of Gray Levels | $\dfrac{50}{200} = 0.25$ | $\dfrac{4{,}472}{200} = 22.4$ |
| Total Noise | $\sqrt{200^2 + \left(\sqrt{50}\right)^2} = 200.12$ electrons | $\sqrt{200^2 + \left(\sqrt{100{,}000}\right)^2} = 374.2$ electrons |
| SNR of Amplified Signal | $\dfrac{50}{200} = 0.25$ | $\dfrac{4{,}472}{347.2} = 12.0$ |
| Dominant Noise | Detector noise | Photon noise |

The second table below shows how even an extremely feeble signal from a tiny defect can become a detectable signal through a large noiseless amplification provided by the strong specular component and a large dynamic range of the image sensor. Notice that, in this case, the signal is weak compared even with its intrinsic noise. However, the signal-to-noise ratio increased from 0.005 to a sizable 1.69 by the noiseless amplification process. It shows the possibility of relatively reliable detection of even a single photon signal.

of small or tiny defects in the future. Noiseless amplification allows us to detect very weak defect signals reliably even with a noisy image sensor as long as the intrinsic signal-to-noise ratio of the signal is reasonably high. It would be quite hopeless to detect such tiny defects without the noiseless amplification of defect signals.

In the real world, especially in high speed applications such as high throughput defect detection, if the defect signal is as weak as the example signal shown in the second table, it may

|  | Without Noiseless Amplification | With Noiseless Amplification |
|---|---|---|
| Signal: $\|s\|^2$ | 1 electron | 1 electron |
| Intrinsic Noise | $\sqrt{1} = 1$ electron | $\sqrt{1} = 1$ electron |
| Intrinsic SNR | 1 | 1 |
| Detector Full Well Capacity | 200,000 electrons | 200,000 electrons |
| Detector Noise | 200 electrons | 200 electrons |
| Min Detectable Signal | 200 electrons | 200 electrons |
| Dynamic Range | $\dfrac{200{,}000}{200} = 1{,}000$ | $\dfrac{200{,}000}{200} = 1{,}000$ |
| Specular Component: $\|b\|^2$ | 0 | 100,000 electrons |
| Gain: | 1× | $\dfrac{2 \times \sqrt{100{,}000} \times \sqrt{1}}{1} = 632.5\times$ |
| Amplified Signal | 1 electron | $1 \times 632.5 = 632.5$ electrons |
| Raw Image Contrast | $\dfrac{1 - 0}{1 + 0} = 100\%$ | $\dfrac{100{,}632.5 - 100{,}000}{100{,}632.5 + 100{,}000} = 0.32\%$ |
| # of Gray Levels | $\dfrac{1}{200} = 0.005$ | $\dfrac{632.5}{200} = 3.16$ |
| Total Noise | $\sqrt{200^2 + \left(\sqrt{1}\right)^2} = 200$ electrons | $\sqrt{200^2 + \left(\sqrt{100{,}000}\right)^2} = 374.2$ electrons |
| SNR of Amplified Signal | $\dfrac{1}{200} = 0.005$ | $\dfrac{632.5}{374.2} = 1.69$ |
| Dominant Noise | Detector noise | Photon noise |

In both cases, the signal-to-noise ratio of the amplified signal is larger than the intrinsic signal-to-noise ratio of the signal itself. This is one of the amazing powers of the technique disclosed herein that to the inventor's knowledge has not been previously appreciated or expected. The signal-to-noise ratios are still less than two times the intrinsic signal-to-noise ratios due to the limited amplification of the signals. The tables show us the importance of the noiseless amplification of signals by the specular component for the detection not be easy to find the defect even with a large amount of noiseless amplification of the signal. Note that in high speed applications, the read-out noise often becomes the major noise component. However, the relative advantage of the systems and methods disclosed herein over existing technologies such as bright field or dark field technology is maintained. In both examples, the noiseless amplification increased the signal-to-noise ratio by a large amount. Basically, a large noiseless amplification drops detector noise out of the equation. Only the intrinsic signal-to-noise ratio matters. The intrinsic signal-to-noise ratio is the ratio between the signal and the signal-noise which is the noise contained in the signal itself. It will be shown through examples in the later section of Limitations of Dark Field Mode that a large amount of noiseless signal amplification by the specular component can be achieved even with samples having low reflectivity.

In signal amplification, the quality of the first stage amplifier is the most important. The specular component provides the possibility of noiseless first stage signal amplification. The systems and methods disclosed herein can take advantage of this by controlling the amplitude of the specular component and by controlling the relative phase between the defect signal amplitude and the specular component. By realizing this noiseless amplification of the signal, a high signal-to-noise ratio can be achieved with the disclosed techniques even if the original signal is weak. A high signal-to-noise ratio means high sensitivity and a low false detection rate in defect detection. Noiseless amplification of the defect signal using the specular component is one of the key features of interferometric defect detection and classification technology disclosed herein. Generally, the higher the noiseless amplification, the better the signal-to-noise ratio.

High noiseless amplification benefits from a strong specular component. Therefore, an unattenuated strong specular component is generally preferred herein. This is the opposite of conventional microscopy where the specular component is either blocked off or severely attenuated to enhance the contrast of the raw images. In the systems and methods disclosed herein, the specular component should be attenuated when the dynamic range of the image sensor is too limited for the application.

The phase controller can also be used for the deamplification of unwanted defect signals. A good example is wafer pattern noise which is actually not a noise but an unwanted defect signal. In most defect detection applications, it is desirable to suppress wafer pattern noise. If the suppression of wafer pattern noise is more important than amplifying the defect signals of interest, the phase controller can be set to minimize the wafer pattern noise rather than maximizing the defect signals of interest. More concrete discussions on pattern noise will be presented later. The terms "sample pattern noise", "wafer pattern noise", "pattern noise", "sample noise" and "wafer noise" refer to the same kind of noise and will be used interchangeably herein.

Another important fact revealed by examining the signal equation is that the spatial frequency band width of the interference term is different from that of the dark field term. The spatial frequency band width of the interference term is smaller than that of the dark field term in a common path configuration. (See FIG. 40 for example.) Less accurately but more intuitively speaking, the defect image formed by the interference term is spatially wider than the defect image formed by the dark field term. This implies that the frequency bandwidth of the interference term is narrower. This can be beneficial because it can lead to a higher throughput. A smaller bandwidth allows a coarser sampling of the sample image which allows a larger field of view for the imaging system with an image sensor of the same size. A higher throughput can normally be achieved with a larger field of view. The bandwidth of the dark field term is fixed as long as the numerical aperture of the imaging system is fixed; it does not depend on the ray angle of the specular component. However, the bandwidth of the interference term depends not only on the numerical aperture of the imaging system but also on the ray angle of the specular component.

The spatial frequency bandwidth of the interference term can be minimized by minimizing the ray angle of the specular component. The ray angle of the specular component becomes a minimum when the direction of the illumination light is normal or near-normal to the sample surface. Thus, when only the interference term is used or is dominant, a normal or near-normal illumination of the sample can be chosen for a higher throughput. Normal or near-normal illumination carries an additional advantage, in that it makes the polarization more uniform across the pupil compared to a high angle incidence illumination. A more uniform polarization across the pupil leads to a higher interference term. Another important fact to notice is that if the defect is much smaller than the wavelength, the spatial shape of the interference term is just the shape of the amplitude point spread function (APSF) of the imaging system and is thus fixed. Even if the spatial frequency of the specular component is not zero, it does not change the shape of the interference term. Its only effect is to provide the interference term with a non-zero carrier frequency.

If the specular component comprises a single ray, the interference term can be expressed as the multiplication of the amplitude point spread function, APSF, with the carrier frequency term. That is, the carrier frequency term can always be factored out and be treated separately. If we treat the carrier frequency term separately, there is no difference between the shape of the subtracted image of a tiny defect and the APSF. This allows a fast numerical deconvolution of the defect image with the sampling functions of finite width attributable to a detector array.

The width of the sampling function is the width of the light-sensitive area in each pixel of the image sensor. A high sensitivity or a high dynamic range usually requires a large light-sensitive area. Thus the finite size of the detectors in the array serves to reduce maximum signal amplitude somewhat and deconvolution is equivalent to magnifying the image. Thus, the optical image magnification can be replaced with a fast numerical deconvolution. Replacing optical magnification with a numerical deconvolution reduces optical system cost. These issues are addressed in greater detail in the later section of Spatial Frequency Bandwidth.

It is sometimes useful to control the penetration depth of the illumination light into the sample surface. For example, if a defect that needs to be detected is located on or close to the sample surface, a shallow penetration of the illumination light will be generally preferred to detect the defect more reliably. In an opposite case where a defect that needs to be detected is located at the bottom of a deep trench, a deep penetration of the illumination light will generally be preferred to detect the defect more reliably. The penetration depth of the illumination light cannot be controlled arbitrarily. However, if the printed patterns around the defect on the sample are oriented in one direction, the penetration depth of the illumination light can be controlled to some degree by controlling the polarization of the illumination light. For example, if the polarization direction of the illumination light is set to be parallel to the direction of the printed patterns on the sample, the illumination light penetrates the least amount.

If the polarization direction of the illumination light is set to be perpendicular to the direction of the printed patterns, the illumination light penetrates most deeply. This way of controlling the penetration depth of the illumination light can be useful in defect detection because a high proportion of printed patterns have a preferred edge direction.

Sometimes, the penetration of the illumination light can still be too deep even with the polarization of the illumination light oriented parallel to the direction of printed patterns. In this case, we can consider implementing a high incidence angle for the illumination. Note that an incidence angle is defined as the angle between the light ray and the surface normal, not the surface itself.

High incidence angle illumination can lead to throughput reduction because it requires a finer sampling grid in order to accurately sense the signal. This leads to either a higher magnification ratio or a smaller field of view for the same detector size. However, there can be a beneficial effect with a high angle illumination. If a high angle illumination is combined with s-polarized light, it can reduce the penetration of the illumination light into the surface of the sample much more effectively than a low incidence angle illumination. Note that an extremely high angle incidence is called "grazing incidence".

The reduction of the penetration of the illumination light into the wafer surface can also reduce the so-called "wafer pattern noise". Wafer pattern noise arises when the printed patterns on the wafer vary slightly from die to die due to variations in the manufacturing processes across the wafer. There are two kinds of wafer pattern noise. One is called axial or longitudinal wafer pattern noise and the other is called lateral wafer pattern noise. High angle illumination can reduce the longitudinal wafer pattern noise. Lateral wafer pattern noise can be reduced by good Fourier filtering and softening the edges of apertures and obscurations. An effective and practical way of softening the edges of apertures and obscurations is described in a later section called Serrated Aperture.

Strictly speaking, wafer pattern noise is actually not a noise at all. It is rather a kind of defect signal that we are not interested in. The reduction of the illumination light penetration can be significant if the surface profile of the wafer is relatively flat or if the direction of wafer pattern edges tend to be parallel to the direction of the s-polarization of the illumination light. However, the benefit can be less significant if the wafer has as many x-direction edges as y-direction edges or the directions of the pattern edges are not substantially parallel to the direction of the s-polarization of illumination light.

The implementation of high angle incidence illumination can be very costly. Therefore, the benefit against cost should be carefully analyzed before making a decision to employ high incidence angle illumination.

Penetration depth control of the illumination light is not the only reason for the polarization control of the illumination light. The interaction of the polarized light with the defect and its surrounding patterns is usually complicated and needs experimental measurement and/or numerical modeling to predict. Real cases often defy intuition. In some instances the polarization direction can be varied to improve defect detection. There is more discussion about the high angle illumination and polarization control in a later section of High Incidence-angle Illumination.

II. System Configuration:

The interferometric defect detection systems, according to embodiments, can be configured in many different ways. Many examples include a common path and a provision for controlling the relative phase between the defect signal and the specular component. In this section, general system configurations will be provided. Concrete design examples and subsystem examples will be presented later in other sections.

1. Example of System Configuration. FIG. 1 shows an example of an interferometric defect detection system 100. A light beam 118 is generated by illumination source 112 which in one example is a coherent source such as a laser. Any wavelength can be used provided it is possible to make the basic components of the interferometric imaging system. Examples of wavelengths that can be used include the ultraviolet, deep ultraviolet, vacuum ultraviolet, extreme ultraviolet, visible, infrared, far-infrared, etc.

In FIG. 1 Beam 118 is reflected towards the surface of the sample 110 and illuminates the sample surface as shown. Beam 118 covers the field-of-view of the image sensor at the surface of sample 110. Sample 110 can be a wafer, reticle, or other sample being inspected. The sample 110 scatters (or diffracts) part of the illumination beam and specularly reflects another part (and a part may be absorbed). The scattered and specularly reflected portions of the incident beam are referred to herein as the "scattered component" and "specular component" respectively. The scattered component is represented by beams 128, and the specular component is represented by beam 124.

A high-resolution optical imaging system including a front-end lens system 116 and a back-end lens system 114 is arranged to collect both the scattered and specular components of light and directs them to an image sensor 140. Aberrations in the imaging system can cause the relative phase between the specular and the scattered components to vary from one scattered ray to another scattered ray. This kind of phase variation can degrade the system performance. Therefore, the imaging system is preferably substantially diffraction-limited, i.e., has only small amounts of aberrations. It should be understood that while ray optics terminology is used herein, counterpart diffraction optics terminology could have been used, and that persons skilled in the relevant technology will understand the equivalence and the limitations of both ray optics and diffraction optics explanations of optical phenomena.

The design and manufacturing of such imaging systems are well-known arts. The front-end lens system is usually designed to be telecentric on the sample side in order to achieve uniform performance across the field. The telecentricity does not need to be perfect. A substantial amount of telecentricity error, such as a few degrees is usually tolerable. Back-end lens system 114 does not need to be telecentric.

In most applications including defect detection, the image of the sample needs to be magnified by a large amount, typically 100× or even more. The magnification of the sample image is usually achieved by making the focal length of back-end lens system 114 longer than that of front-end lens system 116. In order to achieve high performance, the focus of the imaging system needs to be accurately maintained during the sample scan. Accurate maintenance of the imaging system focus usually requires a servo-controlled autofocus system. Examples of a servo-controlled focus system are presented in a later section called Autofocus System.

Note that many different kinds of image sensors could be used for system 100. Two-dimensional image sensors such as CCD, Time Delay and Integration CCD (TDI CCD), and the like, have been found to be appropriate for many applications. Note that the term "image sensor" as the term used herein means the whole image sensing hardware system, not just the light-receiving part. For example, in certain embodiments, image sensor 140 may also include controller 142, which is described in greater detail below.

A high sensitivity and high dynamic range are preferred in the image sensor. In order to detect small signals, a high noiseless amplification of the signal is usually desired. However, a high noiseless amplification of the signal requires a high dynamic range in the image sensor. Therefore, the dynamic range of the image sensor or sensor system will become an important issue in the future when extremely tiny defects need to be detected.

In an example embodiment of system 100 as shown in FIG. 1 includes a controller 142, such as a computer or like machine, that is adapted (e.g., via instructions such as software embodied in a computer-readable or machine-readable medium) to control the operation of the various components of the system. Controller 142 is configured to control the operation of system 100 and includes a processing unit ("processor") 152 electrically connected to sensor system 140 and adapted to receive and process digitized raw electronic signal therefrom and form processed image signals, as described in greater detail below. In an example embodiment, processor 152 is configured to process raw signal and compare it to other signals (e.g., digital images of adjacent fields, or idealized fields, such as stored in memory unit 154) to determine if a defect is present, and to characterize the defect, as explained in greater detail below. As used herein, the term "electronic or electrical signal" includes both analog and digital representations of analog physical quantities or other information.

Controller 142 is configured to receive electronic raw signal from sensor system 140 and process the signal to characterize or classify the defect in the sample. As described, controller 142 includes a processor 152, which is or includes any processor or device capable of executing a series of software instructions and includes, without limitation, a general- or special-purpose microprocessor, finite state machine, controller, computer, central-processing unit (CPU), graphical-processing unit (GPU), field-programmable gate array (FPGA), or digital signal processor.

Memory unit ("memory") 154 is operably coupled to processor 152. As used herein, the term "memory" refers to any processor-readable medium, including but not limited to RAM, ROM, EPROM, PROM, EEPROM, disk, floppy disk, hard disk, CD-ROM, DVD, or the like, on which may be stored a series of instructions executable by processor 152. In an example embodiment, controller 142 includes a port or drive 156 adapted to accommodate a removable processor-readable medium 158, such as CD-ROM, DVD, memory stick or like storage medium.

The defect detection and classification methods described herein may be implemented in various embodiments in a machine-readable medium (e.g., memory 154) comprising machine readable instructions (e.g., computer programs and/or software modules) for causing controller 142 to perform the methods and the controlling operations for operating system 100. In an example embodiment, the computer programs run on processor 152 out of memory 154, and may be transferred to main memory from permanent storage via disk drive or port 156 when stored on removable media 158, or via a network connection or modem connection when stored outside of controller 142, or via other types of computer or machine-readable media from which it can be read and utilized.

The computer programs and/or software modules may comprise multiple modules or objects to perform the various methods of the present invention, and control the operation and function of the various components in system 100. The type of computer programming languages used for the code may vary between procedural code-type languages to object-oriented languages. The files or objects need not have a one to one correspondence to the modules or method steps described depending on the desires of the programmer. Further, the method and apparatus may comprise combinations of software, hardware and firmware. Firmware can be downloaded into processor 142 for implementing the various example embodiments of the invention.

Controller 142 also optionally includes a display unit 146 that can be used to display information using a wide variety of alphanumeric and graphical representations. For example, display unit 146 is useful for displaying raw signals or processes signals. Controller 142 also optionally includes a data-entry device 148, such as a keyboard, that allows a user of system 100 to input information into controller 142 to manually control the operation of system 100.

In an example embodiment, controller 142 is operably connected to or is part of sensor system 140. In another example embodiment, controller 142 is operably connected to a sample positioning system 150 for positioning the sample and an actuator 144 for adjusting the phase using phase controller and attenuator 122. Controller 142 is shown only in system 100 of FIG. 1 for ease of illustration, however it can be included in all example embodiments described herein.

As shown in FIG. 1, both the scattered component 128 and specular components 124 pass through the same optical system. Thus, this embodiment is a type of common path interferometer system. This feature is advantageous for the stability of the system performance. This is because any disturbances to the common path interferometer are likely to affect both optical paths by the same amount and the relative phase difference between scattered and specular components is likely to be maintained.

In some embodiments, the phase controller and attenuator 122 is installed in the path of the specular component 124. The specular component passes through a phase controller 122 and its relative phase can be adjusted to maximize defect detection sensitivity or to determine both the phase and the amplitude of each defect signal. Scattered light beams 128 are passed through a compensation plate 130 to compensate the otherwise large amount of path length difference between the specular and scattered components. The axial position of the compensation plate is very flexible because the optical path length of the light ray does not depend on the axial location of the compensation plate. That is, the compensation plate does not need to be placed in the same plane with the phase controller even though most of the figures show the compensation plate and the phase controller in the same plane in order to emphasize the fact that the compensation plate compensates for the otherwise longer optical path length of the phase controller. It can be placed significantly above or below the phase controller. The flexibility in the axial location of the compensation plate facilitates the mechanical designs around the compensation plate.

Phase control is an advantageous feature and can be utilized to dramatically improve the defect detection capability and is discussed in greater detail below. According to some embodiments, especially where the dynamic range of the image sensor is too small for the application, the specular component 124 can also be attenuated to improve image contrast by adding a pinhole stop in its path or a reflective coating on one of the surfaces of phase controller components. The reflected portion of specular component 124 is represented in FIG. 1 with beam 126. Note that the phase controller and attenuator are located at the primary pupil plane or aperture stop, which advantageously avoids power loss and complexity due to an additional pupil relay system, beam splitters and other components that may be needed otherwise.

Many different kinds of light sources can be used for source 118. Bright sources are preferred in many applications because they allow a clean spatial separation of the specular component from the scattered component at a pupil conjugate plane of the optical imaging system. Bright sources also make the Fourier filtering very effective thanks to a small footprint for the specular component at the pupil plane. Both a clean separation of the specular component from the scattered component and an effective Fourier filter are important for the best performance of the systems and methods disclosed herein. In general, the brighter the source, the better. The brightest sources currently available are lasers. Therefore, lasers are the preferred sources for many applications.

The sample can be illuminated with a laser in either coherent or incoherent fashion. However, incoherent illumination with a laser has significant drawbacks in that it not only usually requires a costly speckle buster but also makes Fourier filtering much less effective compared with coherent illumination. Therefore, coherent illumination with a laser source is preferred. The methods of achieving uniform illumination intensity across the whole field are presented in a later section on Coherent Uniform Illuminator.

Many different types of lasers are suitable for the illumination source. For example, the laser can be either a continuous-wave type or a pulsed type such as mode-locked or Q-switched laser. The laser can have multiple temporal modes or a finite temporal bandwidth. However, a single spatial mode is usually preferred for the coherent illumination. Other sources, such as an arc lamp, light emitting diodes (LED), etc, can also be used. However, it is difficult to separate the specular component from the scattered component with these extended sources. This is because some part of the scattered component can overlap with the specular component even at the pupil plane. This makes precise control of the relative phase between the scattered and specular components difficult. Imprecision in phase control usually results in poorer performance. It is also hard to implement an effective Fourier filter with an extended source due to the relatively large footprint of the specular component at the pupil plane.

Note that the use of lasers as a light source can create damaging hot spots on or in some lens components. This problem can be mitigated by lens design and by the use of durable lens materials such as specially formulated fused silica, calcium fluoride, lithium fluoride, etc.

The phase controller 122 should be placed at or close to the pupil or a pupil conjugate of the optical imaging system in order to be able to spatially separate the specular component from the scattered component in a clean fashion and also to achieve uniform performance over the whole imaging field. Ideally the optical system is relatively simple and there is no need for a conjugate of the aperture stop of the optical imaging system. The phase controller 122 is placed at or close to the aperture stop plane of the imaging system in FIG. 1. Placing the phase controller at or close to the aperture stop plane of the optical imaging system is preferred for many applications because it does not require additional optical parts that are not only bulky and costly but also can reduce image quality and energy efficiency. It has been found that in cases where a laser is used as the light source 112 and the sample 110 is illuminated coherently, the size of the specular component at the pupil conjugate plane becomes tiny, usually smaller than 1 mm, and consequently, the phase controller can be made quite small and does not to take much space or interfere with other system components.

The ability to place the phase controller directly at or close to the aperture stop plane of the optical imaging system even if the area is narrow and crowded with other parts is a practical advantage in many applications. This advantage is especially valuable in the current and future defect detection system designs because it is difficult and also costly to add more optical elements to relay the aperture stop into a less crowded area. In some alternate embodiments, where the area of aperture stop is too narrow or crowded to allow a phase controller, the aperture stop plane can be relayed out to a less crowed area by designing in a high quality pupil relay system. However, this design brings with it undesirable side effects. It is difficult and costly to design in a suitable pupil relay system for a high-etendue, DUV optical system.

Figure 2A:
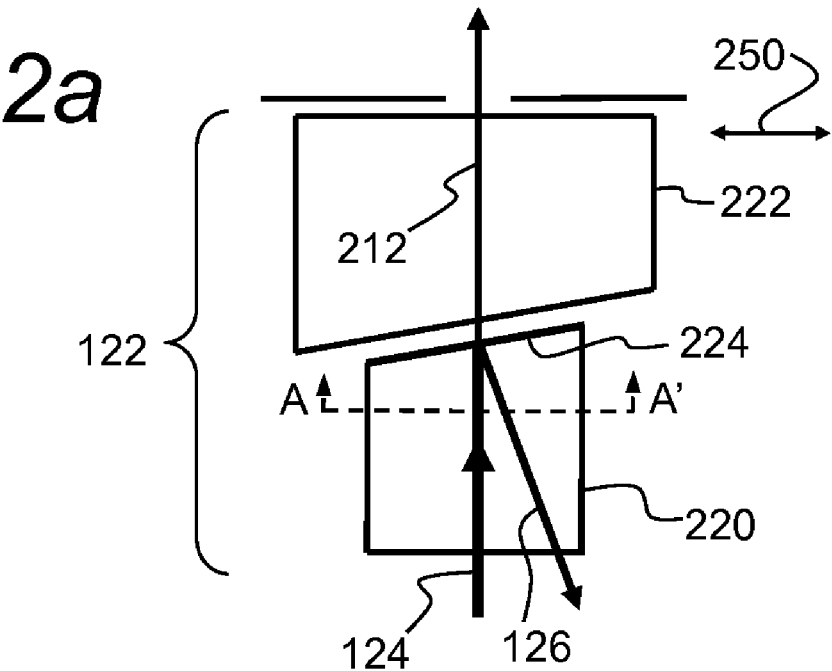
FIGS. 2a and 2b show an example of a phase controller and attenuator, according to some embodiments.
Figure 2B:
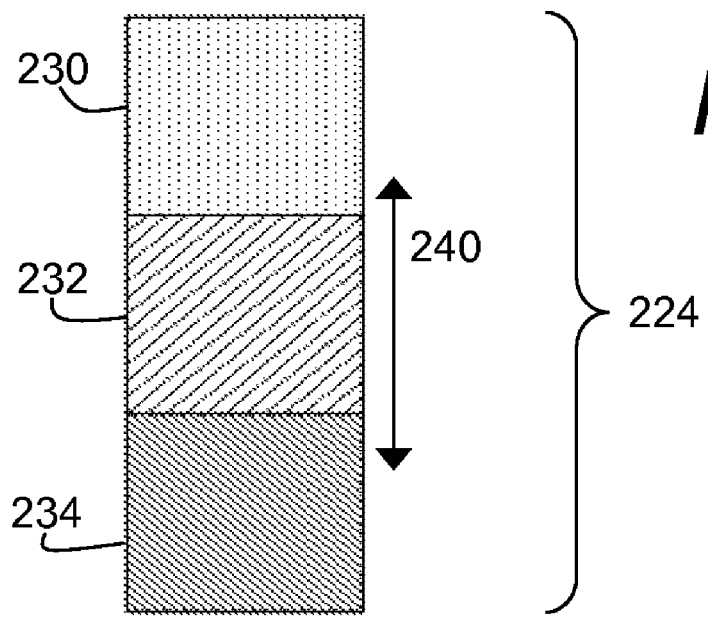

2. Phase Controller. FIGS. 2a and 2b show an example of a phase controller and attenuator. A phase controller is used to change the relative phase between scattered and specular components of light from the sample. Note that absolute phase is generally not of interest. Rather, it is the relative phase between scattered and specular components that is generally of interest. Therefore, the phase controller can be installed in the path of either the specular or scattered component.

While most figures herein show the phase controller installed in the path of the specular component, in some embodiments, the phase controller may be installed in the path of the scattered component. There are a variety of ways of changing the phase of a beam of light. One technique for changing the phase is to change the optical path length of the beam. The optical path length can be changed easily by varying the thickness of the optical material that the beam passes through. These kinds of phase controllers can be made in many different ways. One way is to overlap two wedged glass plates as shown in FIG. 2a. Phase controller 122 makes use of an upper glass wedge 222 and a lower glass wedge 220. Incoming light beam 124 enters the lower wedge 220 and at least a portion passes through the upper wedge 222 as light beam 212. By moving one of the wedged plates in directions indicated by arrow 250, the optical path length of the passing-through beam is changed. For example, the upper wedge 222 can be moved rightward to increase the path length and leftward to decrease the path length.

The air gap between the upper wedge and lower wedge can cause the specular component beam to walk off the desired path. This can cause the wavefront of the specular component to be tilted at the image plane. The tilted wavefront can lead to performance variation across the field, especially in the high sensitivity mode of operation which will be described in later sections. However, this problem can be fixed easily. The specular component beam can be brought back to its desired path by slightly tilting the whole phase controller block in the opposite direction to the beam walk-off direction. The amount of tilt required can be determined by measuring the wavefront tilt of the specular component at the image plane. The wavefront tilt appears as a linear phase variation of the specular component across the field. Therefore, it can be measured during the phase controller calibration process which will be described in the next paragraph. To bring the beam back to its desired path, a couple of iterations of the phase block tilting are expected.

The phase controller needs to be calibrated before use. The calibration can be done purely mechanically by precisely measuring the dimensions and positions of the optical parts of the controller. However, a better way is doing it optically, which can be done without difficulty. For example, the phase controller can be calibrated using a step-phase object, such as phase mask consisting of a two-dimensional array of islands, each island having a small path difference from its surrounds. The image of the step-phase object shows contrast reversal around the phase-step area as the phase of the specular component passes the 90° point. The image contrast hits the extrema at zero and at a 180° phase angle of the specular component. Using this phenomenon and the mechanical properties of the phase controller, the phase controller can be accurately calibrated. Other patterns such as a small pit, small island, a narrow valley, narrow mesa, etc. can also be used for the calibration. This calibration process provides the phase reference, or zero phase shift point, as well.

If multiple identical patterns are arranged across the field and the calibration is performed simultaneously across the field, we can achieve not only a more accurate calibration of the phase controller but also establish phase references across the field. The values of phase references should all be the same if the imaging system is perfect. However, real imaging systems cannot be made perfect. Some variation of phase reference values across the field is expected to exist due to phase controller tilt, aberrations, field curvature, etc. The linear part of the variation of phase reference values across the field can be removed by slightly tilting the whole phase controller block. The nonlinear parts of the variation originate from the imperfections in the imaging system.

The first order effect of an imaging system imperfection is a variation of phase reference values across the field. Therefore, the magnitude of the variation of phase reference values across the field is a good indicator of the quality of the imaging system. The variation of phase reference values across the field is less important for the catch-all mode and dark field mode of operation which is presented in later sections. However, this can become an issue for the high sensitivity mode of operation which will be presented in a later section. This is because it can make the performance of the high sensitivity mode of operation vary across the field. Therefore, it is important to maintain the quality of the imaging system high.

It is noted that there is another phase called Gouy phase that needs to be calibrated. However, the calibration of the Gouy phase is straightforward as long as the phase controller is calibrated. Gouy phase is described below in a later section called Variable Pinhole Stop.

In an example embodiment, an attenuator is added to the kind of phase controller shown in FIG. 2a by putting a reflective coating on one or more of the surfaces of phase controller components. For example, in FIG. 2a a reflective coating 224 is positioned at a surface of lower wedge 220 as shown. According to this example, a portion of incoming beam 124 is reflected by coating 224 and dumped as represented by dump beam 126. According to some embodiments, the attenuation amount can be step-varied by putting several coatings with different reflectance in a row and making the component movable.

FIG. 2b shows an example of a reflective coating 224 a viewed along the line A-A' of FIG. 2a. In this example, coating 224 is made up of three different reflective coatings 230, 232 and 234, arranged as shown in the direction of arrow 240. By moving lower wedge 220, different levels of attenuation can be achieved.

Figure 3:
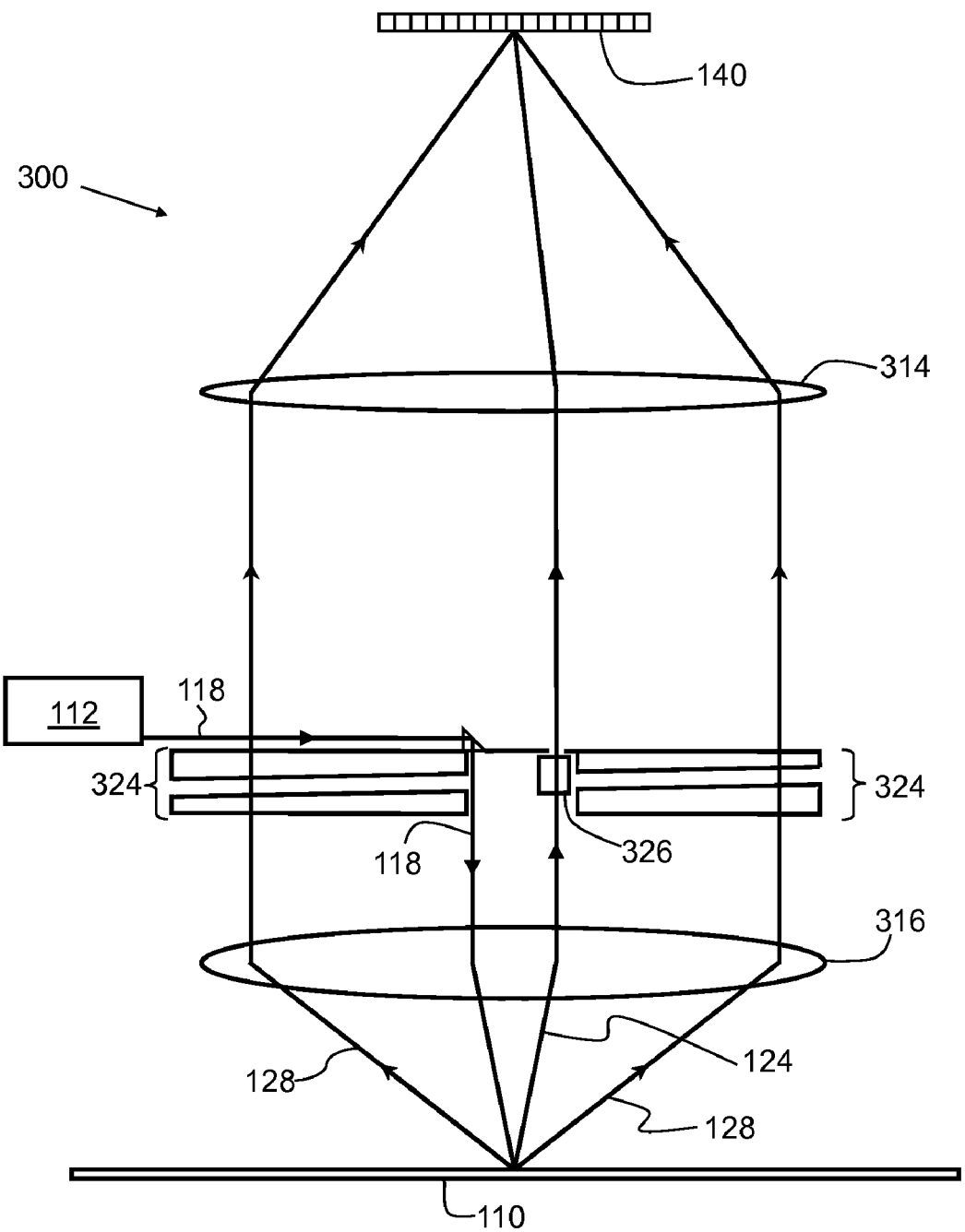
FIG. 3 shows an example of an interferometric defect detection system, according to some embodiments.

FIG. 3 shows another example of an interferometric defect detection system 300. In FIG. 3, the phase of the scattered component, represented by beams 128 are varied using the glass wedges 324. Coherent light source 112 generates illumination beam 118 which is reflected toward the surface of sample 110. The scattered component of the reflected light is represented by beams 128 and the specular component is represented by beam 124. By moving the upper wedge relative to the lower wedge, the effective path length and therefore the phase of the scattered component is changed. Specular component 124 passes through compensation block 326 to compensate for path length difference between the specular and scattered components. Front-end lens system 316 and back-end lens system 314 collect the light from sample 110 and focus the light on the image sensor 140.

Figure 4A:
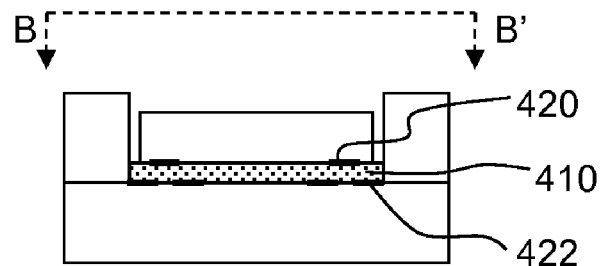
FIGS. 4a and 4b show an example for changing optical path length, according to some embodiments.
Figure 4B:
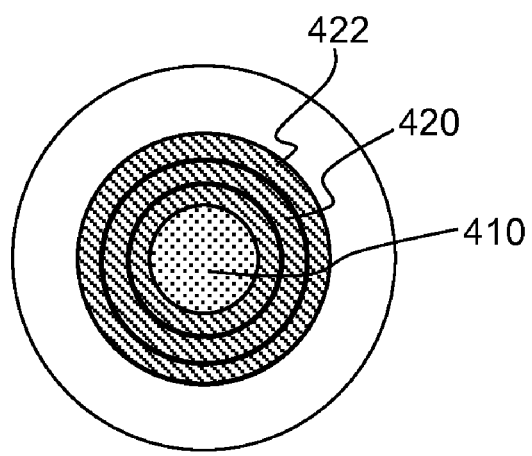

Another way of changing the optical path length is shown in FIGS. 4a and 4b. In this example, as shown in FIG. 4a, an optically transparent liquid 410 is injected between electrodes 420 and 422 of a ring capacitor. The thickness of the liquid 410 is varied by varying the voltage across the capacitor electrodes 420 and 422. Liquid crystal rather than regular liquid can also be used for liquid 410. In this case, the optical path length is varied by just changing the average orientation of the liquid crystal molecules. FIG. 4b shows a plan view of the structure of FIG. 4a in the direction along B-B'. Upper electrode 420 is shown along with liquid 410.

A movable slightly wedged glass plate or transparent film strip can also be used as a simple continuously-variable phase controller. However, this kind of phase-controller inevitably deviates the ray path from its ideal path and consequently affects the system performance adversely.

Figure 5:
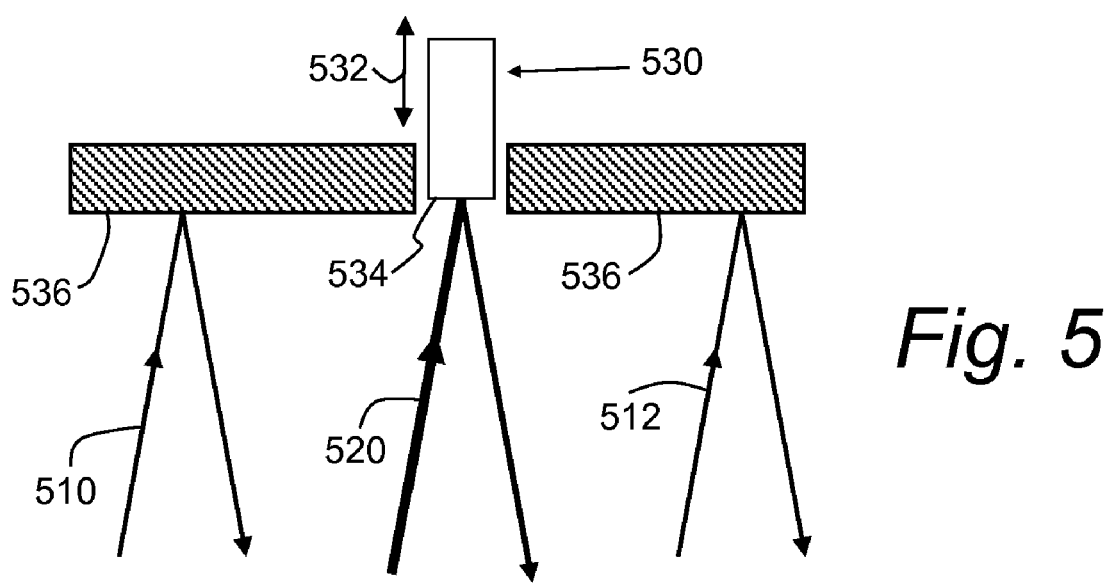
FIG. 5 shows an example of a movable mirror used to change the optical path length, according to some embodiments.

FIG. 5 shows an example of a movable mirror used to change the optical path length, according to some embodiments. The system includes a movable member 530 having a reflective surface. Incoming specular reflection beam 520 is partially reflected from surface 534 of member 530. Scattered light beams 510 and 512 are reflected from fixed reflective member 536. A movable mirror type phase controller has been found to be especially useful for applications using extremely short wavelength light, like a vacuum ultraviolet light or extreme ultraviolet light which might be used in future generation defect detection systems. This is because it is relatively difficult to find or develop transmissive optical materials for these wavelengths.

It is noted that the phase controlling mirror does not always need to be highly reflective. For many applications, especially when the dynamic range of the image sensor is low, a low reflectivity is preferred because attenuating the specular component is useful in achieving proper image contrast. For example, it has been found that bare glass without any coating can provide adequate reflectivity in some instances. In other embodiments, especially where a fast response is desirable, a phase controller can be constructed using electro-optical components.

Figure 6:
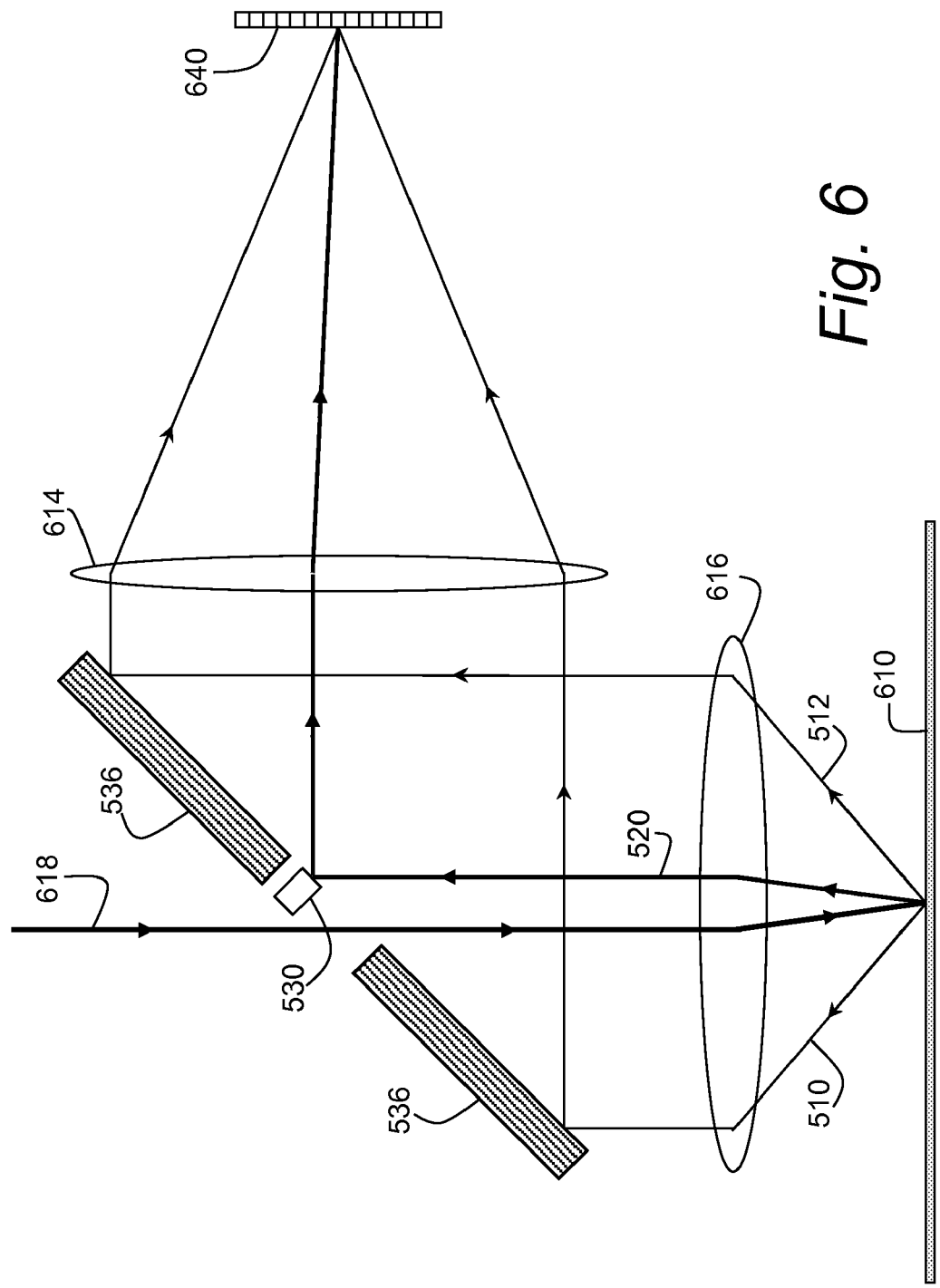
FIG. 6 shows an example of an interferometric defect detection system making use of a moveable mirror phase controller, according to some embodiments.

FIG. 6 shows an example of an interferometric defect detection system making use of a moveable mirror phase controller. Incoming light beam 618 is directed toward the surface of sample 610 which could be a wafer, reticle, or other sample being inspected. The scattered component, represented by beams 510 and 512, pass through lens system 616 and are reflected from reflective member 536 before passing through lens system 614 which directs the beams toward the image sensor 640. The specular component beam 520 is reflected from the surface of moveable reflective member 530 as described with respect to FIG. 5.

Note that although a continuously-variable phase controller is shown for many of the embodiments described herein, according to some embodiments, a discretely-variable phase controller can be used. For example, if the total number of phase selections is limited to four, one choice of phase values for the discretely-variable phase controller is 0°, ±180°, and ±90°. Even three discrete phase selections may work in some applications such as catch-all mode of operation which will be described in a later section. In this case, one choice of phase values is 0°, and ±120°. Reducing the number of phase selections to two, e.g. {0°, 180°} or {90°, −90°} is less preferred for many applications since the sign of the interference term cannot be matched to that of the dark field term for both amplitude-type defects and phase-type defects.

A discretely variable phase controller can be made in many different ways. One way of making a discretely variable phase controller is by either depositing thin films of the correct thickness on a substrate or etching out the substrate by a correct depth. Here, even if discretely variable phase controllers can have different physical shapes than continuously variable phase controllers, they are not conceptually considered as a different kind of phase controller but considered as a subset of continuously variable phase controllers because a continuously variable phase can be operated in a discrete fashion.

A single phase controller can be shared by multiple wavelengths or employed with broadband illumination. However, in this case, precise phase controls for all wavelengths is relatively difficult to achieve.

If the phase of the phase controller can be varied rapidly, the system can be operated in a heterodyne mode. Heterodyne mode is a good choice if there is significant amount of 1/f noise. A rapid change of the phase of the phase controller can be achieved in many different ways. For example, it can be achieved by rapidly moving one of the glass pieces of the phase controller shown in FIG. 2a. If the phase controller is made of electro-optical materials, a very rapid phase change can be achieved by controlling the phase controller electro-optically. A heterodyne system is relatively difficult to implement in scanning systems, especially in fast scanning systems, but is relatively easy to implement in non-scanning systems such as static or stepping systems.

3. Fourier Filtering. Blocking unwanted light at a pupil plane or aperture stop is called Fourier filtering because the light amplitude distribution at a pupil plane or aperture stop is the Fourier transform of the light amplitude distribution at the object plane. Fourier filtering is a desirable feature in many applications because it can effectively reduce the amount of light reaching the detector array that is diffracted by the Manhattan mask or wafer patterns. It reduces not only photon noise but also sample pattern noise. It also makes the intensity of the light more uniform across the field.

A more uniform light intensity allows for better use of the dynamic range of the image sensor for noiseless signal amplification. The majority of circuit patterns are formed from x- or y-direction edges and consequently scatter (or diffract) light along two narrow bands in the pupil corresponding to the y- and x-directions of the circuit pattern. This kind of scattered light does not carry much information about defects but generates photon noise and pattern noise and can saturate the image sensors.

Therefore, it is desirable to filter out this kind of light. FIGS. 7a-7c show an example of a compensation plate with opaque Fourier filter strips for use with an interferometric defect detection system having near normal illumination. In FIG. 7a, compensation plate 730 is shown with narrow Fourier filter strip members 750, 752, 754 and 756. Scattered light near the specular beam is blocked by an opaque blocking plate 732, which contains an aperture of width p just wide enough to pass the specular beam. In this example, light scattered by the x- and y-wafer pattern geometries lands on the filter strip members 750, 752, 754 and 756 at the pupil plane or aperture stop. In this way, this kind of unwanted light can be filtered out very effectively. A couple of crossed strips of opaque material such as metal are all that is needed.

Notice that the Fourier filters block not only the diffracted light from periodic patterns, but also the diffracted light from non-periodic patterns such as long lines or edges oriented in the perpendicular direction to the Fourier filter strips. Note that strip members 750, 752, 754 and 756 do not block much of the defect signal light while blocking most of the unwanted light generated by the Manhattan patterns on the mask or wafer. This kind of Fourier filter that blocks unwanted light in two-directions is called a two-dimensional Fourier filter. Two-dimensional Fourier filtering is much more effective than a one-dimensional Fourier filter in blocking unwanted light from a 2-dimensional pattern on the sample. This also means that a two dimensional Fourier filter makes the intensity of the image much more uniform across the field compared with a one dimensional Fourier filter.

Uniform image intensity is important for many applications because it allows us to fully utilize the dynamic range of image sensor for the amplification of the defect signal. Thus, an effective two dimensional Fourier filter is essential for a high, noiseless amplification of weak defect signals. It improves the useful dynamic range of the image sensor.

The width of the Fourier filter does not need to be uniform and can be varied across the pupil in order to block the unwanted light more effectively. The unwanted light is usually more intense in the proximity of the specular component at the pupil plane. Therefore, Fourier filter strips usually need to be tapered to optimize their performance Tapered Fourier filter strips, which are wider in the middle and narrower at their extremities, will be generally more effective in blocking the unwanted light while minimizing their impact on obscuring signal light.

The location of the strips does not need to be varied as long as the illumination beam 718 and prism 780 remain in the same position. Therefore, the Fourier filter does not need any driving mechanism and can be installed in a permanent fashion.

It is noted that Fourier filters can have dual functions. Fourier filter strips can also be used as an aperture stop for the specular component by extending their inner ends to the region where the specular component passes. If the aperture stop needs to be variable, then the Fourier filter strips should be made movable along their length directions. Mechanical abrasion between moving Fourier filters and the fixed compensation plate can easily be avoided by putting a big enough gap between the Fourier filter strips and the compensation plate. Putting a sizable gap between the Fourier filter strips and the compensation plate does not affect the performance of the imaging system because moving the compensation plate in any direction does not affect the optical path length of any ray.

Thus, two-dimensional Fourier filtering is achieved not only simply and easily but also with minimal impact to the signal light. Also shown in FIG. 7a are an upper glass wedge 722 and a lower glass wedge 720. FIG. 7b shows a cross-sectional view of the arrangement of FIG. 7a along the line C-C' according to some embodiments. Compensation plate 730 is shown with an opening, in which are disposed upper glass wedge 722 and lower glass wedge 720. The upper surface of lower glass wedge 720 has a variable reflective surface as shown and described with respect to FIGS. 2a-2b.

FIG. 7c shows a cross-sectional view of the arrangement of FIG. 7a along the line D-D' according to some embodiments. Compensation plate 730 is shown with an opening in which are disposed upper glass wedge 722 and lower glass wedge 720 having a reflective surface 724. Relative motion between the upper and lower glass wedges is achieved by extension arm 726 and actuator 770, which are connected to the upper glass wedge 722. As is to be expected, the center of the illumination input prism 780 and the small pupil stop of diameter p for the specular beam are diagonally opposite each other in FIGS. 7 and 8.

Note that in most of the figures, the compensation plate and phase controller are located in the same or nearly the same plane in order to emphasize the fact that the compensation plate compensates optical path lengths for the phase controller. However, this is not necessary because the axial location of the compensation plate is very flexible, as previously explained. The flexibility in the axial location of the compensation plate can alleviate mechanical conflicts or difficulties around the Fourier filters and phase controller.

According to other embodiments, Fourier plane blockers to eliminate pattern diffraction other than that arising from the Manhattan patterns on the sample are added if needed. This kind of special Fourier blockers usually needs to be custom-designed and can be implemented in many different ways. For example, additional metal strips can be introduced in the pupil plane. Another way is to insert a glass plate or a pellicle containing printed patterns in the pupil plane. This kind of flexibility allows an almost perfect filtering of noise-generating light for almost any kind of wafer or mask pattern. This is another advantageous feature of the systems and methods disclosed herein.

It has been found that too much Fourier filtering can be detrimental because the Fourier filter blocks defect signal light as well as noise-generating light. The blocking of signal light can impact the final defect signal in two ways: it not only reduces the total amount of signal light but also makes the image of a defect a little fuzzier through diffraction. There is usually an optimum amount of Fourier filtering that depends on the patterns on the wafer. Thus the amount of Fourier filtering which is desirable depends on the particular application and can be determined without undue experimentation by one skilled in the art.

A Fourier filter does not always need to be made with opaque materials like metal strips. It can be made with semi-transparent materials or even completely transparent materials such as dielectric films. These kinds of Fourier filters can be very effective in increasing the signal or the visibility of some patterns or features. For some applications such as the observation of complicated patterns or features, a very sophisticated Fourier filter can be used in order to increase the image visibility.

The Fourier filter made of an absorbing material like metal can become hot during operation, especially in industrial applications where powerful light sources are usually used. A hot Fourier filter not only causes mechanical problems but also optical problems because it can heat the surrounding air, which in turn can distort the wavefront of the signal light. However, this kind of heat problem can be resolved or mitigated by flowing gas with high heat conductivity like helium around the Fourier filter. Helium gas is especially suitable because its refractive index is very low and therefore not very sensitive to its density.

4. Variable Pinhole Stop. Note that the systems and methods disclosed herein work with a fixed pinhole stop or even without any pinhole or pinhole stop in the path of the specular component. However, it has been found that in many applications, a variable pinhole stop in the path of the specular component can improve the system performance.

Most figures, i.e. FIGS. 2a, 7b, 7c, 9, 10, 11, 13b, 13c, and 14 illustrating a phase controller herein, also show a small stop for the specular beam on the top of the phase controller. The ideal location for the specular beam stop is the pupil plane. This is because the system performance can vary across the field if the pinhole stop is located away from the pupil plane. The primary pupil plane is the back focal plane of the front-end lens system in the case of telecentric designs.

The term "specular component" cannot be precisely defined because there are no clear boundaries between specular and scattered components. The specular component must be of finite size and therefore contain some, even an extremely tiny amount of scattered (or diffracted) component. Therefore, the specular component actually means a combination of both unscattered (or undiffracted) light and low angle scattered light. The term "specular component" as used herein is allowed to contain some amount of low angle scattered component.

Since the specular component contains some amount of low angle scattered light, the characteristics of the specular component can be varied by changing the amount of low angle scattered light it contains. Varying the size of the specular stop is one of the simplest devices that can be used to change the amount of scattered light in the specular beam. A larger specular stop puts more scattered components into the specular beam and vice versa. The important thing is that the stop size is directly related to the spatial uniformity of the specular component at the image plane. A larger stop provides less spatial uniformity of specular component at the image plane because it passes more scattered light and vice versa. In other words, a larger specular stop averages less of the local variations of image intensity and vice versa.

More accurately speaking, a larger specular stop spatially averages less of the local variations of the complex amplitude of the specular component at the image plane and vice versa. That is, the specular stop averages spatially not only the intensity or amplitude but also the phase variation of the specular component across the field of view. Mathematically speaking, the complex amplitude of the specular component at the image plane is a convolution of sample reflectivity function with the diffraction pattern of the specular stop at the image plane.

Thus, not only can we change the total amount of the specular component that can reach image sensor, but also the spatial uniformity of the specular component at an image plane by varying the specular stop size. The size of the variable specular stop diameter is shown in FIGS. 7b and 7c as dimension "p." This variable of the specular component can be utilized to improve the defect detection capability. The specular stop can also be used for the attenuation of the specular component because a smaller stop transmits less of the specular component. Other ways of attenuating the specular component are described in a later section called Amplitude Attenuation.

If the dynamic range of the image sensor is not large enough, the defect signal may be poorly characterized by the limited number of gray levels available, even though the whole dynamic range of the detector is fully utilized by the noiseless amplification of the signal. In this case, some amount of attenuation of the specular component is needed to achieve proper contrast in the raw images. By adjusting the size of the specular stop, a proper attenuation of the specular component can easily be achieved. The attenuation of the specular component using the specular stop has an incidental effect of making the specular component more uniform across the field.

Another advantageous feature with the specular aperture is that it does not create a ghost image because the reflected light can be easily removed from the optical system. As is well known, an attenuator with a reflective coating can produce a ghost image through a second reflection with another surface. However, there are drawbacks as well. First, the specular stop may have to absorb a lot of light energy for proper attenuation of the specular component and consequently will become very hot. This can cause not only mechanical problems but also optical problems because the hot stop can heat the surrounding air and the heated air in turn can distort the wavefront. However, this kind of heat problem can be mitigated by filling the lens cavities with a gas with high heat conductivity and low refractive index like helium. Helium gas is a good choice because its refractive index is very low and therefore insensitive to its density.

The second drawback is the phase change of the specular component with the pinhole size. This kind of phase change is called "Gouy phase shift". This is an intrinsic phenomenon and therefore cannot be easily avoided. However, Gouy phase shift is static and therefore can easily be mapped over the field and compensated. Therefore, the phase change of the specular component associated with specular stop size needs to be attended to but is not a show stopper. In practice the specular stop may well turn out to be the size of a pinhole. The reflective counterpart of a pinhole is a tiny mirror (pinmirror) that reflects a portion of incoming light. The choice of specular aperture type and shape depends on the application and the design of the optical system. Transmissive and reflective pinholes share the same optical properties. Therefore, all the descriptions related to transmissive specular stop can be applied directly to a reflective specular beam stop.

In most figures, the specular beam stop and Fourier filter components are shown as separate components to emphasize their separate functions. However, in actual system designs, it may be preferable to combine the two separate components into one to simplify the mechanical design and also to minimize potential mechanical conflicts. The two components can be combined into one by either extending the Fourier filter strips inwards or extending the specular beam or pinhole aperture outwards. In the combined design, the size of the pinhole stop can be adjusted by moving the Fourier filter strips along their long directions.

5. Actuators. A variable phase controller requires some kind of mechanical or electrical actuator. The most convenient place to put an actuator may be right next to the phase controller. However, placing an actuator right next to the phase controller may block too much of the signal light. In some examples, the actuator is placed at the periphery of the optical imaging system, which is an attractive choice because it provides more space for the actuator. However, the drawback of this choice is that it requires some mechanism to transfer the actuator motion to the phase controller. The motion transfer mechanism must span the pupil radius and can block the signal light. However, according to some embodiments, the problem of light blocking is resolved by making use of the fixed locations of Fourier filters. By installing the motion transfer mechanism like moving or rotating wires on the top of or below Fourier filter blocking strips, further blocking of light can be avoided.

In FIGS. 7a and 7c, a motion transfer member 726 is provided that runs along the path of Fourier filter member 754. Motion transfer member 726 is driven by actuator 770 and moves the top wedge shaped glass piece in the variable phase shift mechanism. Similarly, motion transfer mechanisms for other parts like variable pinhole stops or wave plates can also be implemented in much the same way to minimize additional light blockage. Enough space for motion transfer mechanisms can easily be procured because the axial location of the compensation plate is very flexible.

6. Obscuration. The phase controller and its actuator unavoidably obscure (or block) some of the signal light. This kind of light blockage reduces not only the total amount of signal light that can reach the image sensor but also reduces the resolving power of the optical system by diffracting light. This is an undesirable side effect which is minimized to the maximum extent possible. In order to accomplish this, both optical components and the actuator of the phase controller should be made as small as possible or the actuator should be placed at the periphery of the optical imaging system.

Figure 8:
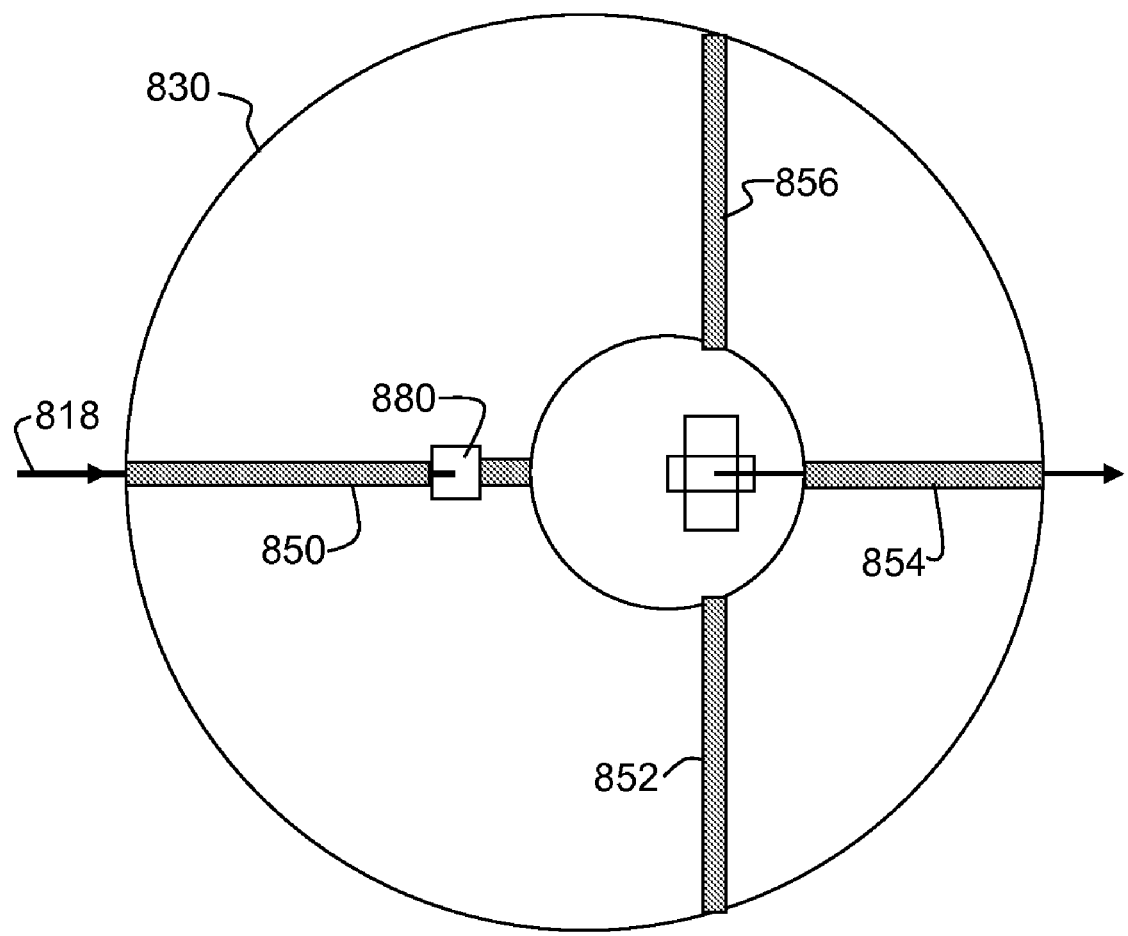
FIG. 8 shows an example of a placement of a folding prism for the illumination light, according to some embodiments.

FIG. 8 shows an example of a placement of a folding prism for the illumination light, according to some embodiments. Compensation plate 830 is arranged with Fourier filter strips 850, 852, 854 and 856 in a fashion similar to that shown in FIG. 7a. In the example of FIG. 8, an additional small reduction of obscuration can be achieved by placing the folding prism 880 for the illumination light beam 818 in line with the Fourier filter strip 850 as shown. Also, softening of the edges of the obscurations and the optical imaging system's aperture stop can reduce the undesirable side effect of edge diffraction. An effective and practical way of softening the edges of apertures and obscurations is described in a later section of Serrated Aperture.

Note that there is a beneficial side effect from the rather large obscuration caused by the blocking plate 732. This obscuration works as the guard band in dark field mode. This large guard band along with two-dimensional Fourier filter makes the dark field mode very dark. This means that the dark field mode is characterized by low noise and, consequently, can maintain higher defect detection sensitivity compared with dark field systems with less obscuration.

7. Polarization Control of Illumination Light. Penetration depth control of the illumination light into a sample surface by controlling the polarization direction of the illumination light was described previously. However, penetration depth control is not the only reason for polarizing the illumination light. The detection sensitivity for some types of defects depends on the polarization of the illumination light. Therefore, the capability of varying the polarization direction of the illumination light can be an important feature. Polarization of the illumination light can be easily and precisely controlled in the arrangements described herein because the etendue of the illumination light beam is small. Existing polarization control devices can be used. If the polarization of the illumination light is altered during passage through the illumination system then this can be measured and compensated. As long as a defect and its surrounding patterns do not have any helical structure, no polarizations other than linear polarizations are needed to maximize the defect detection sensitivity. This has been found to be the case for semiconductor wafers and reticles. However, if both of the mutually orthogonal linear polarizations need to be provided simultaneously, diagonally linear or circular polarization can be used. In this case however, the defect detection sensitivity can be compromised.

8. Polarization Control of Collected Light. The polarization of the signal light can be different than that of the specular component. In order to achieve high defect detection sensitivity, the polarization of the specular component should be made the same as that of the signal light to as great a degree as is possible. Therefore, in some embodiments, the polarization of the specular component is varied in the path between the sample and the detector. This can be done easily and precisely because the etendue of the specular component is small.

Figure 9:
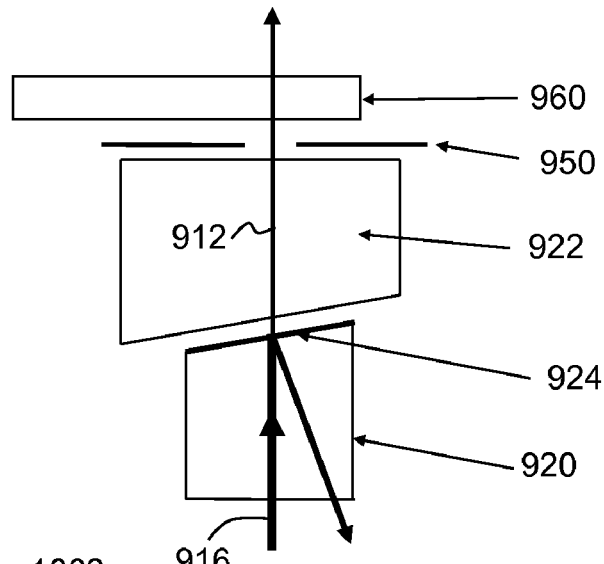
FIG. 9 shows a phase controller combined with a polarization rotator, according to some embodiments.

FIG. 9 shows a phase controller combined with a polarization rotator suitable for some embodiments. FIG. 9 shows a lower wedged glass plate 920 having a reflective coating 924, an upper moveable wedged glass plate 922 and a variable specular stop 950. A rotatable $\lambda/2$ plate 960 is positioned above the variable pinhole stop 950. Incoming specular light beam 916 is partially reflected by coating 924, and a portion of the beam 912 passes through the moveable wedged glass plate 922, the stop 950 and the rotatable $\lambda/2$ plate 960. The polarization controllability of the arrangement shown in FIG. 9 is somewhat limited in that it cannot transform the polarization of an incoming specular component to an arbitrary type of polarization. However, the arrangement can rotate an incoming linear polarization in any direction. As long as the defect and its surrounding patterns do not have any helical structure, no polarizations other than linear polarizations are needed to maximize the defect detection sensitivity. This has been found to be the case for semiconductor wafers and reticles. Therefore, a simple polarization control device shown in FIG. 9 will be adequate for a wafer or reticle defect detection.

Figure 10:
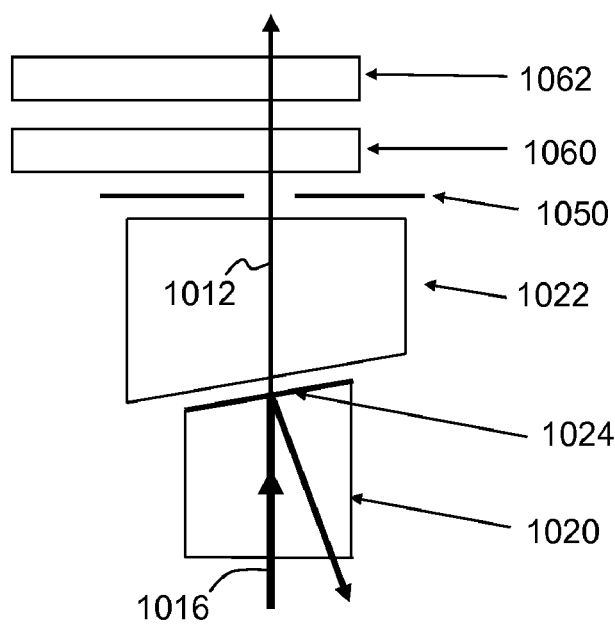
FIG. 10 shows an example of a polarization controller, according to some embodiments.

If a more general polarization control is needed, a slightly more complicated polarization controller shown in FIG. 10 can be employed. FIG. 10 shows a lower wedged glass plate 1020 having a reflective coating 1024, an upper moveable wedged glass plate 1022 and a variable stop 1050. A rotatable λ/2 plate 1060 and a rotatable λ/4 plate 1062 are positioned above the variable pinhole stop 1050. Incoming specular light beam 1016 is partially reflected by coating 1024, and a portion of the beam 1012 passes through the moveable wedged glass plate 1022, the stop 1050, the rotatable λ/2 plate 1060 and the rotatable λ/4 plate 1062. The arrangement shown in FIG. 10 can convert any incoming polarization to any type of polarization. Its working principle is described in: R. M. A. Azzam and N. M. Bashara, "Ellipsometry and Polarized Light" Elsevier Science B. V., 1999, pp 72-84, which is incorporated by reference herein.

The portion of the scattered component whose polarization is orthogonal to that of specular component does not interfere with the specular component and consequently contributes to the dark field part of the image. For some applications, this portion of the orthogonal polarization in the scattered component can be filtered out in order to increase the image contrast or reduce photon noise. Filtering the orthogonal polarization in the scattered light beam can be achieved by inserting appropriate waveplates into the path of the scattered component to linearly polarize the unwanted polarization component, removing this unwanted component with a linear polarizer and then converting the remaining light to match the polarization of the interfering specular beam.

9. Amplitude Attenuation. As mentioned previously, the specular component amplifies the defect signal. The stronger the specular component is, the more the amplification. Therefore, an unattenuated or a strong specular component is preferred in most cases. Note that this is the opposite of conventional microscopy where the specular component is either blocked off or severely attenuated to achieve a high contrast in the raw images. However, too strong specular component can saturate the image sensor. Saturation of the image sensor not only reduces but also distorts the defect signal in an undesirable way. In other words, if the dynamic range is saturated by the specular component, then the defect signal cannot span the required number of gray levels even if it is amplified as much as possible by the specular component. In this case, some attenuation of the specular component, sometimes along with an increase in the illumination light intensity to increase the scattered component, is needed to enhance the contrast of the raw images.

The attenuation of the specular component using the specular aperture stop to avoid detector saturation was described previously. In this section, other attenuation methods are described. The simplest method is absorbing the specular component using some light absorbing material. However, this simple attenuation method may not be suitable for wafer or reticle defect detection due to the high power of the specular component which is very likely to damage any light-absorbing attenuators.

A more suitable way of attenuating the specular component is to reflect the excessive portion of the specular component away from the sensor plane. This kind of attenuator can easily be constructed by putting a reflective dielectric coating on one of the phase controller components as shown in FIGS. 2a and 2b. The amount of attenuation can be varied by putting several different reflective coatings in a row, each having a different reflectivity, and make them movable as shown in FIG. 2b. This kind of attenuator is simple and does not require additional optical components. However, these kinds of attenuators can generate a ghost image due to the highly reflective surface.

Figure 11:
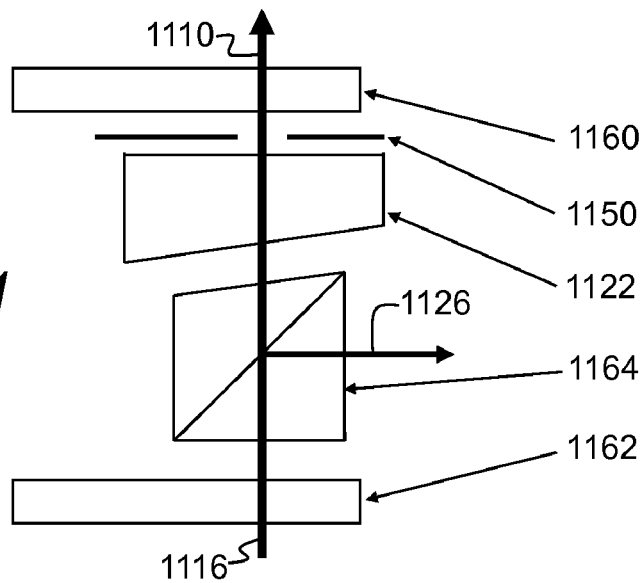
FIG. 11 shows an example of a continuously-variable attenuator using polarization, according to some embodiments.
Figure 12:
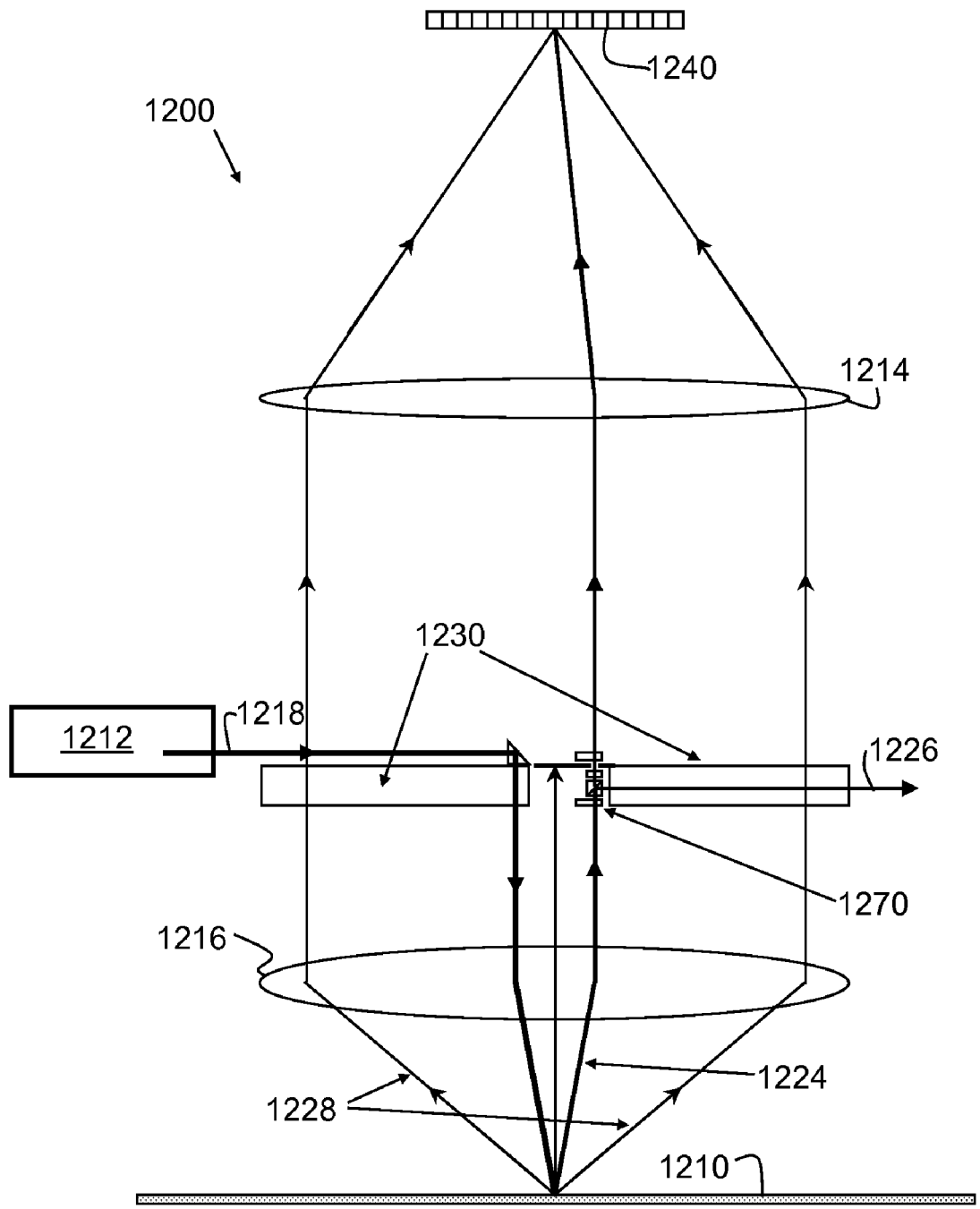
FIG. 12 shows an example implementation of a system using the type of attenuator shown in FIG. 11.
Figure 13A:
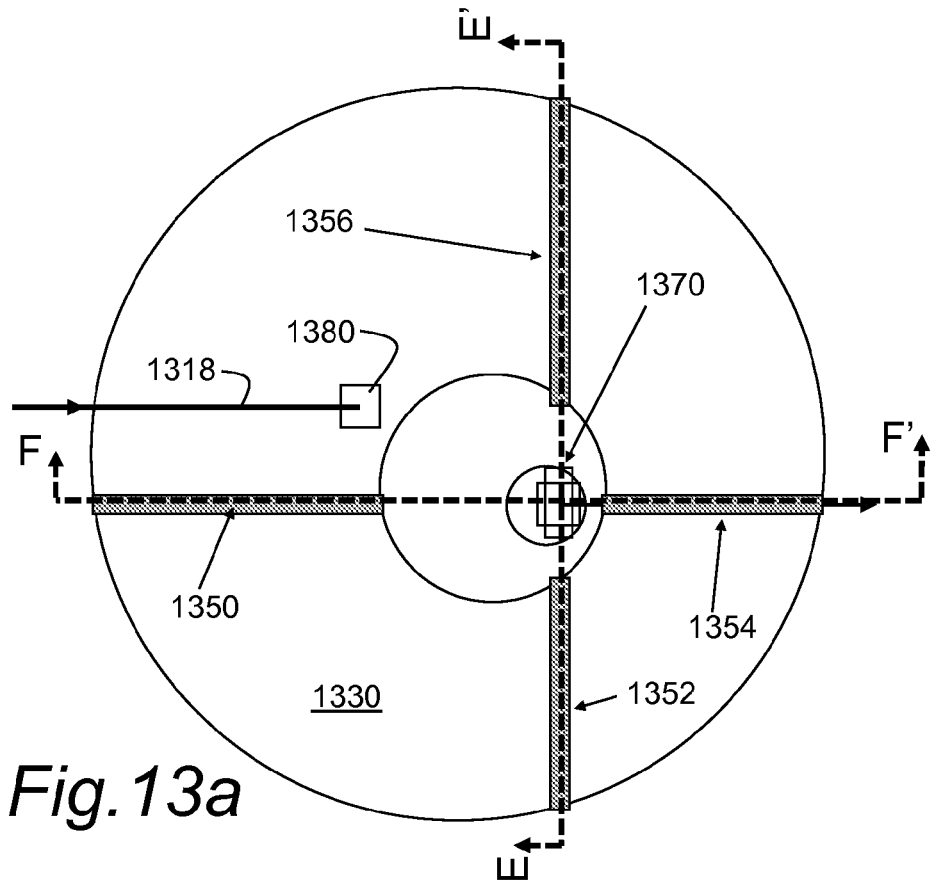
FIGS. 13a-13c show further detail of the system in the vicinity of the pupil or aperture stop, according to some embodiments.
Figure 13B:
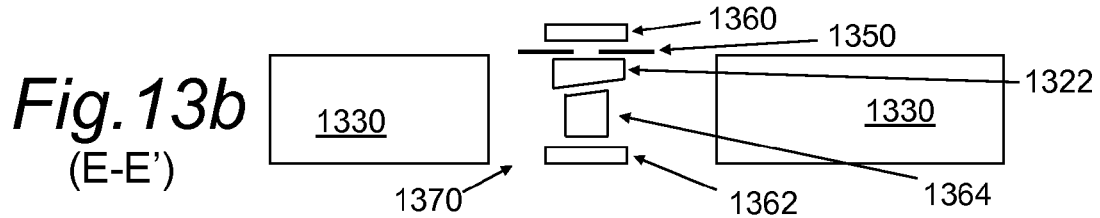
Figure 13C:
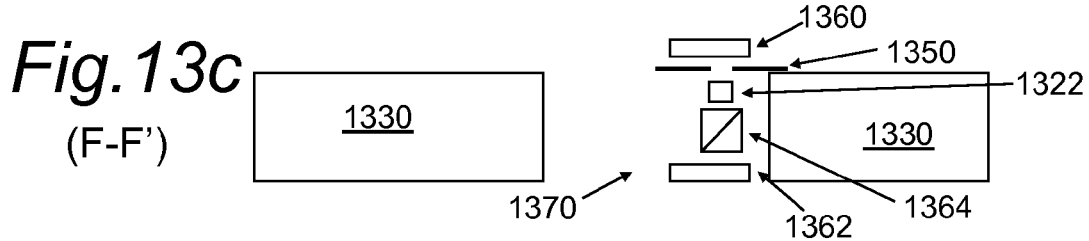

It is also difficult to achieve a continuous variation of attenuation with this kind of simple attenuator. For increased performance, a continuously-variable attenuator can be used. One way to make a continuously-variable attenuator is to utilize the polarization property of light. It is well-known that a continuously-variable attenuator can be constructed by rotating a polarizer around the axis of a linearly polarized beam, or alternatively, rotating the polarization direction of a beam passing through a fixed polarizer. FIG. 11 shows an example of a continuously-variable attenuator using a polarizing beam splitter. FIG. 12 shows an example implementation of a system using the type of attenuator shown in FIG. 11. FIGS. 13a-13c show further detail of the system in the vicinity of the pupil or aperture stop, according to some embodiments.

Referring to FIG. 11, polarized laser beam 1116 enters a polarization beam splitter 1164 which reflects s-polarized light 1126 while transmitting p-polarized light 1110. By controlling the polarization direction of the incoming light using the rotatable λ/2 plate 1162, the amount of specular component that passes through the polarization beam splitter can be controlled in a continuous fashion. After passing through the beamsplitter 1164 the p-polarized light beam 1110 pass through moveable wedged glass plate 1122 and variable aperture stop 1150 as previously described. The rotatable λ/2 plate 1160 on the output side can be used to reorient the polarization of the exiting light in any direction. This attenuation method is well suited for wafer or reticle inspection. However, this method is not completely general. It works nicely manipulating linear polarizations. If more general polarization states need to be used, additional optical components can to be added to the attenuator.

Figure 14:
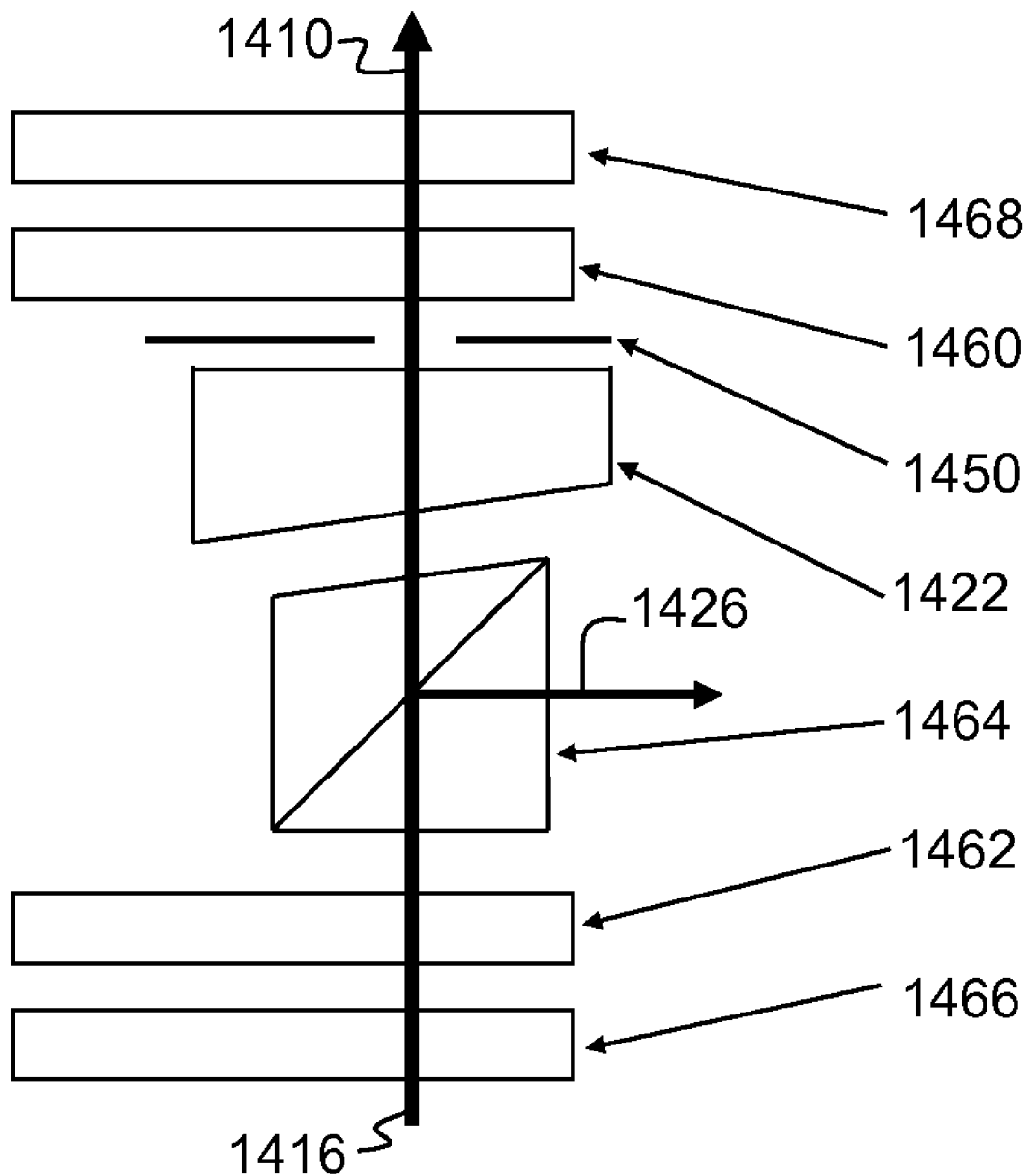
FIG. 14 shows an example of an attenuator having both $\lambda/2$ and $\lambda/4$ plates, according to some embodiments.

FIG. 14 shows an example of an attenuator having both λ/2 and λ/4 plates which can be used to achieve any polarization state. Beam 1416 enters a fixed polarization beam splitter 1464 which reflects the s-polarized light 1426 while transmitting p-polarized light 1410. By controlling the polarization direction of incoming light using both the rotatable λ/4 plate 1466 and the rotatable λ/2 plate 1462, the amount of specular component that passes through the polarization beam splitter can be controlled in continuous fashion. After passing through the fixed beamsplitting polarizer 1464 the p-polarized light 1410 passes through moveable wedged glass plate 1422 and variable stop 1450 as previously described. The rotatable λ/2 plate 1460 and the rotatable λ/4 plate 1468 on the output side can be used to reorient the polarization of the exiting light in any state. By rotating both λ/2 and λ/4 plates, any kind of polarization of the specular component can be obtained with proper attenuation.

Referring to FIG. 12, interferometric defect detection system 1200, includes an illumination source 1212 which generates a coherent beam 1218. Beam 1218 is directed towards the surface of the sample 1210 as shown. The sample 1210 can be a wafer, reticle, or other sample being inspected. The scattered component from sample 1210 is represented by beams 1228, and the specular component is represented by beam 1224. A high-resolution optical system including lens systems 1214 and 1216 collects both the scattered and specular components of light and directs them to an image sensor 1240. Subsystem 1270 is positioned in the path of specular component 1224 and includes a phase controller, variable attenuator, and one or more polarization rotators such as described and shown with respect to FIGS. 11 and 14. Scattered light beams 1228 are passed through a compensation plate 1230 to compensate for the path length difference between the specular and scattered components. A beam dump 1226 accepts the portion of specular component 1224 that is attenuated by the variable attenuator.

Referring to FIG. 13*a*, compensation plate 1330 is shown with narrow Fourier filter strip members 1350, 1352, 1354 and 1356. Illumination beam 1318 is reflected toward the sample (not shown) using prism 1380. Subsystem 1370 is positioned as shown and includes a phase controller, variable attenuator, and one or more polarization rotators such as described and shown with respect to FIGS. 11 and 14. FIGS. 13*b* and 13*c* show cross-sectional views of the arrangement of FIG. 13*a* along the line E-E' and F-F' respectively. In both FIGS. 13*b* and 13*c*, compensation plate 1330 is shown with an opening in which are disposed the various components of subsystem 1370. Polarization beam splitter 1364 reflects the s-polarized light while transmitting p-polarized light. By controlling the polarization direction of the incoming light using the rotatable λ/2 plate 1362, the amount of specular component that passes through the polarization beam splitter can be controlled in a continuous fashion. P-polarized light passes through moveable wedged glass plate 1322 and variable stop 1350. The rotatable λ/2 plate 1360 on the output side can be used to reorient the polarization of the exiting light in any direction.

10. High incidence-angle illumination. One source of noise that can be considered is the wafer pattern noise that arises when the printed patterns on the wafer vary slightly from die to die due to the variation of manufacturing process across the wafer. The wafer pattern noise increases with the penetration depth of the illumination light into the wafer surface. Therefore, it is sometimes desirable to reduce the penetration of the illumination light into the wafer surface.

Light of short wavelength such as deep or extreme ultraviolet light does not penetrate the wafer surface much because most materials used for wafer patterning are opaque to short wavelength light, thanks to their strong absorption of short wavelength light. However, light of longer wavelengths, such as visible or near ultraviolet light, can penetrate the wafer surface relatively more deeply because of the lower absorption of the light by most materials at these wavelengths. One of the most popular ways of reducing the penetration of illumination light into the sample surface is to illuminate the sample at a high incidence angle with s-polarized light. Note that an incidence angle is defined as the angle between the light ray and the surface normal, not the surface itself. Extremely high angle incidence is called grazing incidence.

This method, however, has a couple of drawbacks. First, it can reduce the strength of the defect signal light as well as the wafer pattern noise. Second, it can increase the spatial frequency bandwidth of the interference term shown in equation (2c) at the image plane. The increase of spatial frequency bandwidth requires a finer sampling of the image to detect the interference term faithfully. This can reduce the throughput of the catch-all mode of operation which will be described in later sections.

Even with these drawbacks, for some applications, especially where the benefit is greater than the harm, it is desirable to increase the incidence angle of the illumination light to reduce the wafer pattern noise. The systems and methods disclosed herein are flexible with respect to the incidence angle of illumination. The systems and methods can accommodate not only a low incidence angle but also a high incidence angle. FIGS. 15 through 18 show examples of this.

Figure 15:
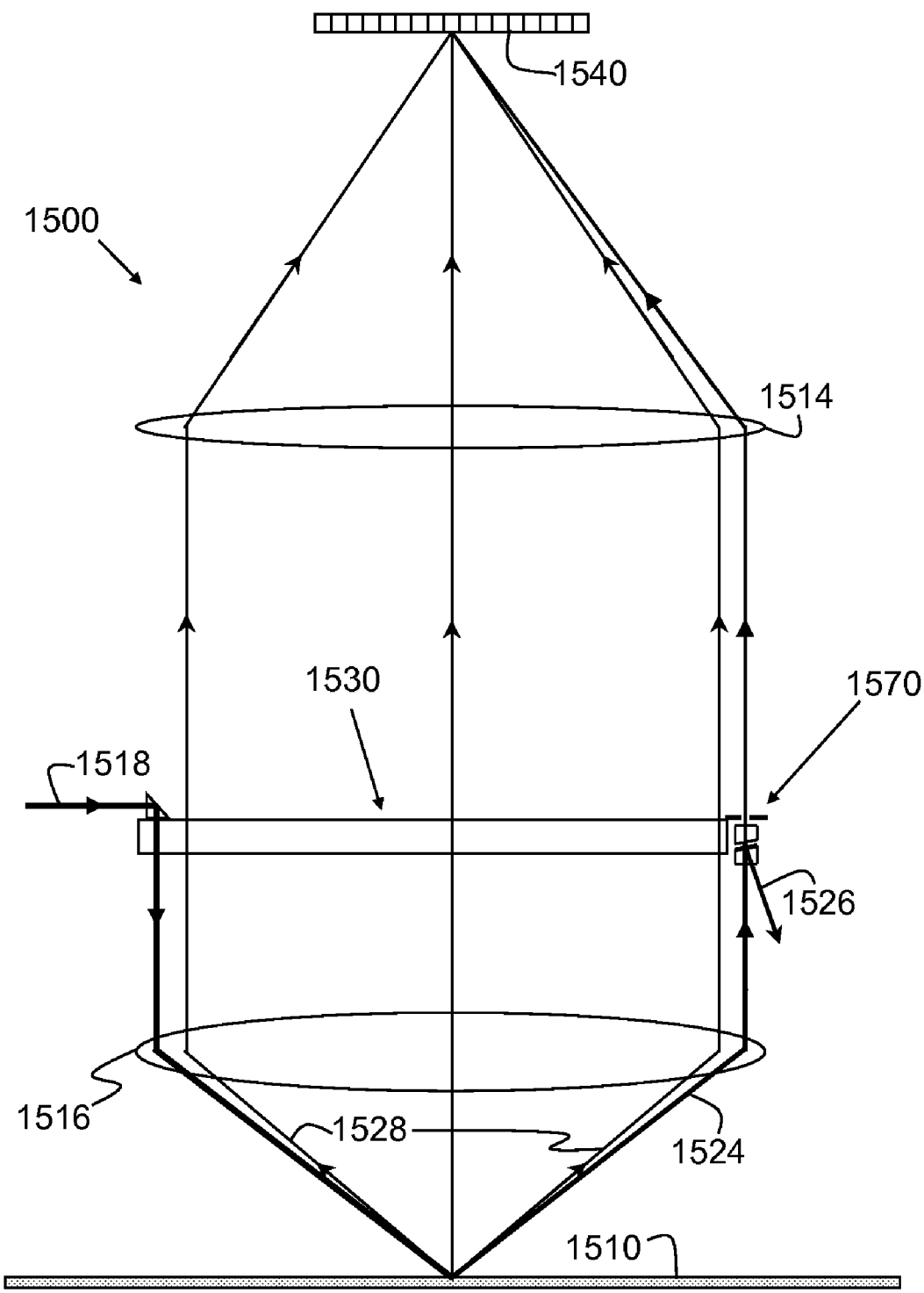
FIG. 15 shows an example of an interferometric defect detection system with high incidence angle illumination, according to some embodiments.

FIG. 15 shows an example of an interferometric defect detection system with high incidence angle illumination. Interferometric defect detection system 1500 includes an illumination source beam 1518 which is directed towards the surface of the sample 1510 as shown. The sample 1510 can be a wafer, reticle, or other sample being inspected. The scattered component from sample 1510 is represented by beams 1528, and the specular component is represented by beam 1524.

A high-resolution optical system including lens systems 1514 and 1516 collects both the scattered and specular components of light and directs them to an image sensor 1540. Subsystem 1570 is positioned in the path of specular component 1524 and includes a phase controller and attenuator such as described and shown with respect to FIGS. 2*a* and 2*b*. Scattered light beams 1528 are passed through a compensation plate 1530 to equalize path lengths for the specular and scattered components. A beam dump 1526 accepts the portion of the specular component 1524 that is rejected by the attenuator.

Figure 16:
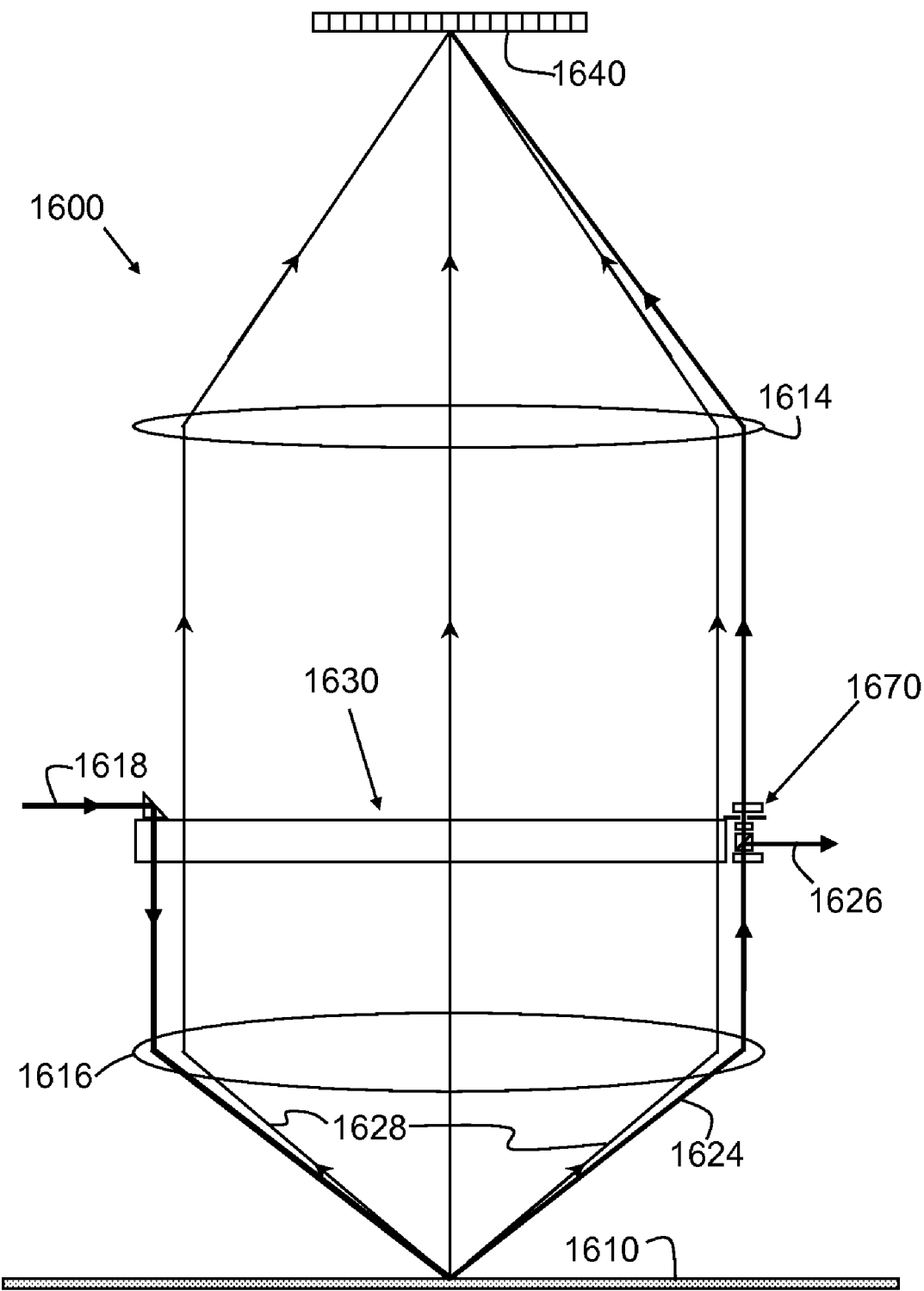
FIG. 16 shows an example of an interferometric defect detection system with high incidence angle illumination and a variable attenuator, according to some embodiments.

FIG. 16 shows an example of an interferometric defect detection system with high incidence angle illumination and a variable attenuator. Interferometric defect detection system 1600 includes an illumination source beam 1618 which is directed towards the surface of the sample 1610 as shown. The sample 1610 can be a wafer, reticle, or other sample being inspected. The scattered component from sample 1610 is represented by beams 1628, and the specular component is represented by beam 1624. A high-resolution optical system, which includes lens systems 1614 and 1616, collects both the scattered and specular components of light and directs them to an image sensor 1640. Subsystem 1670 is positioned in the path of specular component 1624 and includes a phase controller and variable attenuator such as described and shown with respect to FIGS. 9-11 and 14. Scattered light beams 1628 are passed through a compensation plate 1630 to equalize the path lengths of the specular and scattered components. A beam dump 1626 accepts the portion of the specular component 1624 that is rejected by the variable attenuator.

Figure 17:
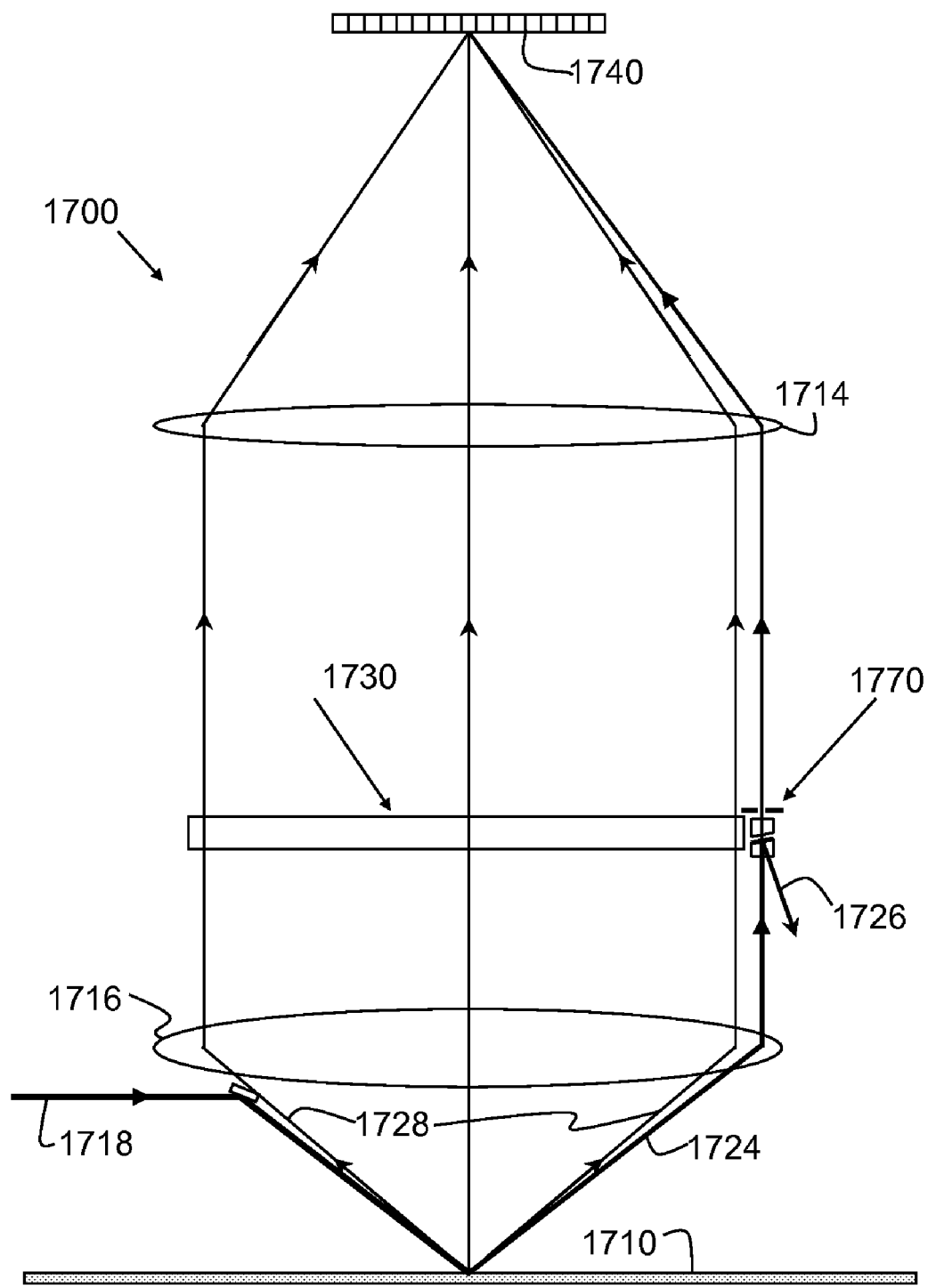
FIG. 17 shows an example of an interferometric defect detection system with a low-flare high-incidence angle illumination, according to some embodiments.

FIG. 17 shows an example of an interferometric defect detection system with a low image flare and high-incidence angle illumination. Flare is illumination light reflected or scattered by the lens surfaces on its way to the sample which winds up on the sensing plane. Interferometric defect detection system 1700 includes an illumination source beam 1718 which is directed towards the surface of the sample 1710 as shown. The sample 1710 can be a wafer, reticle, or other sample being inspected. The scattered component from sample 1710 is represented by beams 1728, and the specular component is represented by beam 1724. A high-resolution optical imaging system including lens systems 1714 and 1716 collects both the scattered and specular components of light and directs them to an image sensor 1740. Subsystem 1770 is positioned in the path of specular component 1724 and includes a phase controller and attenuator such as described and shown with respect to FIGS. 2*a* and 2*b*. Scattered light beams 1728 are passed through a compensation plate 1730 to equalize the path lengths of the specular and scattered components. A beam dump 1726 accepts the portion of specular component 1724 that is rejected by the attenuator.

Figure 18:
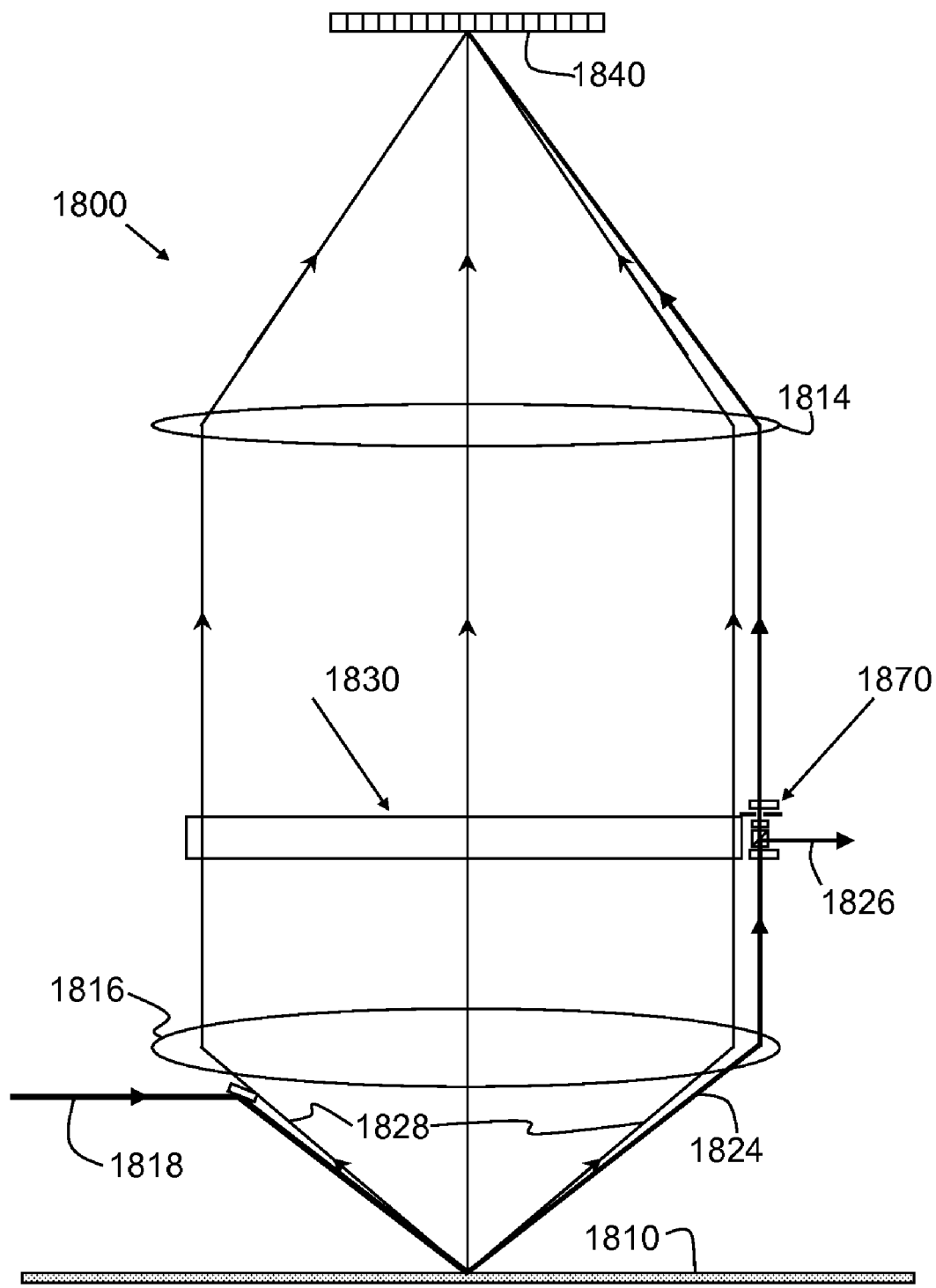
FIG. 18 shows an example of an interferometric defect detection system with low-flare high-incidence angle illumination and a variable attenuator, according to some embodiments.

FIG. 18 shows an example of an interferometric defect detection system with low image flare and high-incidence angle illumination and a variable attenuator, according to some embodiments. Interferometric defect detection system 1800 includes an illumination source beam 1818 which is directed towards the surface of the sample 1810 as shown. The sample 1810 can be a wafer, reticle, or other sample being inspected. The scattered component from sample 1810 is represented by beams 1828, and the specular component is represented by beam 1824. A high-resolution optical system including lens systems 1814 and 1816 collects both the scattered and specular light components and images them on an image sensor 1840. Subsystem 1870 is positioned in the path of specular component 1824 and includes a phase controller and variable attenuator such as described and shown with respect to FIGS. 9-11 and 14. Scattered light beams 1828 are passed through a compensation plate 1830 to equalize the path lengths of the specular and scattered components. A beam dump 1826 accepts the portion of specular component 1824 that is rejected by the variable attenuator.

As shown in FIGS. 15 through 18, by shifting the beam location toward the edge of the pupil plane/aperture stop or by feeding the illumination light onto the sample externally, a high incidence angle of illumination can be achieved. External routing of the illumination light to the sample will reduce the flare and stray light significantly. All of the aforementioned techniques of phase control, amplitude attenuation, and polarization control of the specular component can be employed.

Figure 19:
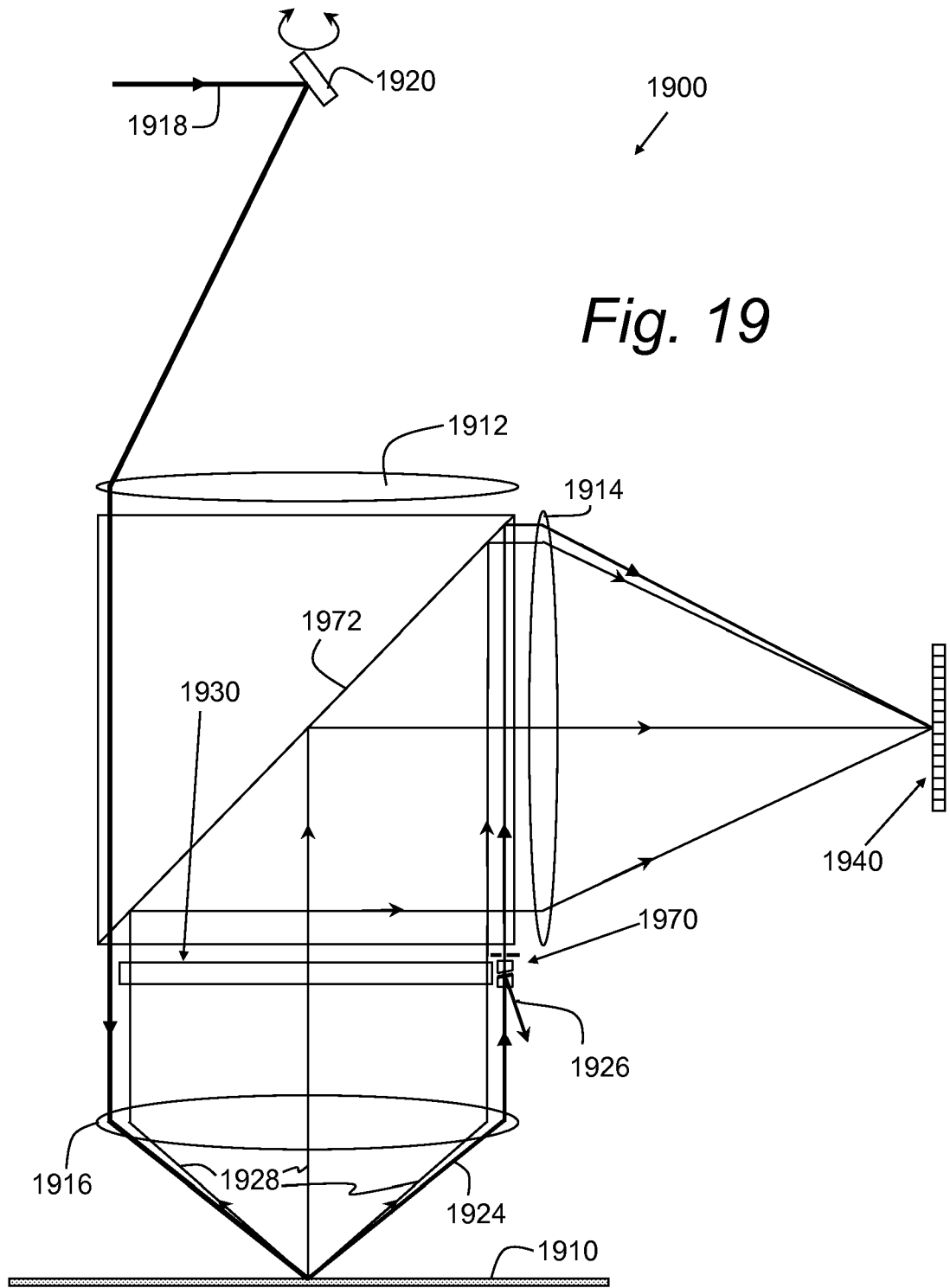
FIG. 19 shows an example of an interferometric defect detection system with an azimuthally rotatable high incidence angle illumination, according to some embodiments.
Figure 20:
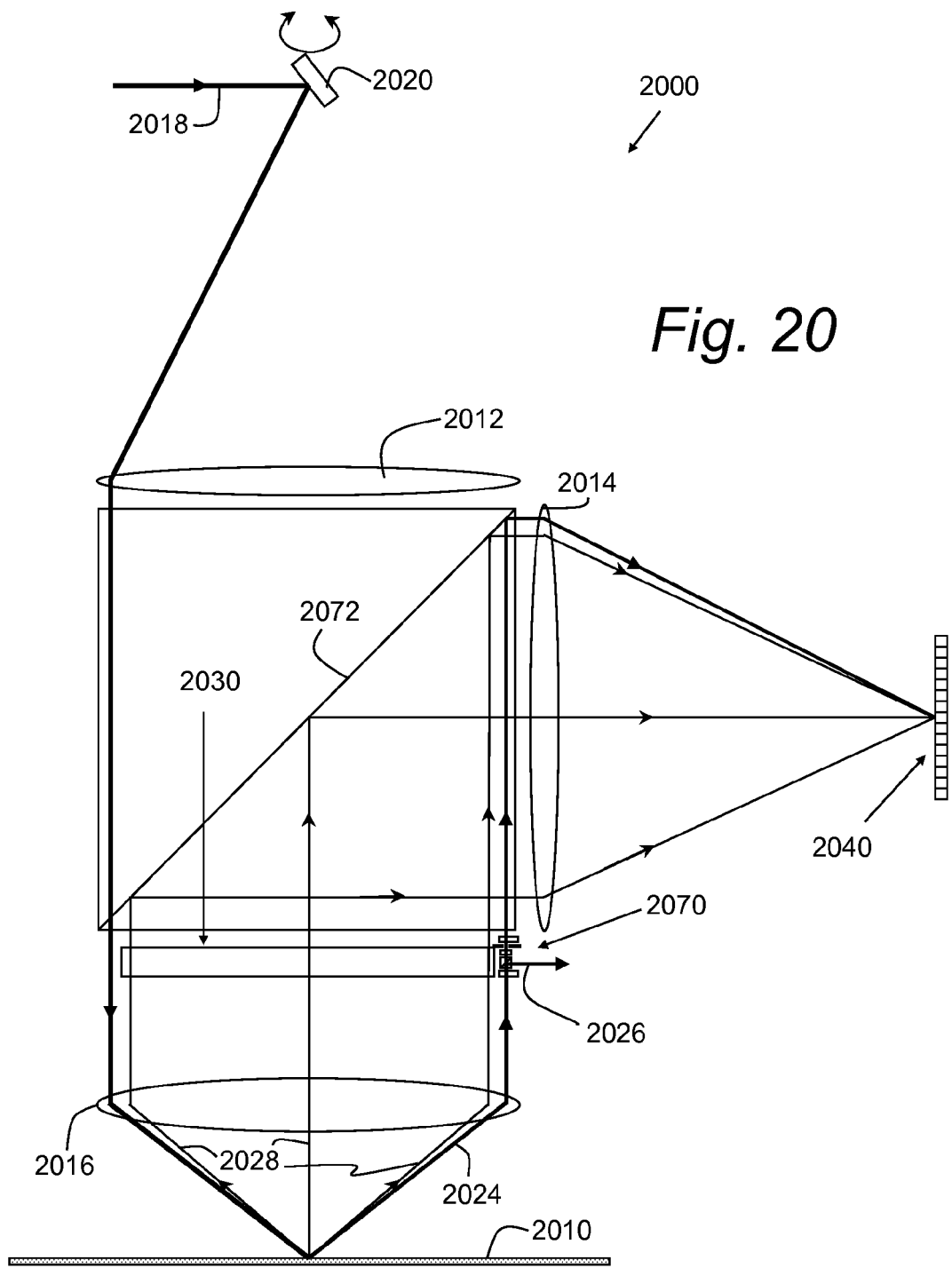
FIG. 20 shows an example of an interferometric defect detection system with an azimuthally rotatable high incidence angle illumination with a variable attenuator for the specular component, according to some embodiments.

11. Azimuthal Rotation of Illumination Light. Defect detection sensitivity generally depends not only on the polar angle but also on the azimuthal angle of incidence of the illumination light. Azimuthal angle is defined as the angle between the pattern on the sample and a normal projection of the incident beam onto the sample. In order to maximize the defect detection sensitivity for some applications, it is desirable to vary the illumination azimuthal angle so that an optimum angle can be found. An effective way of covering the practical azimuthal angles is to put a rotatable prism or mirror at the conjugate location of the sample. This scheme is shown in FIGS. 19 through 22. The configuration of FIGS. 19 and 20 is more flexible because the illumination system and collection system share only the high power part of lens system.

FIG. 19 shows an example of an interferometric defect detection system with an azimuthally rotatable high incidence angle illumination. Interferometric defect detection system 1900 includes an illumination source beam 1918 which is directed towards a rotatable and tiltable surface 1920 such as a mirror or prism. The reflected beam passes through lens systems 1912 and 1916 and is directed towards the surface of the sample 1910 as shown. The sample 1910 can be a wafer, reticle, or other sample being inspected. The scattered component from sample 1910 is represented by beams 1928, and the specular component is represented by beam 1924.

A high-resolution optical system including lens systems 1914 and 1916, and beam splitter 1972 collects both the scattered and specular components of light and directs them to an image sensor 1940. Subsystem 1970 is positioned in the path of specular component 1924 and includes a phase controller and attenuator such as described and shown with respect to FIGS. 2a and 2b. Scattered light beams 1928 are passed through a compensation plate 1930 to compensate for path length differences between the specular and scattered components. A beam dump 1926 accepts the portion of specular component 1924 that is rejected by the attenuator. Subsystem 1970 has to move with the rotation of the mirror 1920 to follow the beam around the periphery of the pupil. If a 50/50 beamsplitter is employed on surface 1972 then the optical efficiency of this scheme can be no greater than 25% because of the transmission and reflection through the beamsplitter. If a polarizing beamsplitter is used for surface 1972 and a quarter wave plate is employed in the illumination path between the beamsplitter and the sample then a much higher efficiency is possible.

FIG. 20 shows an example of an interferometric defect detection system with an azimuthally rotatable high incidence angle illumination and with a variable attenuator for the specular component, which may find applications. Interferometric defect detection system 2000 includes an illumination source beam 2018 which is directed towards a rotatable surface 2020 such as a mirror or prism. The reflected beam passes through lens systems 2012 and 2016 and is directed towards the surface of the sample 2010 as shown. The sample 2010 can be a wafer, reticle, or other sample being inspected. The scattered component from sample 2010 is represented by beams 2028, and the specular component is represented by beam 2024. A high-resolution optical system including lens systems 2014 and 2016, and beam splitter 2072 collects both the scattered and specular components from the sample and directs them to an image sensor 2040. Subsystem 2070, positioned in the path of specular component 2024, includes a phase controller and variable attenuator such as described and shown with respect to FIGS. 9-11 and 14. Subsystem 2070 should move with the rotation of the mirror 2020 to follow the beam around the periphery of the pupil. Scattered light beams 2028 are passed through a compensation plate 2030 to equalize path lengths for the specular and scattered components. A beam dump 2026 accepts the portion of the specular component 2024 that is attenuated by the variable attenuator.

Figure 21:
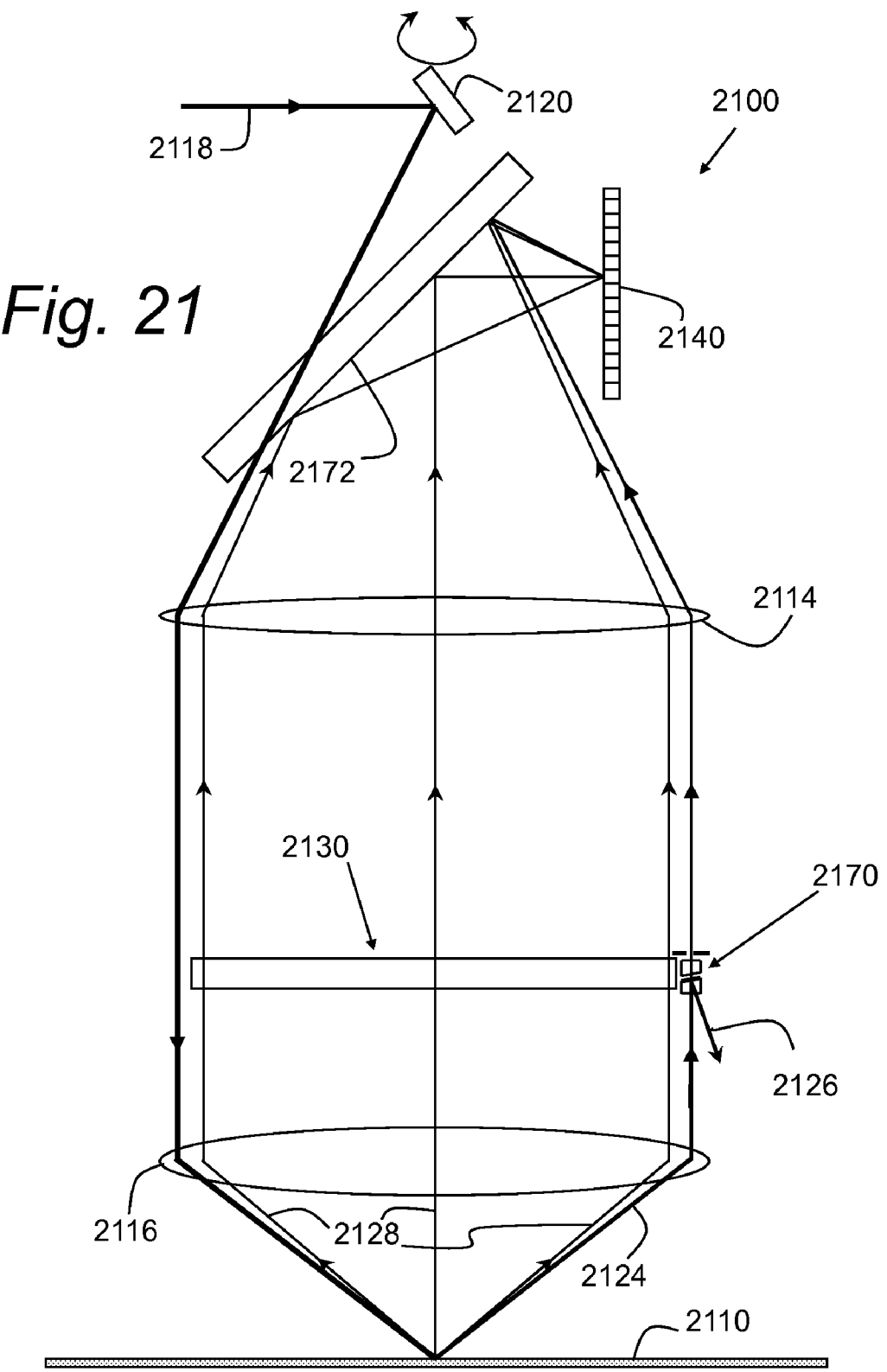
FIG. 21 shows an example of an interferometric defect detection system with an azimuthally rotatable high incidence angle illumination, according to some embodiments.
Figure 22:
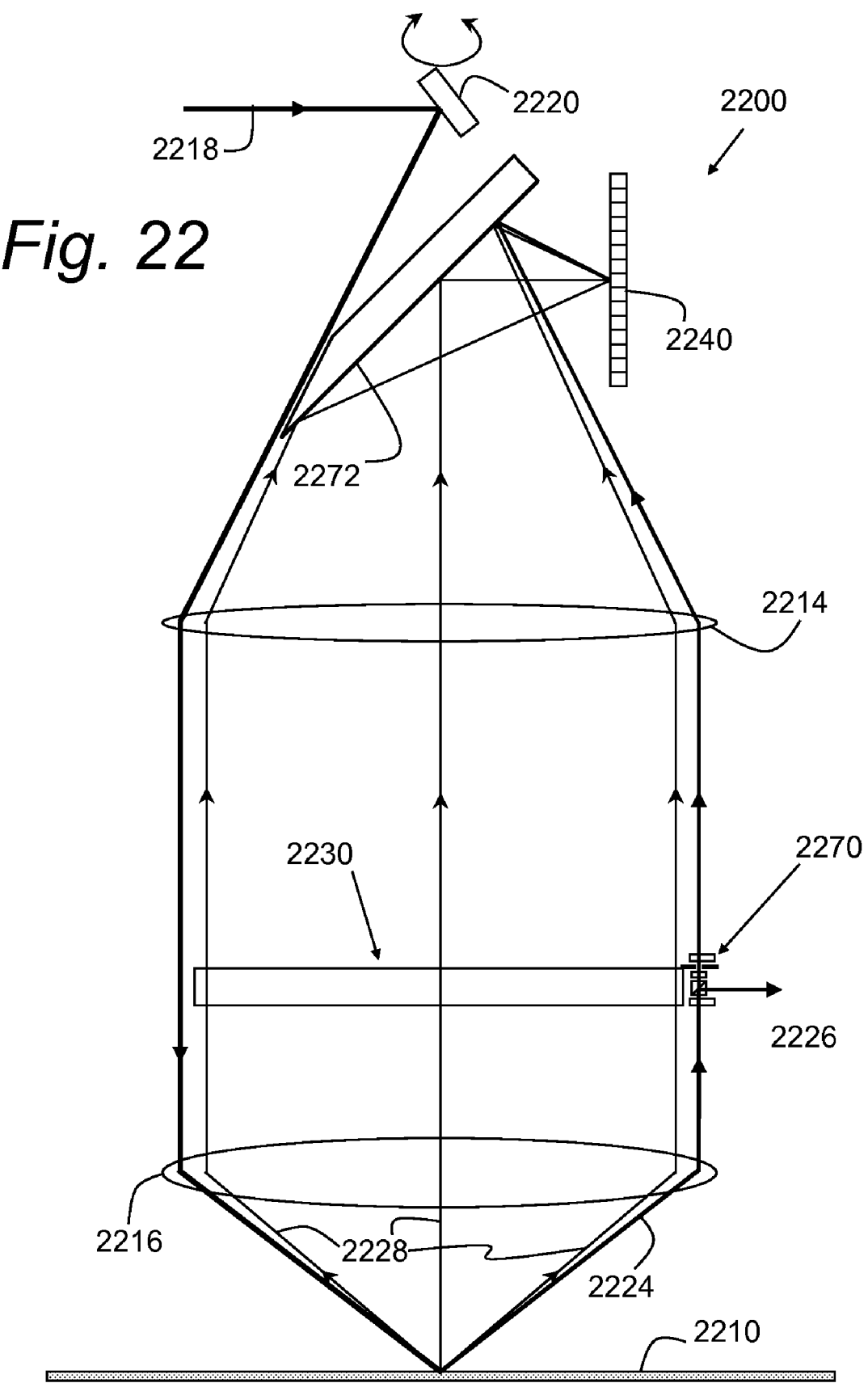
FIG. 22 shows an example of an interferometric defect detection system with an azimuthally rotatable high incidence angle illumination with a variable attenuator for the specular component, according to some embodiments.

For some applications, especially in large etendue systems, there may be little space available in the middle section of lens system for the beam splitter. In this case, the beam splitter can be replaced with a beam splitter or a mirror positioned where more space is available. FIGS. 21 and 22 show possible configurations. FIG. 21 shows an example of an interferometric defect detection system with an azimuthally rotatable, high incidence angle illumination. Interferometric defect detection system 2100 includes an illumination source beam 2118 which is directed towards a rotatable and tiltable surface 2120 such as a mirror or prism. The reflected beam is directed towards the surface of the sample 2110 as shown. The sample 2110 can be a wafer, reticle, or other sample being inspected. The scattered component from sample 2110 is represented by beams 2128, and the specular component is represented by beam 2124. A high-resolution optical system including lens systems 2114 and 2116, and beam splitter 2172 collects both the scattered and specular components of light and directs them to an image sensor 2140. Subsystem 2170 is positioned in the path of specular component 2124 and includes a phase controller and attenuator such as described and shown with respect to FIGS. 2a and 2b. Subsystem 2170 should move with the rotation of the mirror 2120 to follow the beam around the periphery of the pupil. Scattered light beams 2128 are passed through a compensation plate 2130 to equalize path lengths of the specular and scattered components. A beam dump 2126 accepts the portion of specular component 2124 that is rejected by the attenuator.

FIG. 22 shows an example of an interferometric defect detection system with an azimuthally rotatable high incidence angle illumination with a variable attenuator for the specular component that may be suitable for some applications. Interferometric defect detection system 2200 includes an illumination source beam 2218 which is directed towards a rotatable and tiltable surface 2220 such as a mirror or prism. The reflected beam is directed towards the surface of the sample 2210 as shown. The sample 2210 can be a wafer, reticle, or other sample being inspected. The scattered component from sample 2210 is represented by beams 2228, and the specular component is represented by beam 2224.

A high-resolution optical system including lens systems 2214 and 2216, and mirror 2272 collects both the scattered and specular components of light and directs them to an image sensor 2240. Subsystem 2270 positioned in the path of specular component 2224 and includes a phase controller and variable attenuator such as described and shown with respect to FIGS. 9-11 and 14. Subsystem 2270 should move with the rotation of the mirror 2220 to follow the beam around the periphery of the pupil. Scattered light beams 2228 are passed through a compensation plate 2230 to equalize path lengths of the specular and scattered components. A beam dump 2226 accepts the portion of specular component 2224 that is attenuated by the variable attenuator.

By rotating the prism or mirror located in the virtual conjugate focal plane of the sample, it is, in principle, possible to rotate the azimuthal angle of the illumination beam by 360 degrees. However, a 360 degree azimuthal rotatability of illumination light is rather difficult to achieve in practice because of mechanical collisions with other mechanical or optical parts. In some embodiments, a 180 degree azimuthal rotation of illumination light may be used. In these cases, 360 degree coverage of azimuthal rotation of illumination light relative to the sample is achieved by rotating the sample by 180 degrees. A 180 degree rotation of the sample usually does not cause problems because the patterns on the wafers or reticles are predominantly oriented in the 0°-180° or the 90°-270° directions. An azimuthal rotation of the illumination beam can be very effective in increasing the defect detection sensitivity, if it is combined with polarization control. Polarization control of the illumination does not need to be mechanically coupled with the azimuthal rotation of the illumination light. Therefore, the two controls can be implemented independently without difficulty. Note that when the azimuthal direction of the illumination beam is changed, then the phase controller in the path of the specular component should also be rotated around the lens axis in order to follow the illumination beam path.

12. Transmissive Configuration. Some samples like reticles and biological tissues can be more transmissive than reflective. In order to inspect transmissive samples, the system can be configured in a transmission mode.

Figure 23:
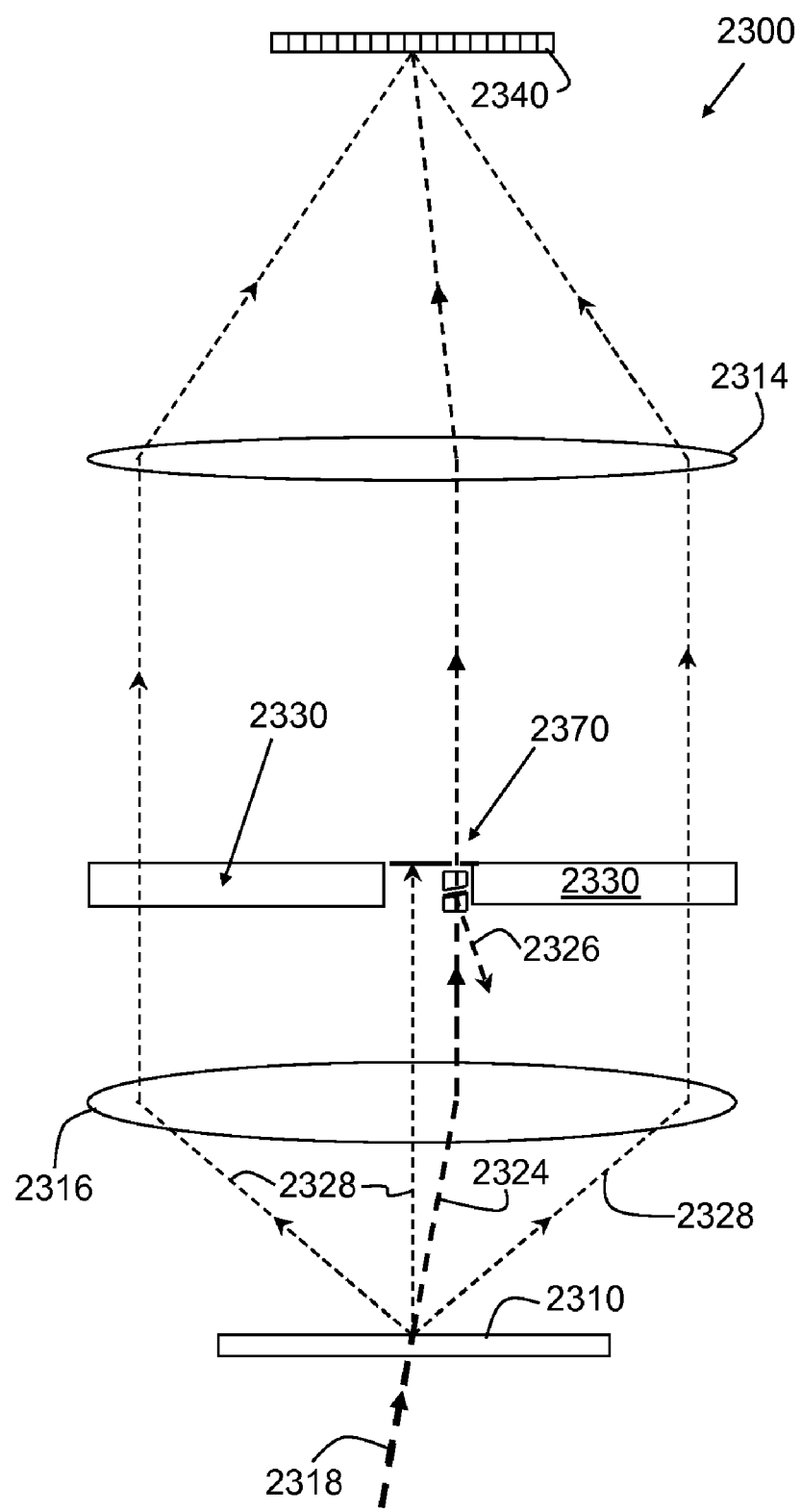
FIG. 23 shows an example of an interferometric defect detection system with illumination through transmissive samples, according to some embodiments.

FIG. 23 shows an example of an interferometric defect detection system designed to pass illumination through transmissive samples. The only significant difference from the embodiments previously described is the illumination path.

Other aspects remain the same. Interferometric defect detection system 2300 includes an illumination source which generates a coherent beam 2318. Beam 2318 is directed towards the transmissive sample 2310 as shown. The sample 2310 can be, for example, a reticle or a biological sample being inspected. The scattered component from sample 2310 is represented by beams 2328, and the specular component is represented by beam 2324.

A high-resolution optical system including lens systems 2314 and 2316 collects both the scattered and specular components of light and directs them to an image sensor 2340. Subsystem 2370 is positioned in the path of the specular component 2324 and can include a phase controller, an attenuator, and/or one or more polarization controllers such as described and shown with respect to FIGS. 2a-b, 9-11 and 14. Scattered light beams 2328 are passed through a compensation plate 2330 to equalize the path lengths of the specular and scattered components. A beam dump 2326 accepts the portion of specular component 2324 that is rejected by the variable attenuator.

Most reticles are both transmissive and reflective. However, they are usually used in transmission mode. In this case, the transmission, not the reflectivity, of the reticle is the final concern. Unlike conventional reticle inspection tools, the complex transmission coefficient of a point on a reticle can be determined by measuring the intensity of the transmitted light using a number of different phase shifts. Therefore, the transmissive configuration described herein can be used for the inspection of reticles, especially phase-shift reticles, very effectively in terms of both performance and cost.

13. Dual Mode Configuration. Some samples can be both reflective and transmissive. A good example is a reticle. In order to inspect this kind of sample in a more thorough fashion, the system can incorporate both reflection and transmission modes at the same time.

Figure 24:
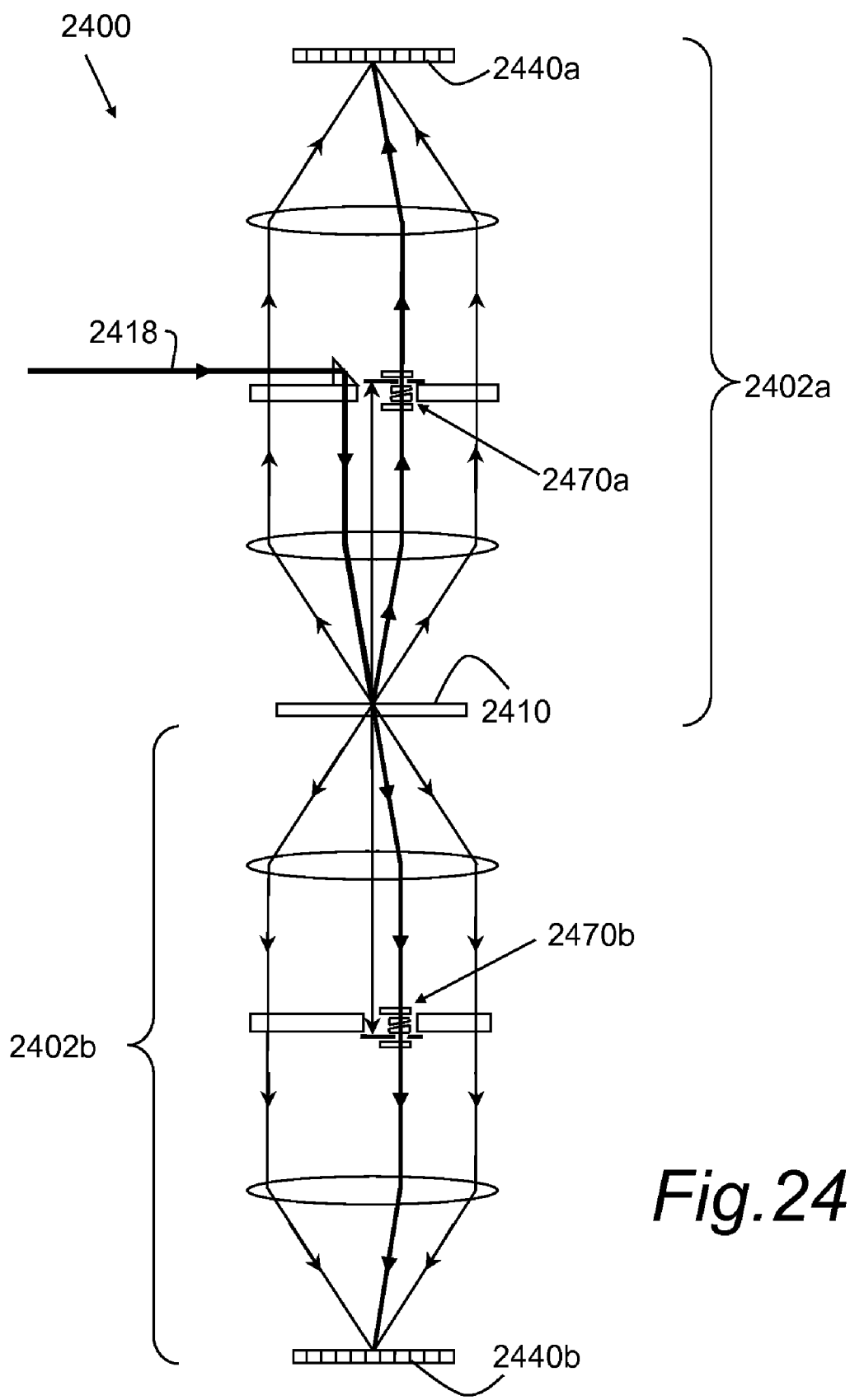
FIG. 24 shows an example of a sample inspection system incorporating both reflection and transmission modes, according to some embodiments.

An example configuration of this kind of system is shown in FIG. 24. System 2400 includes a reflective inspection subsystem 2402a and a transmissive inspection subsystem 2402b. A single source beam 2418 is directed toward sample 2410, which is, for example, a reticle. The reflected and transmitted light beams are detected by two separate image sensors 2440a and 2440b simultaneously. Phase control and attenuation are achieved through each respective subsystem 2470a and 2470b. There is no change of working principles from those previously described herein. The aforementioned controls of relative phase, specular amplitude, azimuthal rotation and polarization can be implemented.

In the case of reticle inspection, a die-to-die image subtraction technique usually cannot be used. In this case the reference image of a defect-free reticle can be generated from reticle data used to make the reticle pattern. This is a heavy computational task usually done by computer. Then, the image of an actual reticle is compared with the computer-generated image of a defect-free reticle to find defects. In order to facilitate fast data processing, the image of a defect-free reticle must be generated very quickly. A fully coherent illumination source such as a laser minimizes the amount of computation required for reticle image construction, thus allowing fast image construction with minimal computational resources.

14. Multiple Wavelength Configurations. Generally, a shorter wavelength provides higher defect detection sensitivity. However, the detection sensitivity of some defects does not follow this general rule. Therefore, for some applications, multiple wavelengths can be used to detect a variety of defects more effectively. Multiple wavelengths can be implemented cost-effectively in either a sequentially-operational or a simultaneously-operational configuration.

Sequential Multiple Wavelengths: In this configuration, only one image sensor may be used and one wavelength at a time may be used to detect defects. The hardware is simpler but the operation takes more time compared with the configuration for simultaneous multiple wavelength operation. The continuously variable phase controller does not need to be modified to accommodate different wavelengths but wave plates for amplitude attenuation and polarization control should be modified to handle different wavelengths.

Figure 25:
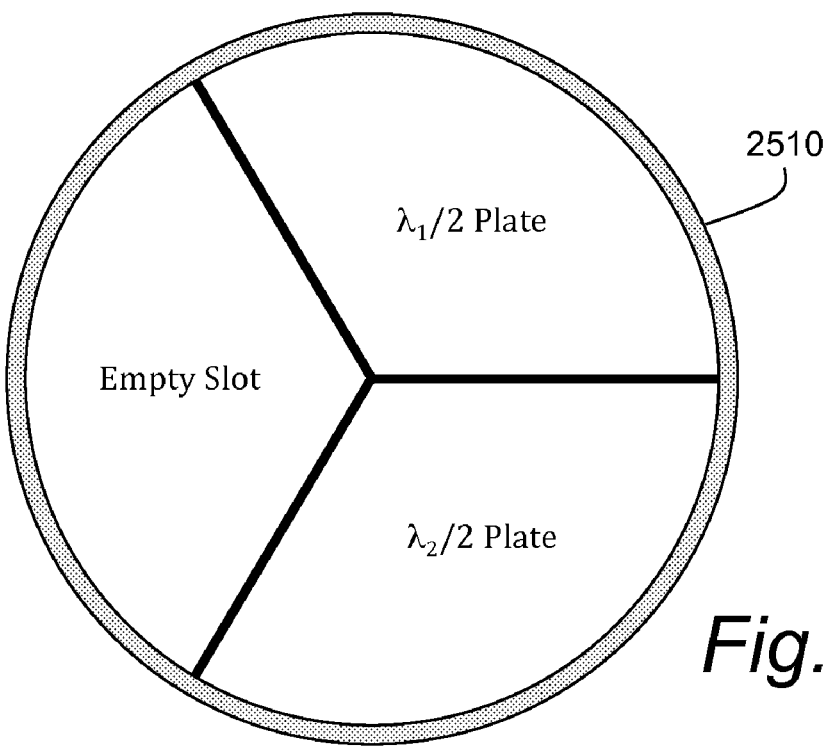
FIGS. 25 through 27 show various examples of waveplates for use in operation of a detection system in a sequential multiple wavelength mode, according to some embodiments.
Figure 26:
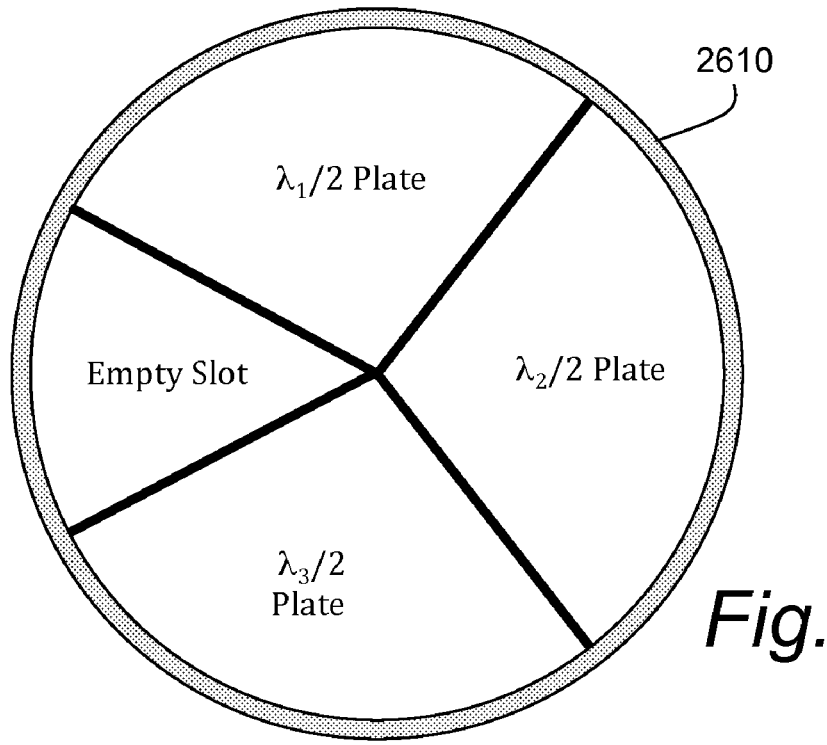
Figure 27:
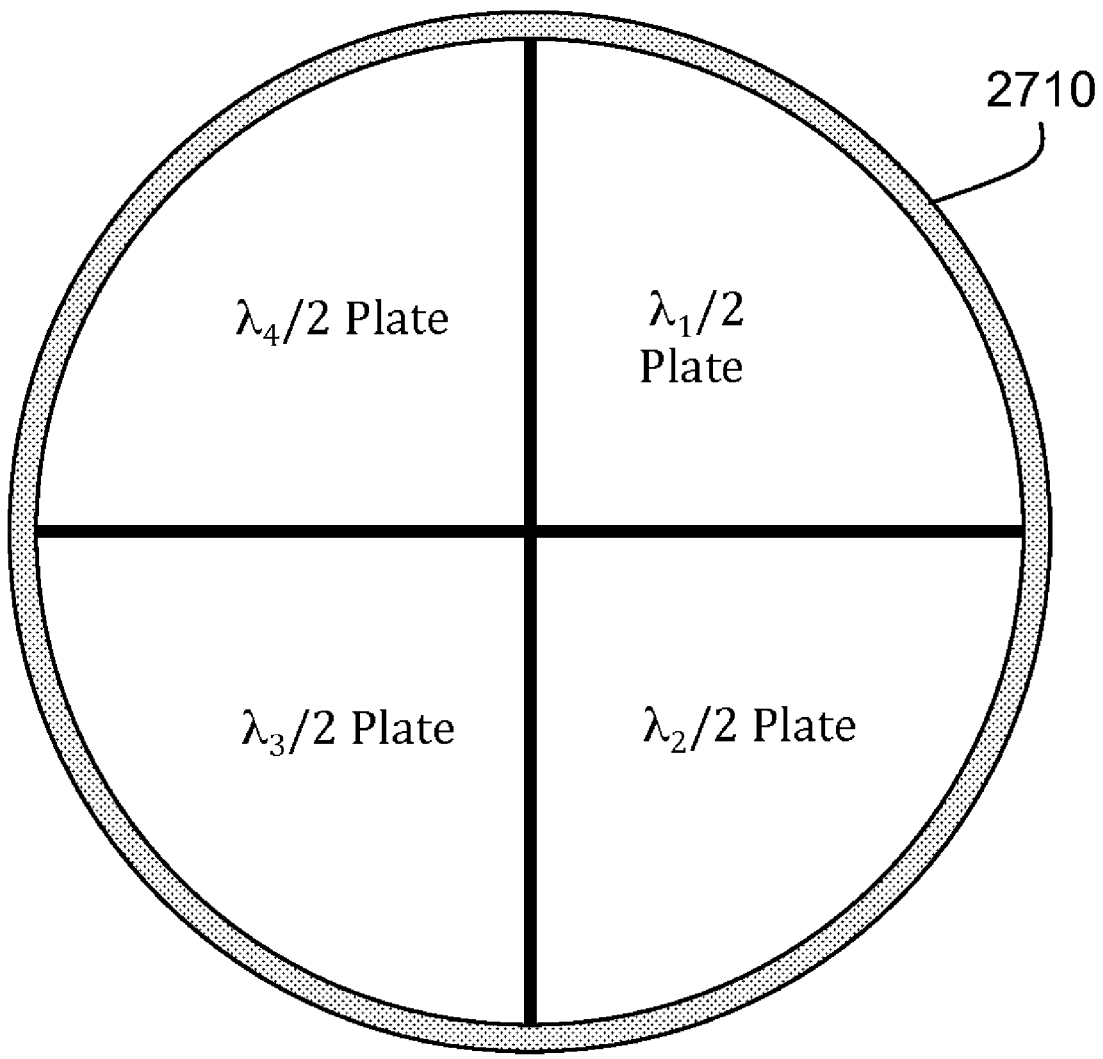

FIGS. 25 through 27 show some possible means for changing the $\lambda/2$ plates. FIG. 25 shows an example of a carousel 2510 holding two $\lambda/2$ wave plates, each for a different inspection wavelength. FIG. 26 shows an example of a carousel 2610 holding three $\lambda/2$ wave plates, each optimal for a different wavelength. FIG. 27 shows an example of a carousel 2710 holding four $\lambda/2$ wave plates for four different wavelengths. Modifications analogous to those shown in FIGS. 25-27 can be applied to $\lambda/4$ plates. When the wavelength is switched, the wave plates are switched accordingly. Wave plate switching is achieved by rotating the waveplate carousel by an appropriate amount. The wave plates are rotated by a maximum of 90° to cover all possible amplitude attenuation and polarization states. Therefore, a maximum of four wave plates for four different wavelengths can be packaged in a single mount as shown in FIG. 27. If the beam size is not very small compared with the area of each wave plate, then two or three plates in the single mount, as shown in FIGS. 25 and 26, is more practical.

Figure 28:
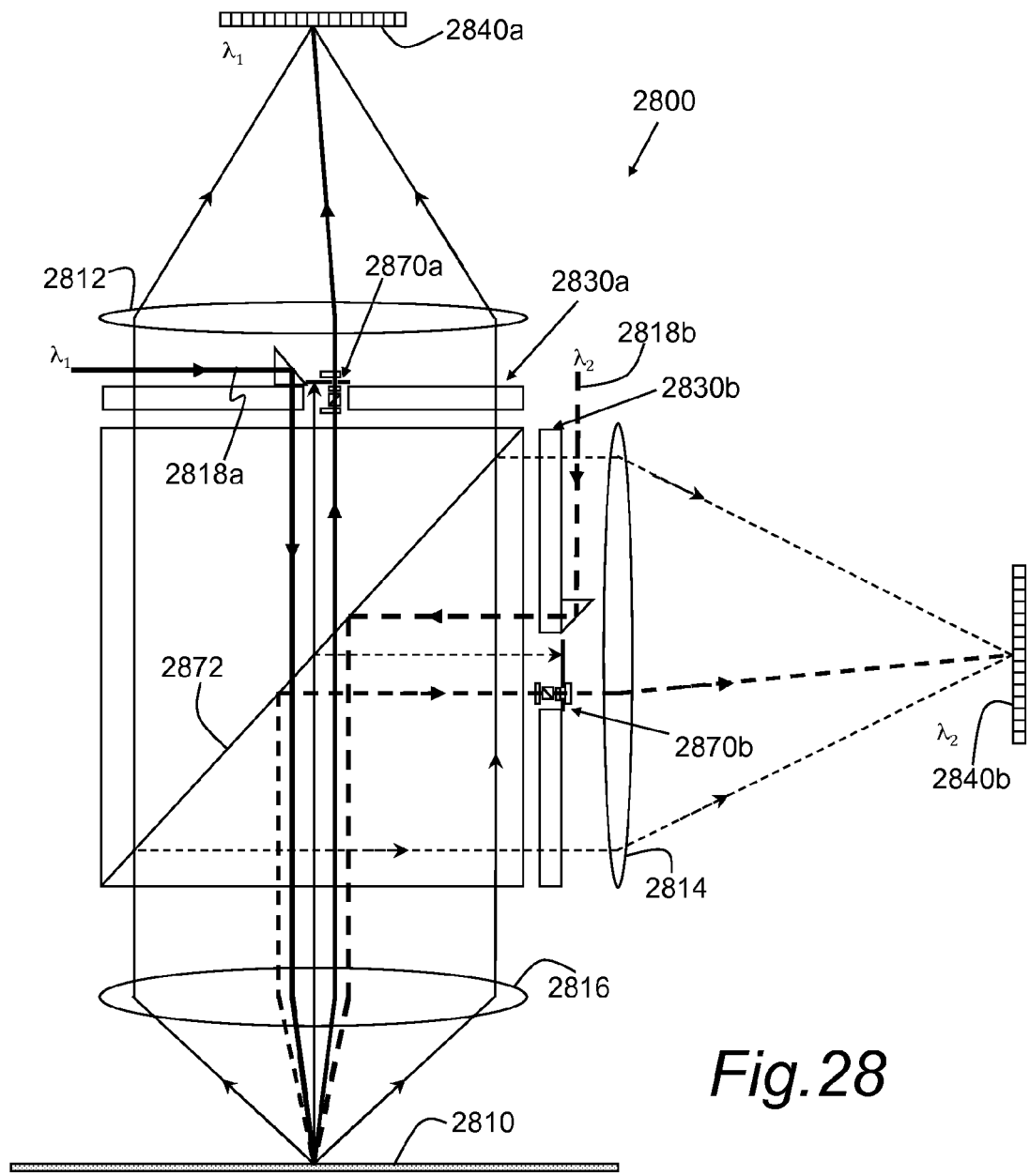
FIG. 28 shows an example system configuration for two wavelengths, according to some embodiments.

Simultaneous Multiple Wavelengths: Multiple wavelengths can be used simultaneously by adding a wavelength splitter and a separate image sensor for each wavelength. FIG. 28 shows an example system configuration for two wavelengths. System 2800 for inspection of sample 2810 uses two separate illumination source beams 2818*a* and 2818*b* having two different wavelengths. The two wavelengths are combined and separated by a dichroic wavelength splitter 2872. The two wavelengths share the same front end of the collection optics 2816, which is usually the most critical and also the most expensive part of the whole optical system. By sharing the front end of the collection optics 2816, the system achieves not only simplicity but also stability. The back-end lens components, 2812 and 2814, which are usually of low optical power and therefore are less expensive, are separated in order to give maximum flexibility in phase control, magnification adjustment, and sensor choices. Subsystems 2870*a* and 2870*b* are used to control the phase and attenuation such as shown and described with respect to FIGS. 2*a-b*, 9-11 and 14.

Each wavelength also uses its own compensation plate 2830*a* and 2830*b*, and image sensor 2840*a* and 2840*b*. In some embodiments, 266 nm and 532 nm wavelengths are used. The technology for producing these two wavelengths is mature and a single laser system can provide both wavelengths, thus reducing cost. Note that shorter wavelengths such as 193 nm, vacuum ultraviolet, extreme ultraviolet, etc., can be used to get higher sensitivity. However, shorter wavelengths are harder to handle. In some embodiments, more than two wavelengths are implemented by adding more wavelength splitters in the back-end optical paths.

It is also possible to arrange things so that all the phase controllers can be placed in the same pupil plane next to each other to eliminate wavelength splitters and save image sensors. However, such a configuration makes the mechanical designs more difficult and increases the pupil obscuration. Furthermore, the system can be configured so that multiple wavelengths or broad band illumination share the same phase controller. Such a configuration saves on the number of phase controllers but makes a precise control of the phases difficult.

Figure 29:
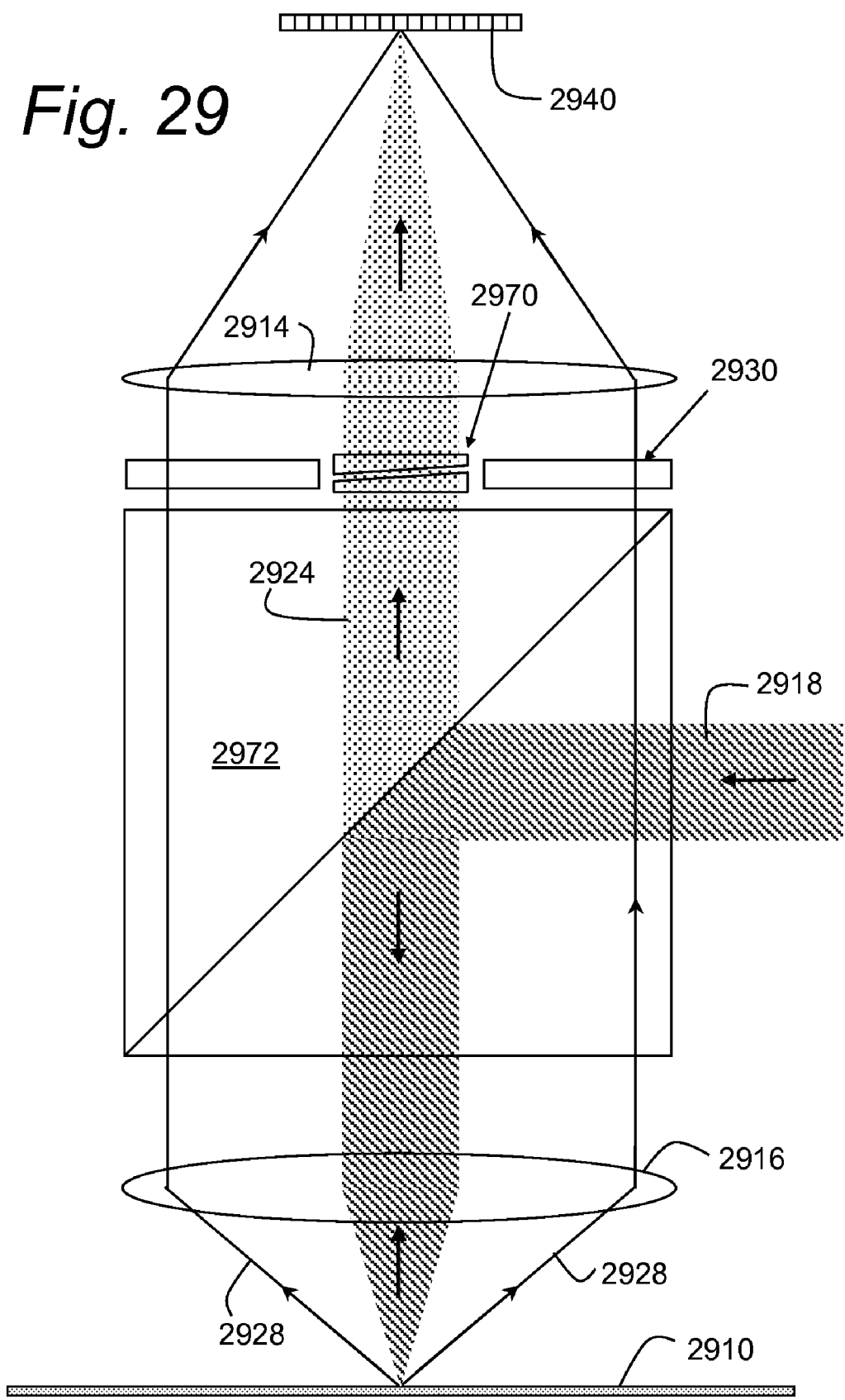
FIG. 29 shows an example of an interferometric defect detection system having a low incidence angle illumination with an extended light source, according to some embodiments.
Figure 30:
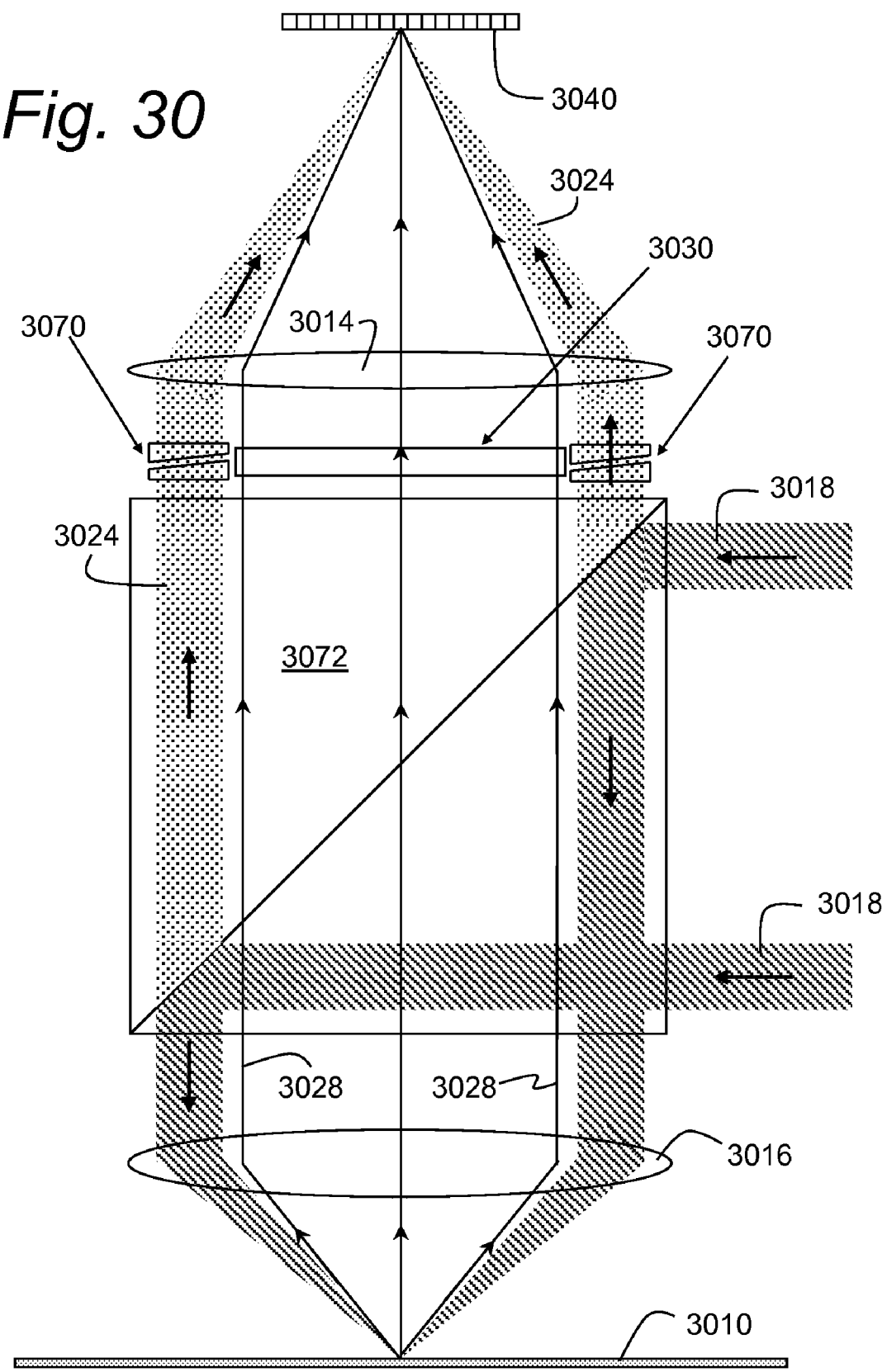
FIG. 30 shows an example of an interferometric defect detection system having a high incidence angle illumination with an extended light source, according to some embodiments.
Figure 31:
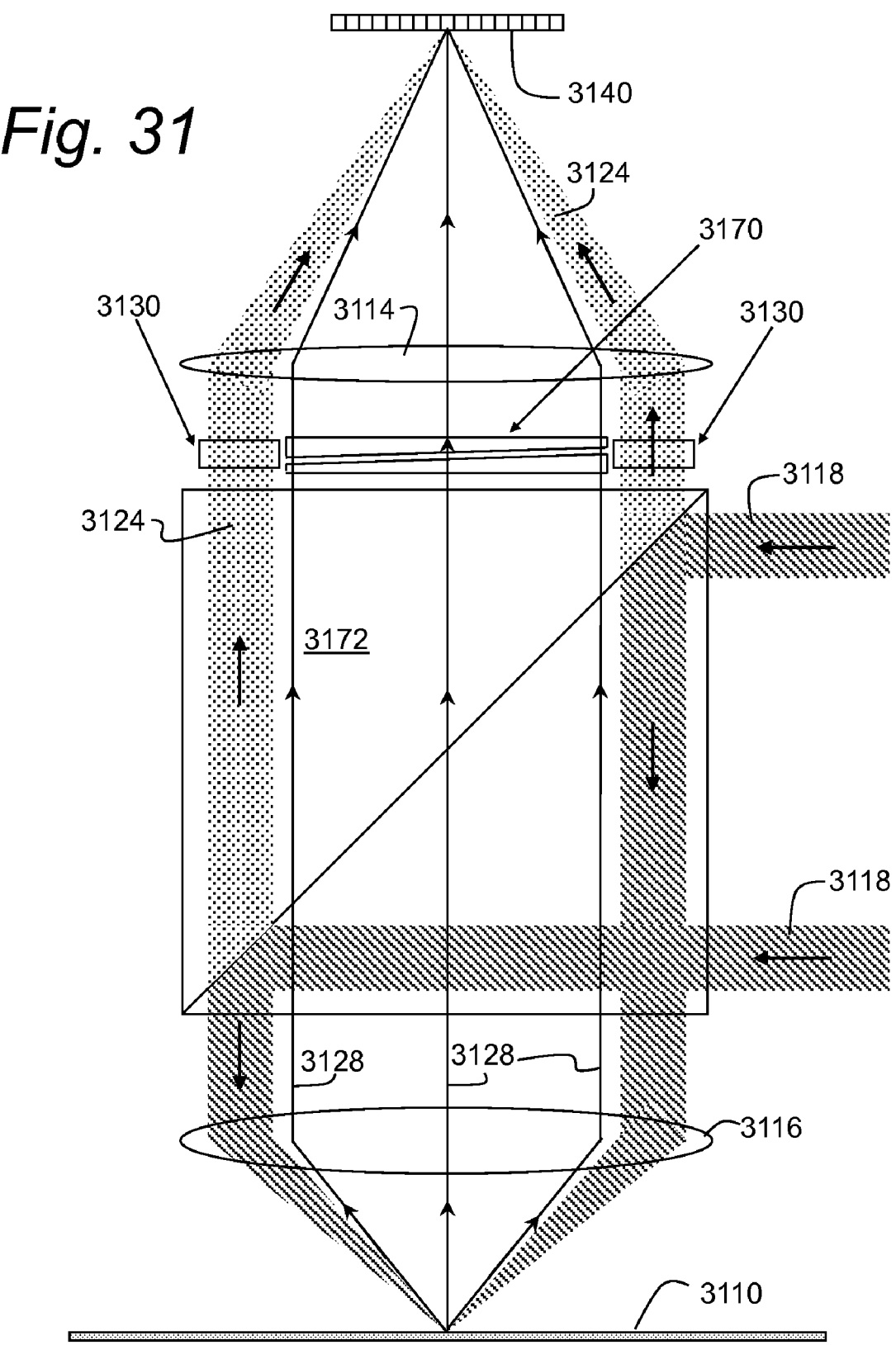
FIG. 31 shows an example of an interferometric defect detection system having a high incidence angle illumination with an extended light source and phase control in the path of the scattered light, according to some embodiments.

15. Extended Source. For many applications single spatial mode lasers, which produce a very coherent beam, are the preferred light sources as previously discussed. However, in some embodiments, light sources other than single mode lasers can also be used. For example, an extended source like an arc lamp can be used as shown in FIGS. 29 through 31. An extended source is defined herein as an incoherent source whose etendue is much larger than the square of its wavelength.

FIG. 29 shows an example of an interferometric defect detection system having a low incidence angle illumination system and employing an extended source. Incoming illumination beam 2918 is directed toward sample 2910 using beam splitter 2972. The specular reflected component is represented by beam 2924 and passes through a phase controller and attenuator 2970 that is analogous to any of the subsystems shown and described with respect to FIGS. 2*a-b*, 9-11 and 14. The scattered component represented by beams 2928 pass through a compensation plate 2930. Front end optical system 2916 and back end optical system 2914 collect and direct the light from the sample towards imaging sensor 2940.

FIG. 30 shows an example of an interferometric defect detection system having a high incidence angle illumination with an extended light source. Incoming light beams 3018 are directed toward sample 3010 using beam splitter 3072. The specular reflected component is represented by beam 3024 which passes through a phase controller and attenuator 3070 that are analogous to any of the subsystems shown and described with respect to FIGS. 2*a-b*, 9-11 and 14. The scattered component represented by beams 3028 pass through compensation plate 3030. Front end optical system 3016 and back end optical system 3014 collect and direct the light towards imaging sensor 3040.

FIG. 31 shows an example of an interferometric defect detection system having a high incidence angle illumination with an extended light source and phase control in the path of the scattered light. Incoming illumination beam 3118 is directed toward sample 3110 using beam splitter 3172. The specular reflected component is represented by beam 3124 and passes through a compensation plate 3130. The scattered component represented by beams 3128 pass though phase controllers and attenuators 3170 that are analogous to any of the subsystems shown and described with respect to FIGS. 2*a-b*, 9-11 and 14. Front end optical system 3116 and back end optical system 3114 collect and direct the light towards imaging sensor 3140.

An extended source has an advantage of spreading light energy uniformly over wider areas of the imaging system lens components. This reduces the possibility of lens damage by the high power density of the illumination beam or the specular beam component. However, there are disadvantages associated with extended light sources. For example, it is hard to spatially separate the specular component from the scattered component. Some part of the scattered component unavoidably overlaps with the specular component even at the pupil plane. This makes precise control of the relative phase between the scattered and specular components difficult. Imprecision in phase control usually results in poorer performance. Another disadvantage is that the collection efficiency of the signal light tends to be reduced because of increased pupil obscuration. Also, it is generally more difficult to implement a Fourier filter to discriminate against pattern noise with extended sources because of the relatively large footprint of the blocking strips at the pupil plane.

III. Operation Modes.

The systems described herein can be operated in many different ways. Further details on several different operation modes will now be provided.

1. High Sensitivity Mode. This mode targets specific types of defects, particularly the kinds of defects which can adversely affect chip production yield. The relative phase between the scattered component and the specular component is usually set to maximize the defect signal. However, the relative phase can also be set to minimize wafer pattern noise or maximize the signal-to-noise ratio of defect signals. In most cases, these are equivalent to each other.

As explained previously, the signal-to-noise ratio can be increased up to two times the intrinsic signal-to-noise ratio through noiseless amplification of the signal by the specular component. As shown previously, noiseless amplification is important for the detection of weak defect signals. If the detailed physical characteristics of the defect and surrounding circuit patterns are unknown, the desirable or ideal relative phase value can be determined experimentally. For example, the catch-all-mode which will be introduced in the next section can be run on the sample to determine the optimal phase value experimentally. On the other hand, if the physical characteristics of the defects are known, the optimum relative phase for detection can be set based on theory or numerical simulations.

Equation (2c) shows that $\phi_s$, the relative phase between the defect signal amplitude and specular component, is an important variable for maximizing the defect signal. It shows that extrema of the defect signal happen when $\phi_s=0°$ or 180°. If $\phi_s=0°$, the value of the interference term becomes positive and if $\phi_s=180°$, the value of the interference term becomes negative. As mentioned previously, the total defect signal is composed of both dark field terms and the interference term. Therefore, in order to maximize the total defect signal, the sign of the interference term should be modified to be the same sign as the whole dark field term. The sign of the whole dark field term cannot be controlled. It can either be positive or negative depending on the physical characteristics of the defect and surrounding patterns. Therefore, to get the maximum defect signal the phase of the interference term can be controlled.

If the sign of the whole dark field term is positive, the choice of $\phi_s=0°$ maximizes the total defect signal. If the sign of the whole dark field term is negative, the choice of $\phi_s=180°$ maximizes the total defect signal. In order to show the benefit of the disclosed systems and methods clearly, a realistic but simple defect is chosen for numerical simulation.

Also, as mentioned previously, the relative phase can be varied by changing the phase of either or both the specular or scattered component. But, in practice it is usually much easier to change the phase of the specular component because the specular component usually has a lower etendue. Therefore, in all numerical simulations, the phase of the specular component is varied to get optimum relative phase values. Even though the numerical simulations are limited to specific type of defects, the systems and methods disclosed herein are generally applicable for the detection of any kind of defects.

Figure 32A:
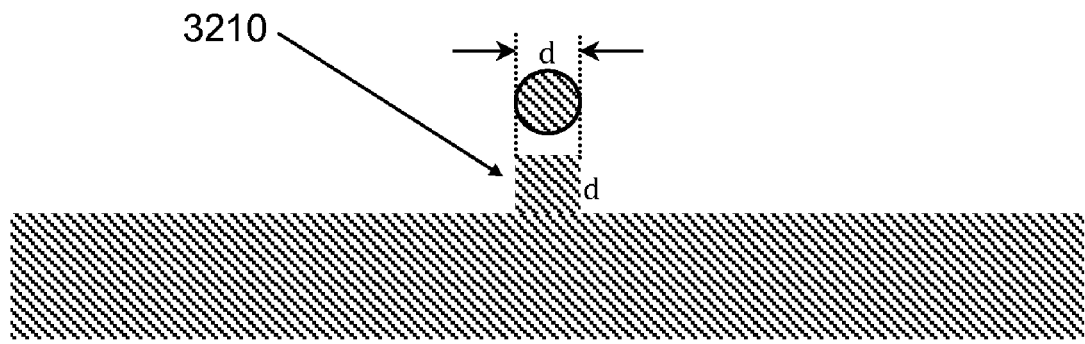
FIGS. 32a and 32b show the shapes of the defects used for numerical simulations herein.
Figure 32B:
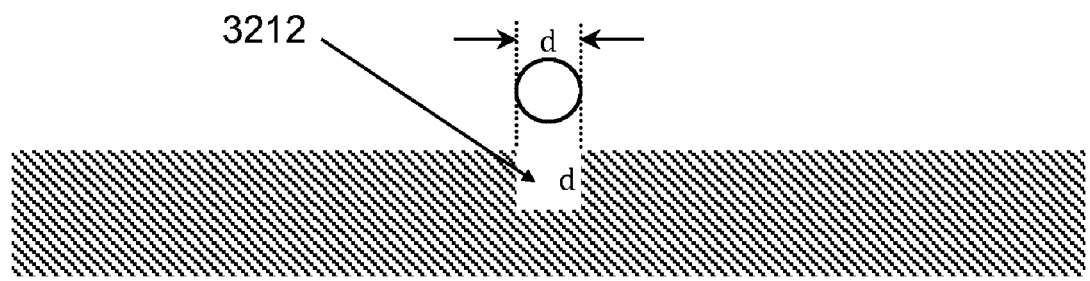

FIGS. 32a and 32b show the shapes of the defects used for the numerical simulations herein. The defects are cylindrically-shaped having a height or depth the same as their diameter. FIG. 32a shows a particle type defect 3210 having a height and diameter of "d." FIG. 32b shows a void type defect 3212 having a depth and diameter of "d." The defect material is assumed to be the same as the sample material. These kinds of defects are called phase defects because they introduce phase change, not amplitude change, to the reflected light. Being phase only, they are at an extreme end of a full spectrum of possible defect types.

Another extreme type of defect is an amplitude-only defect Amplitude only defects have opposite characteristics to phase defects; they have zero height but different reflectivity than their surrounding areas. Most real defects are neither a pure phase type nor a pure amplitude type. They generally have both phase and amplitude differences from their surrounds. Only the signals from phase type defects are simulated in this section, however, the equations and computer program used for the simulations are so general that they can handle other types of isolated cylindrical defects.

In the simulation discussed here, a wavelength of 266 nm was used and the numerical aperture (NA) of the signal collection system was assumed to be 0.9. The central obscuration due to the phase controller and its mount was assumed to be 0.2 NA.

The equations for image formation are derived below and are based on the scalar theory of diffraction. Scalar equations are less accurate than vector equations. However, they are accurate enough for the performance comparison between conventional technologies and the systems and methods disclosed herein. They also provide quite an accurate quantitative estimation of signal strength and shape for defects smaller than a quarter of a wavelength, which is our main interest here. Also, scalar equations usually allow much clearer physical insights than vector equations and therefore, are more suitable for explaining the important concepts contained in the systems and methods disclosed herein. The effect of the defect height is approximated as a sudden phase change. This approximation is justified assuming the imaging system collects only the radiative part of the light wave. It is not suitable in near-field microscopy, which collects the non-radiative part of the light wave. The derived equations are sufficiently general that they can handle other types of isolated cylindrical defects. The following notations are used in the equations:

h: Defect height
a: Reflectivity amplitude of the defect
b: Reflectivity amplitude of surrounding area
$\rho_1$: Numerical aperture of the central obscuration of imaging system
$\rho_2$: Numerical aperture of the aperture stop of the imaging system
t: Transmission amplitude of the attenuator
$\phi$: Phase added to the specular component by the phase controller (radians)

The complex amplitude of the sample reflectivity, O(r), can be expressed as follows.

$$O(r) = \begin{bmatrix} a\exp(i2kh) & \text{for } r \leq r_0 \\ b & \text{for } r > r_0 \end{bmatrix}; \text{Defect and surrounding area} \quad (3)$$

$$= (a\exp(i2kh) - b)circ\left(\frac{r}{r_0}\right) + b \text{ where}$$

$$k = \frac{2\pi}{\lambda}$$

$$circ(r) \equiv \begin{cases} 1 & \text{for } r \leq 1 \\ 0 & \text{for } r > 1 \end{cases}$$

Equation (3) can be rewritten as follows.

$$O(r) = \left[(a\exp(i2kh) - a)circ\left(\frac{r}{r_0}\right) + a\right] + \left[(0 - (b-a))circ\left(\frac{r}{r_0}\right) + (b-a)\right] \quad (4)$$

The part in the first angled bracket represents a pure phase object and the part in the second angled bracket represents a pure amplitude object with zero reflectivity. Therefore, we can generally say that any tiny defect can be decomposed into a pure phase defect and a pure amplitude defect.

Normal illumination is adopted to maintain the circular symmetry of the system. Circular symmetry is maintained in order to make the signal graphs less distractive. Oblique illumination can be modeled as easily as a normal illumination. Normal illumination with unit intensity can be simply expressed as follows.

$$Illu(x,y)=1; \text{Illumination} \quad (5)$$

The complex amplitude of reflected light, W(x,y), is expressed as follows:

$$W(x, y) \equiv O(x) \times Illu(x, y) \quad (6)$$

$$= \left[(a\exp(i2kh) - b)circ\left(\frac{r}{r_0}\right) + b\right]$$

If the coordinates are resealed with wavelength:

$$W(x', y') = \left[(a\exp(i2kh) - b)\mathrm{circ}\left(\frac{r'}{r'_0}\right) + b\right] \text{ where} \quad (7)$$

$$x' \equiv \frac{x}{\lambda}, y' \equiv \frac{y}{\lambda}, r' \equiv \frac{r}{\lambda} \text{ and } r'_0 \equiv \frac{r_0}{\lambda}$$

The diffraction pattern amplitude observed at the pupil plane, $Q(\alpha,\beta)$, is the Fourier transform of $W(x',y')$. Therefore, the complex amplitude at the pupil plane becomes:

$$Q(\alpha, \beta) \equiv FT\{W(x', y')\} = Q_1(\alpha, \beta) + Q_2(\alpha, \beta) \text{ where} \quad (8)$$

$$Q_1(\alpha) \equiv 2\pi(a\exp(i2kh) - b)(r'_0)^2 \frac{J_1(2\pi r'_0 \sqrt{\alpha^2 + \beta^2})}{2\pi r'_0 \sqrt{\alpha^2 + \beta^2}} \quad (9)$$

$$Q_2(\alpha) \equiv b\delta(\alpha)\delta(\beta) \quad (10)$$

The pupil transmission, $\mathrm{Pupil}(\rho)$, and the phase control on the specular component are expressed as follows:

$$\mathrm{Pupil}(\rho) = \begin{vmatrix} t\exp(i\phi) & \text{for } \rho = 0 \\ 0 & \text{for } \rho < \rho_1 \text{ or } \rho > \rho_2 \\ 1 & \text{for } \rho_1 \leq \rho \leq \rho_2 \end{vmatrix} \quad (11)$$

The effect of sample defocus on the detector or sensing plane can also be introduced at the pupil as follows:

$$\mathrm{Defocus}(\rho) = \exp\left(ikz\left(1 - \sqrt{1 - \rho^2}\right)\right) \text{ where } z = \text{sample defocus} \quad (12)$$

If the pupil transmission and defocus effect are combined:

$$P(\rho) = \begin{vmatrix} t\exp(i\phi) & \text{for } \rho = 0 \\ 0 & \text{for } 0 < \rho < \rho_1 \text{ or } \rho > \rho_2 \\ \exp(ikz(1 - \sqrt{1-\rho^2})) & \text{for } \rho_1 \leq \rho \leq \rho_2 \end{vmatrix} \quad (13)$$

The complex amplitude of the reflected light, $V(\alpha,\beta)$, at the pupil becomes:

$$V(\alpha, \beta) \equiv \mathrm{Pupil}(\rho) \times \mathrm{Defocus}(\rho) \times Q(\alpha, \beta) \quad (14)$$

$$= \begin{vmatrix} bt\exp(i\phi)\delta(\alpha)\delta(\beta) & \text{for } \rho = 0 \\ 0 & \text{for } 0 < \rho < \rho_1 \text{ or } \rho > \rho_2 \\ Q_1(\alpha, \beta)\exp(ikz(1 - \sqrt{1-\rho^2})) & \text{for } \rho_1 \leq \rho \leq \rho_2 \end{vmatrix}$$

The complex amplitude of light at the image plane is the inverse Fourier transform of $V(\alpha,\beta)$. It becomes $$U(x', y') = FT^{-1}\{V(\alpha, \beta)\} \quad (15)$$

$$= \int\int V(\alpha, \beta)\exp(i2\pi(\alpha x' + \beta y'))d\alpha d\beta$$

$$= \int\int \begin{pmatrix} Q_1(\alpha, \beta) + \\ Q_2(\alpha, \beta) \end{pmatrix} P(\alpha, \beta)\exp(i2\pi(\alpha x' + \beta y'))d\alpha d\beta$$

$$= \int\int Q_1(\alpha, \beta)P(\alpha, \beta)\exp(i2\pi(\alpha x' + \beta y'))d\alpha d\beta + bt\exp(i\phi)$$

The light intensity at the image plane, $I(x')$, becomes $$I(x') = |U(x')|^2 \quad (16)$$

The above equations are used for all of the defect signal simulations. The values of equation (15) are numerically calculated using, for example, the Python programming language.

Figure 33:
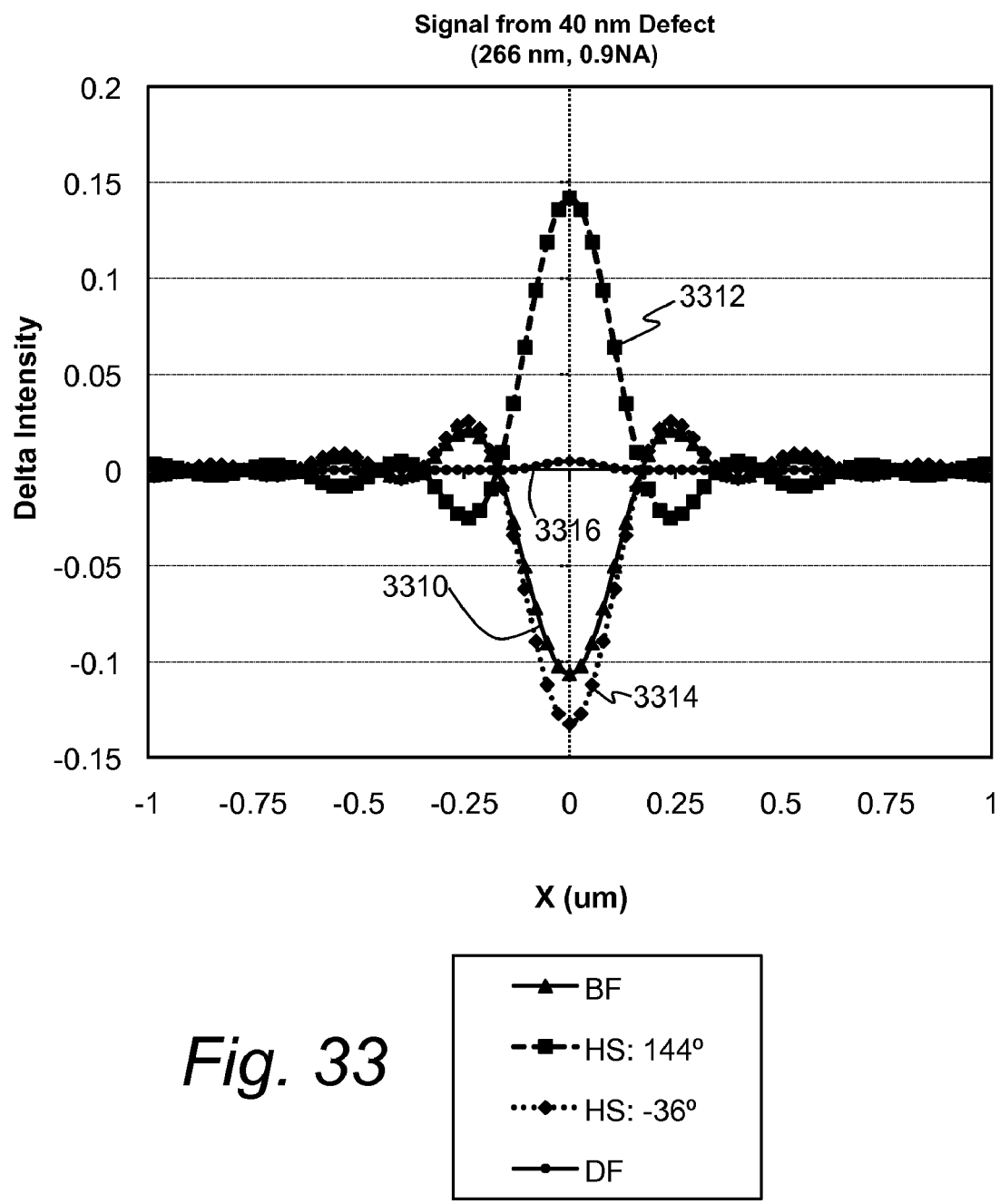

FIGS. 33-35b show numerical simulation results using the above program. FIG. 33 shows simulation results for a 40 nm diameter defect. Curve 3310 shows simulated results for a conventional bright field mode system and curves 3312 and 3314 show simulated results of the interferometric methods disclosed herein using a high sensitivity mode and phase angles of 144° and −36° applied to the specular component, respectively. Curve 3316 shows simulated results for a conventional dark field system.

FIG. 34 shows simulation results for a 20 nm diameter defect. Curve 3410 shows simulated results for a conventional bright field mode system. Curves 3412 and 3414 show simulated results for the interferometric methods disclosed herein using a high sensitivity mode introducing phase angles of 117° and −63° to the specular component, respectively. Curve 3416 plots simulated results for a conventional dark field system.

Figure 35A:
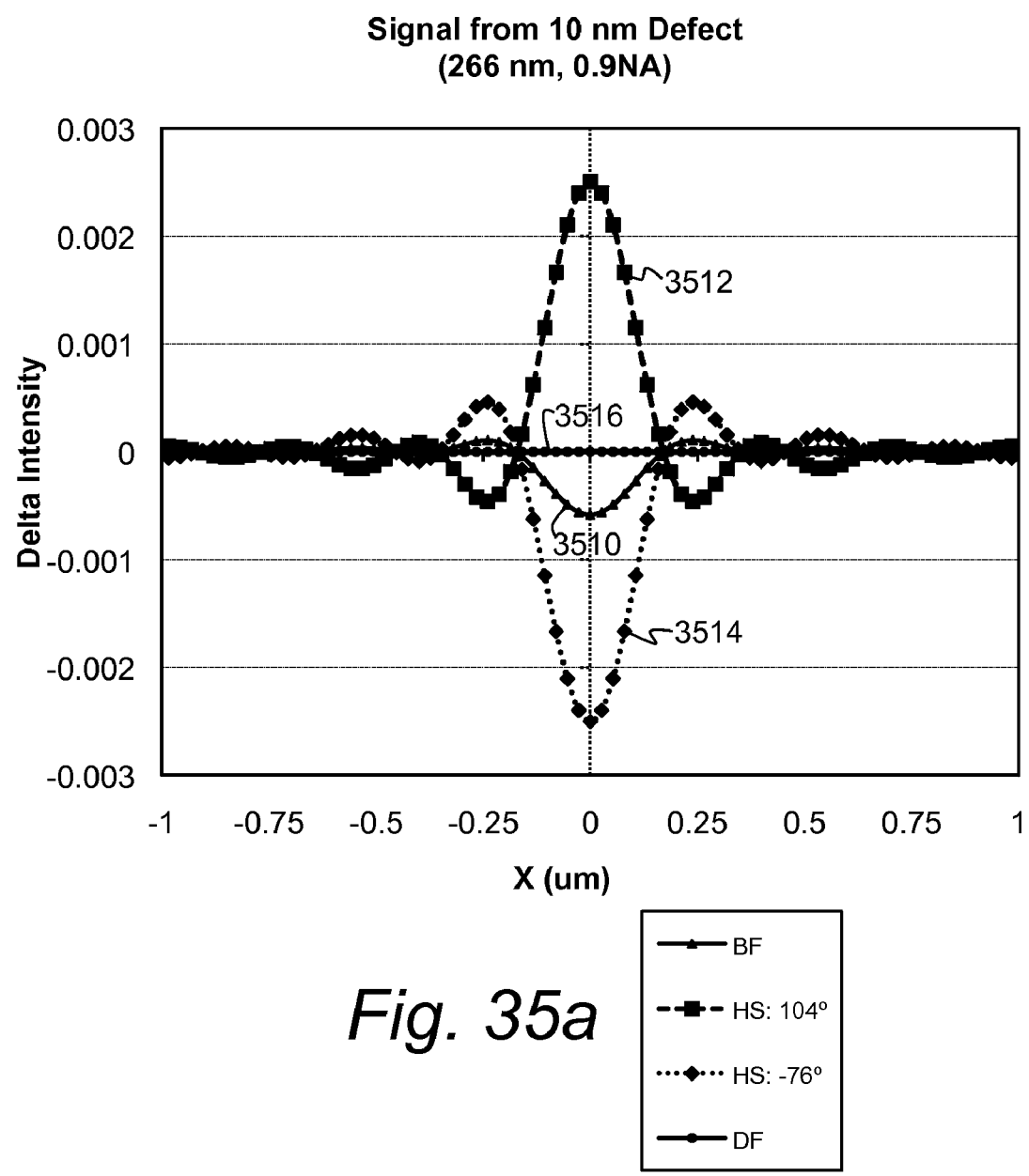

FIG. 35a shows simulation results for a 10 nm diameter defect. Curve 3510 shows simulated results of a conventional bright field mode system. Curves 3512 and 3514 show simulated results of the interferometric methods disclosed herein using a high sensitivity mode introducing phase angles of 104° and −76° to the specular component, respectively. Curve 3516 shows simulated results for a conventional dark field system. "BF" in the figure's legend means a conventional system using bright field mode and is included in the figures for comparison purposes. "HS" in the figure's legend means high sensitivity mode. The angle values are the phase angles introduced to the specular component to get the two extrema of defect signals as mentioned previously. The positive angles correspond to $\phi_s=0°$ cases and negative angles correspond to $\phi_s=\pm180°$ cases.

The angle $\phi_s$ is not the phase angle introduced to the specular component. Rather, $\phi_s$ is the sum of the phase angle introduced to the specular component and the innate phase angle difference between the defect signal and the specular component. The innate phase angle difference is the phase angle difference that a conventional bright field mode system will have. The innate phase angle differences in the simulated defect signals are −144°, −117° and −104° for 40 nm, 20 nm and 10 nm defects respectively. These innate phase angle differences are quite different from 0° or ±180°. This is the reason why a conventional bright field inspection mode can perform neither well nor stably.

The phase controller either adds or subtracts an appropriate amount of phase angle to make the total phase angle difference 0° or ±180° between the defect and its surround. In the simulated defect signals, the phase controller added 144°, 117° and 104° respectively to the innate signals from 40 nm, 20 nm, and 10 nm defects to make the total phase differences 0°. The phase controller also adds −36°, −63° and −76° respectively to the innate defect signals from 40 nm, 20 nm, and 10 nm defects to make the total phase difference −180°.

The legends in the FIGS. 33 through 35b shows the phase angles the phase controller added to the innate phase angle differences. "BF" means no phase angle addition (or subtraction). Therefore, "BF" is equivalent to "HS:0°", the high sensitivity mode with no phase addition to the specular component. Also, notice from the figures' legends that the difference between the two phase angles corresponding to the two extreme defect signals is 180°. "DF" in the Figures' legends represents dark field systems.

Several important facts can be derived from the simulation results. First, the strength of the dark field signal decreases very quickly as the size of the defect becomes smaller than a quarter of the wavelength. The dark field signal could be higher than those shown in the figures if it happens to interfere constructively with the scattered light by the surrounding patterns. That kind of interference is not controllable and relies completely on luck. Therefore, it is generally expected that the dark field defect signal will become too low to be detected reliably for defects whose size is smaller than a quarter of the wavelength. In the near future, a significant portion of critical defects in semiconductor wafers are expected to be much smaller than a quarter of the wavelength. In fact, line widths are expected to approach a quarter wavelength where the wavelength is 193 nm divided by the index of refraction of water at 193 nm. Therefore, the future of current dark field inspection technologies looks poor.

Second, the required phase change on the specular component to make the relative phase between the defect signal and the specular component be 0° or 180° is not necessarily ±90°, even though the defects used in simulations are phase objects. Actually, the amount of phase change required on the specular component for a maximum defect signal depends on the size of the phase object. This is a critical difference between this inspection technology and phase-contrast microscopy where a fixed ±90° phase is added to the specular component for maximum image contrast. Even these simple examples show that continuous variability of the relative phase between the defect signal and the specular component is desirable for reliable defect detection. If the signals from more general defects were simulated, they would show even more clearly the desirability of having continuous variability in the phase controller.

For example, if the signals from pure amplitude defects are simulated, the optimum phase value for the phase controller will be 0° or 180°. These phase values are very different from those shown in the examples of pure phase defects. Actually, the phase controller should be able to provide any phase shift value in order to be able to detect all kinds of defects reliably. Thus, the continuous variability of the phase controller is not just desirable but really necessary if we want to reliably detect defects. The systems and methods disclosed herein employ a phase controller that can vary the relative phase in a substantially continuous manner.

Third, the defect signals are boosted or amplified significantly over the conventional bright field signal by varying the relative phase appropriately. Furthermore, the signal amplification becomes more significant when the defect size gets smaller. Another advantage of operating in a maximum defect signal mode is improved signal stability. This is because the first order signal sensitivity to external perturbation is zero if the signal intensity is an extremum. Thus, the systems and methods disclosed herein can provide much higher defect detection sensitivity along with better stability.

The phase controller can also be used for the deamplification of unwanted defect signals. A good example is wafer pattern noise, which is actually not a noise but a defect signal. In most defect detection situations, it is desirable to suppress wafer pattern noise. If suppression of wafer pattern noise is more important than amplifying the defect signals of interest, the phase controller can be set to minimize the wafer pattern noise rather than maximizing the defect signals of interest.

In all three FIGS. 33, 34 and 35a, the bright field signal is still sizable. However, the important thing is that this is true for the defect type used in the simulation. The bright field signal can be much smaller for some types of real defects. In order to understand this issue, the defect signal can be written more explicitly. The defect signal, s, is the difference between the raw signal from the defect and the specular component. (Refer to equation (3).) Therefore, the defect signal amplitude at the location of the defect becomes $$s = \sqrt{R_d} \exp\left(\frac{i4\pi h}{\lambda}\right) - b \qquad (17)$$
$$= \left(\sqrt{R_d} \cos\left(\frac{4\pi h}{\lambda}\right) - b\right) + i\sqrt{R_d} \sin\left(\frac{4\pi h}{\lambda}\right)$$

where $R_d$ is the reflectivity of the defect
h is the height of the defect
Equation (17) tells us that if $$R_{sur} = b^2 = R_d \cos^2\left(\frac{4\pi h}{\lambda}\right) \qquad (18)$$

where $R_{sur}$ is the reflectivity of the surrounding area
the defect signal is purely imaginary. That is, $\phi_s$ the phase difference between the defect signal and specular component is $$\pm \frac{\pi}{2}.$$

In this case, the interference term shown in equation (2c) becomes zero and does not contribute to the bright field signal. Consequently, the bright field signal is the same as the dark field signal, which is very low for a small defect. This shows that bright field systems can be fatally blind to some types of defects.

Figure 35B:
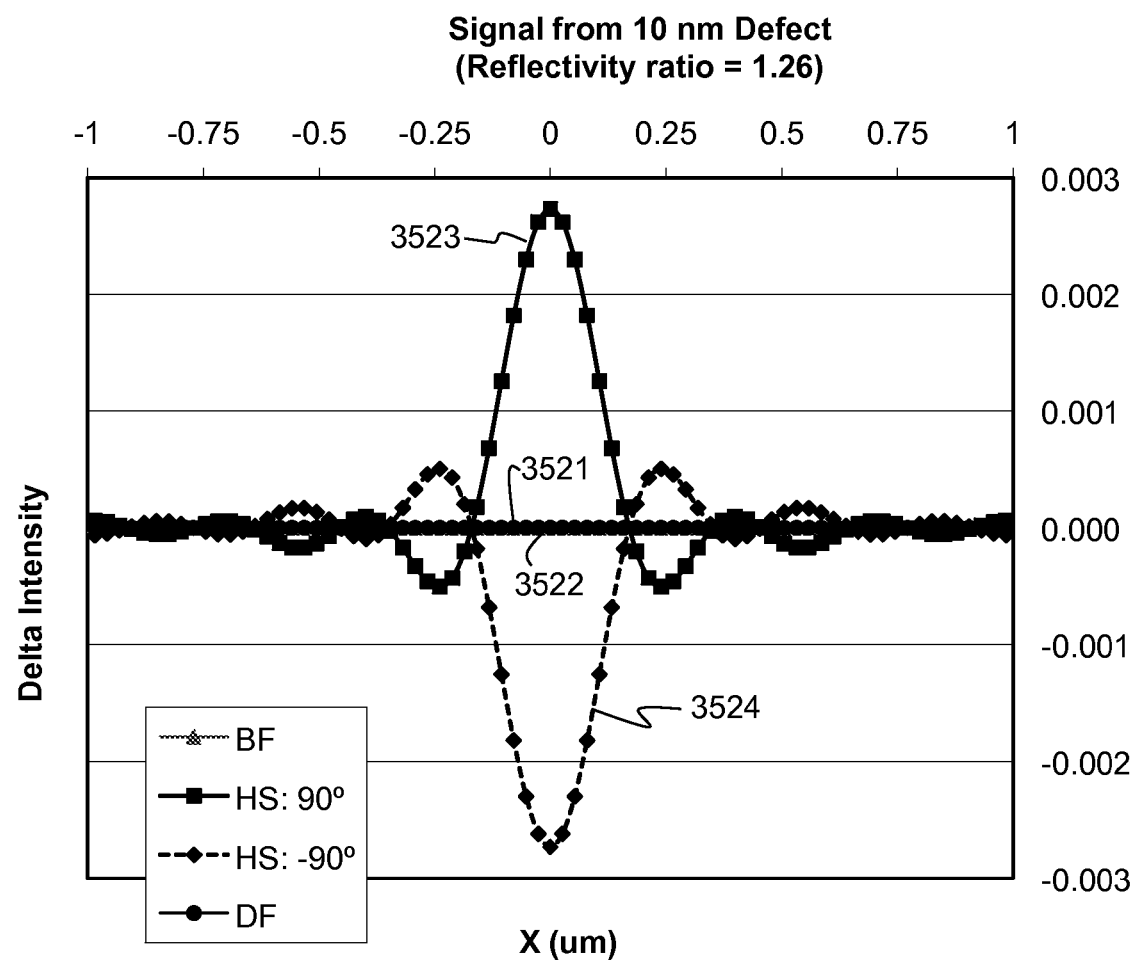

A good example is a small highly reflective particle on the top of a silicon wafer. The reflectivity of the particle can satisfy equation (18) because its reflectivity is higher than that of silicon. If the particle satisfies equation (18) even approximately, the bright field system will have difficulty in finding it. FIG. 35b shows the problem clearly. The defect size is 10 nm, but its reflectivity is 26% higher than the surrounding area to meet equation (18).

Under these conditions, both the bright field, 3521, and dark field signals, 3522, are virtually zero. However, the signal may be completely recovered by controlling the relative phase between the scattered and specular components. A 90° relative shift generates interference signal 3523, and a −90° relative phase shift generates signal 3524. This example demonstrates the power of the interferometric detection systems and methods disclosed herein.

It seems counterintuitive that the bright field systems can be very blind to bright defects. But, actually, there is a reason. This is understood at least qualitatively by thinking of two extreme situations. We know from our intuition that if the reflectivity of the defect is the same or lower than that of the surrounding area, the bright field signal should have a negative sign, i.e., a dip in its raw image, the signal before subtracting the reference. However, we also know from our intuition that if the reflectivity of the defect is much higher than that of the surrounding area, the bright field signal should have a positive sign, i.e., a peak in its raw image. This tells us that the bright field signal must be zero for some intermediate reflectivity of the defect. Therefore, the fatal blindness of the bright field system for some types of defects does exist. If the defect is relatively large, the chance for the defect to satisfy equation (18) is slim.

Consequently, the chance for the bright field system to be blind to some large defects is slim. However, if defects are much smaller than a quarter wavelength, the chance for defects to satisfy equation (18) becomes significant. Defect sizes are shrinking rapidly. Therefore, the bright field system is expected to be incapable of detecting defects reliably for the rapidly shrinking defect sizes associated with future technologies. The systems and methods disclosed herein exploit the relative phase between the defect signal and the specular component. In the above example, if the phase controller changes the phase of the specular component by $$\pm \frac{\pi}{2},$$

the interference term regains its full strength.

In FIG. 33, signal curve 3312 is slightly larger in absolute amplitude than signal curve 3314. This is because the dark field term and the interference term shown in equation (2c) carry the same signs and add constructively for curve 3312. However, for curve 3314, the dark field term and the interference term carry opposite signs and add destructively. Therefore, in this specific example, curve 3312 is a better choice for defect detection than curve 3312. In this specific example, the difference between the two choices is small. However, in cases of real defects, the difference between the two choices can be significant. The high sensitivity mode of operation allows us to choose the optimum signal curve for any specific type of defect.

Due to the diffraction from the sharp edge of the imaging system aperture, the defect signal usually changes signs as the signal measurement point moves toward the peripheral part of the signal as shown in FIG. 33 through FIG. 35b. Therefore, if the signal needs to be integrated spatially to maximize the total signal, it is important to convert all parts of the signal to positive values before the integration. The amount of noise is spatially uniform because the main noise sources are the detector noise and the photon noise from the specular component, both of which are spatially uniform. Therefore, the signal has the highest signal-to-noise ratio at the center or peak of the signal and a lower signal-to-noise ratio in its periphery.

It is beneficial if the signal conversion process puts higher weights towards the high signal-to-noise parts of the signal and puts lower weights toward the lower signal-to-noise parts of the signal. For example, both squaring and taking absolute values of the signal converts all parts of the signal to positive values. However, squaring the signal automatically puts more weight towards the higher quality parts of the signal, whereas taking absolute values of the signal puts equal weighting to all parts of the signal. Therefore, squaring the signal is a better conversion process than taking the absolute values of the signal. However, the former process takes more computing time than the latter process. Therefore, in real systems, if computing resources are limited, some compromise between performance and speed may be necessary.

Contrast Enhancement. As stated previously, a strong specular component means high noiseless amplification of the defect signal. High noiseless amplification of defect signals leads to high defect contrast in the subtracted image. This, in turn, leads to a more sensitive and stable defect detection system. Therefore, a strong specular component is generally preferred. Note that a strong specular component increases the contrast of subtracted images, but decreases the contrast of raw images. The contrast of concern for defect detection is the contrast of the subtracted images, not the raw, images before subtraction. This criterion is quite the opposite of all conventional microscopes including phase-contrast types and their derivatives, which endeavor to increase the contrast of raw images. However, too strong a specular component can saturate the image sensor if its dynamic range is not very large, and consequently result in the distortion of the defect signal in an undesirable way. This leads to a deficient number of gray levels to the signal. Therefore, when the dynamic range of the image sensor is saturated, the contrast of the raw sample image may need to be increased, and the specular component decreased, in order to avoid the distortion of the defect signal.

If the defect or wafer pattern is much smaller than the wavelength, significant attenuation of the specular component may be useful in order to get a suitably high image contrast. Numerical simulations have confirmed the effectiveness of this method of contrast enhancement.

Figure 36:
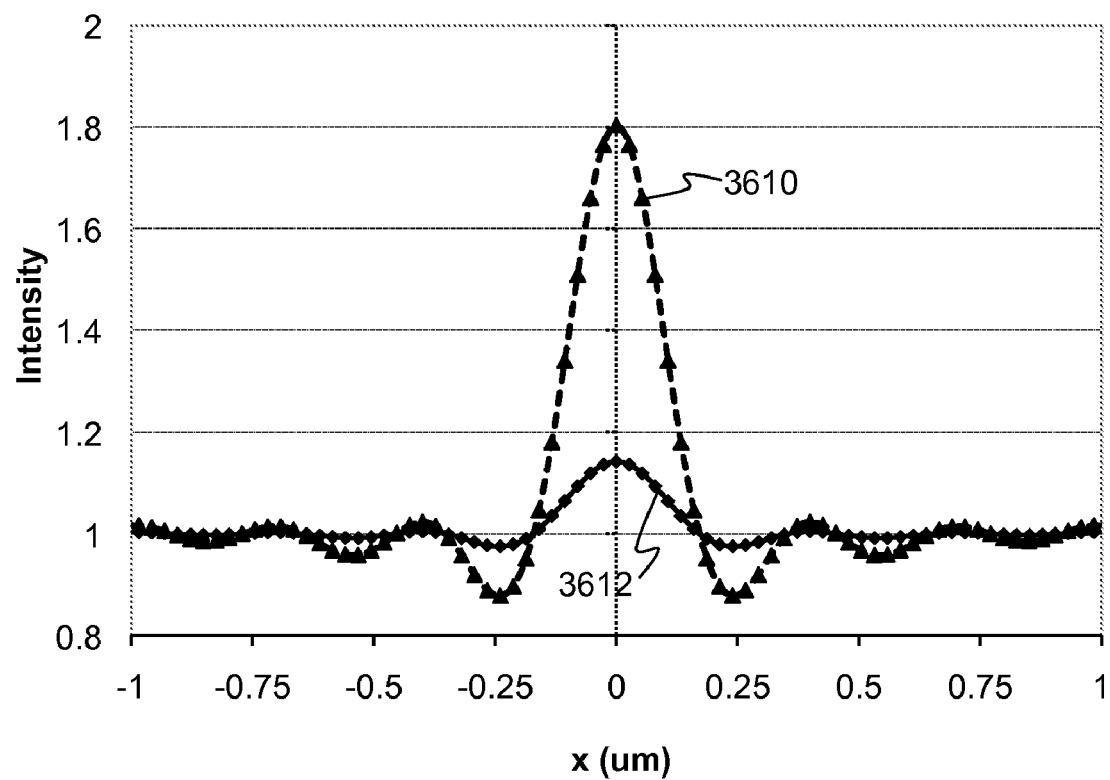
FIG. 36 shows plots of simulated enhanced contrast of an image of a 40 nm defect by attenuating the intensity of the specular component by 96%.

FIG. 36 shows an image of a 40 nm defect that was given enhanced contrast by attenuating the intensity of the specular component by 96%. Curve 3610 shows the results after attenuating the specular component, while curve 3612 shows the results before attenuating the specular component.

Figure 37:
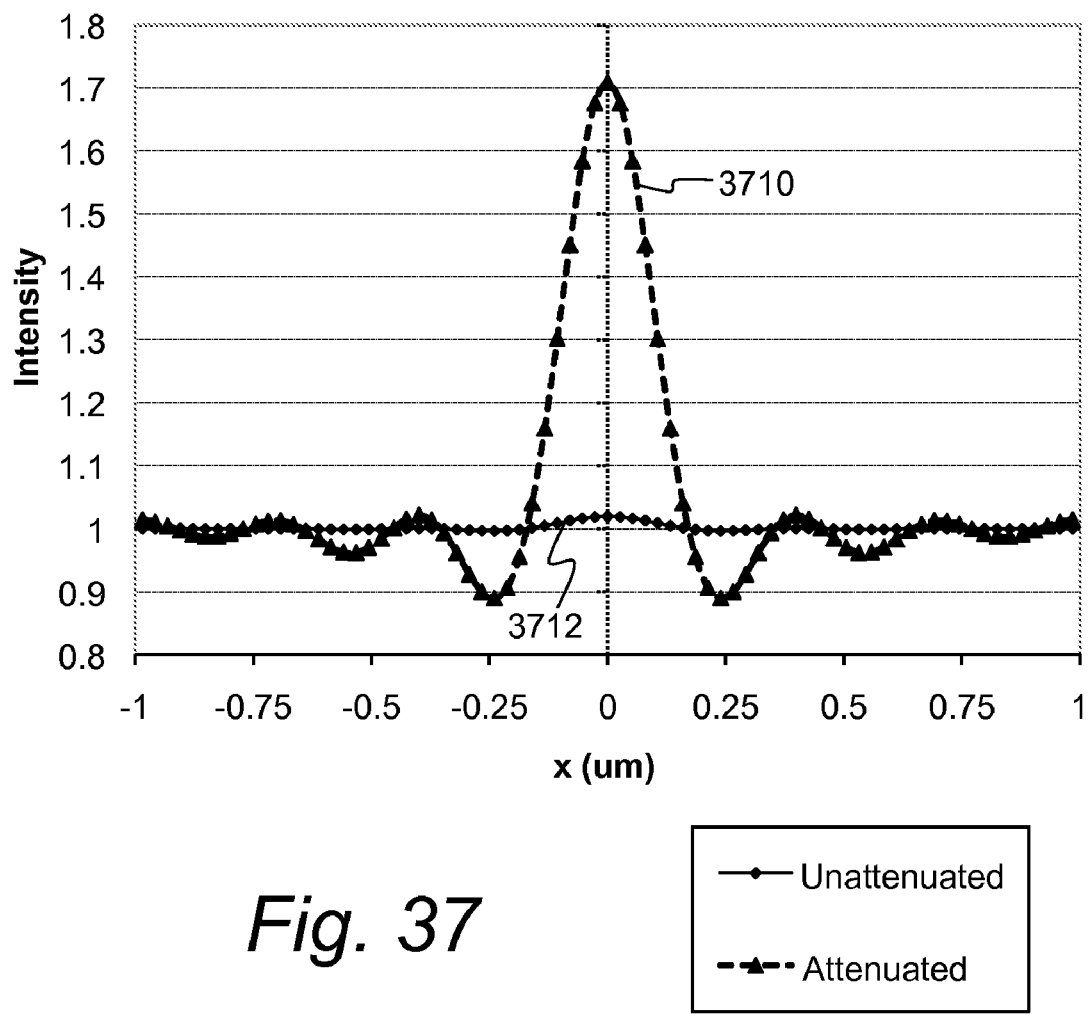
FIG. 37 shows plots of simulated enhanced contrast of an image of a 20 nm defect by attenuating the intensity of the specular component by 99.9%.

FIG. 37 shows an enhanced contrast of the image of 20 nm defect achieved by attenuating the intensity of the specular component by 99.9%. Curve 3710 shows the results after attenuating the specular component, while curve 3712 shows the results before attenuation. Note that the amounts of attenuation used in the simulations are excessive. They are neither recommended nor practical in many cases, but were used to demonstrate the capability of the technique for contrast enhancement.

As expected, smaller defects require stronger attenuation of the specular component to achieve the same image contrast. The size of the defects and circuit patterns on the wafer will continue to be decreased relentlessly and achieving high dynamic range in image sensors can be difficult and costly. Therefore, a strong attenuation of the specular component may be needed to cope with smaller defects in the future. This is why in many embodiments an attenuator is placed in the path of the specular component.

One of the drawbacks of this kind of contrast enhancement technique is the large loss of light energy. In order to compensate for the energy loss due to the attenuation of the specular component, more light can be supplied to the illumination path or the detector signal can be integrated for a longer period of time. In many applications, neither of these options is desirable because an intense illumination beam can damage samples and a longer detector integration time will reduce throughput. Therefore, contrast enhancement must be used with care with these and other undesirable side effects in mind Note that illuminating a larger area on the sample and employing a proportionally larger detector array can reduce the possibility of sample damage by intense illumination light while preserving throughput, but this usually requires a more expensive instrument design.

Fortunately, even though the specular component was attenuated severely in the simulations to show the contrast enhancement clearly, most actual cases do not require that much contrast enhancement thanks to a large dynamic range of the image sensors used in current defect detection systems. Moderate contrast enhancement is not only very acceptable with current practice but also preferred considering the current need for signal amplification, the efficiency of light energy use and system throughput.

An important conclusion can be derived from the shape of the defect images 3610 in FIGS. 36 and 3710 in FIG. 37. The shape of the defect images indicates that the interference term is dominant even with a large amount of attenuation of the specular component. Even if the attenuation is 99.9%, the interference term is still dominant. The interference term is formed by the noiseless amplification of the signal by the specular component and a low reflectivity of the sample has nearly the same effect as a high attenuation of the specular component. Therefore, the dominance of the interference term even with a very high attenuation of the specular component can be interpreted to mean that the noiseless signal amplification by the specular component works very effectively, even with samples of extremely low reflectivity. This means that all the systems and methods disclosed herein which depend on the noiseless signal amplification by the specular component work well with virtually any kind of sample. Actually, the smaller the defect, the more effective the noiseless amplification of the defect signal by the specular component. More accurate supporting examples will be shown in a later section on "The Limitations of Dark Field Mode."

Selection of Polarization. As mentioned previously, in most cases, the signal-to-noise ratio of the defect signal depends on the polarization states of the illumination light and the collected light. Therefore, it is important to select correct polarizations for the defects of interest. The selection of correct polarizations can be done with intuition, theoretical modeling, numerical simulations or experimentation. However, it is usually impractical to test all the different polarization combinations because of their large number. As long as the defect and its neighboring patterns do not have helical structures, the polarization choices can be limited to combinations of linear polarizations.

2. Catch-all Mode. Defects can alter not only the amplitude but also the phase of the scattered light. Different kinds of defects affect both the amplitude and the phase of the scattered light differently. Therefore, if both the amplitude and phase of the scattered light are measured, not only can more defects be caught but also more information about the defects can be obtained. The catch-all mode is based on the determination of both the amplitude and the phase of the defect signal. Because the defect signal is completely determined by its amplitude and the phase, if the noise is low enough, the catch-all mode can, in principle, catch virtually all the different kinds of defects in one run.

Defects can be classified much more accurately if both their amplitude and the phase information is available. For example, the size of the defect can be estimated from the amplitude information and from the phase information it can be determined if the defect is a particle type or void type, or mesa type or valley type. An example will be given in the section "Three Scan Method."

If other data such as the sample substrate and pattern materials, and the surrounding patterns geometries, etc, are additionally used, an even more accurate defect classification may be possible.

A more accurate defect classification is a huge time saver in the defect review process, which is usually very costly. The defect review usually requires the use of expensive but slow electron microscopes. In addition, the information collected in the catch-all mode of operation can be very useful for the proper setup of other modes of operation. The utilization of the catch-all mode for the proper setup of other operation modes will not only cut down the setup time but also make a fast automatic setup possible.

The catch-all mode can also be used for the setup of the catch-all mode itself. For example, the catch-all mode can be operated multiple times with different numbers of sample scans, each corresponding to a different phase shift, and also with different polarizations. Then, the results can be compared with each other to determine the optimum number of sample scans and the best polarization settings for the optimum use of the catch-all mode itself. Thus, the catch-all mode is a powerful mode. A single run of the catch-all mode requires multiple scans of the sample. However, its throughput is not expected to be much lower compared with other modes because it can catch all different kinds of defects with a single run and there is no need for sample loading/unloading between multiple scans. Also, the throughput reduction will be handsomely compensated by the throughput increase in the defect review process. Therefore, the catch-all-mode is expected to be a popular mode of operation even with its lower throughput.

Three Scan Method. Equation (2c) shows that the interference term contains the amplitude and cosine of the relative phase of the defect signal. In order to determine the amplitude and relative phase of the defect signal completely, at least three scans of the sample need be used. Two scans are not enough because there is another unknown, the whole dark field term. The phase of the specular component needs to be set differently for each scan. This can be achieved by calibrating the phase controller. A calibration method for the phase controller is described in a previous section.

The initial phase value of the specular component is not important, so any phase setting of the specular component can be used. For example, if the phase value of the specular component for the first scan of sample is $\phi_b$ and the phase changes are $\theta_1$ and $\theta_2$ for second and third scan, then, the complex amplitudes of the specular component for the first, second and third scans are expressed as follows:

$$b_0 \equiv b = |b|\exp(i\phi_b) \tag{19}$$

$$b_1 \equiv |b|\exp(i(\phi_b+\theta_1)) \tag{20}$$

$$b_2 \equiv |b|\exp(i(\phi_b+\theta_2)) \tag{21}$$

Then, the image intensities for the three sample scans are expressed as follows:

$$I_0 \equiv |b_0 + a + s|^2 + |q_a + q_s|^2 + |g|^2 \tag{22}$$

$$= |b|^2 + |a+s|^2 + |q_a+q_s|^2 + |g|^2 + 2|b|(a_x+s_x) \tag{22a}$$

$$I_1 \equiv |b_1 + a + s|^2 + |q_a + q_s|^2 + |g|^2 \tag{23}$$

$$= |b|^2 + |a+s|^2 + |q_a+q_s|^2 + |g|^2 + 2|b|((a_x+s_x)\cos(\theta_1) + \tag{23a}$$
$$(a_y+s_y)\sin(\theta_1))$$

$$I_2 \equiv |b_2 + a + s|^2 + |q_a + q_s|^2 + |g|^2 \tag{24}$$

$$= |b|^2 + |a+s|^2 + |q_a+q_s|^2 + |g|^2 + 2|b|((a_x+s_x)\cos(\theta_2) + \tag{24a}$$
$$(a_y+s_y)\sin(\theta_2))$$

Then, the die-to-die (or cell-to-cell) subtracted intensities are:

$$\Delta I_0 \equiv I_0 - I_0(s = q_s = 0) \quad (25)$$
$$= |a+s|^2 - |a|^2 + |q_a + q_s|^2 - |q_a|^2 + 2|b|s_x$$

$$\Delta I_1 \equiv I_1 - I_1(s = q_s = 0) \quad (26)$$
$$= |a+s|^2 - |a|^2 + |q_a + q_s|^2 - |q_a|^2 + 2|b|(s_x\cos(\theta_1) + s_y\sin(\theta_1))$$

$$\Delta I_2 \equiv I_2 - I_2(s = q_s = 0) \quad (27)$$
$$= |a+s|^2 - |a|^2 + |q_a + q_s|^2 - |q_a|^2 + 2|b|(s_x\cos(\theta_2) + s_y\sin(\theta_2))$$

These die-to-die subtracted intensities contain the needed amplitude and phase information of the defect signal. Therefore, these die-to-die subtracted intensities need to be stored for the whole wafer. This seems to require an unrealistic amount of memory space. But, in reality, it does not require much memory space because the data are non-zero only in areas around defects, which are extremely sparse in reality. Only data of non-zero or larger values than the predetermined threshold value need to be stored. Data of zero or values smaller than the threshold value do not need to be stored.

If $\theta_1$ and $\theta_2$ are not zero and $\theta_1 \neq \theta_2$, then we can determine the complex amplitude (or equivalently the amplitude and phase) of the defect signal from equations (25), (26) and (27). The real and imaginary parts of the complex amplitude of the amplified defect signal are:

$$2|b|s_x = \frac{\Delta I_1 \sin(\theta_2) - \Delta I_2 \sin(\theta_1) - \Delta I_0(\sin(\theta_2) - \sin(\theta_1))}{\sin(\theta_2 - \theta_1) - (\sin(\theta_2) - \sin(\theta_1))} \quad (28)$$

$$2|b|s_y = \frac{1}{\sin(\theta_2 - \theta_1)} \quad (29)$$
$$\left\{\begin{array}{l} -\left[\cos(\theta_2) + \frac{\sin(\theta_2)(\cos(\theta_2) - \cos(\theta_1))}{\sin(\theta_2 - \theta_1) - (\sin(\theta_2) - \sin(\theta_1))}\right]\Delta I_1 + \\ \left[\cos(\theta_1) + \frac{\sin(\theta_1)(\cos(\theta_2) - \cos(\theta_1))}{\sin(\theta_2 - \theta_1) - (\sin(\theta_2) - \sin(\theta_1))}\right]\Delta I_2 + \\ (\cos(\theta_2) - \cos(\theta_1))\left[1 + \frac{(\sin(\theta_2) - \sin(\theta_1))}{\sin(\theta_2 - \theta_1) - (\sin(\theta_2) - \sin(\theta_1))}\right]\Delta I_0 \end{array}\right\}$$

We can also see that the whole dark field term is expressed as follows.

$$D = \frac{\Delta I_0 \sin(\theta_2 - \theta_1) - \Delta I_1 \sin(\theta_2) + \Delta I_2 \sin(\theta_1)}{\sin(\theta_2 - \theta_1) - (\sin(\theta_2) - \sin(\theta_1))} \quad (30)$$

where $D \equiv |a+s|^2 - |a|^2 + |q_a + q_s|^2 - |q_a|^2$ :dark field term $\quad (31)$ If $\theta_1 = -\theta_2 = \theta \neq 0$, then, equations (28), (29), and (30) reduce to the following equations:

$$2|b|s_x = \frac{(2\Delta I_0 - \Delta I_1 - \Delta I_2)\sin(\theta)}{2\sin(\theta) - \sin(2\theta)} \quad (32)$$

$$2|b|s_y = \frac{(\Delta I_1 - \Delta I_2)\cos\theta}{\sin(2\theta)} \quad (33)$$

$$D = \frac{(\Delta I_1 + \Delta I_2)\sin(\theta) - \Delta I_0 \sin(2\theta)}{2\sin(\theta) - \sin(2\theta)} \quad (34)$$

There are several good choices for $\theta_1$ and $\theta_2$ values. But, the best choice will be $$\theta_1 = -\theta_2 = \frac{2\pi}{3}$$

because of the resulting simplicity of signal intensity equation as shown by equation (38). Other choices like $$\theta_1 = -\theta_2 = \frac{\pi}{3} \text{ or } \theta_1 = \frac{\pi}{3}, \theta_2 = \frac{2\pi}{3}$$

will work as well, but the expression of signal intensity will not be as simple and symmetric as equation (38). If $$\theta_1 = -\theta_2 = \frac{2\pi}{3},$$

then, equations (32), (33) and (34) further reduce to the following equations:

$$2|b|s_x = \frac{2\Delta I_0 - \Delta I_1 - \Delta I_2}{3} \quad (35)$$

$$2|b|s_y = \frac{\Delta I_1 - \Delta I_2}{\sqrt{3}} \quad (36)$$

$$D = \frac{\Delta I_0 + \Delta I_1 + \Delta I_2}{3} \quad (37)$$

The amplified defect signal intensity, $I_s$, for this case has the following simple expression:

$$I_s^2 \equiv (2|b|s_x)^2 + (2|b|s_y)^2 \quad (38)$$
$$= \frac{4}{9}(\Delta I_0^2 + \Delta I_1^2 + \Delta I_2^2 - \Delta I_0 \Delta I_1 - \Delta I_1 \Delta I_2 - \Delta I_2 \Delta I_0)$$
$$= \frac{2}{9}[(\Delta I_0 - \Delta I_1)^2 + (\Delta I_1 - \Delta I_2)^2 + (\Delta I_2 - \Delta I_0)^2]$$

$I_s$ is a raw signal intensity. Its magnitude depends not only on the intensity of illumination light but also on the intensity of the specular component. Therefore, in order to make the defect signal more consistent, $I_s$ should be normalized against the intensities of the illumination light beam and the specular component.

The illumination can be made relatively uniform across the field but the intensity of the specular component can vary significantly over the whole field. An exact measurement of the intensity variation of the specular component is difficult. Fortunately, exact values of the local intensity of the specular component are not needed. Approximate values are fine for normalization purpose. Local intensity values of the specular component can be approximated by the local average of the total light intensity in most cases. Therefore, the raw amplified defect signal intensity, $I_s$ can be properly normalized as follows.

$$I_s'^2 \approx \frac{2}{9} \frac{[(\Delta I_0 - \Delta I_1)^2 + (\Delta I_1 - \Delta I_2)^2 + (\Delta I_2 - \Delta I_0)^2]}{I_{ill} \cdot I_{local}} \quad (39)$$

where $I_{ill}$ is the intensity of illumination at sample plane.

$I_{local}$ is the local average of total light intensity at image plane $I'_s$ is the normalized intensity of the amplified defect signal. $I_{ill}$ normalizes $|s|^2$ and $I_{local}$ normalizes $|b|^2$. Defects are usually detected by comparing the peak value of $I'_s$ with a preset value called threshold. More elaborate defect detection algorithms can also be used to improve the overall performance.

For example, $I'^2_s$ can be spatially integrated and the integrated value, rather than the peak value, can be compared with a predefined threshold value. Also, a numerical deconvolution of the defect image with the finite width of detector element can also be applied along with other methods. A fast numerical deconvolution method will be described in the section "Spatial Frequency Bandwidth." The normalized intensity of the amplified defect signal not only reveals the existence of a defect but also provides crucial information about the size of the defect.

The optical signal does not directly provide the physical size information of defects. Rather, it provides only the 'optical size' of defects directly. The relationship between the physical size and the optical size can be complicated. Therefore, it is hard to estimate the physical size of the defect accurately from the optical signal alone. However, we can establish a general relationship between the physical and optical sizes of defects through experiments or simulations. Then, the physical size of defects can be approximately estimated from the general relationship. If other data such as defect composition data, reticle pattern data, etc, are additionally used, more accurate characterization of defects will be possible.

The phase of the defect signal $\phi_s$, relative to the specular component, becomes:

$$\varphi_s = \tan^{-1}\left(\frac{s_y}{s_x}\right) = \tan^{-1}\left(\frac{\sqrt{3}(\Delta I_1 - \Delta I_2)}{2\Delta I_0 - \Delta I_1 - \Delta I_2}\right) \quad (40)$$

A more meaningful phase value is the difference between $\phi_s$ and the reference phase value which is discussed in the "Phase Controller" section. Therefore, if the value of the reference phase is not zero, we should subtract the reference phase value from $\phi_s$. The phase information provides additional critical information for a more accurate defect classification. For example, phase information determines immediately if the defect is a particle, void, mesa, or a valley type. An accurate and reliable defect classification is just as important as reliable defect detection. Existing technologies rely on partial amplitude information only for defect classification, and this results in very unreliable defect classification. The systems and methods disclosed herein allow using both amplitude and phase information for defect classification. The use of both quantities allows a much more accurate and reliable defect classification.

If additional information such as defect composition data, reticle pattern data, etc, are also used, an even more accurate defect classification will be possible. More accurate and reliable defect classification capability is one of the important features of the systems and methods disclosed herein. Defect phase information can also be used to set the phase controller properly for the high sensitivity mode of operation.

The defects of no interest such as wafer pattern noise, false defects, etc. are actually real defects. The catch-all mode can also be used very effectively to study or characterize these kinds of defects, so they can be discriminated against most effectively.

Figure 38:
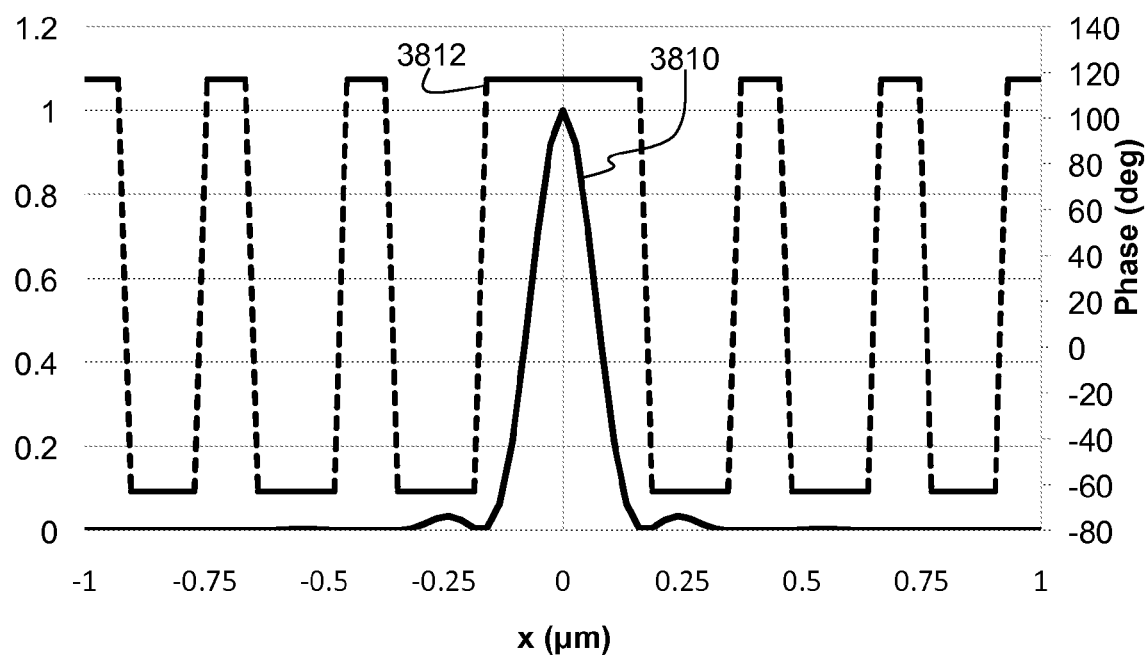
FIG. 38 shows plots of simulated signal intensity and the phase of 20 nm defect as an example.

FIG. 38 shows plots of the signal intensity and the phase of a 20 nm defect as an example. Curve 3810 is the signal intensity and curve 3812 is the corresponding phase. For the detection of this defect, only the peak value of the signal intensity is usually needed.

Equation (37) can be normalized with illumination intensity and used to evaluate the strength of the dark field signal and this will determine if the dark field mode of operation can be used to reliably find defects.

Equations (35) through (39) can be especially useful in real systems because it does not take much computing time to calculate them and they are the least sensitive to random noise thanks to an equal division of the phase angle. By choosing $$\theta_1 = -\theta_2 = \frac{2\pi}{3}$$

and by using those equations, the three scan method can determine the complex amplitude of the defect signal completely in a very effective manner.

The equations allow pixel-by-pixel parallel computing. Therefore, real time computing can be realized without difficulty by employing massively parallel computing technology. For example, with current technology, a powerful, massively parallel computer can be constructed inexpensively by using a large number of graphics processing units (GPU) and the supporting chip sets.

The amplified defect signal intensity, equation (38) or (39), is the intensity of the whole, not just the real part, of the defect signal and, therefore, a true indicator of the existence of the defect. By comparing it with a predefined threshold, we can tell if the defect is sufficiently large to be of concern. If the defect is of concern, we can characterize it by calculating the complex amplitude of its signal using equations (35) and (36). This gives some crucial information about what kind of defect it is.

Figure 39:
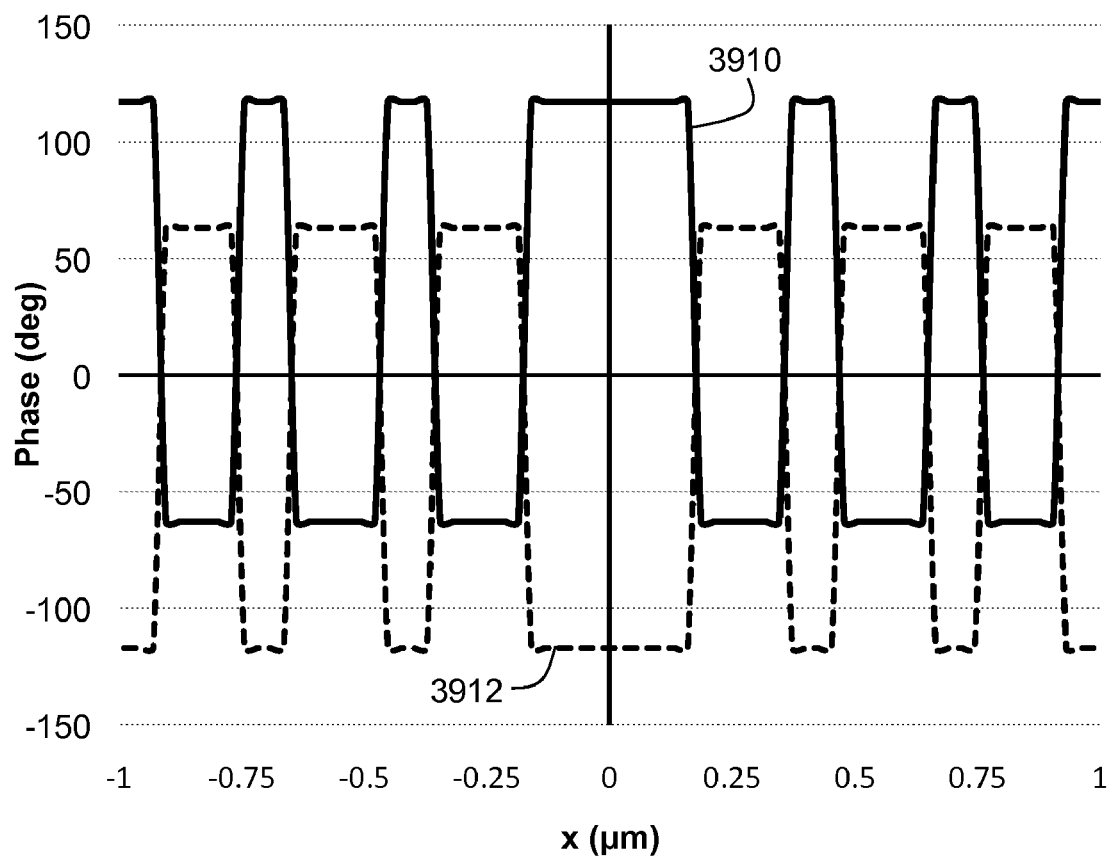
FIG. 39 shows plots of simulated phases of defect signals from 20 nm particle and 20 nm void.

For example, FIG. 39 shows plots of the phases of defect signals from a 20 nm particle and a 20 nm void. Curve 3910 shows the phases of the 20 nm void, and curve 3912 shows the phase of the 20 nm particle. From FIG. 39, it can be seen that the particle and voids give phase angles of opposite sign to the complex amplitudes of the defect signal. Therefore, even if the amplitudes of the defect signals are the same, we can tell which ones are particle type defects and which ones are void type defects.

If the defect size is comparable to or larger than the resolution of the collection optics and noise is also low, we can even deconvolve the complex amplitude of the defect signal with the complex amplitude of the point spread function of the imaging optics to get a more detailed picture of the defect. This capability will help defect classification become much more accurate. More accurate defect classification leads to significant time saving in the defect review process which is usually a very costly and slow because defect review usually requires the use of expensive but slow electron microscopes. Therefore, the throughput reduction due to multiple sample scans will be handsomely compensated by the throughput increase in the defect review process.

Another important fact is that the strength of the amplified defect signal intensity, equation (38) or (39), does not depend on the phase value of the defect signal. This means that the catch-all mode can potentially catch any kind of defects surrounded by any kind of pattern. This is why the catch-all mode is such a powerful mode. Conventional technologies cannot support the catch-all mode because they cannot measure both the real and imaginary parts of the complex amplitude of the defect signal. They can only measure the real part. In this case, the signal intensity critically depends on the relative phase value between the defect signal and its surrounding pattern. Consequently, conventional technologies cannot find all of the different kinds of defects. Rather, conventional technologies are likely to miss a significant number defects.

Two Scan Method. As stated previously, in general, it takes at least three sample scans in order to determine the complex amplitude of the defect signal completely. However, if the dark field part of the whole signal is negligible compared with the interference part, then two sample scans suffice to determine the complex amplitude of the defect signal. This can be seen from equations (25) and (26). If we ignore the dark field part in the equations and set $$\theta_1 = \pm \frac{\pi}{2},$$

then, those equations give $$2|b|s_x \approx \Delta I_0 \quad (41)$$

$$2|b|s_y \approx \pm \Delta I_1 \quad (42)$$

The amplified defect signal intensity, $I_s$, becomes $$I_s^2 \equiv (2|b|s_x)^2 + (2|b|s_y)^2 \quad (43)$$
$$\approx \Delta I_0^2 + \Delta I_1^2$$

The normalized amplified defect signal intensity, $I_s'$ becomes $$I_s'^2 \approx \frac{\Delta I_0^2 + \Delta I_1^2}{I_m \cdot I_{local}} \quad (44)$$

If the image sensor has a large dynamic range, then we can boost the interference part of the whole signal by a large amount. In this case, the dark field part of the whole signal can be so small that we may be able to use the two scan method to speed up the catch-all mode of the operation.

Four Scan Method. A simple choice for the four phase values of the specular component is 0, π, $$\frac{\pi}{2} \text{ and } -\frac{\pi}{2}.$$

If we scan the sample four times with 0, π, $$\frac{\pi}{2} \text{ and } -\frac{\pi}{2}$$

phase changes of the specular component per scan, then:

$$b_0 \equiv b = |b|\exp(i\varphi_b) \quad (45)$$

$$b_1 \equiv |b|\exp(i(\varphi_b + \pi)) \quad (46)$$

-continued $$b_2 \equiv |b|\exp\left(i\left(\varphi_b + \frac{\pi}{2}\right)\right) \quad (47)$$

$$b_3 \equiv |b|\exp\left(i\left(\varphi_b + \frac{\pi}{2}\right)\right) \quad (48)$$

Die-to-die subtracted intensities become:

$$\Delta I_0 \equiv I_0 - I_0(s = q_s = 0) \quad (49)$$
$$= |a + s|^2 - |a|^2 + |q_a + q_a|^2 - |q_a|^2 + 2|b|s_x$$

$$\Delta I_1 \equiv I_1 - I_1(s = q_s = 0) \quad (50)$$
$$= |a + s|^2 - |a|^2 + |q_a + q_a|^2 - |q_a|^2 - 2|b|s_x$$

$$\Delta I_2 \equiv I_2 - I_2(s = q_s = 0) \quad (51)$$
$$= |a + s|^2 - |a|^2 + |q_a + q_a|^2 - |q_a|^2 + 2|b|s_y$$

$$\Delta I_3 \equiv I_3 - I_3(s = q_s = 0) \quad (52)$$
$$= |a + s|^2 - |a|^2 + |q_a + q_a|^2 - |q_a|^2 - 2|b|s_y$$

The real and imaginary parts of the complex amplitude of the amplified defect signal become:

$$2|b|s_x = \frac{\Delta I_0 - \Delta I_1}{2} \quad (53)$$

$$2|b|s_y = \frac{\Delta I_2 - \Delta I_3}{2} \quad (54)$$

$$D = \frac{\Delta I_0 + \Delta I_1}{2} = \frac{\Delta I_2 + \Delta I_3}{2} = \frac{\Delta I_0 + \Delta I_1 + \Delta I_2 + \Delta I_3}{4} \quad (55)$$

The amplified defect signal intensity, $I_s$, for this case has the following simple expression:

$$I_s^2 \equiv (2|b|s_x)^2 + (2|b|s_y)^2 \quad (56)$$
$$= \frac{1}{4}[(\Delta I_0 - \Delta I_1)^2 + (\Delta I_2 - \Delta I_3)^2]$$

The normalized amplified defect signal intensity becomes:

$$I_s'^2 \approx \frac{1}{4} \frac{[(\Delta I_0 - \Delta I_1)^2 + (\Delta I_2 - \Delta I_3)^2]}{I_{ill} \cdot I_{local}} \quad (57)$$

The phase of the defect signal relative to the specular component, $\phi_s$, becomes $$\varphi_s = \tan^{-1}\left(\frac{s_y}{s_x}\right) = \tan^{-1}\left(\frac{\Delta I_2 - \Delta I_3}{\Delta I_0 - \Delta I_1}\right) \quad (58)$$

This four scan method provides simpler equations. However, its main drawback is that the relative phase angle between defect signal and specular component can be as large as 45°. Notice that the maximum relative phase angle for the three scan method is 30°. This fact can make this four scan method less sensitive to some defects than the three scan method. In order to achieve better sensitivity than the three scan method, different phase values than {0, π, $\frac{\pi}{2}$ and $-\frac{\pi}{2}\}$ can be chosen. Possible different choices are $\{0,$ $\frac{\pi}{4}, \frac{\pi}{2}$ and $\frac{3\pi}{4}\}, \{\pm\frac{\pi}{8}, \pm\frac{3\pi}{8}\},$ etc. However, these other choices involve the use of a regression method to determine the defect signal and make the analytical expression of defect signal more complicated. (See next subsection for a general expression of defect signal.) Another drawback of the four scan method is reduced throughput compared with the three scan method thanks to the extra sample scan needed.

Higher Scan Methods. More independent image data leads to a better signal-to-noise ratio. Therefore, to increase the signal-to-noise ratio, sample can be scanned more than four times with a different phase setting of the specular component for each scan. In this case, the amount of data is more than that needed to determine uniquely the complex amplitude of the defect signal. Therefore, a regression method should be adopted to determine the defect signal. There are many different regression methods available with known pros and cons. One of the most popular methods is the least-square regression. It is the preferred choice if the noise is random and it also allows an analytical approach for the current case. Analytical regression is important because it can save a lot of computation time. Other regression methods can be more suitable if noise is not random but they usually do not allow analytical approaches. Therefore, the least-square regression is presented here.

Let us assume that sample is scanned N times with a different phase setting for each scan, then, $\Delta I_n^{(0)}$, the theoretical die-to-die subtracted image intensity for the nth scan, is expressed as follows:

$$\Delta I_n^{(0)} = D + 2|b|(s_x \cos(\theta_n) + s_y \sin(\theta_n)) \quad (59)$$

where $D \equiv |a+s|^2 - |a|^2 + |q_a + q_a|^2 - |q_a|^2$ :dark field term (60)

The error function is defined as follows in a least-square regression.

$$E = \sum_{n=0}^{N-1} (\Delta I_n - \Delta I_n^{(0)})^2 \quad (61)$$

where $\Delta I_n$ is the actual die-to-die subtracted image intensity for nth scan and $\Delta I_n^{(0)}$ is the theoretical die-to-die subtracted image intensity for nth scan We have to find D, $s_x$ and $s_y$ values that minimize the error function. The slopes of error function with respect to D, $s_x$ and $s_y$ become zero at its minimum. Therefore, the solution satisfies following three equations:

$$\frac{-1}{2}\frac{\partial E}{\partial D} = \sum_{n=0}^{N-1} (\Delta I_n - \Delta I_n^{(0)}) = 0 \quad (62)$$

$$= \sum_{n=0}^{N-1} \Delta I_n - \sum_{n=0}^{N-1} [D + 2|b|(s_x \cos(\theta_n) + s_y \sin(\theta_n))]$$

$$= \sum_{n=0}^{N-1} \Delta I_n - ND - 2|b|\sum_{n=0}^{N-1} (s_x \cos(\theta_n) + s_y \sin(\theta_n))$$

$$\frac{-1}{4|b|}\frac{\partial E}{\partial s_x} = \sum_{n=0}^{N-1} \cos(\theta_n)(\Delta I_n - \Delta I_n^{(0)}) = 0 \quad (63)$$

$$= \sum_{n=0}^{N-1} \Delta I_n \cos(\theta_n) - \sum_{n=0}^{N-1} [D\cos(\theta_n) + 2|b|(s_x \cos^2(\theta_n) + s_y \sin(\theta_n)\cos(\theta_n))]$$

$$= \sum_{n=0}^{N-1} \Delta I_n \cos(\theta_n) - D\sum_{n=0}^{N-1} \cos(\theta_n) - |b|s_x\left[N + \sum_{n=0}^{N-1} \cos(2\theta_n)\right] - |b|s_y \sum_{n=0}^{N-1} \sin(2\theta_n)$$

$$\frac{-1}{4|b|}\frac{\partial E}{\partial s_y} = \sum_{n=0}^{N-1} \sin(\theta_n)(\Delta I_n - \Delta I_n^{(0)}) = 0 \quad (64)$$

$$= \sum_{n=0}^{N-1} \Delta I_n \sin(\theta_n) - \sum_{n=0}^{N-1} [D\sin(\theta_n) + 2|b|(s_x \sin(\theta_n)\cos(\theta_n) + s_y \sin^2(\theta_n))]$$

$$= \sum_{n=0}^{N-1} \Delta I_n \sin(\theta_n) - D\sum_{n=0}^{N-1} \sin(\theta_n) - |b|s_x \sum_{n=0}^{N-1} \sin(2\theta_n) - |b|s_y\left[N - \sum_{n=0}^{N-1} \cos(2\theta_n)\right]$$

Then, from equation (62):

$$D = \frac{1}{N}\sum_{n=0}^{N-1} \Delta I_n - \frac{2|b|}{N}\sum_{n=0}^{N-1} (s_x \cos(\theta_n) + s_y \sin(\theta_n)) \quad (65)$$

By substituting equation (65) into equations (63) and (64):

$$\frac{-1}{4|b|}\frac{\partial E}{\partial s_x} = A - B|b|s_x - C|b|s_y = 0 \quad (66)$$

$$\frac{-1}{4|b|}\frac{\partial E}{\partial s_y} = A' - C|b|s_x - B'|b|s_y = 0 \quad (67)$$

-continued $$\text{where } A \equiv \sum_{n=0}^{N-1} \Delta I_n \cos(\theta_n) - \frac{1}{N}\left(\sum_{n=0}^{N-1} \Delta I_n\right)\left(\sum_{n=0}^{N-1} \cos(\theta_n)\right) \quad (68)$$

$$B \equiv N + \sum_{n=0}^{N-1} \cos(2\theta_n) - \frac{2}{N}\left(\sum_{n=0}^{N-1} \cos(\theta_n)\right)^2 \quad (69)$$

$$C \equiv \sum_{n=0}^{N-1} \sin(2\theta_n) - \frac{2}{N}\left(\sum_{n=0}^{N-1} \cos(\theta_n)\right)\left(\sum_{n=0}^{N-1} \sin(\theta_n)\right) \quad (70)$$

$$A' \equiv \sum_{n=0}^{N-1} \Delta I_n \sin(\theta_n) - \frac{1}{N}\left(\sum_{n=0}^{N-1} \Delta I_n\right)\left(\sum_{n=0}^{N-1} \sin(\theta_n)\right) \quad (71)$$

$$B' \equiv N - \sum_{n=0}^{N-1} \cos(2\theta_n) - \frac{2}{N}\left(\sum_{n=0}^{N-1} \sin(\theta_n)\right)^2 \quad (72)$$

From equations (66) and (67):

$$|b|s_x = \frac{AB' - A'C}{BB' - C^2} \quad (73)$$

$$|b|s_y = \frac{A'B - AC}{BB' - C^2} \quad (74)$$

Equations (73) and (74) are the general best solutions for the complex amplitude of amplified defect signal. By substituting equations (73) and (74) into equation (65), $$D = \frac{1}{N}\sum_{n=0}^{N-1} \Delta I_n - \frac{2}{N}\left[\left(\frac{AB' - A'C}{BB' - C^2}\right)\left(\sum_{n=0}^{N-1} \cos(\theta_n)\right) + \left(\frac{A'B - AC}{BB' - C^2}\right)\left(\sum_{n=0}^{N-1} \sin(\theta_n)\right)\right] \quad (75)$$

The signal intensity and phase can be computed quickly and be used for defect detection and classification in the manner described previously. Equation (75) can be normalized with illumination intensity and used to evaluate the strength of the dark field signal. By evaluating the strength of the dark field signal, we can tell if the dark field mode of operation can be used to find the defects.

Generally, if $N \geq 4$, we can also estimate the integrity of the measurement data by computing the amount of residual error after the regression. The residual error can be computed quickly by substituting equations (73), (74) and (75) into equation (61) and summing up each term in the equation. By comparing the residual error with a preset value, we can tell the soundness of measurements. Checking the residual error is especially helpful in system trouble shooting. It is usually the first step in a system trouble-shooting process.

Equations (73) through (75) reduce to equations (28) through (30) respectively when N=3.

If the phase settings are chosen to meet following condition, $$\sum_{n=0}^{N-1} \cos(\theta_n) = \sum_{n=0}^{N-1} \sin(\theta_n) = \sum_{n=0}^{N-1} \cos(2\theta_n) = \sum_{n=0}^{N-1} \sin(2\theta_n) = 0 \quad (76)$$

(As an example, the above condition can be met if all the $\theta_n$ are chosen with even angular intervals between them.)

then, $$A = \sum_{n=0}^{N-1} \Delta I_n \cos(\theta_n), \; A' = \sum_{n=0}^{N-1} \Delta I_n \sin(\theta_n), \; B = B' = N, \; C = 0 \quad (77)$$

and, consequently, in this case, $$|b|s_x = \frac{A}{N} = \frac{1}{N}\sum_{n=0}^{N-1} \Delta I_n \cos(\theta_n) \quad (78)$$

$$|b|s_y = \frac{A'}{N} = \frac{1}{N}\sum_{n=0}^{N-1} \Delta I_n \sin(\theta_n) \quad (79)$$

$$D = \frac{1}{N}\sum_{n=0}^{N-1} \Delta I_n \quad (80)$$

From equations (78) and (79), $$I_s \equiv (2|b|s_x)^2 + (2|b|s_y)^2 \quad (81)$$

$$= \frac{4}{N^2}\sum_{m=0}^{N-1}\sum_{n=0}^{N-1} \Delta I_m \Delta I_n \cos(\theta_m - \theta_n)$$

It is easy to see that equations (78) through (81) reduce to equations (35) through (38) respectively when N=3 and $\theta_0 = 0$, $$\theta_1 = -\theta_2 = \frac{2\pi}{3}.$$

They also reduce to equations (53) through (56) when N=4 and $\theta_0 = 0$, $\theta_1 = \pi$, $$\theta_2 = -\theta_3 = \frac{\pi}{2}.$$

As shown above, the regression process for the catch-all mode can be done analytically. Therefore, operation in the catch-all mode does not require excessive computing time even if the sample is scanned a lot more than three times in order to obtain more reliable defect signals. Definitely, more scans mean lower throughput. However, if the signal-to-noise ratio is low or a high signal-to-noise ratio is needed, more sample scans can significantly help. For example, an accurate study of defect signals can benefit from a supply of defect signals of high signal-to-noise ratio and this can be easily obtained by running the catch-all mode with a large number of sample scans.

If N is large and the relative phase can be changed rapidly and the measurement data can be collected rapidly, then the system can be operated in heterodyne mode. Heterodyne mode suffers less 1/f noise and so is able to provide cleaner measurement data generally. The heterodyne method can be implemented with relative ease in static or stepping systems, however, it is usually hard to implement in scanning systems, especially in fast scanning systems.

Contrast Enhancement. If the dynamic range of the image sensor is saturated, then, the contrast of the image needs to be increased in the catch-all mode to preserve signal integrity. In this case the same contrast enhancement technique described in the high sensitivity mode section can be used.

Polarization Diversity. As mentioned previously, the strength of the defect signal can depend on the polarization states of the illumination light and also the scattered light. Therefore, if the defects of interest are composed of different kinds of defects, whose signal strengths depend on polarization states differently, then in order to capture all the different kinds of defects, images need to be collected with multiple different polarization states. This is called polarization diversity. In theory coping with polarization diversity could take a lot of scans with different combinations of phase shift and polarization settings. In practice this is not usually practical, and good judgment is required to balance throughput with the probability of missing a small defect or two. A basic understanding of optical physics can help in coping with polarization diversity. For example, as long as the defect and its neighboring patterns do not have helical structures, the polarization combinations employed can be limited to linear polarization combinations.

Spatial Frequency Bandwidth. The maximum spatial frequency of the complex amplitude distribution of the optical signal collected by the collection lens is $$\frac{NA}{\lambda}$$

where NA is the numerical aperture of the collection lens. However, the maximum spatial frequency for the intensity distribution is $$\frac{2NA}{\lambda}$$

because the intensity is the absolute square of the complex amplitude. But, if we take a look at equation (1) in more detail, we find that in actuality, only the dark field terms have a maximum spatial frequency of $$\frac{2NA}{\lambda}.$$

Figure 40:
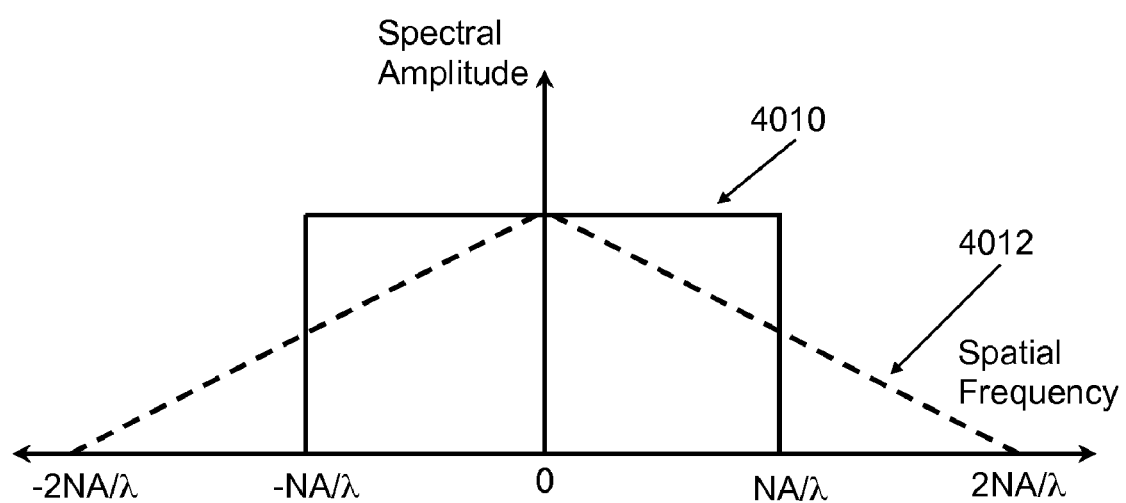
FIG. 40 shows plots of spatial frequency bandwidths of defect signal components.

The maximum spatial frequency of the interference term can be only $$\frac{NA}{\lambda}$$

approximately. This is because the maximum spatial frequency of the specular component can be made very small by illuminating the sample from a near-normal direction. This fact is depicted in FIG. 40, which compares the spatial frequency bandwidth of the defect signal component with normal incidence of illumination, with the dark field spatial frequency bandwidth. Curve 4010 shows the interference term and curve 4012 shows the dark field term. The maximum spatial frequency for the high sensitivity mode and dark field mode is $$\frac{2NA}{\lambda}$$

because they have dark field terms in their image measurements and utilize them. However, the catch-all mode drops out all dark field terms during the signal processing and utilizes only interference terms. Therefore, the maximum spatial frequency for the catch-all mode is $$\frac{NA}{\lambda},$$

not $$\frac{2NA}{\lambda}.$$

This has a significant implication. The Nyquist-Shannon sampling theorem states that the spatial frequency of the image sampling should be at least two times the maximum spatial frequency of the image in order to pick up all information in the image and to avoid signal aliasing. Note that the Nyquist-Shannon sampling theorem applies to image sensors because image sensors are a kind of sampling device.

This means that if we use the same image sensor for all modes, the image magnification for the catch-all mode does not need to be as high as that of the high sensitivity mode or dark field mode to pick up all the needed information about the defect and to prevent signal aliasing. This means that the same image sensor can cover a larger field of view at the sample plane in the catch-all mode. A larger field of view means a higher throughput. Thus, in theory at least, the throughput reduction of the catch-all mode due to multiple sample scans can be significantly compensated by the increase in the field of view.

If the dark field signal is small or negligible compared with the interference signal, we can reduce the magnification of the imaging system even for a high sensitivity mode of operation in order to increase the throughput without affecting performance. The dark field signal becomes less and less important as the defect size gets smaller and smaller. The dark field signal can be extremely small or negligible in the future. Therefore, future generations of interferometric defect detection systems may be able to use the same image magnification for both the high sensitivity mode and the catch-all mode. Also, in future generations of interferometric defect detection systems, the dark field mode may not be operational with an image magnification higher than that for the other modes of operation due to the low intensity of this signal component. If the illumination ray path is fixed, the image magnification does not need to be changed. This suggests that the same fixed image magnification may be used for all modes of operation in future generations of interferometric defect detection systems. A single fixed image magnification will not only make the imaging system more stable while reducing the manufacturing cost of the system but also simplify its operation.

Note that the Nyquist-Shannon sampling theorem assumes a delta function as the sampling function. But, any real sampling function cannot be a delta function. Real sampling functions must have finite widths, otherwise, they cannot sense the signal. Image sensors are a kind of spatial sampling device. The width of the sampling function is the width of the light-sensitive area in each pixel of the image sensor. A high sensitivity or high dynamic range usually requires a large light-sensitive area. Therefore, the Nyquist-Shannon sampling theorem is applied to real systems with appropriate modification. However, the general arguments presented here still hold.

A standard way of eliminating the negative effect of the finite width of sampling functions is to deconvolve the image with the sampling function. This is equivalent to the inverse Fourier filtering in which the Fourier transform of the image is multiplied with the inverse of the Fourier transform of the sampling function. However, the process of deconvolution usually requires too much computing resources to be practical. This is especially true for high speed defect detection.

In order to make the deconvolution process practical, the process can be greatly simplified so it can be performed quickly. Simplification of the deconvolution process is very limited for arbitrary images. However, great simplification of the deconvolution process is possible for the subtracted images of tiny defects whose sizes are much smaller than the wavelength. This is because the interference term is dominant in the subtracted image of the tiny defect and the shape of the interference term is the same as the shape of the amplitude point spread function (APSF) of the imaging system and thus fixed as long as the numerical aperture of the imaging system is fixed.

FIG. 33 through FIG. 37 confirm this fact. Even if the spatial frequency of the specular component is not zero, it does not change the shape of the interference term. Its effect is to provide the interference term with a nonzero carrier frequency.

If the specular component is composed of a single ray, the interference term can be expressed as the multiplication of the APSF with the carrier frequency term. That is, the carrier frequency term can be factored out and be treated separately. If we treat the carrier frequency term separately, the difference between the subtracted image of a tiny defect and the APSF is their strengths. In this case, thanks to the fact that only one kind of signal function needs to be handled, the deconvolution process reduces to the point-by-point resealing of the signal function. The resealing function can easily be generated by taking the ratio between the ideal APSF, which is not affected by the finite width of the sampling function, and the real APSF which is affected by the finite width of the sampling function.

The deconvolution process is a simple point-by-point multiplication of the defect image with the resealing function. This is an extremely fast process in modern computers. Thus, in this case, the deconvolution process can be performed extremely fast for the images of tiny defects. Notice that noise is not amplified or affected in a statistical sense by the deconvolution process as long as it is evenly distributed statistically in the spatial frequency domain. Deconvolution makes the image look like it is being sampled with an array of delta-functions, referred to as a comb-function, with the same spacing as the detector array. With the data in this form it possible to accurately fit a function corresponding to the ideal signal shape and then shift this signal slightly so that subtraction of the reference signal gives a nearly null result if a defect is not present. In the event that deconvolution of the entire signal proves to be computationally impractical in a given system example, then this de-convolution technique can be selectively applied only to feeble or border-line defect signals to improve the accuracy of the detection process. Therefore, the fast deconvolution method presented herein will be a key factor in the design of a low-cost, highly-stable, high-performing, high-throughput defect detection system Reduction in the Number of Sample Scans. One way of increasing the throughput is to reduce the number of sample scans. The number of sample scans can be reduced by splitting the original beam of light into multiple beams and installing a phase controller in each beam path.

Figure 41:
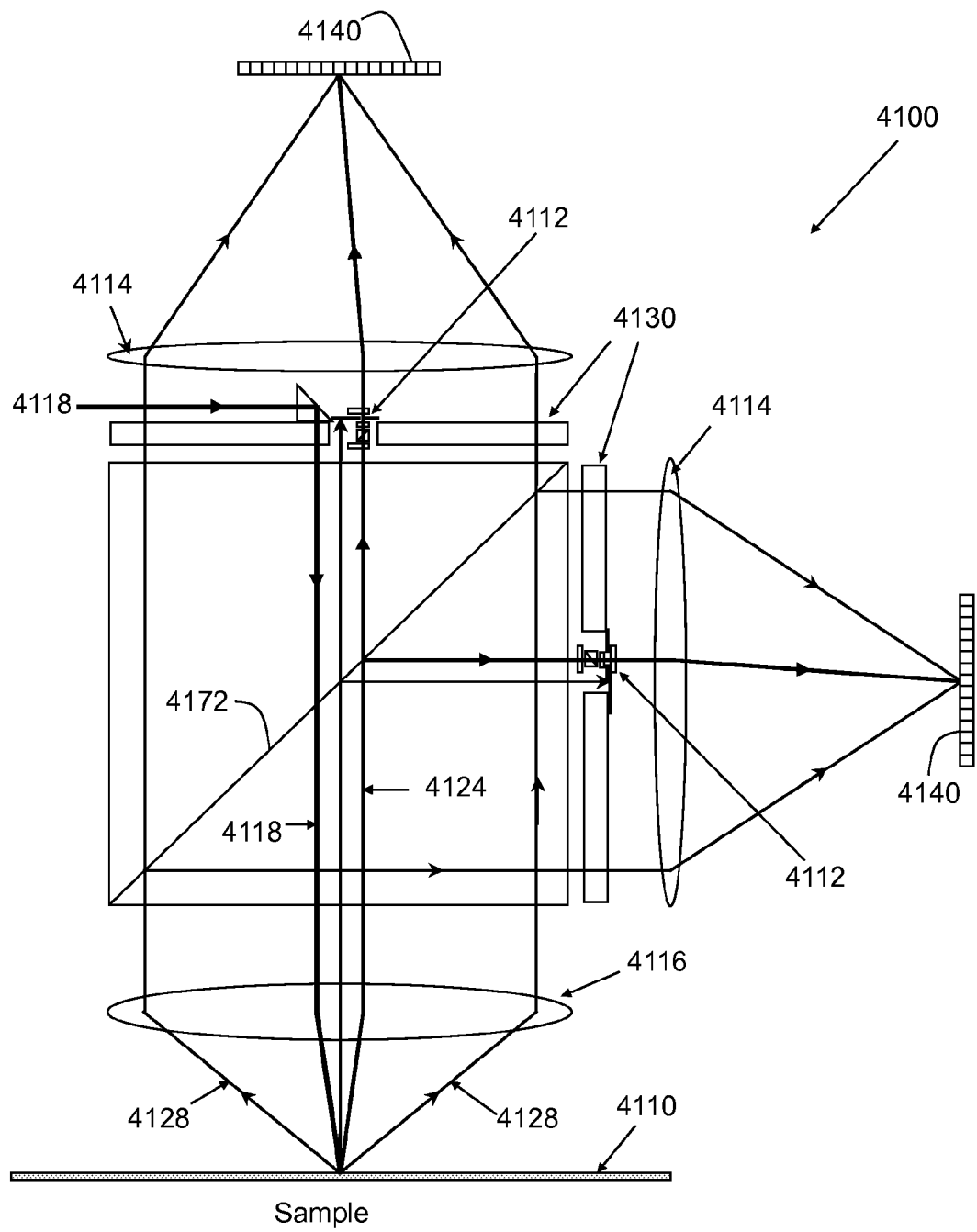
FIG. 41 shows an example of system configuration for the reduction of the number of sample scans.

FIG. 41 shows an example system 4100. The illumination beam 4118 enters the imaging system near the pupil plane and is folded by a small prism so that it strikes the sample at near normal incidence. The specular beam component, 4124, and the scattered component, 4128, from the sample 4110, are split into two beams using a beam splitter, 4172, located near the pupil and between the high NA lens assembly, 4116, and the low NA lens assembly, 4114. After the split, a phase controller 4112 and a compensation plate, 4130, is installed in each beam path. Each phase controller sets the relative phase between scattered and specular components to one of the pre-selected values. Two separate image sensors, 4140, measure the intensities of two separate images simultaneously. Thus, a single sample scan can produce two image data sets at the same time. Consequently, the total number of sample scans can be reduced to half in the example system. Further reduction of the number of sample scans can easily be achieved by further splitting each of the two beams using additional beam splitters.

An additional phase controller and image sensor need to be installed in each of the additional beam paths. Each phase controller sets the relative phase between scattered and specular components to one of the pre-selected values. Multiple separate image sensors simultaneously measure the intensities of multiple separate images. Thus, a single sample scan can produce multiple image data sets at the same time. Consequently, the total number of sample scans can be reduced accordingly. Cascaded beam splittings can be performed as many times as needed as long as the physical space allows them. This method can also be applied to a high-sensitivity mode of operation when the targeted defects contain multiple different kinds of defects each of which require a different phase setting for optimum detection. In this case, each phase controller is set to an optimal phase value for the best detection of each different kind of defect. The net effect is the running of multiple high-sensitivity modes simultaneously. This kind of scan number reduction can also be applied to the polarization-diverse measurements by making the beam splitter polarization-sensitive. However, this kind of scan number reduction carries its own drawbacks. It not only increases the complexity and cost of the optical system but also reduces signal intensity. If the signal intensity becomes too low, the scan speed must be reduced to boost the signal intensity to an acceptable level. The reduction of the scan speed can reduce the throughput gain obtainable with the reduction of the number of scans.

3. Dark Field Mode. The dark field mode is realized by completely blocking out the specular component. The additional two-dimensional Fourier filtering of noise-generating light in this scheme will make the dark field mode very quiet (or the noise level very low). It will have much less photon noise than the dark field modes in currently available equipment, which typically employs line illumination, which allows only one dimensional Fourier filtering. However, as explained previously, even with two-dimensional Fourier filtering, the dark field mode is not a good choice for the detection of tiny defects whose sizes are smaller than $$\frac{\lambda}{4}.$$

However, the dark field mode is a good choice for the speedy detection of large defects because it produces strong enough signals for a variety of different kinds of large defects and a single scan of the sample is usually enough. Note that if one wants to know the strength of the dark field signal beforehand, the catch-all mode may be employed on the sample first.

Another good use of the dark field mode is finding the best focus for the image sensor. This is because the dark field mode blocks out the specular component which does not carry any focus information but still can affect the image critically during image focusing through its interference with the scattered component. The dark field mode does not need as high a dynamic range on the image sensor as other operational modes because it does not have a specular component. More important characteristics of the image sensor system for the dark field mode are high sensitivity and finer pixels.

Limitations of Dark Field Mode. The dark field mode is easy to operate because it does not require the manipulation of a phase controller. Also, it can catch a variety of defects with a single sample scan. Therefore, the dark field mode is usually the first choice if the signal is strong enough or the noiseless amplification of the signal by the specular component is insignificant due to the weak specular component. However, as explained previously, the dark field mode has severe limitations in finding tiny defects due to its lack of noiseless signal amplification capability.

The limitations of the dark field need to be known more clearly in order to avoid futile trials using the dark field mode. In order to understand the limitations of the dark field mode more clearly, the signals from isolated defects are simulated and then are divided into a dark field part and an interference part. A wavelength of 266 nm and the numerical aperture of 0.9 of the imaging system were assumed. The central obscuration was assumed to be 0.2 NA. The phase controller was adjusted to maximize the interference term.

Figure 42A:
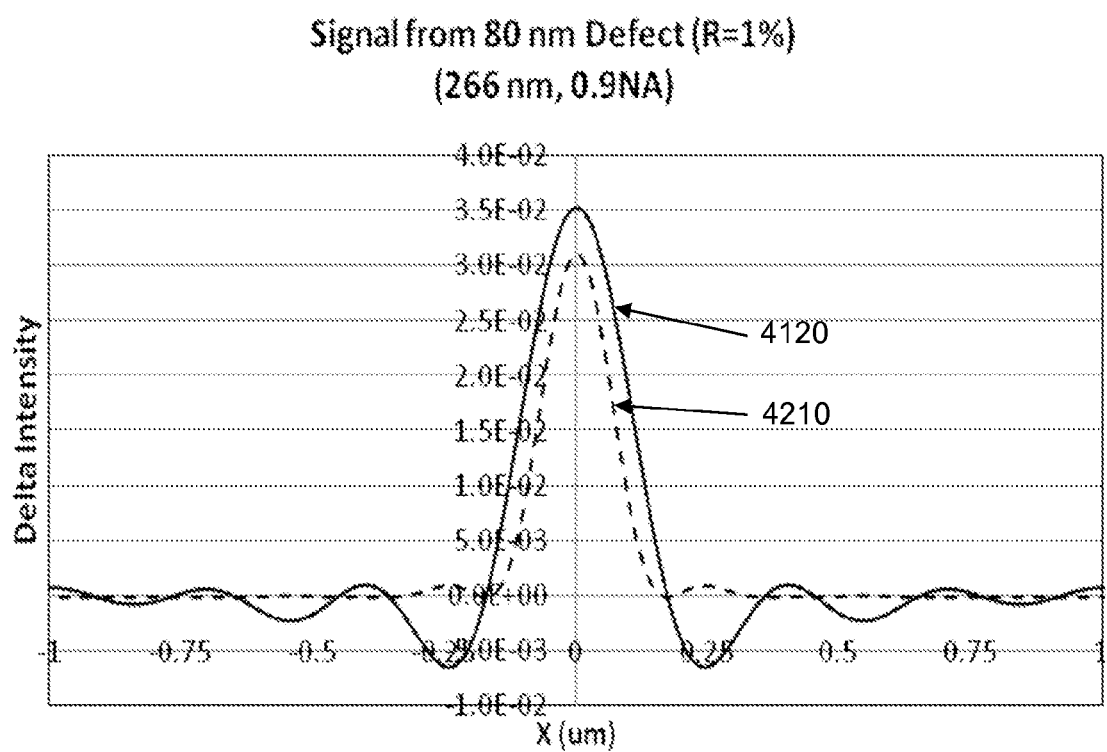
FIGS. 42a through 42c compare the magnitude of interference term with that of dark field term for different defect sizes and sample reflectivities.
Figure 42B:
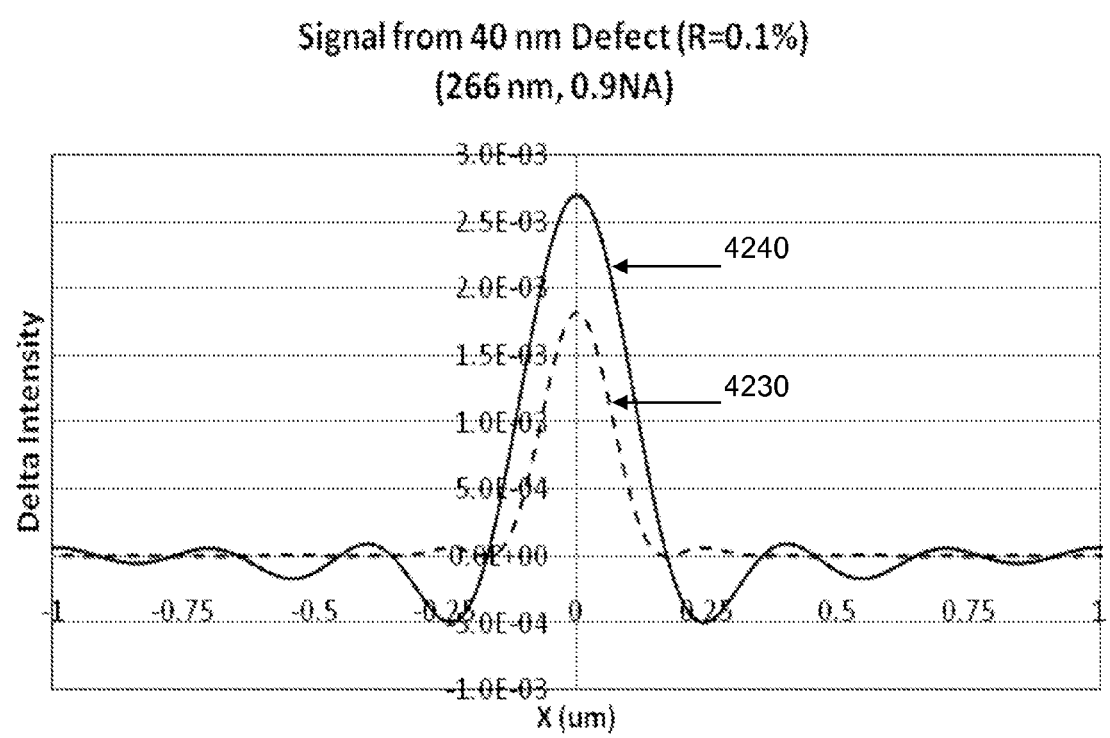

FIG. 42a shows the dark field part, 4210, and interference part, 4220, of the defect signal from a 80 nm isolated defect on a sample surface of only 1% reflectivity. The reflectivity of the defect itself is assumed to be 100% in all simulated cases. FIG. 42a shows that even if the defect is relatively large and the reflectivity of the sample surface is very low, the interference part of the signal is larger than the dark field part. FIG. 42b shows the dark field part, 4230, and interference part, 4240, of the defect signal from a 40 nm isolated defect on a sample surface of only 0.1% reflectivity. That is, the reflectivity of the surrounding area is only one thousandth of the defect reflectivity. This shows that if the size of the defect is smaller than quarter wavelength, even with extremely low reflectivity of the sample, the interference part of the defect signal is larger than the dark field part.

Figure 42C:
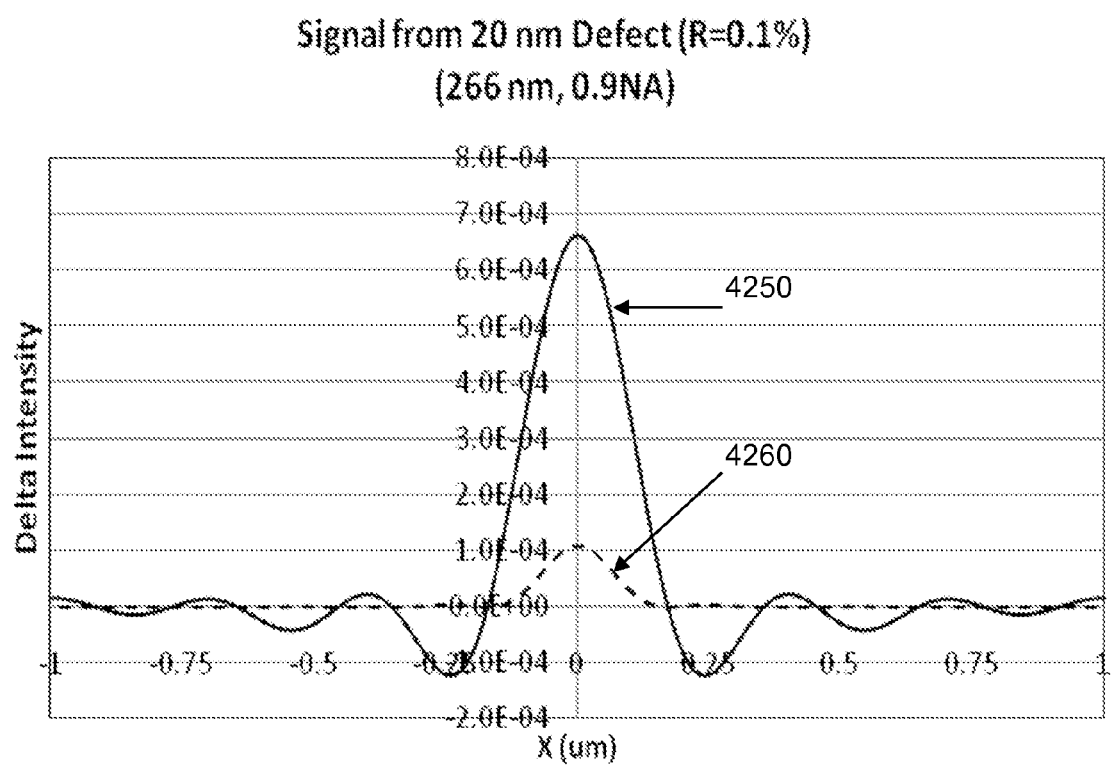

FIG. 42c shows the dark field part, 4260, and interference part, 4250, of the defect signal from a 20 nm isolated defect on a sample of only 0.1% reflectivity. In this case, the dark field part is significantly smaller than the interference part. If the reflectivity of the sample is larger, the interference part dominates even more. Therefore, we can say that in almost all practical situations, the interference term will dominate for all samples. That is, the technique of the phase control and noiseless amplification described herein work well for all the different types of wafers and reticles likely to be encountered in practice. This is another important advantage of the systems and methods disclosed herein. It turns out that dark field mode is useful only when the size of the defect is roughly larger than a quarter wavelength. However, most critical defects in the future are expected to be much smaller than a quarter wavelength. Also, the dark field mode cannot classify defects accurately and therefore, it is not expected to be a popular mode of operation in the future.

Most actual defects are not isolated from other features. Therefore, the conclusions we arrived at by simulating signals from isolated defects should not be interpreted as the last word. However, the isolated defect case represents an average of many different kinds of cases and therefore, the conclusions should be at least roughly correct. Similar conclusions can be reached for transmissive samples because transmissive samples are mathematically very similar to reflective samples.

IV. Design Examples of the Imaging System

A high quality imaging system is one of the key components and the most expensive part of most optics-based inspection systems. As stated previously, the systems and methods disclosed herein can be used with a wide variety of imaging systems including dioptric, catoptric, and catadioptric systems. Dioptric and catoptric designs are better known for this type of application. Numerous books, patents, and other literature exhaustively cover dioptric and catoptric designs.

Figure 43A:
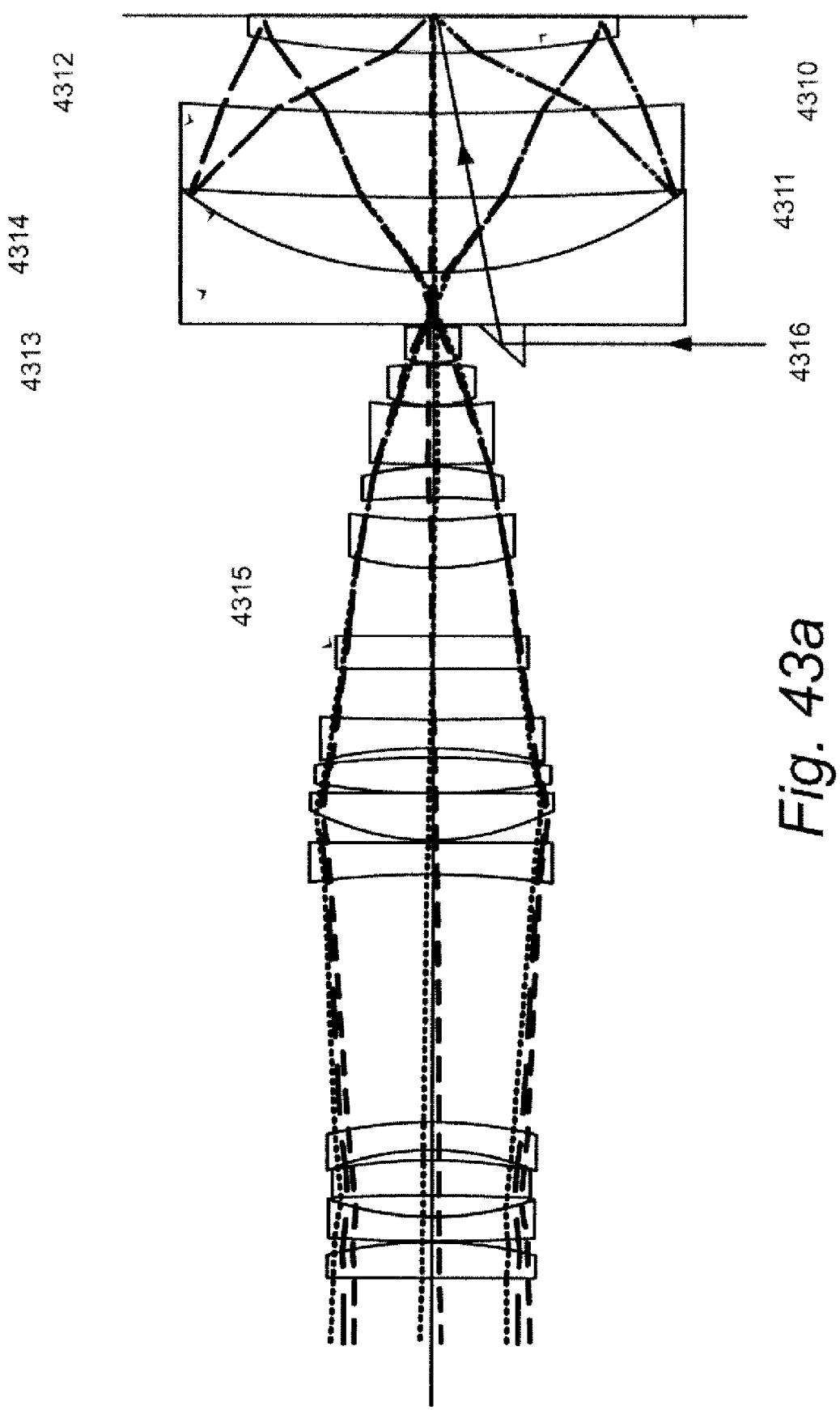
FIGS. 43a and 43b show the design examples of catadioptric imaging system.

Catadioptric designs are less known but can be very high performing. Design examples of two high performing catadioptric imaging systems will be presented here. The designs are based on U.S. Pat. No. 5,031,976. The first design example is shown in FIG. 43a. The design prescription is shown below.

| SURFACE NO. | RADIUS OF CURVATURE | THICKNESS | LENS MATERIAL |
| --- | --- | --- | --- |
| IMAGE PLANE | INFINITY | 0 | |
| 1: | INFINITY | 2522.782646 | |
| PUPIL | INFINITY | −2522.782646 | |
| 3: | INFINITY | 2094.43911 | |
| 4: | −217.65754 | 10 | FUSED SILICA |
| 5: | 184.03778 | 98.463605 | |
| 6: | −298.46859 | 13 | FUSED SILICA |
| 7: | −120.22474 | 1 | |
| 8: | 260.02259 | 13 | FUSED SILICA |
| 9: | −4448.91929 | 3.697875 | |
| 10: | −259.03744 | 10 | FUSED SILICA |
| 11: | −2241.09909 | 983.562232 | |
| 12: | −479.70522 | 10 | FUSED SILICA |
| 13: | −103.66125 | 0.2 | |
| 14: | 242.54669 | 8 | FUSED SILICA |
| 15: | 55.83421 | 6.381699 | |
| 16: | −390.65626 | 11 | FUSED SILICA |
| 17: | −91.48058 | 2.47366 | |
| 18: | −58.19481 | 9 | FUSED SILICA |
| 19: | −88.66288 | 75.067704 | |
| 20: | −170.66791 | 10 | FUSED SILICA |
| 21: | −956.52725 | 0.212011 | |
| 22: | 57.35537 | 14 | FUSED SILICA |
| 23: | 747.14858 | 0.2 | |
| 24: | 151.31445 | 11 | FUSED SILICA |
| 25: | −202.79292 | 2.708846 | |
| 26: | −93.25341 | 9 | FUSED SILICA |
| 27: | 384.81581 | 15 | |
| COMP. PLATE | INFINITY | 10 | FUSED SILICA |
| 29: | INFINITY | 20.572398 | |
| 30: | 70.02973 | 15.28383 | FUSED SILICA |
| 31: | 120.97319 | 5.671358 | |
| 32: | −235.82704 | 9.972695 | FUSED SILICA |

-continued

| SURFACE NO. | RADIUS OF CURVATURE | THICKNESS | LENS MATERIAL |
|---|---|---|---|
| 33: | −51.95654 | 0.2 | |
| 34: | 170.05902 | 18.000029 | FUSED SILICA |
| 35: | 36.10217 | 0.2 | |
| 36: | 29.65551 | 12.387074 | FUSED SILICA |
| 37: | −164.61485 | 0.820227 | |
| 38: | 34.06431 | 11.675753 | FUSED SILICA |
| 39: | INFINITY | 0 | |
| 40: | INFINITY | 15 | FUSED SILICA |
| 41: | 93.01526 | 23.058061 | |
| 42: | 695.78458 | 25.676922 | FUSED SILICA |
| 43: | 464.68469 | 18.387944 | |
| 44: | 300.42881 | 9.894583 | FUSED SILICA |
| 45: | INFINITY | −9.894583 | MIRROR |
| 46: | 300.42881 | −18.387944 | |
| 47: | 464.68469 | −25.676922 | FUSED SILICA |
| 48: | 695.78458 | −23.058061 | |
| 49: | 93.01526 | 23.058061 | MIRROR |
| 50: | 695.78458 | 25.676922 | FUSED SILICA |
| 51: | 464.68469 | 18.387944 | |
| 52: | 300.42881 | 9.894583 | FUSED SILICA |
| 53: | INFINITY | 1.5 | |
| SAMPLE PLANE | INFINITY | 0 | |

This design is for single wavelength applications. A wavelength of 266 nm was chosen for the example design. All lenses and the two catadioptric components 4313, 4311 are made of fused silica in the example design. The refractive index value of fused silica is assumed to be 1.499684 for 266 nm wavelength. However, other lens materials such as calcium fluoride, lithium fluoride, etc. can also be used.

Lens component 4311 is a plano-convex lens with a reflective coating on the flat side, which faces the sample 4310 spaced 1.5 mm away. The central part of the reflective coating is removed to allow the light from the sample to pass through the lens. After passing through the lens 4311 the image beam passes through another lens element 4312 and is reflected by a coating on surface 4314 on mirror element 4313, from which it passes again through lens element 4312 and through to the flat side of element 4311 containing the reflective coating. After a second reflection the light emerges from element 4311, passes for a third time through element 4312 and this time passes through a central hole in the reflective coating on surface 4314 to an intermediate focus near the rear of element 4313. The other lens elements in the optical train are all refractive and simply reimage the intermediate image on a detector array far to the left of the drawing.

Illumination can be introduced through the compensation plate 4315 using the scheme shown in FIG. 1. Another way of introducing the near normal incidence illumination beam 4316 is through a second, small, off-axis hole in the reflective coating on surface 4314 on lens/mirror element 4313. This assures that the specular component from the sample 4310 is reflected from the opposite side of surface 4314 and therefore follows a very similar path as the scattered component from the sample to the detector plane. This illumination method produces less flare because the illumination beam passes through fewer optical components.

All the lens elements do not need to be made of the same material. For example, lenses located at a high laser intensity area can be made with a more laser-damage-resistant material like calcium fluoride and the rest can be made with fused silica. All lens surfaces are spherical. No aspheric surface is needed even though aspheric surfaces can be used to improve performance further or to reduce the number of lens components.

No lens surface has extreme curvature either. All these lens characteristics lead to moderate manufacturing tolerances. Thus, the lens system shown in FIG. 43a can be manufactured without any extreme difficulty. The numerical aperture of the design is 0.9. Its field of view covers quite a large 1.0 mm diameter field. The magnification is chosen to be 200×, but it can be changed easily without affecting the quality or performance of the system. The design Strehl ratio is 0.996 or higher over the whole field. The diameter of the aperture stop is 47 mm. The compensation plate 4315 lies close the lens pupil and in an interferometric imaging application would contain the phase controller and the Fourier filter blocking strips. The clear aperture diameter of the compensation plate is nearly the same as the 47 mm diameter of the aperture stop. This is large enough to install a phase controller in the middle without incurring excessive central obscuration. The design also has very low field curvature and distortion. The only drawback of the design is its small working distance which is 1.5 mm in the example design. The example design may not work for applications such as reticle inspection, which typically requires a large working distance because of the pellicle protection. However, the design is well suited for other applications such wafer inspection, which do not require a large working distance.

Figure 43B:
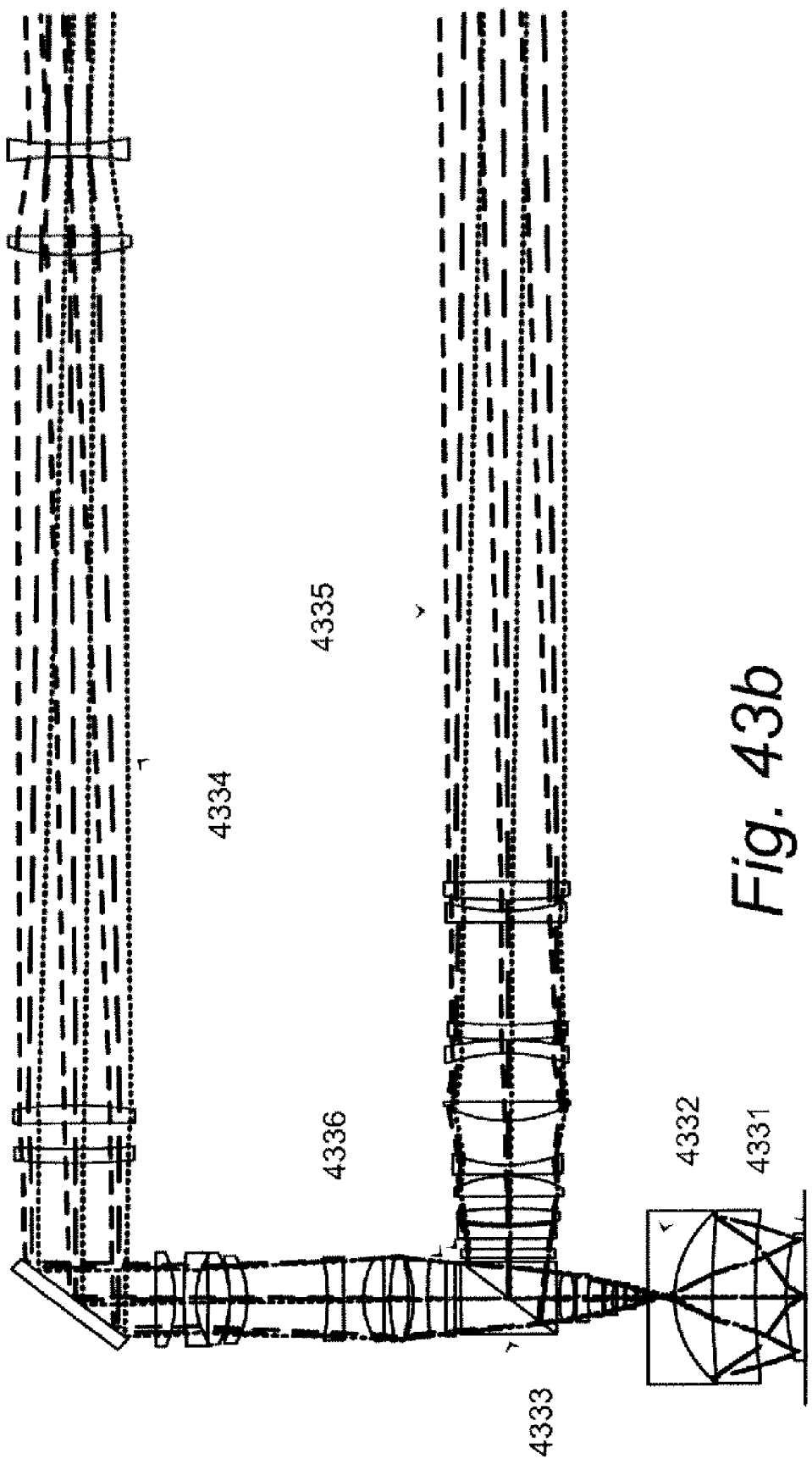

FIG. 43b shows another catadioptric design example. The design prescriptions are shown below.

| | 266 nm Path | | |
|---|---|---|---|
| SURFACE NO. | RADIUS OF CURVATURE | THICKNESS | LENS MATERIAL |
| IMAGE PLANE | INFINITY | 0 | |
| 1: | INFINITY | 3066.335876 | |
| PUPIL | INFINITY | −3066.335876 | |
| 3: | INFINITY | 2694.957429 | |
| 4: | −163.28603 | 10 | FUSED SILICA |
| 5: | 216.26862 | 61.379602 | |
| 6: | −517.65262 | 13 | FUSED SILICA |
| 7: | −123.63976 | 660.088432 | |
| 8: | 245.34768 | 13 | FUSED SILICA |
| 9: | −1713.51106 | 22.12615 | |
| 10: | −253.37027 | 10 | FUSED SILICA |
| 11: | −1290.34822 | 153.955659 | |
| 12: | −455.09619 | 10 | FUSED SILICA |
| 13: | −104.69229 | 4.798484 | |
| 14: | 247.46505 | 8 | FUSED SILICA |
| 15: | 57.02186 | 7.317064 | |
| 16: | −350.74834 | 11 | FUSED SILICA |
| 17: | −91.92925 | 2.750436 | |
| 18: | −58.78037 | 9 | FUSED SILICA |
| 19: | −89.13846 | 49.161367 | |
| 20: | −170.29791 | 10 | FUSED SILICA |
| 21: | −963.86275 | 10.239229 | |
| 22: | 57.96681 | 14 | FUSED SILICA |
| 23: | 707.70698 | 4.045678 | |
| 24: | 151.63696 | 11 | FUSED SILICA |
| 25: | −203.5169 | 2.965125 | |
| 26: | −90.61124 | 9 | FUSED SILICA |
| 27: | 371.34632 | 10 | |
| COMP. PLATE | INFINITY | 6 | FUSED SILICA |
| 29: | INFINITY | 2 | |
| WAVE SPLITTER | INFINITY | 56 | FUSED SILICA |
| 31: | INFINITY | 2.669311 | |
| 32: | 100.33748 | 9.510003 | FUSED SILICA |
| 33: | −60.8163 | 0.20347 | |
| 34: | INFINITY | 8.873905 | FUSED SILICA |
| 35: | 64.51709 | 0.555192 | |
| 36: | 65.19822 | 8.790183 | FUSED SILICA |
| 37: | 124.97631 | 0.209881 | |
| 38: | 69.26197 | 5.80478 | FUSED SILICA |
| 39: | 21.89578 | 0.2 | |

266 nm Path

| SURFACE NO. | RADIUS OF CURVATURE | THICKNESS | LENS MATERIAL |
|---|---|---|---|
| 40: | 20.23207 | 6.3765 | CALCIUM FLUORIDE |
| 41: | -485.32987 | 0.47477 | |
| 42: | 50.61378 | 5.057388 | FUSED SILICA |
| 43: | 99.48525 | 0.667202 | |
| 44: | 48.81849 | 6.637569 | FUSED SILICA |
| 45: | INFINITY | 0 | |
| 46: | INFINITY | 15 | FUSED SILICA |
| 47: | 92.94259 | 23.127191 | |
| 48: | 656.66565 | 25.830118 | FUSED SILICA |
| 49: | 439.13539 | 18.505918 | |
| 50: | 306.48465 | 9.907152 | FUSED SILICA |
| 51: | INFINITY | -9.907152 | MIRROR |
| 52: | 306.48465 | -18.505918 | |
| 53: | 439.13539 | -25.830118 | FUSED SILICA |
| 54: | 656.66565 | -23.127191 | |
| 55: | 92.94259 | 23.127191 | MIRROR |
| 56: | 656.66565 | 25.830118 | FUSED SILICA |
| 57: | 439.13539 | 18.505918 | |
| 58: | 306.48465 | 9.907152 | FUSED SILICA |
| 59: | INFINITY | 1.5 | |
| SAMPLE PLANE | INFINITY | 0 | |

532 nm Path

| SURFACE NO. | RADIUS OF CURVATURE | THICKNESS | LENS MATERIAL |
|---|---|---|---|
| IMAGE PLANE | INFINITY | 0 | |
| 1: | INFINITY | 3632.88769 | |
| PUPIL | INFINITY | -3632.88769 | |
| 3: | INFINITY | 3347.66316 | |
| 4: | INFINITY | 0 | |
| 5: | INFINITY | 0 | |
| 6: | INFINITY | 0 | |
| 7: | INFINITY | 0 | |
| 8: | 216.96892 | 13 | BK7 |
| 9: | -658.16044 | 8.19496 | |
| 10: | -125.51497 | 10 | BK7 |
| 11: | -834.80474 | 80.01999 | |
| 12: | -403.85737 | 10 | BK7 |
| 13: | -140.67609 | 0.21459 | |
| 14: | 162.98508 | 10 | BK7 |
| 15: | 62.6621 | 37.7104 | |
| 16: | -793.57915 | 15 | BK7 |
| 17: | -69.83886 | 34.20348 | |
| 18: | -57.48694 | 10 | BK7 |
| 19: | -833.75848 | 0.71388 | |
| 20: | INFINITY | 0 | |
| 21: | INFINITY | 0 | |
| 22: | 60.7612 | 14 | BK7 |
| 23: | 392.0481 | 9.87199 | |
| 24: | 169.0556 | 11 | BK7 |
| 25: | -266.0879 | 2.31345 | |
| 26: | -114.62355 | 9 | BK7 |
| 27: | 571.92482 | 10 | |
| COMP. PLATE | INFINITY | 6 | BK7 |
| 29: | INFINITY | 2 | |
| WAVE SPLITTER | INFINITY | 56 | FUSED SILICA |
| 31: | INFINITY | 2.669311 | |
| 32: | 100.33748 | 9.510003 | FUSED SILICA |
| 33: | -60.8163 | 0.20347 | |
| 34: | INFINITY | 8.873905 | FUSED SILICA |
| 35: | 64.51709 | 0.555192 | |
| 36: | 65.19822 | 8.790183 | FUSED SILICA |
| 37: | 124.97631 | 0.209881 | |
| 38: | 69.26197 | 5.80478 | FUSED SILICA |
| 39: | 21.89578 | 0.2 | |
| 40: | 20.23207 | 6.3765 | CALCIUM FLUORIDE |
| 41: | -485.32987 | 0.47477 | |
| 42: | 50.61378 | 5.057388 | FUSED SILICA |
| 43: | 99.48525 | 0.667202 | |
| 44: | 48.81849 | 6.637569 | FUSED SILICA |
| 45: | INFINITY | 0 | |
| 46: | INFINITY | 15 | FUSED SILICA |
| 47: | 92.94259 | 23.127191 | |
| 48: | 656.66565 | 25.830118 | FUSED SILICA |
| 49: | 439.13539 | 18.505918 | |
| 50: | 306.48465 | 9.907152 | FUSED SILICA |
| 51: | INFINITY | -9.907152 | MIRROR |
| 52: | 306.48465 | -18.505918 | |
| 53: | 439.13539 | -25.830118 | FUSED SILICA |
| 54: | 656.66565 | -23.127191 | |
| 55: | 92.94259 | 23.127191 | MIRROR |
| 56: | 656.66565 | 25.830118 | FUSED SILICA |
| 57: | 439.13539 | 18.505918 | |
| 58: | 306.48465 | 9.907152 | FUSED SILICA |
| 59: | INFINITY | 1.5 | |
| SAMPLE PLANE | INFINITY | 0 | |

This design is similar to the previous design in the part between the sample surface 4331 and the intermediate image 4332, however near the pupil plane it contains a dichroic wavelength splitter 4333 which divides the beam in two legs, with one leg 4334 being the 266 nm portion and the other 4335 the 532 nm portion. Each leg contains its own compensation plate 4336 and phase controller (not shown). The refractive index values of fused silica are assumed to be 1.499684 for 266 nm and 1.460705 for the 532 nm wavelength. The refractive index values of calcium fluoride are assumed to be 1.462084 for the 266 nm and 1.435358 for the 532 nm wavelength. The refractive index value of BK7 glass is assumed to be 1.519473 for the 532 nm wavelength. The design has similar characteristics to the single wavelength design. The lens system can be manufactured without extreme difficulty. The numerical aperture and the field of view are the same as those of the previous design. The physical size is also similar. However, it is designed for two wavelength applications. The wavelengths are chosen to be 266 nm and 532 nm. Other wavelengths can also be chosen with the same design form. It has a wavelength splitter and two separate phase controllers contained in each compensation plate so as to be able to independently handle two wavelengths.

As seen from the prescriptions, the front-end lens system is shared by both wavelengths. The back-end lens systems are completely separated to maximize the design flexibility. The design Strehl ratios are at least 0.996 for the 266 nm wavelength and at least 0.985 for the 532 nm wavelength over the whole field. The field curvature and distortion are also very low. The design can be easily modified to accommodate more wavelengths by inserting more wavelength splitters into the back-end lens systems. These design examples are applicable to the defect detection systems described herein.

V. Subsystems

The systems and methods disclosed herein do not rely on any specific illumination or focus subsystems. They can accommodate almost any subsystem. However, optimizing the whole inspection instrument in terms of both performance and cost requires not only an excellent imaging system design but also inspired design of the complimentary illumination and autofocus systems.

Another simple but important part is suppressing diffraction from the aperture stop. In coming sections, new illumination systems and new autofocus systems will be presented first. Then, a new way of making low-diffraction apertures will be presented with a complete theory. The subsystems presented are especially well suited for interferometric inspection systems. However, they can also be used effectively for other optical instruments.

1. Coherent Uniform Illuminator

For some applications such as interferometry, optical Fourier filtering, etc, completely coherent illumination rather than partially coherent or incoherent illumination is preferred. For most of these applications, uniform illumination over the object plane with a tophat beam profile is preferred or required. However, achieving uniform illumination efficiently requires a sophisticated approach because the output beams from coherent sources like lasers have gaussian rather than tophat intensity profiles and many of the tools used to achieve good uniformity with incoherent beams, such as lens arrays and light pipes, simply do not work with a coherent illumination source. There are a number of well known energy-efficient ways of converting a gaussian beam profile to a tophat beam profile. According to some embodiments, another method is provided for converting a gaussian beam profile to a tophat beam profile.

The most straightforward way of converting a gaussian beam into a tophat beam is to partially absorb the high intensity part of the beam using an absorbing material. However, this method is not only energy-inefficient but also prone to damaging the absorbing material if the input beam is intense or made up of short pulses. A more energy-efficient and a less damage-prone way of converting a gaussian beam to a tophat beam is to redistribute the light energy in the beam. This can be done using a couple of lenses (or lens groups) that are separated from each other.

Figure 44A:
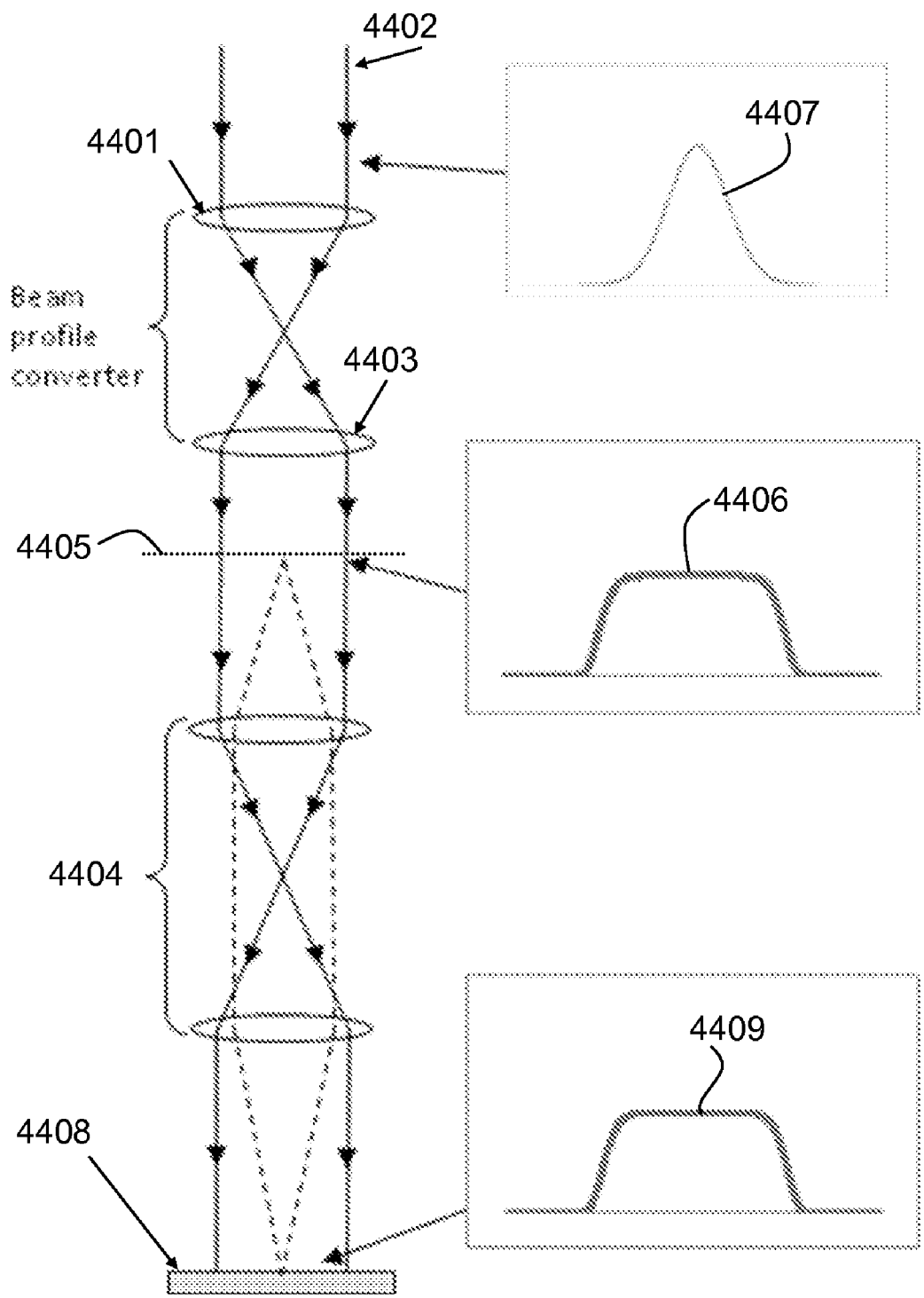
FIGS. 44a through 44f show coherent uniform illuminator designs.

FIG. 44a shows this method. The first lens 4401 purposely introduces an appropriate amount of spherical aberration to the input beam 4402 which has a gaussian shape as shown in curve 4407. Spherical aberration from the first lens redistributes the energy in the beam as it propagates through free space. By adjusting the form and the amount of spherical aberration and the propagation distance, a gaussian beam can be converted into a tophat-shaped uniform beam. The second lens 4403 is used because the spherical aberration not only redistributes light energy but also introduces wavefront distortion. The second lens corrects the wavefront distortion introduced by the first lens so that the energy distribution at focal plane 4405 is shown by curve 4406. Thus, two lenses can convert a gaussian beam into a tophat beam without distorting the wavefront.

This method is quite energy-efficient and can handle a high power beam. However, there is a drawback with this method; it usually needs an additional image relay system 4404 as shown in FIG. 44a. An image relay system is used because the beam profile converter provides limited working space close to the desired uniform illumination field. Consequently, the tophat-shaped output beam profile from the beam profile converter is relayed to the illumination field 4408 using an imaging system. Otherwise, the tophat beam profile can change significantly if the beam has to propagate a long distance from its ideal focus conjugate. Note that the light distribution in the relay image plane shown by curve 4409 is the same as that in focal plane 4405 and shown by curve 4406.

The relay system usually needs at least two lenses separated from each other. This is because the relay system not only needs to relay the tophat beam profile but also has to preserve the flat wavefront at the illumination field. Sometimes, it is very hard to procure space for the relay system. Usually, lots of mechanical interference problems arise. The problem becomes more severe if the relay system needs to be a zoom system. The embodiments described herein can alleviate these problems.

Figure 44B:
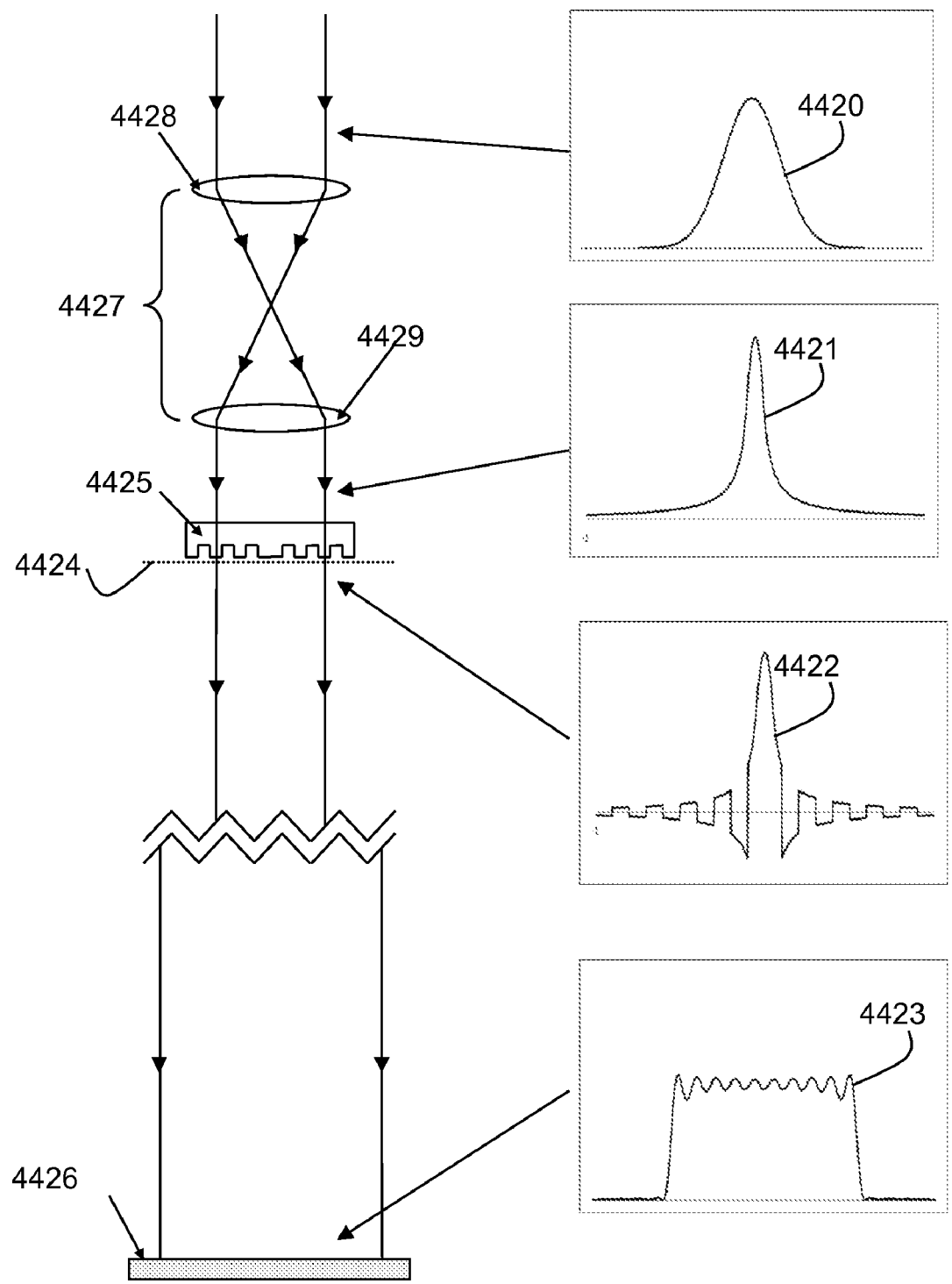

FIG. 44b shows the workings of the present invention according to some embodiments. In brief, the gaussian input beam profile 4420 is converted into a profile 4421 that is shaped to form an envelope over a sinc-function. At the sinc function location 4424 the beam is incident on a phase plate 4425 that has grooves positioned where the sinc function goes negative that produce 180 degree phase changes in the transmitted beam. Further propagation of the beam through free space converts it into a tophat intensity profile 4423 at the sample plane 4426.

Diffraction theory tells us that the far-field diffraction pattern of a sinc-function-like beam is tophat-shaped. The described embodiments, like the prior art, use a beam profile converter 4427 but, the beam profile converter does not convert an input beam profile to a tophat profile. It converts the input gaussian beam profile into another nonuniform beam profile 4421. The converted beam profile 4421 at image plane 4424 is actually more nonuniform than the input beam profile 4420. The profile of the converted beam 4421 should look more or less like the envelope of a sinc-function. The beam profile converter 4427 converts the input beam profile to a desirable profile without introducing a wavefront distortion. The beam profile converter introduces an appropriate amount of spherical aberration through the first lens 4428 (or lens group) and corrects the wavefront distortion introduced by lens 4428 with the second lens 4429 (or lens group).

The present embodiment uses another optical component called a "phase-stepper" placed after the beam profile converter. The phase stepper can be made by forming unequally spaced grooves with a square profile on a glass substrate as shown in FIG. 44b. Precision grooves on a glass substrate can be made in many different ways. For example, they can be made by patterning the grooves with a lithography technique followed by either precision etching or deposition of a glass material. The phase stepper changes the phases of selected portions of the incident wavefront in a discreet fashion. The amount of phase step needed is about 180°.

After being phase-stepped, the nonuniform beam 4422 that emerges looks more or less like a sinc-function and is allowed to propagate through free space for a long distance. While the beam propagates through free space, the beam profile changes to a tophat shape. The minimum distance it needs to propagate to become a tophat beam is:

$$\text{Minimum propagation distance} = \frac{2D^2}{\lambda} \tag{82}$$

where D=Diameter of the beam at the phase stepper
λ=Wavelength
(Reference: "Introduction to Fourier Optics, Third edition", Joseph W. Goodman, Roberts & Company, Englewood, Colo., 2005, page 75.) There is a relationship between the size of the beam at the start of free space propagation and the size of the tophat beam at the illumination field. This relationship is known and can be found in the same reference book. The beam at the illumination field 4426 is not completely uniform but includes ringing as shown in FIG. 44b. This is because the beam profile at the starting plane of propagation 4424 is an imperfect sinc-function and has a finite size. The former discrepancy might be fixed by judiciously adding absorbers to the phase stepper, which might be damaged by a high input beam power. By omitting any absorbers, the present embodiment trades off some amount of residual intensity nonuniformity for the capability of handling high power.

Most applications tolerate some amount of intensity nonuniformity. Therefore, many of the described embodiments are still valuable for many applications, including optical inspection. As stated previously, an important beneficial feature of the described embodiments is that it does not require an image relay system, which can cause serious mechanical conflicts with other parts or subsystems. This feature can be very helpful in designing real systems.

Figure 44C:
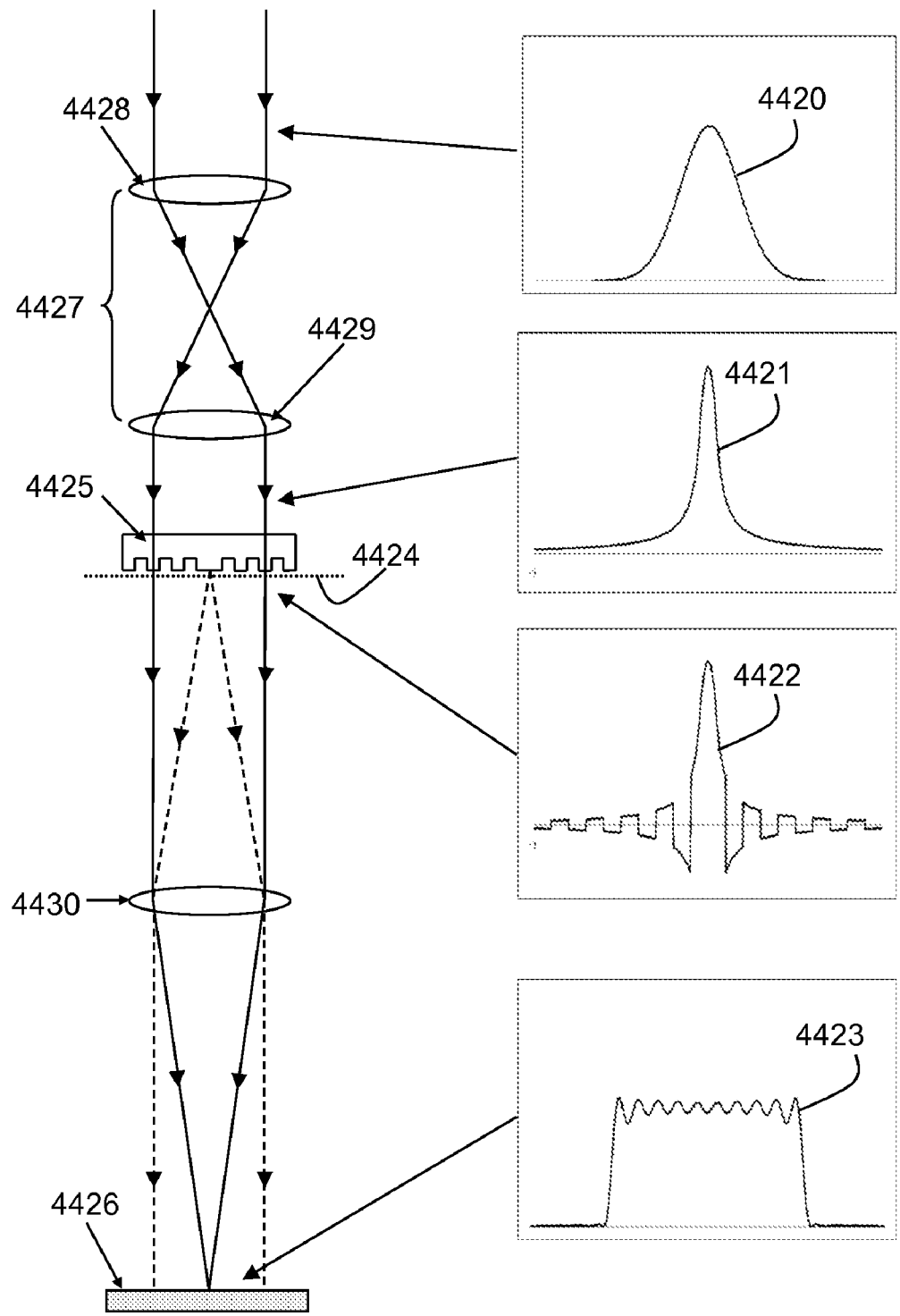

FIG. 44*c* shows a configuration according to another embodiment. It has a transform lens 4430 which transforms the sinc-function-like beam 4422 into a tophat beam at its focal plane 4426. Thus, the function of the transform lens in this design is the same as a long free space propagation path in the previous design. Basically, both free space propagation and the transform lens perform a Fourier transform of the input beam profile. The size of the tophat beam depends on the size of the input beam to the transform lens and also on the focal length of the transform lens; it is inversely proportional to the size of the input beam and proportional to the focal length of the transform lens.

By choosing the right input beam size and/or focal length for the transform lens, the size of the tophat beam at the illumination field can be controlled. A transform lens becomes a valuable alternative to free space propagation when space is too limited to meet the distance requirement of equation (82). If a transform lens needs to have a longer focal length than the physical path length available, a telephoto lens can be used as a transform lens. In the opposite cases where a longer overall length is desired, a reverse-telephoto lens can be used as a transform lens.

In the embodiment of FIG. 44*c*, a lens or lenses are in the beam propagation path. However, the transform lens is simpler and more flexible in its configuration than the image relay lenses needed in the prior art systems. Thus, the embodiments have advantages over the prior art including those employing lenses in the beam propagation path.

Figure 44D:
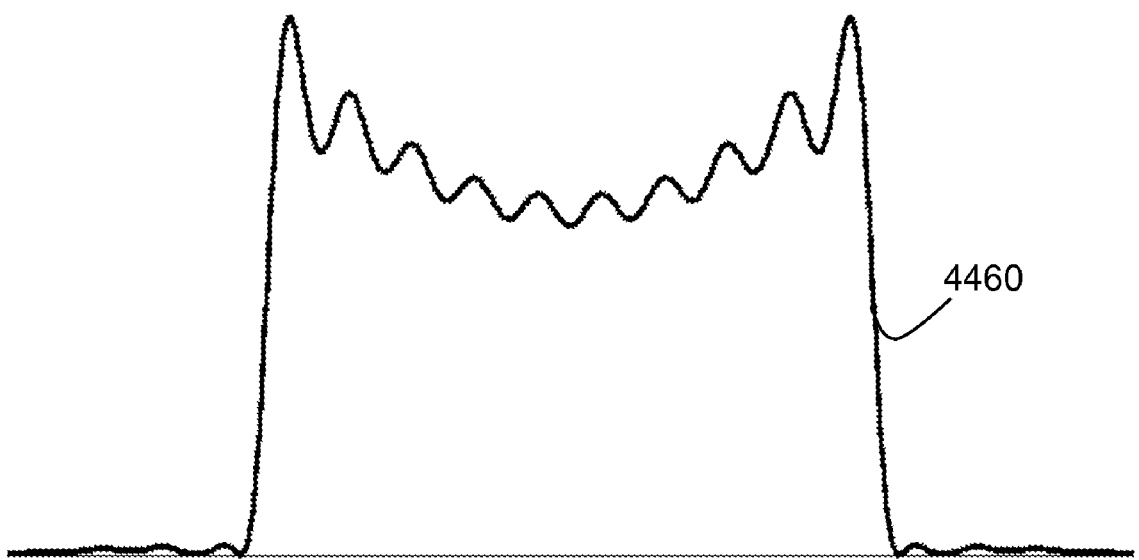

In many practical applications, a higher intensity at the edge of the beam is preferred. This kind of beam is called a "superuniform beam" or a "supertophat beam". FIG. 44*d* shows an example of a superuniform beam profile 4460. The described techniques are well-suited for the generation of a superuniform beam which can be easily generated by shaping the beam profile on the input side of the phase-stepper like an envelope of the Fourier transform of the targeted superuniform beam profile. Actually, the described techniques are so flexible that it can be used for the generation of a wide variety of other beam profiles such as a beam profile with multiple humps.

Figure 44E:
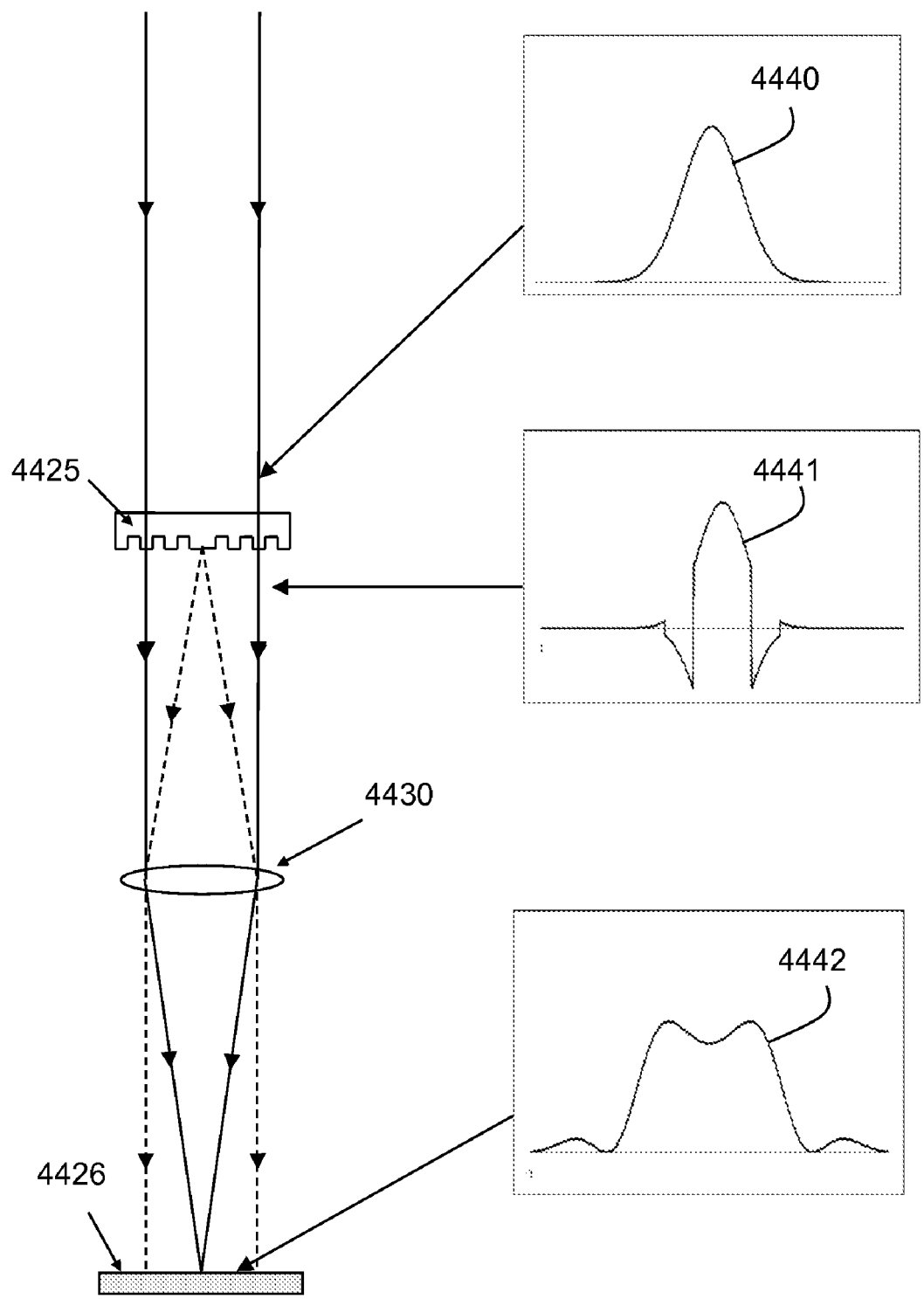

FIG. 44*e* shows the result of trying to achieve a tophat profile without using a beam profile converter. The input gaussian beam, 4440, is passed through a phase-stepper, 4425, which changes the phase without changing the general beam profile as shown by curve 4441. The final result at the illumination field 4426, curve 4442, is preferable to a gaussian profile but not as good as is obtained with a profile converter. This system is simpler because it does not need a beam profile converter. However, the beam at the illumination field is either less uniform and/or less energy-efficient than those shown in FIGS. 44*b* and 44*c*.

So far uniform illumination in one dimension has been considered. However, according to some embodiments, an extension to two dimensional distribution is straightforward because the gaussian beam profile of the input beam is in a separated-variable form. According to these embodiments, the x- and y-directions can be treated completely separately and independently. Thus, these embodiments can be applied to obtain not only one dimensional but also two dimensional illumination distributions.

Figure 44F:
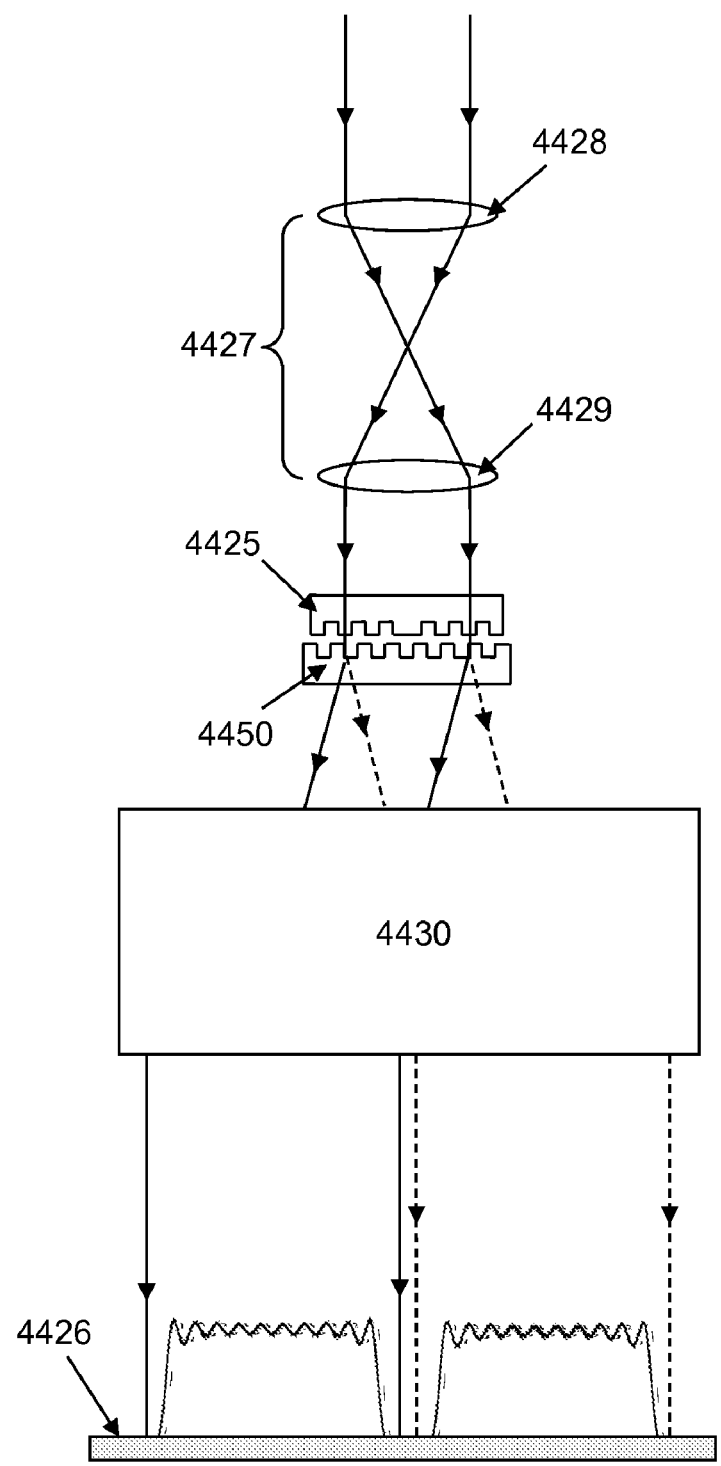

Some applications require illuminating multiple fields simultaneously. Examples are systems with multiple image sensors which are separated spatially. The simultaneous illumination of multiple fields can be achieved easily. FIG. 44*f* shows an example. Multiple field illumination can be achieved by inserting a diffraction grating, 4450, in front of or behind the phase stepper, 4425. The grating diffracts the incoming coherent beam into multiple diffraction orders. Each diffraction order illuminates one field.

FIG. 44*f* shows only two separate illumination fields to illustrate the working principle clearly. However, more than two illumination fields can be achieved easily by inserting a grating which generates more than two diffraction orders or by inserting multiple diffraction gratings. The locations of the illumination fields can be controlled by choosing the pitch and orientation of the grating(s) properly. In FIG. 44*f*, the orientation of the grating is set to be the same as that of phase stepper in order to show the working principle clearly, but, that is not a requirement. The grating orientation can be set to any direction in order to place the illumination fields at predetermined positions.

High energy efficiency and good inter-field uniformity can also be achieved by designing the profile of the grating grooves properly. For example, the depth and shape of the groove can be adjusted to achieve well matched illumination uniformity in each field. Also, extremely high energy efficiency can be achieved by blazing the grating groove profiles.

Thus, energy-efficient, uniform, coherent illumination is provided for multiple as well as single fields. The important features of the present coherent uniform illuminator are summarized below.

1. It can generate a tophat illumination profile without using a relay lens system. A transform lens or transform lens system may be needed. But, a transform lens or lens system is simpler and more flexible than a relay lens system.
2. It can generate other beam profiles such as a superuniform beam profile.
3. It provides more flexibility in illumination system design.
4. Single or multiple field illumination is readily obtained.

2. Autofocus System

Most high resolution imaging systems require at least one autofocus system as a subsystem. The interferometric defect detection system is not an exception. In principle, interferometric defect detection system can be operated without an autofocus system if the environment is quiet and the sample stage is extremely precise. However, these ideal conditions rarely are available in the real world. Therefore, it will be usually preferred to have an autofocus system to insure stable performance of the whole system.

An autofocus system is usually an important subsystem. Its performance is usually crucial to the performance of the whole system. However, performance alone is not the only requirement for an autofocus system. It must fit to an available space. Also, its cost must be reasonable. Described embodiments of the present invention address these issues.

There are a large number of different autofocus systems. But they can be classified into two types; one type is off-the-lens and the other is through-the-lens. Off-the-lens type autofocus systems have their own advantages. However, most high precision imaging systems require through-the-lens type autofocus systems because they are less sensitive to environmental perturbations like temperature changes, atmospheric pressure variations, etc.

Most prior-art, high precision, through-the-lens autofocus systems use incoherent light sources like light-emitting diodes, arc lamps, etc, which are significantly less bright than lasers. The use of less brighter light sources forced the prior art through-the-lens autofocus systems to employ a large etendue in order to be able to provide enough light to the focus signal detectors. The size of the etendue made the autofocus systems not only physically large and expensive but also sensitive to aberrations and misalignments. According to some embodiments of the present invention, lasers are used as light sources. The change of light sources not only provides a higher focus signal but also allows simplification of the whole autofocus system. Other unique features are provided as well.

Figure 45A:
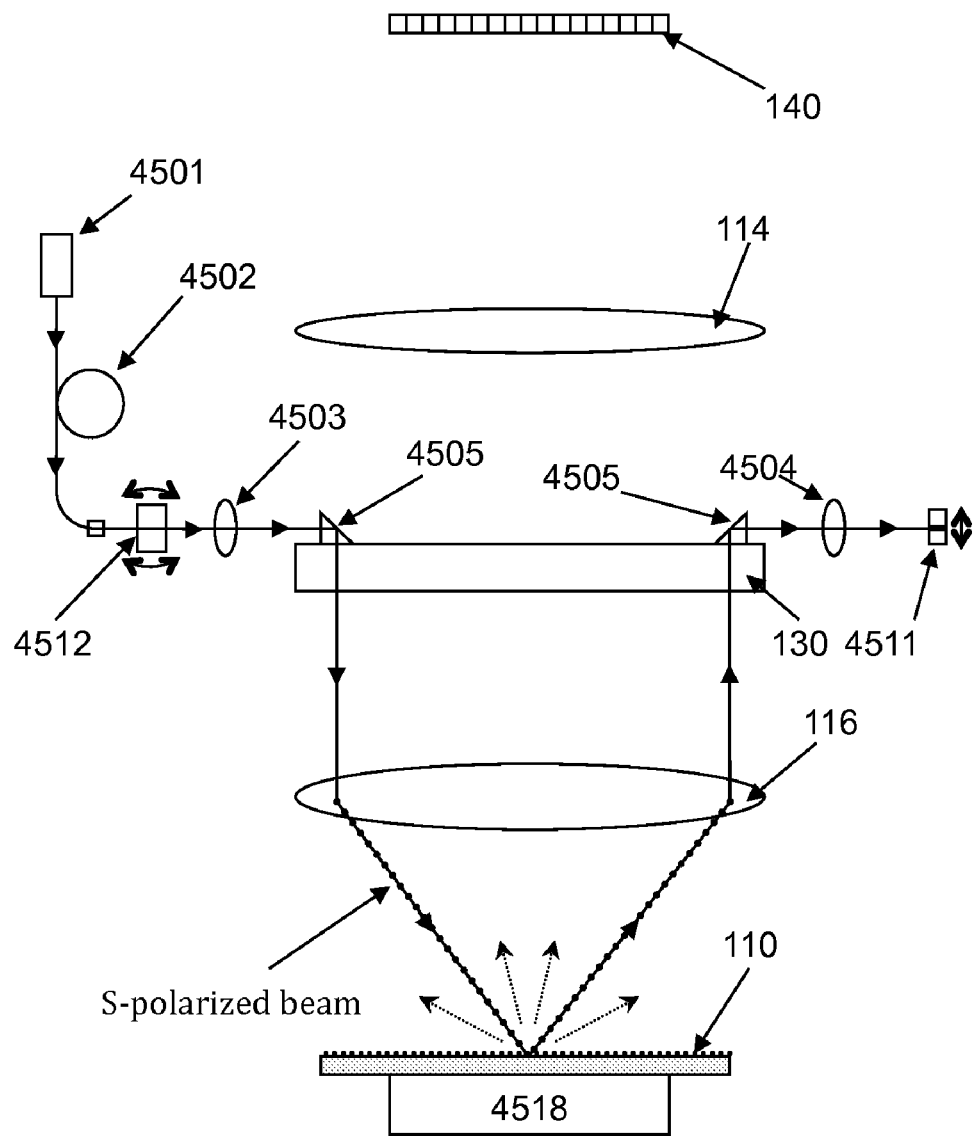
FIGS. 45a through 45f show autofocus system designs.

According to an embodiment, a single channel configuration is shown in FIG. 45*a*, which shows the focus system located relative to the high NA and low NA imaging lens groups 116 and 114 respectively and the compensation plate 130. The focusing system uses a single spatial-mode laser 4501 as a light source. Semiconductor lasers are excellent candidates. However, laser beams are usually not very stable in their position and pointing direction. Because of their inherent instability, it is preferable not to couple lasers directly into an autofocus optical system. Unstable laser beams can introduce errors into the focus signal.

According to some embodiments, lasers are not directly coupled to the autofocus optical system. Instead, the laser beam passes through a long single-mode optical fiber 4502. The single-mode fiber preferably at least a foot long in order to dissipate the cladding modes which are usually excited by an imperfect coupling of the laser light into the fiber. The single-mode optical fiber is a passive device that can stabilize the beam position and pointing direction by converting the original instabilities in the source to an output intensity change which can be calibrated out easily. The variation in beam position and pointing direction changes the coupling efficiency of the laser beam into the single-mode-fiber. The change of coupling efficiency at the input end induces a change of intensity at the output end.

The use of single-mode fiber as a beam stabilizer is an important feature, according to some embodiments. The output end of the fiber is conjugated (or imaged) on the sample plane 110 and on the position sensitive detector (PSD) surface 4511. Because the autofocus ray is focused obliquely on the sample surface by lens 4503, a focal shift of the sample surface causes a lateral movement of the laser beam at the PSD surface 4511. However, a small tilt in the sample moves the beam over the aperture of imaging lens 4504 but does not change its position on the position sensitive detector 4511. Thus the system measures sample focus position but not sample tilt. Thus, by reading the beam position from the PSD, we can determine the amount of focus change of the sample. A computer or controller connected to the PSD reads the PSD output and processes it to estimate the focus error. If the focus error is larger than a predetermined value, the computer or controller takes corrective action by sending an appropriate focus correction signal to the focus actuator 4518. The focus error detection and the corrective action can be run in an open or closed loop. PSDs are readily available and provide a variety of choices.

The described embodiment preferably does not use a beam splitter to couple the autofocus ray into or out of the imaging system. Instead, it uses small prisms (or mirrors) 4505. This method of light coupling has the following advantages over the beam splitter.

1. Simple coupling optics.
2. Takes less space.
3. Less chance of mechanical collisions with other components.
4. Collects specular component only. Rejects scattered light. Note that a portion of the autofocus light can be scattered by the sample. Varying scattered light can cause focus error if it winds up on the focus sensor.
5. Keeps the etendue of the autofocus system small.
6. The aberrations of autofocus optics can be made very small because of the small etendue of the beams.

Therefore, many of the described embodiments are not only expected to perform better but also cost less.

Figure 45B:
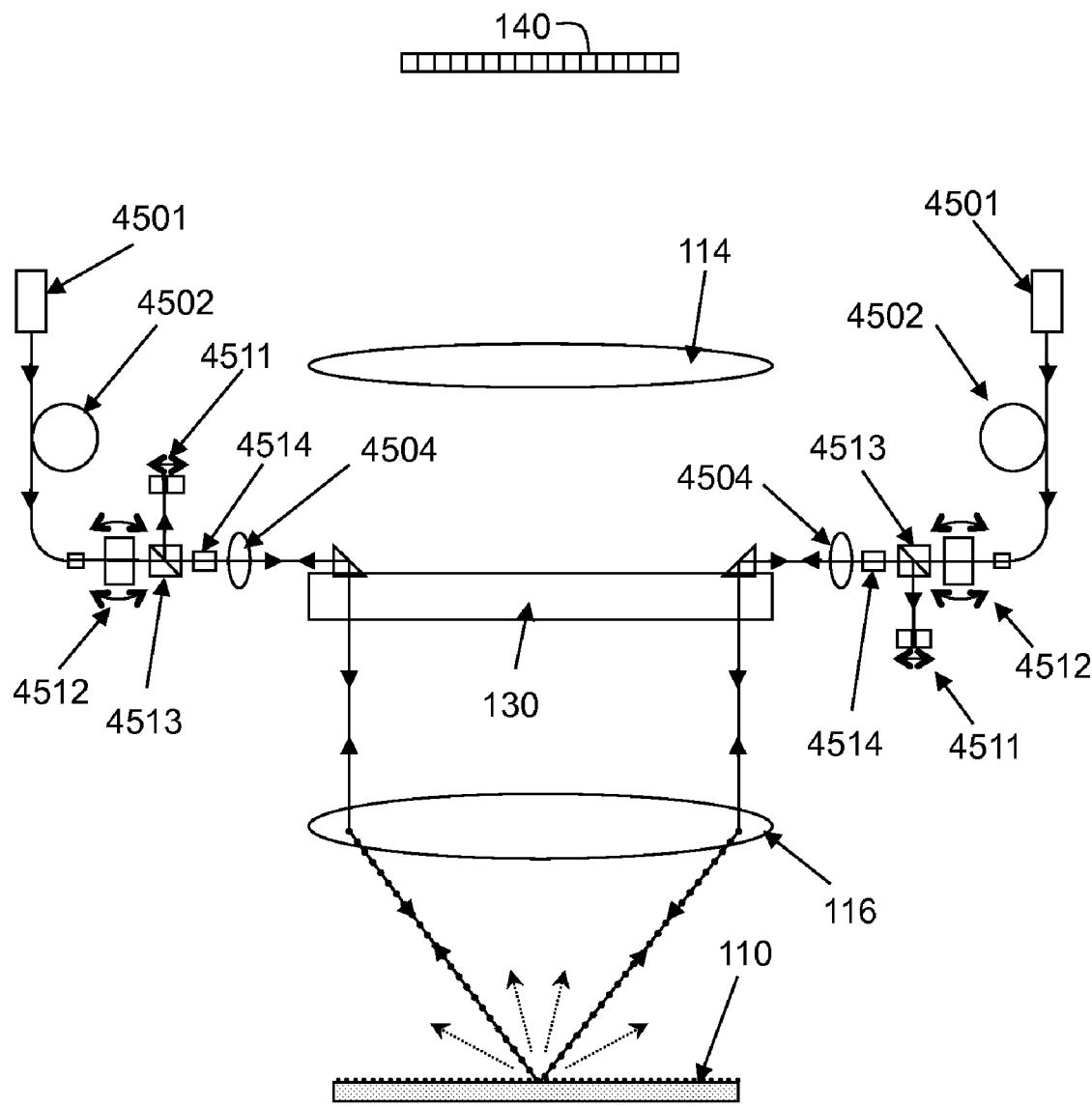
Figure 45C:
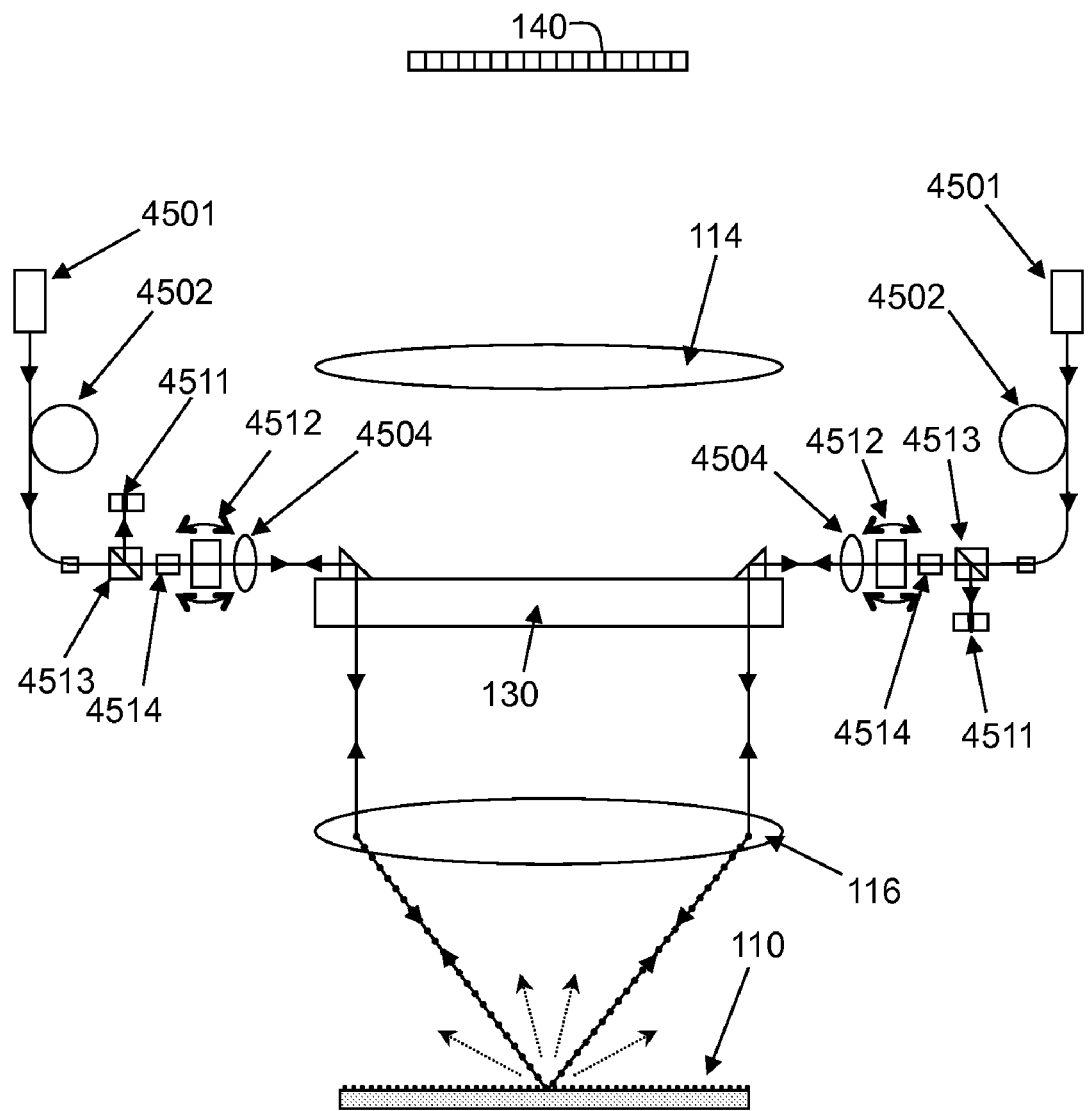

The performance of an autofocus system depends on the choice of polarization significantly. S-polarization, which has the electrical field parallel to the sample surface, has less variation of reflectivity and phase than p-polarization on most samples. This means that s-polarized light can provide more consistent performance than p-polarized light. According to some embodiments, s-polarized light is used as shown in FIG. 45*a* through 45*c*. S-polarization is represented by arrays of circular dots in the beam paths. There are several different ways to ensure that only s-polarized light is picked up from the source. One way is simply to install a polarizer in the beam path. Another way is to use a polarization-preserving single mode fiber between the source laser and the entrance to the autofocus optical system. The polarization-preserving fiber accepts both s- and p-polarizations but transmits one polarization while attenuating the other polarization quickly. By rotating the core of fiber to the correct direction, the polarization-preserving fiber can be made to transmit only s-polarization. If the light coming out from the laser source is polarized, the polarization-preserving single mode fiber can provide significantly higher energy efficiency than other kinds of fibers.

A generic problem of most autofocus systems is that there is a time delay between focus error sensing and its correction due to time delays in the focus signal processor and the slow response of the focus-error correction system. This becomes one of the main focus error sources in high speed scanning systems where a sample is scanned quickly underneath the imaging system. In this case, in order to reduce the focus error, the focus error should be detected in advance of the imaging of the sample and focus error correction signals should be fed-forward to the focus-error correction system.

In order to detect the focus error in advance, the autofocus beam must land on the sample surface at a forward position in the sample scan direction. This requires the autofocus system to shift the autofocus beam position laterally at the sample surface in order to accommodate changes in scan speed and direction. The autofocus beam position at the sample surface can be easily shifted laterally, by laterally moving the output end of the fiber. This method works because, as stated previously, the output end of the fiber is imaged on the sample surface.

If the lateral shift needs to be precisely controlled, a tiltable glass plate 4512 can be used as shown in FIG. 45*a*. The beam can be laterally shifted by tilting the glass plate. If the input beam is shifted, the output beam is shifted a corresponding amount as well. Maintaining the relative position between the beam and the PSD can be done by introducing a tiltable glass plate in front of the PSD or by simply moving the position of the PSD 4511.

A single-channel autofocus system shown in FIG. 45*a* is usually not very stable because it is sensitive to mechanical structure instabilities or temperature changes. One way to reduce this kind of problem is to set up multiple channels in a symmetrical way. The multiple channel autofocus system configured in a symmetrical way can be made to be insensitive to a common mode mechanical shift. FIG. 45*b* shows an example of multi-channel autofocus systems. It has two channels configured in a symmetrical way. The beam position shift at the sample plane is achieved by tilting glass plates 4512. The PSDs are shifted by direct shift mechanisms 4511.

FIG. 45*c* shows another example of a two-channel autofocus system. In this case, both input and output beams are shifted by tilting the glass plates and consequently, the PSDs do not need to be shifted. This configuration uses fewer parts but makes the beam alignments more difficult because the two channels are coupled by sharing the tiltable glass plates.

As shown in FIGS. 45*b* and 45*c*, if the beam path of one channel is overlapped with the beam path of the other channel, beam splitters 4513 are used to direct the return beams to PSDs. However, there are a couple of issues with the use of beam splitters. One issue is the loss of light energy. The use of non-polarizing beam splitters sacrifices at least 75% of the available light energy. Energy loss may be acceptable for most samples but may not be acceptable for samples of very low reflectivity.

Figure 45D:
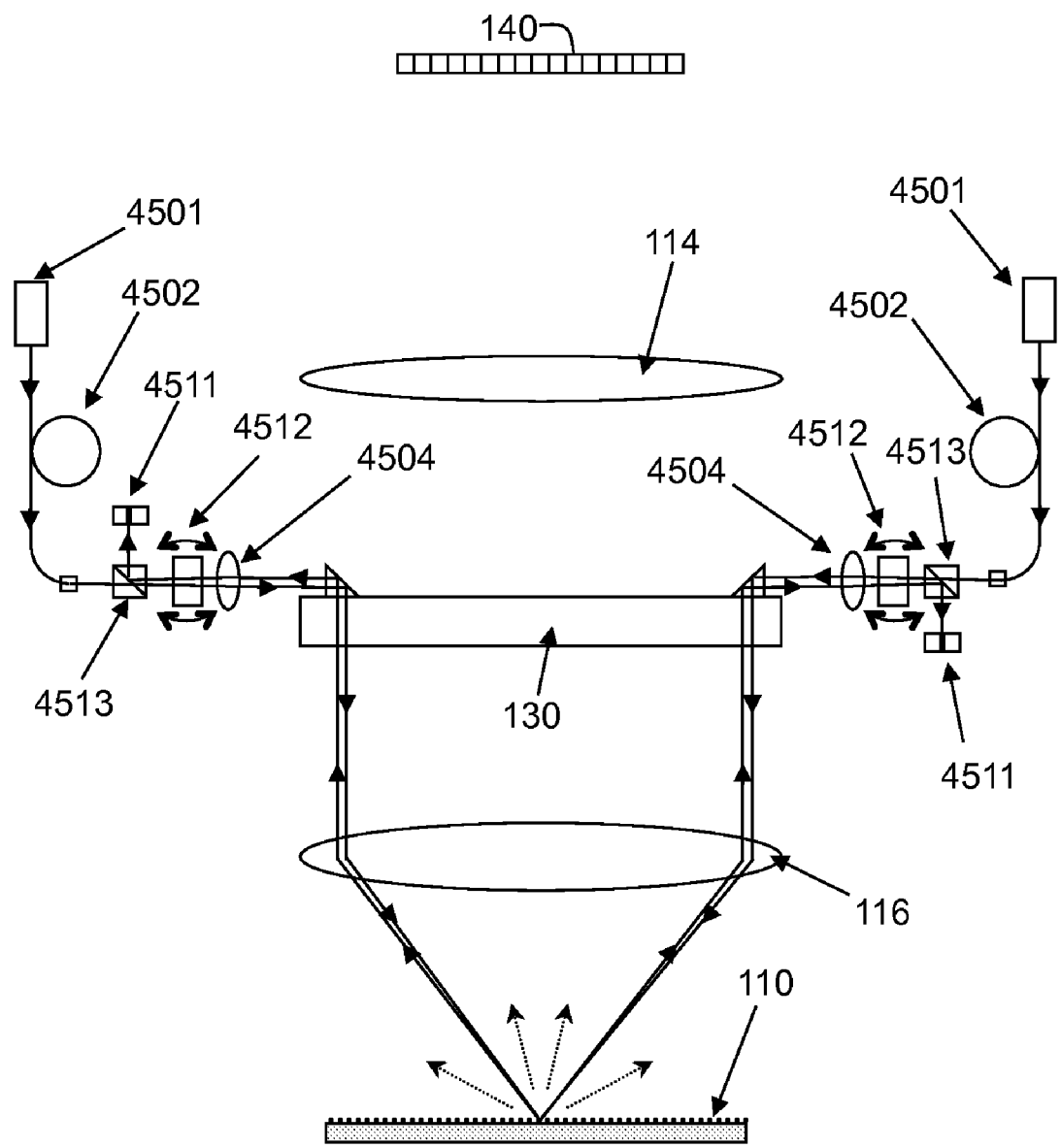

Another issue is that a part of the return beam from one channel enters back into the source laser of the other channel. That is, channels interfere with each other at their sources. This interference destabilizes the source lasers and can cause focus errors. In order to make the source lasers stable, they can be optically isolated from each other. There are two solutions to this problem. One solution is to arrange the beam paths of the two channels so that they do not overlap with each other, as shown in FIG. 45*d*. In this arrangement, the return beam can still hit the core of the optical fiber, however, whenever this happens, the direction of the return beam deviates too far off from the acceptance angle of the single mode fiber for the return beam to be coupled into the fiber.

The other solution is to use polarization beam splitters rather than non-polarizing ones and put Faraday rotators 4514 in the beam paths as shown in FIGS. 45*b* and 45*c*. A polarization beam splitter transmits p-polarization and reflects s-polarization. Therefore, the laser beams that pass through a polarization beam splitter are completely linearly polarized. The Faraday rotators preferably are designed to rotate the angle of the incoming linear polarization by 45°. The beams pass through the Faraday rotators 4514 two times, once in their incoming paths and a second time in their return paths.

Thus, the linear polarization of the laser beams is rotated by 90° by the two Faraday rotators. That is, the originally p-polarized light that passed through the beam splitter in the incoming path is converted into s-polarization at the beam splitter in the return path. The beam splitter in the return path reflects the whole beam toward the PSD and does not transmit the return laser beam toward source laser. Thus, Faraday rotators isolate the source lasers from each other. If the beam splitters 4513 and position sensitive detectors 4511 are rotated properly about the beam axis, the laser beams can be 100% s-polarized when they are incident on the sample. Thus, this method allows us to achieve high energy efficiency, no inter-channel interference and s-polarization on sample surface at the same time.

The use of quarter-wave plates instead of Faraday rotators allows us to achieve high energy efficiency and no inter-channel interference. But it does not allow us to achieve s-polarization on the sample surface. Therefore, Faraday rotators are the preferred choice in many embodiments as compared to quarter-wave plates.

Figure 45E:
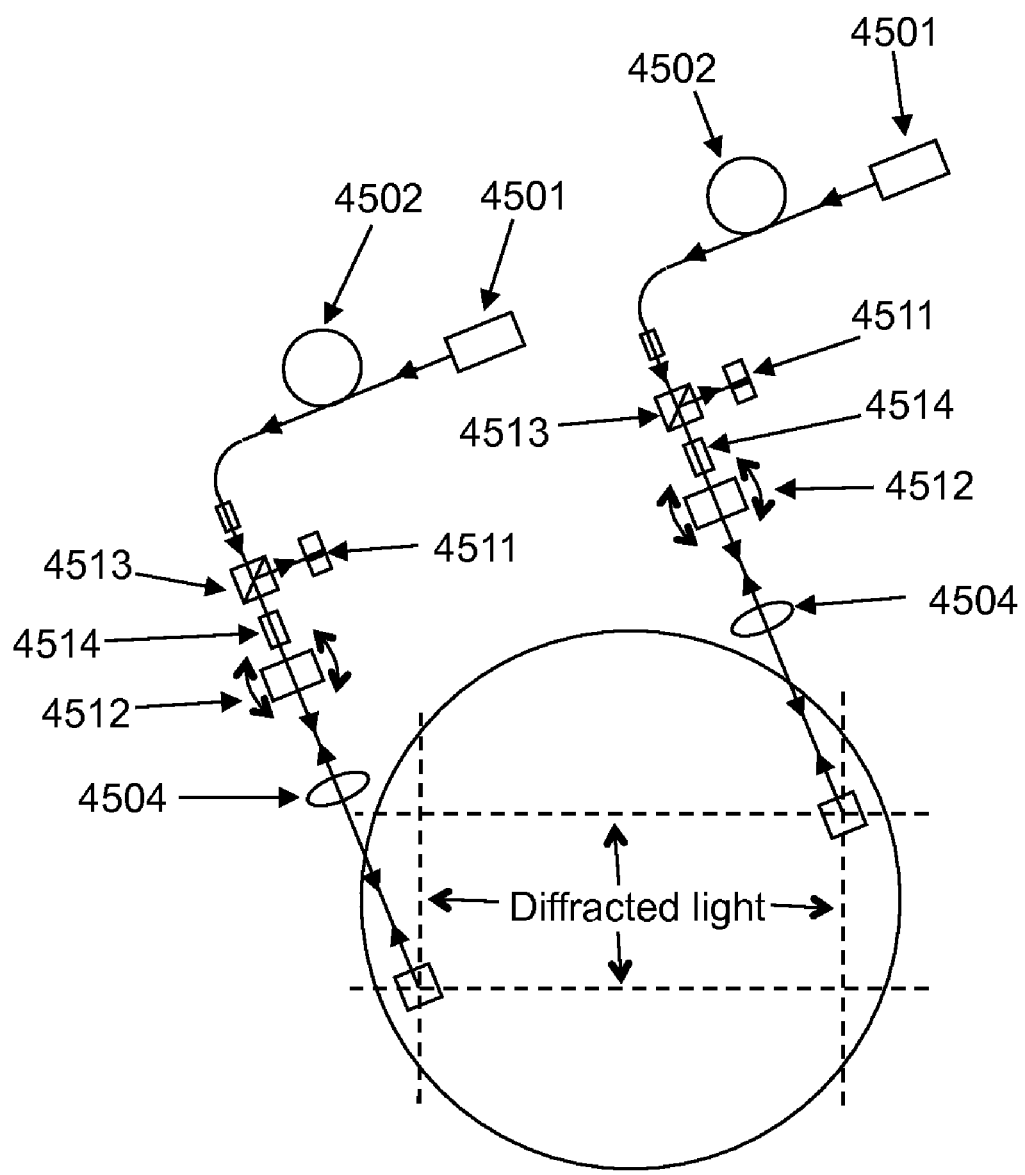

FIG. 45*e* shows the top view of a two-channel autofocus system. The autofocus channels are rotated relative to the sample in order to avoid light from either laser which is diffracted from the sample entering into the outgoing beam path. This method is usually very effective in avoiding diffracted light from the sample because diffracted light is usually very localized in the x- and y-directions at the pupil plane.

In FIG. 45*e*, the two channels are placed close to each other. If there is mechanical drift or creeping, two channels placed close to each other are likely to drift or creep in the same direction. The focus signal extracted from multiple channels can be made insensitive to this kind of common-mode motion of the channels.

Figure 45F:
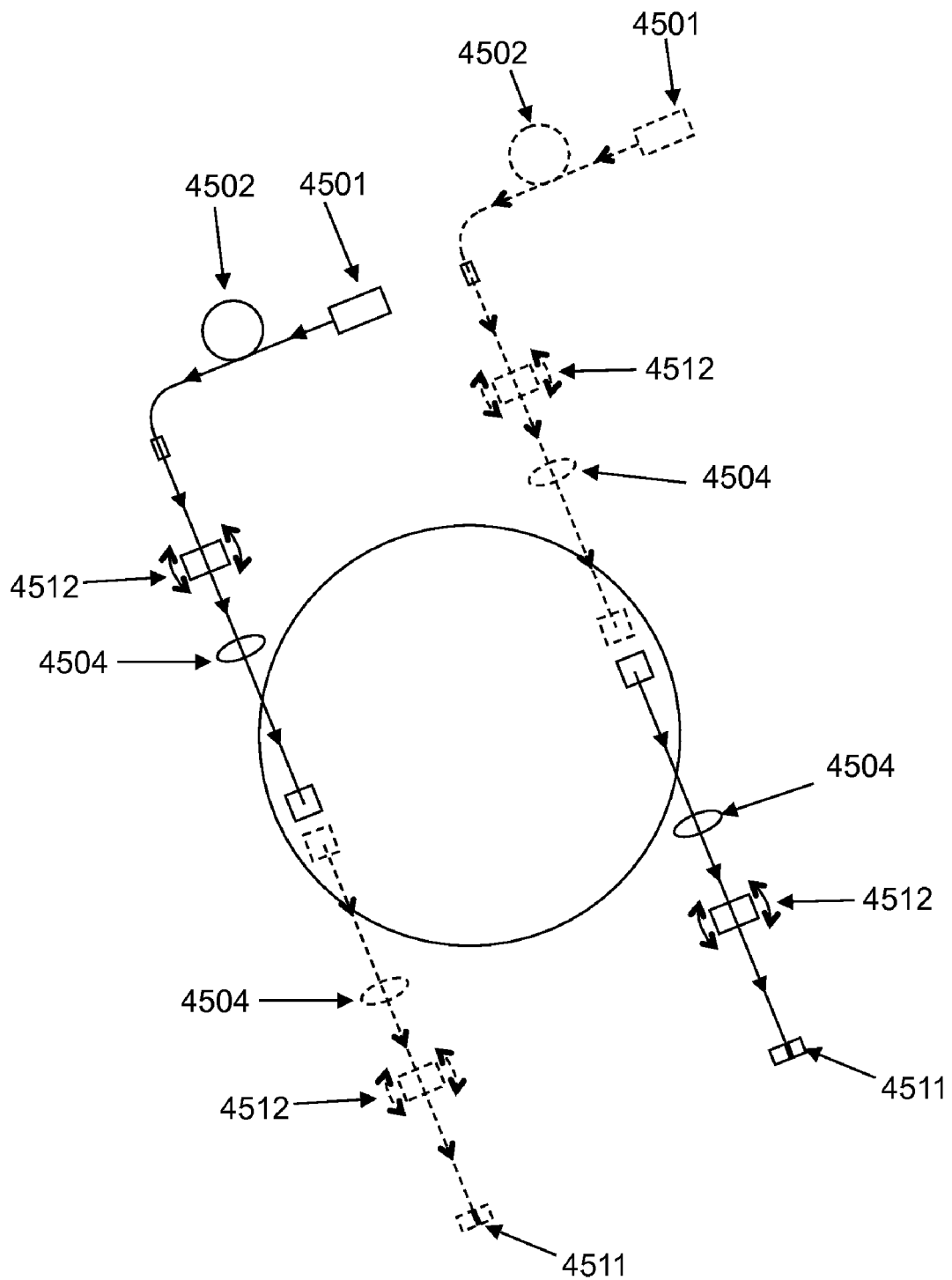

FIG. 45*f* shows another example of a multi-channel configuration. In this case, the optical paths of the two channels cross over at the focus point on the sample but otherwise are completely separated. This configuration requires more parts but is more energy-efficient and also does not require Faraday rotators. Also, the beam path alignments will be easier with this configuration because the two channels are not coupled at all. As shown in the example configurations, the embodiments not only perform better but also are simpler and more flexible in its physical arrangement.

The important features of new autofocus system are summarized below.
1. Through-the-lens configuration.
2. Lasers as light sources.
3. Single ray (small etendue).
4. Source stabilization by the use of single mode fiber.
5. S-polarization on sample surface.
6. No inter-channel interference.
7. Coupling into and out of the imaging system using small prisms or mirror. (No beam splitter/combiner for this purpose.)
8. Good rejection of diffracted light.
9. Capabilities to laterally shift the laser spot at the sample plane for feed-forward focus error correction.
10. Symmetrical dual or multiple channels arranged so as to have less sensitivity to environmental disturbances.

The advantages of new autofocus system are summarized below.
1. Simple system.
2. Plenty of light.
3. High efficiency.
4. Stable performance
5. Less sensitivity to wafer patterns.
6. Less impact to the imaging path.
3. Serrated Aperture Most optical systems require at least one aperture that defines the numerical aperture. Most apertures are made of a thin metal plate with a sizable hole in the middle. These kinds of apertures are easy to produce, however, the sharp edges on these apertures produce a long-range diffraction in the image plane, which in turn causes long-range interferences between the different parts of the image. Long-range interference is one of the major contributors to wafer pattern noise.

In order to reduce this undesirable effect, the aperture edges preferably are softened. That is, the transition between the 100% transmission area and no transmission area should not be abrupt but gradual. A gradual transition can be achieved in many different ways. Aperture edge serration is one of them. An aperture edge serration method is chosen because it has many advantages over other methods if it is done correctly. One advantage is that serrations can be made easily; they can be machined directly into a thin metal plate or they can be created by etching using conventional semiconductor fabrication techniques.

One of the most straightforward ways to make a gradually-transiting aperture is by adding a gradual absorbing coating close to the edges of the aperture. This method is a well-known prior art. However, this method is easy in concept but difficult in practice because a gradual coating is difficult to produce properly and also the coating can introduce undesirable side effects; phase changes in particular. Another prior art uses a negative power lens made with an absorbing material. The effect is very similar to that of the gradual coating. However, it has the same kind of undesirable side effect.

U.S. Pat. No. 6,259,055 talks about the serrated aperture. But it does not provide any diffraction formula that can be used to correctly design a serrated aperture. Also, its qualitative statement about the diffraction property of the serrated aperture is incorrect. According to some embodiments of the present invention, a rigorous diffraction formula is developed for the serrated aperture and uses it to figure out how to make serrated apertures correctly.

Figure 46A:
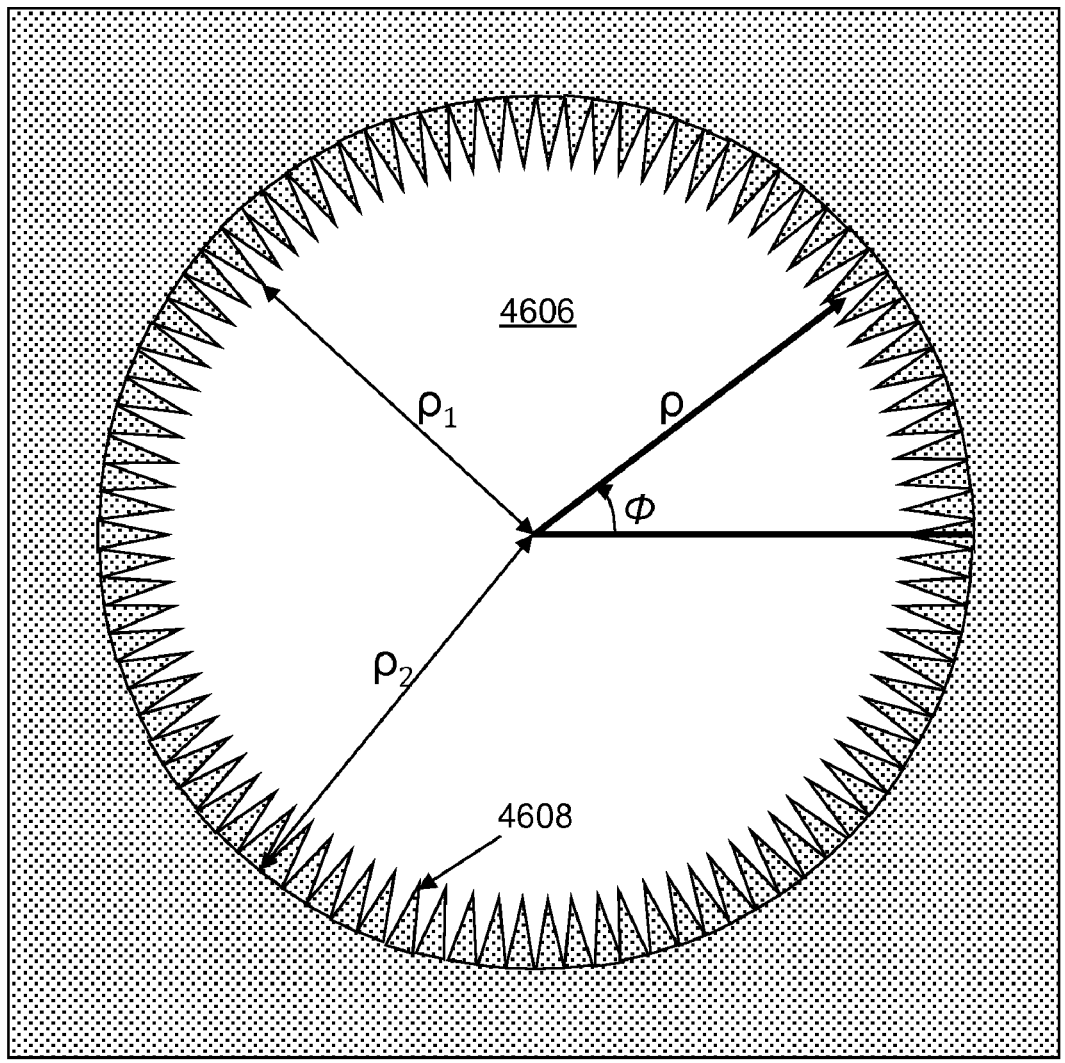
FIGS. 46a through 46e show serrated aperture and its performances.

A schematic diagram of the serrated aperture is shown in FIG. 46a. The serrations of aperture 4606 have periodic structures 4608, not random pitches. Serrations of non-periodic or random structures are not considered in this patent specification because their diffraction patterns do not have desirable forms. Even with perfectly periodic structures, a large amount of diffraction is unavoidable because of sudden transmission changes of the serration edges.

However, the diffraction pattern from periodic serrations can be broken into discrete orders. The lowest order, the zeroth order, originates from the circular average of the transmitted field and consequently is not affected by the sharp edges of the serrations. This means that the diffraction pattern of zeroth order is the same as that from a truly gradually-transiting aperture. Thus, the diffraction pattern of zeroth order is what we want to get from the serrated aperture.

Truly gradually-transiting apertures produce only a zeroth order diffraction. But serrated apertures produce not only zeroth order but also higher diffraction orders. These higher orders are undesirable. In order to make the serrated aperture work like a truly gradually-transiting aperture, we should seek to make sure only the zeroth order passes to the image sensor and all higher diffraction orders miss the image sensor. In the case of linearly-periodic serrations, it is easy to determine if all higher diffraction orders miss the image sensor or not. (Reference: U.S. Pat. No. 7,397,557.) However, in the case of the circularly-periodic serrations, it is not so easy to determine where all the higher diffraction orders go. Thus, we should develop a rigorous diffraction formula to predict where all higher orders go.

The following notations are used in all the equations below.
($\rho,\phi$): Polar coordinates in the aperture plane
($r,\theta$): Polar coordinates in the image plane $$circ(\rho) \equiv \begin{cases} 1 & \text{for } 0 \leq \rho \leq 1 \\ 0 & \text{for } 1 < \rho \end{cases} \text{:Circle function}$$

$$rect(\phi) \equiv \begin{cases} 1 & \text{for } -0.5 \leq \phi \leq 0.5 \\ 0 & \text{for } \phi < -0.5 \text{ or } 0.5 < \phi \end{cases} \text{:Rectangle function}$$

$J_k(r)$: kth order Bessel function of first kind
N: Total number of serrations
$\mathfrak{F}$: Fourier transform operator The far field diffraction pattern produced by an object is the Fourier transform of the object's transmission pattern. However, in order to apply the Fourier transform for the calculation of diffraction by a serrated aperture, the coordinates $\rho$ and r should be scaled properly. There are two lengths that can be used as the scaling units. These are the wavelength and the focal length of the optical system. In order for $\rho$ and r to be a Fourier transform variable pair, if one of $\rho$ and r is scaled with wavelength, the other should be scaled with the focal length. The most popular scaling convention is that $\rho$ is scaled with the focal length and r with the wavelength.

If $\rho$ is expressed with the unit of focal length, it becomes identical with the image space direction cosine of the ray that passes through the pupil point at $\rho$ from the center. The maximum value of $\rho$, expressed in focal length units, is called the numerical aperture (NA) of the optical system. In other words, the image space position coordinate expressed with the wavelength unit and the image space ray direction cosine constitute a convenient Fourier transform variable pair. Changing the scaling convention to the other way, i.e., $\rho$ scaled with wavelength and r scaled with the focal length, works too. In this case, r becomes identical with the aperture space direction cosine of the ray that lands at r in the image plane. The two conventions are equivalent.

The diffraction formula derived uses properly scaled coordinate systems. The diffraction formula does not change when the coordinate scaling is switched between the two conventions. Therefore, the reader can switch between the two scaling conventions freely without worrying about a change in the diffraction formula. Switching the scaling convention is actually equivalent to changing the interpretation of the coordinate variables. Such a change of interpretation can provide more intuition to the diffraction formula.

The diffraction formula will be derived for coherent normal illumination only. This is because the diffraction for an incoherent case is just the intensity summation of multiple coherent cases and the diffraction formula for an oblique illumination case can be immediately derived from a normal illumination case using the "shift theorem" of the Fourier transform. (Reference: "Introduction to Fourier Optics, Third edition", Joseph W. Goodman, Roberts & Company, Englewood, Colo., 2005, page 8.) Serrations can have a variety of different tooth shapes. The details of the diffraction pattern depend on the shape of the teeth. FIG. 46a shows serrations with linear teeth as an example. However, the properties of each diffraction order which are of the most concern do not depend on the shape of the serration teeth but depend on the serration pitch only.

$P(\rho,\phi)$, the amplitude transmission of a serrated aperture, can be expressed as follows.

$$P(\rho, \phi) = \begin{cases} circ\left(\dfrac{\rho}{\rho_1}\right) & \text{for } 0 \leq \rho \leq \rho_1 \\ \displaystyle\sum_{n=1}^{N} rect\left(\dfrac{\phi - \dfrac{2\pi n}{N}}{w(\rho)\dfrac{2\pi}{N}}\right) & \text{for } \rho_1 < \rho \leq \rho_2 \\ 0 & \text{for } \rho_2 < \rho \end{cases} \quad (83)$$

where $w(\rho)$ is the width of opening between two neighboring serration teeth

We need to Fourier-transform equation (83) in order to get the diffraction pattern. If $P(\rho,\phi)$ has a separated-variable form, i.e., $P(\rho,\phi)=f(\rho)\cdot g(\phi)$, we can Fourier-transform it easily using the Weighted Hankel Transform. (Reference: "Introduction to Fourier Optics, Third edition", Joseph W. Goodman, Roberts & Company, Englewood, Colo., 2005, page 10.) Unfortunately, the form of $P(\rho,\phi)$ is not in a separated-variable form. However, we can still Fourier-transform it by taking a few extra steps. There are two ways to do it. One way is to express the sum of N rectangle functions with the weighted sum of exp(jm$\phi$) functions where m is an integer and to follow the process suggested in exercise problem 2-7 in the same reference book. The other way is to convert the sum of N rectangle functions into the integration of separated-variable functions and use the Weighted Hankel Transform.

Both methods are exact and produce the same result, although only the second method is shown herein.

The sum of N rectangle functions can be converted easily into the integration of separated-variable functions using a delta function and a dummy variable $\rho'$. That is:

$$\sum_{n=1}^{N} rect\left(\frac{\phi - \frac{2\pi n}{N}}{w(\rho)\frac{2\pi}{N}}\right) = \int \delta(\rho' - \rho) \sum_{n=1}^{N} rect\left(\frac{\phi - \frac{2\pi n}{N}}{w(\rho')\frac{2\pi}{N}}\right) d\rho' \quad (84)$$

Then, $P(\rho,\phi)$ is converted to the following form.

$$P(\rho, \phi) = \begin{cases} circ\left(\frac{\rho}{\rho_1}\right) & \text{for } 0 \leq \rho \leq \rho_1 \\ \int_{\rho_1}^{\rho_2} \delta(\rho' - \rho) \sum_{n=1}^{N} rect\left(\frac{\phi - \frac{2\pi n}{N}}{w(\rho')\frac{2\pi}{N}}\right) d\rho' & \text{for } \rho_1 < \rho \leq \rho_2 \\ 0 & \text{for } \rho_2 < \rho \end{cases} \quad (85)$$

Now, we apply Fourier-transform to each term of $P(\rho,\phi)$. The Fourier transform of first term can be obtained using the Fourier-Bessel Transform.

$$\Im\left\{circ\left(\frac{\rho}{\rho_1}\right)\right\} = \frac{\rho_1 J_1(2\pi\rho_1 r)}{r} \quad (86)$$

The Fourier transform of second term can be obtained using Weighted Hankel Transform:

$$\Im\left\{\delta(\rho' - \rho) \sum_{n=1}^{N} rect\left(\frac{\phi - \frac{2\pi n}{N}}{w(\rho')\frac{2\pi}{N}}\right)\right\} = \quad (87)$$

$$\sum_{k=-\infty}^{\infty} c_k (-j)^k \exp(jk\theta) H_k\{\delta(\rho' - \rho)\}$$

where:

$$c_k \equiv \frac{1}{2\pi} \int_0^{2\pi} \sum_{n=1}^{N} rect\left(\frac{\phi - \frac{2\pi n}{N}}{w(\rho')\frac{2\pi}{N}}\right) \exp(-jk\phi) d\phi \quad (88)$$

$$= \frac{1}{2\pi} \sum_{n=1}^{N} \int_0^{2\pi} rect\left(\frac{\phi - \frac{2\pi n}{N}}{w(\rho')\frac{2\pi}{N}}\right) \exp(-jk\phi) d\phi \quad (89)$$

and $$H_k\{f(\rho)\} \equiv 2\pi \int_0^{\infty} \rho f(\rho) J_k(2\pi\rho r) d\rho: \text{Hankel transform} \quad (90)$$

The transform of the rectangle function in equation (89) can be carried out as follows:

$$\int_0^{2\pi} rect\left(\frac{\phi - \frac{2\pi n}{N}}{w(\rho')\frac{2\pi}{N}}\right) \exp(-jk\phi) d\phi = \quad (91)$$

$$\int_{\frac{2\pi n}{N} - w(\rho')\frac{\pi}{N}}^{\frac{2\pi n}{N} + w(\rho')\frac{\pi}{N}} \exp(-jk\phi) d\phi = \frac{2}{k} \exp\left(-jk\frac{2\pi n}{N}\right) \sin\left(w(\rho')\frac{k\pi}{N}\right)$$

Now, $c_k$ can be expressed as follows:

$$c_k = \frac{1}{2\pi} \sum_{n=1}^{N} \frac{2}{k} \exp\left(-jk\frac{2\pi n}{N}\right) \sin\left(w(\rho')\frac{k\pi}{N}\right) \quad (92)$$

$$= \frac{1}{\pi k} \sin\left(w(\rho')\frac{k\pi}{N}\right) \sum_{n=1}^{N} \exp\left(-jk\frac{2\pi n}{N}\right)$$

$$= \begin{cases} \frac{N}{\pi k} \sin\left(w(\rho')\frac{k\pi}{N}\right) = \frac{1}{m\pi} \sin(m\pi \cdot w(\rho')) \text{ for} \\ k = mN \text{ where } m = \text{integer} \\ 0 \text{ for } k \neq mN \end{cases}$$

The Hankel transform of a delta function becomes:

$$H_k\{\delta(\rho' - \rho)\} \equiv 2\pi \int_0^{\infty} \rho \delta(\rho' - \rho) J_k(2\pi\rho r) d\rho = 2\pi\rho' J_k(2\pi\rho' r) \quad (93)$$

Now, equation (87) can be expressed as follows:

$$\Im\left\{\delta(\rho' - \rho) \sum_{n=1}^{N} rect\left(\frac{\phi - \frac{2\pi n}{N}}{w(\rho')\frac{2\pi}{N}}\right)\right\} = \quad (94)$$

$$\sum_{m=-\infty}^{\infty} \frac{2}{m} \sin(m\pi \cdot w(\rho'))(-j)^{mN} \exp(jmN\theta) \rho' J_{mN}(2\pi\rho' r)$$

The Fourier transform of $P(\rho,\phi)$ can now be expressed as follows: (The dummy integration variable $\rho'$ was now changed to $\rho$.)

$$\Im\{P(\rho, \phi)\} = \quad (95)$$

$$\frac{\rho_1 J_1(2\pi\rho_1 r)}{r} + \int_{\rho_1}^{\rho_2} \left[\sum_{m=-\infty}^{\infty} \frac{2}{m} \sin(m\pi \cdot w(\rho))(-j)^{mN} \exp(jmN\theta) \rho J_{mN}(2\pi\rho r)\right] d\rho =$$

$$\frac{\rho_1 J_1(2\pi\rho_1 r)}{r} + \sum_{m=-\infty}^{\infty} \frac{2}{m \cdot j^{mN}} \exp(jmN\theta) \int_{\rho_1}^{\rho_2} [\sin(m\pi \cdot w(\rho))\rho J_{mN}(2\pi\rho r)]d\rho$$

Equation (95) shows that whole diffraction is composed of discrete diffraction orders. If we take out the zeroth order from the second term, then:

$$\Im\{P(\rho,\phi)\} = \frac{\rho_1 J_1(2\pi\rho_1 r)}{r} + 2\pi \int_{\rho_1}^{\rho_2} w(\rho)\rho J_0(2\pi\rho r)d\rho + \qquad (96)$$

$$\sum_{\substack{m=-\infty \\ m\neq 0}}^{\infty} \frac{2}{m \cdot j^{mN}} \exp(jmN\theta) \int_{\rho_1}^{\rho_2} [\sin(m\pi \cdot w(\rho))\rho J_{mN}(2\pi\rho r)]d\rho$$

If we combine the +m diffraction order with the −m diffraction order into a single diffraction order using the relationships, sin(−x)=−sin(x) and $$J_{-n}(x) = (-1)^n J_n(x), \text{ then:} \qquad (97)$$

$$\Im\{P(\rho,\phi)\} = \frac{\rho_1 J_1(2\pi\rho_1 r)}{r} + 2\pi \int_{\rho_1}^{\rho_2} w(\rho)\rho J_0(2\pi\rho r)d\rho +$$

$$\sum_{m=1}^{\infty} \frac{4}{m \cdot j^{mN}} \cos(mN\theta) \int_{\rho_1}^{\rho_2} [\sin(m\pi \cdot w(\rho))\rho J_{mN}(2\pi\rho r)]d\rho$$

Equation (97) is the final result of the derivation of the diffraction formula. Unfortunately, it still has a one-dimensional integration that needs to be carried out numerically. However, a numerical one-dimensional integration can be done much more accurately and quickly than the numerical two-dimensional integration that is required for the numerical two-dimensional Fourier transform.

The first two terms in equation (97) constitute the zeroth diffraction order, which is what we want to have from the serrated aperture. If we write down the zeroth diffraction order separately:

$$\text{Zeroth diffraction order} = \frac{\rho_1 J_1(2\pi\rho_1 r)}{r} + 2\pi \int_{\rho_1}^{\rho_2} w(\rho)\rho J_0(2\pi\rho r)d\rho \qquad (98)$$

The last term in equation (97) is all higher diffraction orders which we have to exclude from the image sensor. However, we do not need to care about all nonzero diffraction orders because only the first diffraction order is strongest and comes closest to the zeroth order at the image plane. All other higher orders are not only weaker than the first order but also, more importantly, land further away from the zeroth order at the image plane than the first order. Therefore, in order to make the serrated aperture work, we need to take a look at only the first diffraction order and make sure it lands outside the image sensor. If we take out the first diffraction order from the last term in equation (97), then:

$$\Im\{P(\rho,\phi)\} = \frac{\rho_1 J_1(2\pi\rho_1 r)}{r} + 2\pi \int_{\rho_1}^{\rho_2} w(\rho)\rho J_0(2\pi\rho r)d\rho + \qquad (99)$$

$$(-j)^N 4\cos(N\theta) \int_{\rho_1}^{\rho_2} [\sin(\pi \cdot w(\rho))\rho J_N(2\pi\rho r)]d\rho + \text{Second}$$

and higher diffraction orders

The first order term has its maximum strength along the directions where cos(Nθ)=±1. Therefore, its amplitude along the directions of maximum strength becomes:

$$\text{Max first order amplitude} = 4\int_{\rho_1}^{\rho_2} [\sin(\pi \cdot w(\rho))\rho J_N(2\pi\rho r)]d\rho \qquad (100)$$

In order to make the serrated aperture work, it is sufficient to make sure that the first diffraction order lands outside of the image.

Both the sharp edges of the aperture and any sharp edges of any obscuration can produce long range diffraction effects. The same serration technique used for apertures can be applied to obscurations in order to reduce long range diffraction effects by any obscuration. Thanks to Babinet's principle, the diffraction formula for a serrated obscuration is identical to that for the serrated aperture except for the reversal of the amplitude sign. (Reference: "Principles of Optics", Max Born and Emil Wolf, Cambridge University Press, 1999.) Therefore, no new derivation of diffraction formula for obscurations is needed.

The analytical diffraction formula is so general it can be applied to serrations with any teeth shape. However, we still should do numerical evaluations of the formula to see the behavior of the diffraction pattern. In order to carry out numerical calculation of the diffraction formula, we pick a specific shape of serration teeth and express the function w(ρ) explicitly. The serrations with linear tooth shape as shown in FIG. 46a perform well and are easy to manufacture. Therefore, serrations with linear tooth shape are chosen for the numerical evaluations of the diffraction pattern. In the case of linear serration teeth, the function w(ρ) is expressed as follows:

$$w(\rho) = \frac{\rho_2 - \rho}{\rho_2 - \rho_1} \qquad (101)$$

The diffraction pattern from a serrated aperture with teeth of other shapes can be as easily evaluated as for the linear tooth case by just changing the function w(ρ) properly in the diffraction formula. As stated previously, we need to take a look at only zeroth and first diffraction orders to be able to design a serrated aperture properly. We therefore consider the zeroth order and first order only herein.

Figure 46B:
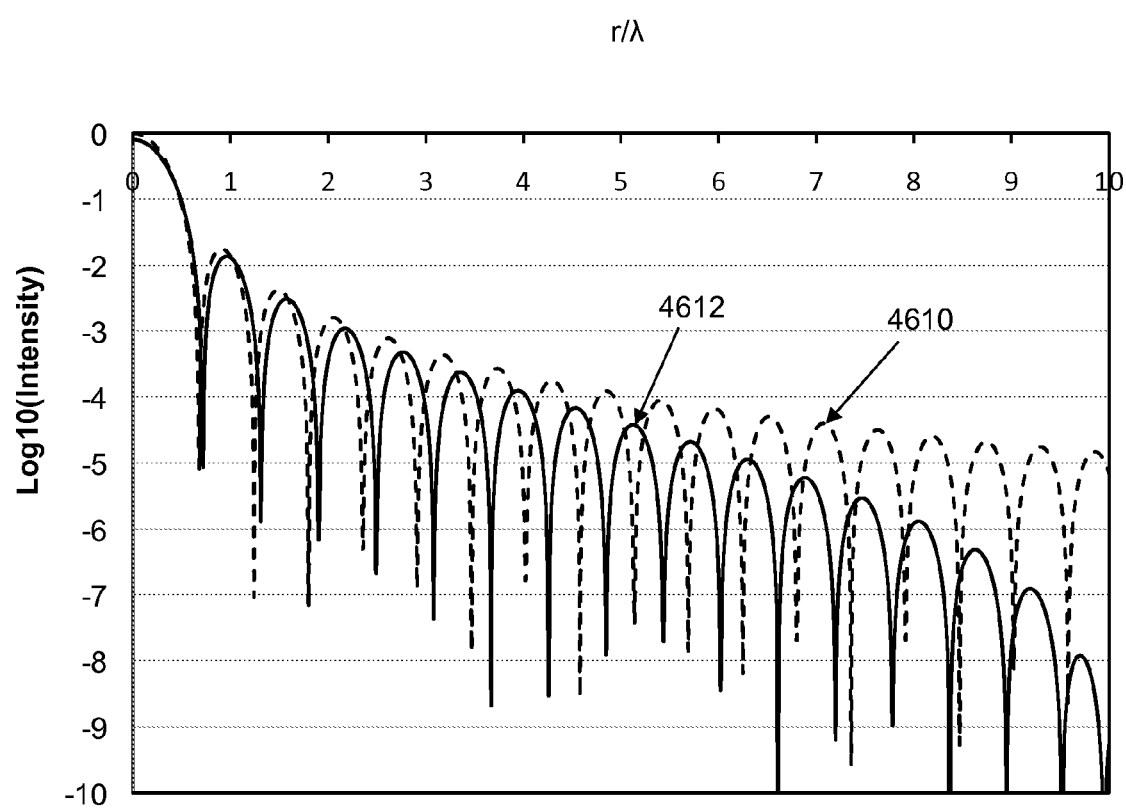
Figure 46C:
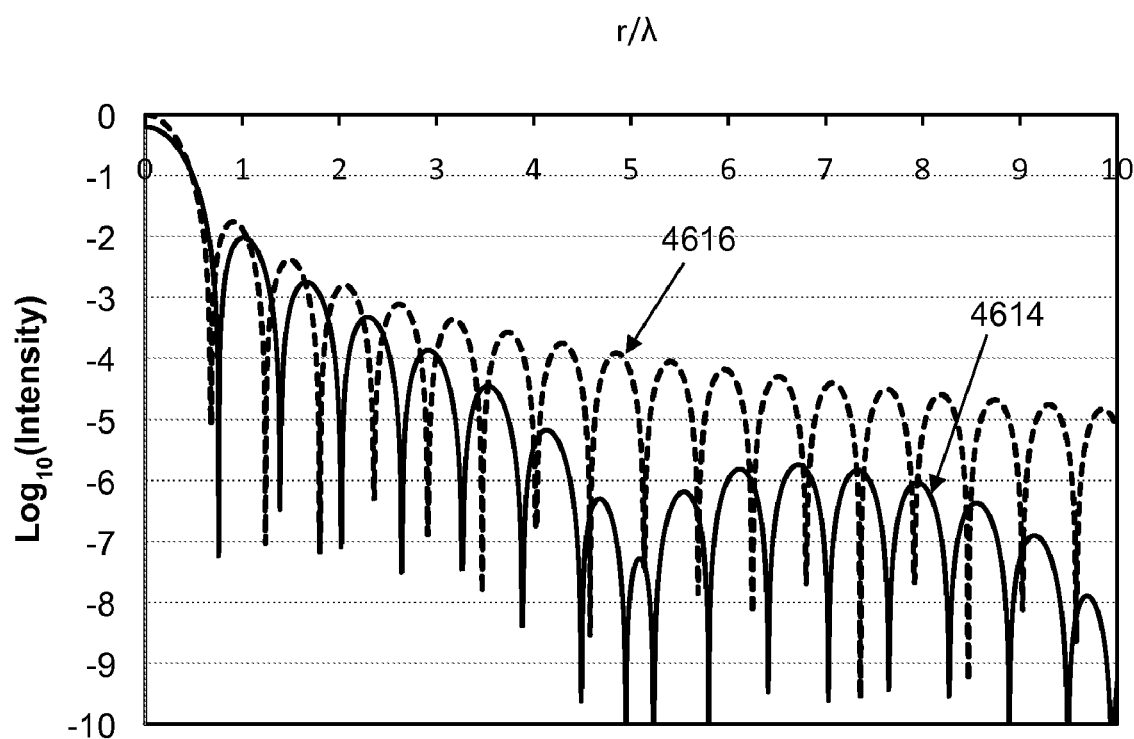

FIGS. 46b and 46c show the radial distribution of the intensity of the zero diffraction order at image plane. Equations (98) and (101) were used for numerical calculations. The values were normalized with the peak amplitude of the diffraction by an un-serrated aperture. The peak amplitude is located at the center of the diffraction pattern (r=0) and its value is:

$$\lim_{r\to 0} \Im\left\{circ\left(\frac{\rho}{\rho_2}\right)\right\} = \lim_{r\to 0} \frac{\rho_2 J_1(2\pi\rho_2 r)}{r} \quad (102)$$

$$= \pi\rho_2^2$$

$$= \text{Area of circle whose radius is } \rho_2$$

The diffraction intensity of the unserrated aperture is included for comparison purpose. Both serrated apertures have a maximum NA=0.9. But, their serration teeth lengths are different. In FIG. 46b, curve 4612 shows the image plane intensity of zeroth diffraction order of serrated aperture ($\rho_1$=0.8 NA, $\rho_2$=0.9 NA), and curve 4610 is for the unserrated aperture. In FIG. 46c, curve 4614 shows the image plane intensity of zeroth diffraction order of serrated aperture ($\rho_1$=0.7 NA, $\rho_2$=0.9 NA), and curve 4616 is for the unserrated aperture. FIGS. 46b and 46c tell us the following.

(1) Serrated apertures produce images which extend less far than an unserrated aperture. This feature is exactly what we wanted from serrated apertures.
(2) The longer the serration width, the less the long range diffraction effects in the image.
(3) Serration is not effective in affecting the image shape near the image center.
(4) The longer the serration width, the smaller the peak intensity of the image.

Serrations reduce long range diffraction amplitudes, but, they also reduce the peak height of the zeroth diffraction order because they unavoidably reduce the effective aperture area. This is an undesirable side effect of serrated apertures and also soft apertures in general. Therefore, in determining the serration width, a good compromise between the two effects needs to be practiced.

As stated previously, in order to make the serrated aperture work, we preferably make sure that only the zeroth diffraction order reaches the image sensor and all higher diffraction orders miss the image sensor. However, second and all higher diffraction orders go further away from the zeroth order than the first order. That is, if the first order misses the image sensor, all higher orders miss the image sensor automatically. Therefore, we can take care of only the first order.

We know from the theory of diffraction by periodic structures that the smaller the serration pitch, the further away the first order goes from zeroth order. If the serrations are made fine enough, we can put the first diffraction order far enough away from the zeroth order. However, serrations are on the edge of a round aperture, not on a straight edge. In this case, the theory of diffraction by periodic structures does not directly apply.

Even if most of the first order light is sufficiently far away from the zeroth order, there can still be a small amount of the first order light landing between the zeroth order and the main part of the first order light. It could be a serious problem if the first order light between the zeroth order and the main part of the first order is not negligible. It does not seem possible to estimate the intensity of this kind of troublesome light in a simple manner. Therefore, numerical calculations are adopted herein.

For the numerical calculations of the first diffraction order intensity distribution, equations (100) and (101) were used. The same normalization factor as the zeroth order case, equation (102), was used for the normalization of intensity.

Figure 46D:
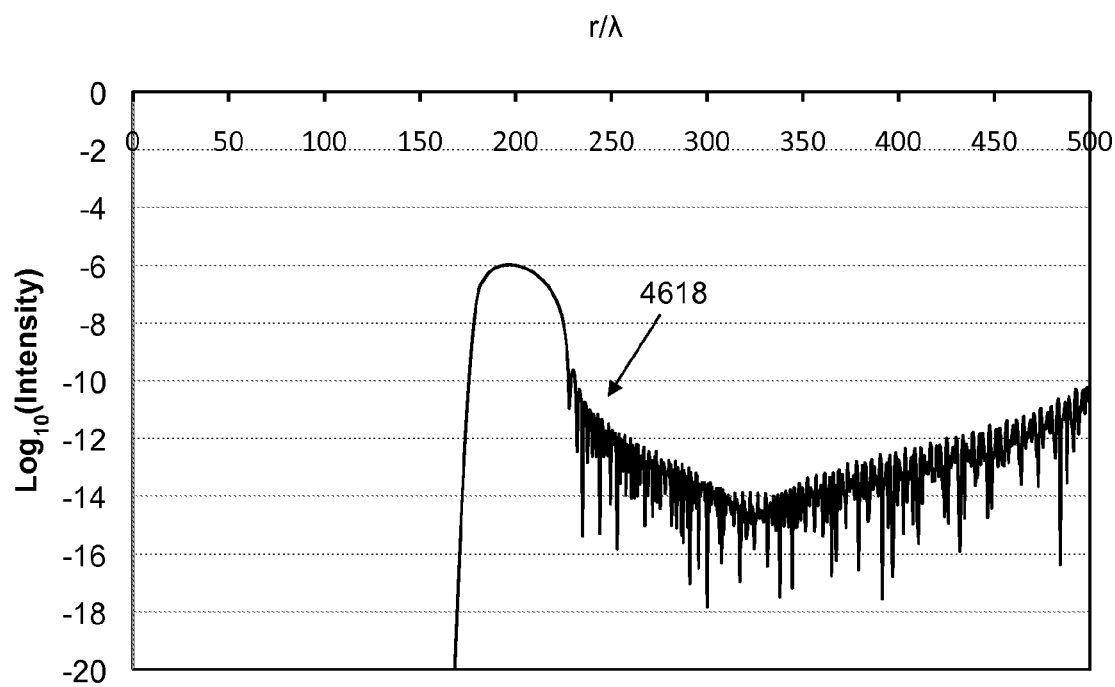

In FIG. 46d, curve 4618 shows the radial distribution of the light in the first diffraction order for N=1000 and indicates the following:

(1) First diffraction order light is spread over a wide range. This is very different from the case for serrations on a straight edge.
(2) There is practically no light between zeroth order and the main part of the first order. This is an amazing and important feature of the serrated aperture. This feature allows serrated apertures to work. We can put the image sensor in the zone where no first order light exists. If the image sensor is too big to be put inside the zone of no first order light, we can increase the number of serrations to increase the area because the radius of the zone is approximately proportional to the number of serrations.

Figure 46E:
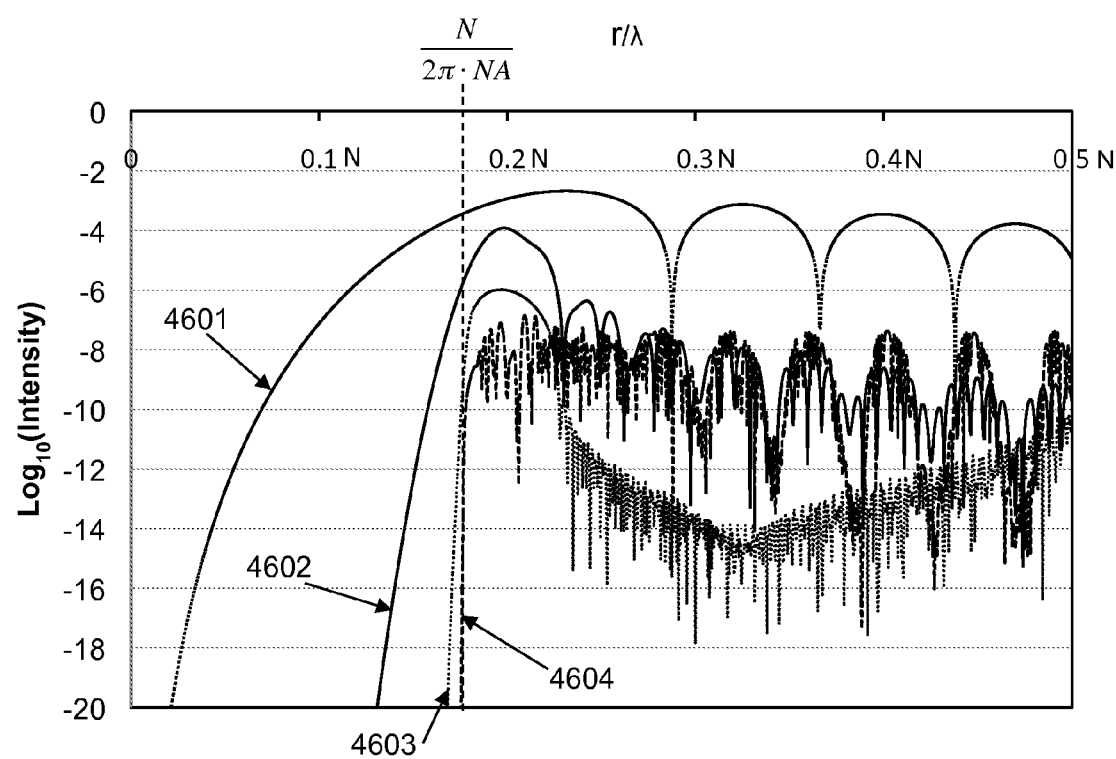

FIG. 46e shows the radial distributions of the first order light for different numbers of serrations around the aperture circumference. Curve 4601 corresponds to 10 serrations around the aperture circumference, curve 4602 corresponds to 100 serrations, curve 4603 to 1000 serrations, and curve 4604 to 10,000 serrations. This analysis indicates the following:

(1) The radius of the no-first-order-light zone is approximately proportional to the number of serrations. This is especially true for a N larger than 1000.
(2) The serrated aperture does not work well when the number of serrations is less than 100 because of the fast shrinkage of the no-first-order-light zone with the decrease of the number of serrations.
(3) For large N, like more than 1000, $$\text{The approximate radius of the no-first-order-light zone} \approx \frac{N\lambda}{2\pi \cdot NA} \quad (103)$$

This value agrees with our intuition, based on diffraction by periodic structures. Equation (103) can be used to determine the number of serrations or an equivalent serration pitch required to put the first and all higher diffraction orders outside the image sensor We can calculate $\theta_1$, the diffraction angle (more precisely the direction cosine) of the first diffraction order, from equation (103) because:

$$\sin(\theta_1) \approx \frac{\text{Radius of no-first-order light zone at image plane}}{f} \quad (104)$$

where f is the focal length of lens system placed between the aperture and image plane and r, the physical radius of the aperture, is expressed as $$r = NA \cdot f \quad (105)$$

and p, the physical pitch of the serration, is expressed as $$p = \frac{2\pi r}{N} \quad (106)$$

From equations (103) through (106), $$\sin(\theta_1) \approx \frac{\lambda}{p} \text{ if } p \ll r \quad (107)$$

Equation (107) is identical to the diffraction angle expression for the serrations on linear edges. The diffraction angle expression for the serrations on linear edges is identical to that for periodical structures like gratings. This means that if the pitch of the serration teeth is much smaller than the radius of curvature of the edge, the curvature of the edge can be ignored and the serrations on curved edges can be treated like those on straight edges.

This also makes sense because a short section of a curve can be considered as a straight line. This tell us that the edge serration technique can be applied to any edge of any shape as long as the edge does not have sharp corners and the pitch of the serrations is much smaller than the radius of curvature of the edge. For example, consider an aperture of irregular shape. In this case, the curvature of the aperture edge varies along the edge. However, as long as the aperture does not have sharp corners, we can make the serration pitch to satisfy equation (107).

The serration pitch does not need to be the same everywhere. As long as the pitch is varied slowly along the edges, the serration technique disclosed herein is expected to work at least to some degree.

The advantages of a serrated aperture are summarized below.
1. Less long-range diffraction. Reduces the height of the diffraction-limited image in regions well removed from the central core of the image.
2. By choosing the serration pitch carefully, the first and higher diffraction orders can be kept away from the image sensor.
3. No phase change introduced.
4. Easy to make.

VI. Applications of Interferometric Defect Detection and Classification

The described embodiments are well-suited to high-resolution optical inspection or making measurements that can benefit from the determination of both the amplitude and phase of the optical signal. The following is a partial list of possible applications: defect detection and defect classification of patterned wafers; defect detection and classification of bare wafers; crystal defect detection; defect review; detection and classification of reticle defects, including defects on reticles having a phase change component.

Many of the advantages of the various embodiments have been described herein. Such advantages include: high defect signal; high defect detection sensitivity; less false defect detections; less sample pattern noise, ability to catch different kinds of defects at a time; ability to distinguish between voids and particles or a mesa and a valley; more accurate and reliable defect classification; improved detection consistency; improved illumination uniformity across the field leading to more effective utilization of image sensor dynamic range for the amplification of defect signals; fast setup of operational modes; the use of a mode-locked laser rather than a CW laser thereby lowering cost; avoidance of the need for speckle busting leading to lower cost; ability to use flood illumination thereby decreasing the chance of wafer damage; ability to use coherent illumination leading to well-defined diffraction orders, thereby providing for straightforward Fourier filtering; simple system configuration leading to lower cost; elimination of pupil or aperture stop relay leading to lower cost and decreasing energy loss; and efficient energy use.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the inventive body of work is not to be limited to the details given herein, which may be modified within the scope and equivalents of the appended claims.

What is claimed is:

1. A common-path interferometry system for detecting a defect in a sample having a surface, the system comprising:
   an illumination source configured to generate light and direct the light toward the sample;
   an optical imaging system configured to collect a portion of the light from the sample including a scattered component that is predominantly scattered by the sample, and a specular component of the light that is predominantly undiffracted by the sample, with the scattered and specular components having a relative phase;
   a variable phase controlling system configured to adjust said relative phase; and
   a sensing system configured to sense at least portions of the scattered component and specular components in a combination thereof after the relative phase is adjusted.

2. A system according to claim 1, wherein the scattered component and the specular component are collected from the same side of the sample as the illumination is incident.

3. A system according to claim 1, wherein the scattered and specular components are transmitted through the sample.

4. A system according to claim 1, wherein the sensing system is configured to compare the sensed portions of the combined scattered and specular components with reference information corresponding to said relative phase.

5. A system of claim 4, wherein the variable phase controlling system is configured to carry out plural adjustments of said relative phase and the sensing system further includes a memory for storing information on the compared sensed portions of the combined scattered and specular components with the reference information for each of said adjustments.

6. A system of claim 5 further including a computation unit configured to use the comparison of the sensed portions of the combined scattered and specular components with the reference information for each of said adjustments to compute a phase and an amplitude of the defect.

7. A system of claim 6, wherein the computation unit further includes a classification unit configured to use a phase and an amplitude related to the defect to categorize the defect.

8. A system according to claim 1, further comprising polarization optical components selected and arranged to impart a polarization to the specular component.

9. A system according to claim 1, wherein the light generated by the illumination source is substantially coherent and is predominantly of a first wavelength.

10. A system according to claim 1, wherein the optical imaging system includes an aperture stop and a Fourier filtering system, with the Fourier filtering system being configured to selectively block light at or near the aperture stop.

11. A system according to claim 1 wherein the specular and scattered components have respective intensities, and wherein the optical system is configured to attenuate at least one of the intensities in a manner that increases image contrast.

12. A defect detection system for detecting one or more defects in a sample having a surface, comprising:
- an illumination unit configured to generate substantially coherent electromagnetic energy of a first and a second wavelength and direct said light to illuminate the sample; and
- optical imaging system means for collecting a scattered component of the light that is predominantly scattered by the sample, and a specular component of the light that is predominantly undiffracted by the sample for each of the first and second wavelengths, wherein for each of said first and second wavelengths said scattered component and said specular component have a respective relative phase; and
- a variable phase controlling means for adjusting the relative phase between the scattered component and the specular component corresponding to each of the first and second wavelengths; and
- a sensing system means for sensing at least portions of a combination of the scattered component and the specular component corresponding to each of the first and second wavelengths after said adjusting of the relative phase.

13. A system according to claim 12, further comprising means for comparing the sensed portions of the combined scattered and specular components with reference information corresponding to the wavelength and the adjusted relative phase of the combined components.

14. A method of using common-path interferometry to observe a sample, the method comprising:
- directing light toward the sample so that the light is incident upon the sample;
- collecting light from the sample with an optical system, the collected light having a scattered component that is predominantly scattered by the sample, and a specular component that is predominantly undiffracted by the sample, with the scattered and specular components having a relative phase;
- adjusting the relative phase with the optical system; and
- sensing at least portions of a combination of the scattered component and the specular component after said relative phase adjustment to create multiple data sets, each corresponding to the sensed light corresponding to a different relative phase.

15. The method of claim 14, wherein the scattered component includes diffracted light.

16. A method according to claim 14, further comprising comparing the sensed portions of the combined scattered and specular components with reference information corresponding to said relative phase shift between the scattered and specular components.

17. A method according to claim 14, further comprising attenuating at least one of the specular component and the scattered component.

18. A method according to claim 14, further comprising independently changing a polarization of the light incident on the sample, a polarization of the specular component, and a polarization of the sensed light.

19. A method according to claim 14, further comprising Fourier filtering light traveling through the optical system.

20. A method according to claim 14, wherein the light directed to the sample is substantially coherent and is predominantly of a first wavelength.

21. A method of using common-path interferometry to observe a sample, the method comprising:
- directing light of a first wavelength and light of a second wavelength toward the sample to be incident thereon;
- collecting, using respective first and second optical systems, light from the sample, the collected light having for each of the first and second wavelengths a scattered component that is predominantly scattered by the sample, and a specular component that is predominantly undiffracted by the sample, with the scattered and specular components having a relative phase for each of the two wavelengths; adjusting said relative phase for each of the first-wavelength light and the second-wavelength light; and
- for each of the first-wavelength light and the second-wavelength light, respectively sensing at least portions of a combination of the scattered component and the specular component after said relative phase adjustment.

22. A method according to claim 21, wherein the scattered component includes diffracted light.

\* \* \* \* \*

UNITED STATES PATENT AND TRADEMARK OFFICE
CERTIFICATE OF CORRECTION

PATENT NO.         : 7,986,412 B2                                    Page 1 of 1
APPLICATION NO.    : 12/959194
DATED              : July 26, 2011
INVENTOR(S)        : Hwan J. Jeong It is certified that error appears in the above-identified patent and that said Letters Patent is hereby corrected as shown below:

On the title page, item [60] Related U.S. Application Data section should read:

This patent application is a continuation of PCT International Application No. PCT/US09/45999 filed Jun. 2, 2009 which claims the benefit of U.S. Patent Application Ser. No. 12/190,144 filed Aug. 12, 2008, of U.S. Provisional Ser. No. 61/130,729 filed Jun. 3, 2008, of U.S. Provisional Ser. No. 61/135,616 filed Jul. 22, 2008, of U.S. Provisional Ser. No. 61/189,508 filed Aug. 20, 2008, of U.S. Provisional Ser. No. 61/189,509 filed Aug. 20, 2008, of U.S. Provisional Ser. No. 61/189,510 filed Aug. 20, 2008 and of U.S. Provisional Ser. No. 61/210,513 filed Mar. 19, 2009.

In the Specifications:
Col. 1, lines 7-15, should be replaced with the following:

--This patent application is a continuation of PCT International Application No. PCT/US09/45999 filed Jun. 2, 2009 which claims the benefit of U.S. Patent Application Ser. No. 12/190,144 filed Aug. 12, 2008, of U.S. Provisional Ser. No. 61/130,729 filed Jun. 3, 2008, of U.S. Provisional Ser. No. 61/135,616 filed Jul. 22, 2008, of U.S. Provisional Ser. No. 61/189,508 filed Aug. 20, 2008, of U.S. Provisional Ser. No. 61/189,509 filed Aug. 20, 2008, of U.S. Provisional Ser. No. 61/189,510 filed Aug. 20, 2008 and of U.S. Provisional Ser. No. 61/210,513 filed Mar. 19, 2009, each of which is incorporated by reference herein.--

Signed and Sealed this
Twenty-first Day of May, 2013

Teresa Stanek Rea
*Acting Director of the United States Patent and Trademark Office*